United States Patent
Joung et al.

(10) Patent No.: US 11,591,601 B2
(45) Date of Patent: Feb. 28, 2023

(54) METHODS FOR IDENTIFICATION AND MODIFICATION OF LNCRNA ASSOCIATED WITH TARGET GENOTYPES AND PHENOTYPES

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Julia Joung, Cambridge, MA (US); Jesse Engreitz, Cambridge, MA (US); Eric S. Lander, Cambridge, MA (US); Feng Zhang, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 16/611,025

(22) PCT Filed: May 4, 2018

(86) PCT No.: PCT/US2018/031075
§ 371 (c)(1),
(2) Date: Nov. 5, 2019

(87) PCT Pub. No.: WO2018/204777
PCT Pub. Date: Nov. 8, 2018

(65) Prior Publication Data
US 2020/0248184 A1 Aug. 6, 2020

Related U.S. Application Data

(60) Provisional application No. 62/564,102, filed on Sep. 27, 2017, provisional application No. 62/502,064, filed on May 5, 2017.

(51) Int. Cl.
| | | |
|---|---|---|
| C07H 21/04 | (2006.01) | |
| C12N 15/113 | (2010.01) | |
| A61P 35/00 | (2006.01) | |
| C12Q 1/6886 | (2018.01) | |
| A61K 45/06 | (2006.01) | |

(52) U.S. Cl.
CPC .......... *C12N 15/1135* (2013.01); *A61P 35/00* (2018.01); *C12Q 1/6886* (2013.01); *A61K 45/06* (2013.01); *C12N 2310/113* (2013.01); *C12N 2310/20* (2017.05); *C12N 2320/31* (2013.01); *C12Q 2600/112* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,769,061 A | 9/1988 | Comai |
| 4,810,648 A | 3/1989 | Stalker |
| 4,940,835 A | 7/1990 | Shah et al. |
| 4,975,374 A | 12/1990 | Goodman et al. |
| 5,266,317 A | 11/1993 | Tomalski et al. |
| 5,273,894 A | 12/1993 | Strauch et al. |
| 5,276,268 A | 1/1994 | Strauch et al. |
| 5,494,813 A | 2/1996 | Hepher et al. |
| 5,543,158 A | 8/1996 | Gref et al. |
| 5,561,236 A | 10/1996 | Leemans et al. |
| 5,563,055 A | 10/1996 | Townsend et al. |
| 5,580,859 A | 12/1996 | Felgner et al. |
| 5,589,466 A | 12/1996 | Felgner et al. |
| 5,593,972 A | 1/1997 | Weiner et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,739,082 A | 4/1998 | Donn |
| 5,789,156 A | 8/1998 | Bujard et al. |

(Continued)

FOREIGN PATENT DOCUMENTS

| | | |
|---|---|---|
| CN | 104004782 A | 8/2014 |
| EP | 0 242 246 A1 | 10/1987 |
| EP | 0 333 033 A1 | 9/1989 |
| EP | 0 571 427 A1 | 12/1993 |
| EP | 0 663 956 A1 | 7/1995 |
| EP | 0 719 338 A1 | 7/1996 |
| EP | 0 728 213 A1 | 8/1996 |
| EP | 1 887 079 A1 | 2/2008 |
| EP | 1 950 303 A1 | 7/2008 |
| EP | 1 999 263 A1 | 12/2008 |

(Continued)

OTHER PUBLICATIONS

Goyal et al. ("Challenges of CRISPR/Cas9 applications for long non-coding RNA genes." Nucleic acids research 45.3 (2017): e12-e12).*

The Broad Institute, Inc., "International Preliminary Report on Patentability issued in International Application No. PCT/US2018/031075", dated Nov. 14, 2019, 16 pages.

(Continued)

*Primary Examiner* — Kimberly Chong
(74) *Attorney, Agent, or Firm* — F. Brent Nix, Esq.; Johnson, Marcou, Isaacs & Nix, LLC

(57) ABSTRACT

The application relates to methods for compositions for identifying lncRNA loci associated with target genotypes or phenotypes, including desirable plant genotypes or phenotype. The application also relates to regulatory regions and genes associated with drug resistance, such as resistance to BRAF-inhibitors. Such regulatory regions and genes form the basis for methods for identifying resistance to BRAF-inhibitors, which is useful for improving disease prognosis, treatment, and likely outcomes. The regulatory regions and genes are also suitable targets for therapy in melanoma that is resistant to BRAF-inhibitors.

9 Claims, 14 Drawing Sheets

Specification includes a Sequence Listing.

(56) References Cited

U.S. PATENT DOCUMENTS

| | | |
|---|---|---|
| 5,814,618 A | 9/1998 | Bujard et al. |
| 5,824,790 A | 10/1998 | Keeling et al. |
| 5,846,946 A | 12/1998 | Huebner et al. |
| 5,855,913 A | 1/1999 | Hanes et al. |
| 5,908,810 A | 6/1999 | Donn |
| 5,908,975 A | 6/1999 | Caimi et al. |
| 5,985,309 A | 11/1999 | Edwards et al. |
| 6,007,845 A | 12/1999 | Domb et al. |
| 6,013,861 A | 1/2000 | Bird et al. |
| 6,248,876 B1 | 6/2001 | Barry et al. |
| 6,284,479 B1 | 9/2001 | Nichols |
| 6,479,626 B1 | 11/2002 | Kim et al. |
| 6,534,261 B1 | 3/2003 | Cox et al. |
| 6,607,882 B1 | 8/2003 | Cox et al. |
| 6,734,341 B2 | 5/2004 | Singletary et al. |
| 6,746,838 B1 | 6/2004 | Choo et al. |
| 6,768,044 B1 | 7/2004 | Boudec et al. |
| 6,794,136 B1 | 9/2004 | Eisenberg et al. |
| 6,824,978 B1 | 11/2004 | Cox et al. |
| 6,866,997 B1 | 3/2005 | Choo et al. |
| 6,903,185 B2 | 6/2005 | Kim et al. |
| 6,933,113 B2 | 8/2005 | Case et al. |
| 6,979,539 B2 | 12/2005 | Cox et al. |
| 7,013,219 B2 | 3/2006 | Case et al. |
| 7,030,215 B2 | 4/2006 | Liu et al. |
| 7,112,665 B1 | 9/2006 | Leemans et al. |
| 7,220,719 B2 | 5/2007 | Case et al. |
| 7,241,573 B2 | 7/2007 | Choo et al. |
| 7,241,574 B2 | 7/2007 | Choo et al. |
| 7,259,015 B2 | 8/2007 | Kingsman et al. |
| 7,303,910 B2 | 12/2007 | Bebbington et al. |
| 7,351,585 B2 | 4/2008 | Mitrophanous et al. |
| 7,585,849 B2 | 9/2009 | Liu et al. |
| 7,595,376 B2 | 9/2009 | Kim et al. |
| 7,745,651 B2 | 6/2010 | Heyes et al. |
| 7,799,565 B2 | 9/2010 | MacLachlan et al. |
| 7,803,397 B2 | 9/2010 | Heyes et al. |
| 7,838,658 B2 | 11/2010 | MacLachlan et al. |
| 7,901,708 B2 | 3/2011 | MacLachlan et al. |
| 7,915,399 B2 | 3/2011 | MacLachlan et al. |
| 7,982,027 B2 | 7/2011 | MacLachlan et al. |
| 8,021,867 B2 | 9/2011 | Smith et al. |
| 8,044,019 B2 | 10/2011 | Uno et al. |
| 8,058,069 B2 | 11/2011 | Yaworski et al. |
| 8,101,741 B2 | 1/2012 | MacLachlan et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,188,263 B2 | 5/2012 | MacLachlan et al. |
| 8,236,943 B2 | 8/2012 | Lee et al. |
| 8,283,333 B2 | 10/2012 | Yaworski et al. |
| 8,372,951 B2 | 2/2013 | Chang et al. |
| 8,404,658 B2 | 3/2013 | Hajjar et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,454,972 B2 | 6/2013 | Nabel et al. |
| 8,507,272 B2 | 8/2013 | Zhang et al. |
| 8,575,305 B2 | 11/2013 | Gait et al. |
| 8,614,194 B1 | 12/2013 | Chen et al. |
| 8,697,359 B1 | 4/2014 | Zhang |
| 8,709,843 B2 | 4/2014 | Shakuda |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2002/0031826 A1 | 3/2002 | Nichols |
| 2004/0013648 A1 | 1/2004 | Kingsman et al. |
| 2004/0142476 A1 | 7/2004 | Evans et al. |
| 2004/0171156 A1 | 9/2004 | Hartley et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2007/0266453 A1 | 11/2007 | Anderson et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0018016 A1 | 1/2009 | Duck et al. |
| 2009/0111106 A1 | 4/2009 | Mitrophanous et al. |
| 2009/0144850 A1 | 6/2009 | Van Winkle et al. |
| 2010/0317109 A1 | 12/2010 | Maden et al. |
| 2011/0117189 A1 | 5/2011 | Mazzone et al. |
| 2011/0195123 A1 | 8/2011 | Shemi |
| 2011/0293571 A1 | 12/2011 | Widdowson et al. |
| 2011/0293703 A1 | 12/2011 | Mahon et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0185823 A1 | 7/2013 | Kuang et al. |
| 2013/0244279 A1 | 9/2013 | de Fougerolles et al. |
| 2013/0245107 A1 | 9/2013 | de Fougerolles et al. |
| 2013/0252281 A1 | 9/2013 | de Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0310830 A1 | 10/2014 | Zhang et al. |
| 2014/0342456 A1 | 11/2014 | Mali et al. |
| 2014/0356959 A1 | 12/2014 | Church et al. |
| 2015/0031132 A1 | 1/2015 | Church et al. |
| 2015/0184139 A1 | 7/2015 | Zhang et al. |
| 2015/0232883 A1 | 8/2015 | Dahlman et al. |
| 2015/0247150 A1 | 9/2015 | Zhang et al. |
| 2015/0291966 A1 | 10/2015 | Zhang et al. |
| 2015/0356239 A1 | 12/2015 | Zhang et al. |
| 2015/0356329 A1 | 12/2015 | Erez et al. |
| 2016/0153004 A1 | 6/2016 | Zhang et al. |
| 2016/0251648 A1 | 9/2016 | Wang et al. |
| 2017/0166903 A1 | 6/2017 | Zhang et al. |
| 2017/0349894 A1 | 12/2017 | Dahlman et al. |
| 2017/0349914 A1 | 12/2017 | Cox et al. |
| 2018/0010134 A1 | 1/2018 | Sharp et al. |
| 2018/0044662 A1 | 2/2018 | Platt et al. |

FOREIGN PATENT DOCUMENTS

| | | |
|---|---|---|
| EP | 2 099 905 A1 | 9/2009 |
| EP | 2 099 915 A1 | 9/2009 |
| EP | 1 519 714 B1 | 10/2010 |
| EP | 1 766 035 B1 | 12/2011 |
| EP | 1 781 593 B1 | 12/2011 |
| EP | 1 664 316 B1 | 8/2012 |
| EP | 2 771 468 B1 | 2/2015 |
| EP | 2 784 162 B1 | 4/2015 |
| EP | 2 764 103 B1 | 8/2015 |
| EP | 2 970 997 A1 | 1/2016 |

(56) References Cited

FOREIGN PATENT DOCUMENTS

| | | |
|---|---|---|
| JP | 2006-304779 A | 11/2006 |
| WO | 93/01294 A1 | 1/1993 |
| WO | 93/02197 A1 | 2/1993 |
| WO | 93/19181 A1 | 9/1993 |
| WO | 94/00992 A1 | 1/1994 |
| WO | 94/04693 A2 | 3/1994 |
| WO | 94/09144 A1 | 4/1994 |
| WO | 94/11520 A2 | 5/1994 |
| WO | 95/04826 A1 | 2/1995 |
| WO | 95/26407 A1 | 10/1995 |
| WO | 95/31553 A1 | 11/1995 |
| WO | 95/35026 A1 | 12/1995 |
| WO | 96/01904 A1 | 1/1996 |
| WO | 96/15248 A1 | 5/1996 |
| WO | 96/19581 A1 | 6/1996 |
| WO | 96/21023 A1 | 7/1996 |
| WO | 96/27674 A1 | 9/1996 |
| WO | 96/30517 A1 | 10/1996 |
| WO | 96/34968 A2 | 11/1996 |
| WO | 96/38567 A2 | 12/1996 |
| WO | 97/11188 A1 | 3/1997 |
| WO | 97/20936 A1 | 6/1997 |
| WO | 97/26362 A1 | 7/1997 |
| WO | 97/32985 A1 | 9/1997 |
| WO | 97/42328 A1 | 11/1997 |
| WO | 97/44472 A1 | 11/1997 |
| WO | 97/45545 A1 | 12/1997 |
| WO | 97/47806 A1 | 12/1997 |
| WO | 97/47807 A1 | 12/1997 |
| WO | 97/47808 A1 | 12/1997 |
| WO | 98/20145 A2 | 5/1998 |
| WO | 98/22604 A1 | 5/1998 |
| WO | 98/27212 A1 | 6/1998 |
| WO | 98/39460 A1 | 9/1998 |
| WO | 98/40503 A1 | 9/1998 |
| WO | 99/12950 A2 | 3/1999 |
| WO | 99/24585 A1 | 5/1999 |
| WO | 99/24586 A1 | 5/1999 |
| WO | 99/24593 A1 | 5/1999 |
| WO | 99/53072 A1 | 10/1999 |
| WO | 99/58654 A2 | 11/1999 |
| WO | 99/58688 A2 | 11/1999 |
| WO | 99/58690 A2 | 11/1999 |
| WO | 98/32326 A3 | 12/1999 |
| WO | 99/66050 A1 | 12/1999 |
| WO | 00/04173 A1 | 1/2000 |
| WO | 00/08175 A2 | 2/2000 |
| WO | 00/08184 A1 | 2/2000 |
| WO | 00/08185 A1 | 2/2000 |
| WO | 00/11192 A2 | 3/2000 |
| WO | 00/14249 A1 | 3/2000 |
| WO | 00/22140 A1 | 4/2000 |
| WO | 00/28052 A2 | 5/2000 |
| WO | 00/47727 A2 | 8/2000 |
| WO | 00/73422 A1 | 12/2000 |
| WO | 00/77229 A2 | 12/2000 |
| WO | 01/12782 A2 | 2/2001 |
| WO | 01/12826 A2 | 2/2001 |
| WO | 01/14569 A2 | 3/2001 |
| WO | 01/19975 A2 | 3/2001 |
| WO | 01/98509 A2 | 12/2001 |
| WO | 02/34923 A2 | 5/2002 |
| WO | 02/46387 A2 | 6/2002 |
| WO | 02/079410 A2 | 10/2002 |
| WO | 02/083911 A1 | 10/2002 |
| WO | 02/101059 A2 | 12/2002 |
| WO | 03/033540 A2 | 4/2003 |
| WO | 03/071860 A2 | 9/2003 |
| WO | 2004/015075 A2 | 2/2004 |
| WO | 2004/056999 A1 | 7/2004 |
| WO | 2004/078983 A2 | 9/2004 |
| WO | 2004/090140 A2 | 10/2004 |
| WO | 2005/002359 A2 | 1/2005 |
| WO | 2005/012515 A2 | 2/2005 |
| WO | 2005/012529 A1 | 2/2005 |
| WO | 2005/030941 A1 | 4/2005 |
| WO | 2005/030942 A1 | 4/2005 |
| WO | 2005/095617 A2 | 10/2005 |
| WO | 2005/095618 A2 | 10/2005 |
| WO | 2005/095619 A1 | 10/2005 |
| WO | 2005/095632 A2 | 10/2005 |
| WO | 2005/107437 A2 | 11/2005 |
| WO | 2005/123927 A1 | 12/2005 |
| WO | 2006/018319 A1 | 2/2006 |
| WO | 2006/032538 A1 | 3/2006 |
| WO | 2006/045633 A1 | 5/2006 |
| WO | 2006/063862 A1 | 6/2006 |
| WO | 2006/072603 A2 | 7/2006 |
| WO | 2006/103107 A1 | 10/2006 |
| WO | 2006/108702 A1 | 10/2006 |
| WO | 2006/133827 A2 | 12/2006 |
| WO | 2007/009823 A1 | 1/2007 |
| WO | 2007/039314 A2 | 4/2007 |
| WO | 2007/039315 A1 | 4/2007 |
| WO | 2007/039316 A1 | 4/2007 |
| WO | 2007/107326 A1 | 9/2007 |
| WO | 2008/042156 A1 | 4/2008 |
| WO | 2008/064289 A2 | 5/2008 |
| WO | 2009/144079 A1 | 12/2009 |
| WO | 2010/061186 A2 | 6/2010 |
| WO | 2010/096488 A1 | 8/2010 |
| WO | 2011/008730 A2 | 1/2011 |
| WO | 2012/135025 A2 | 10/2012 |
| WO | 2013/046247 A1 | 4/2013 |
| WO | 2013/122472 A2 | 8/2013 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/144155 A1 | 9/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015024986 A1 | 2/2015 |
| WO | 2015/058052 A1 | 4/2015 |
| WO | 2015/065964 A1 | 5/2015 |
| WO | 2015/070083 A1 | 5/2015 |
| WO | 2015/086795 A1 | 6/2015 |
| WO | 2015/089351 A1 | 6/2015 |
| WO | 2015/089354 A1 | 6/2015 |
| WO | 2015/089364 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015/109752 A1 | 7/2015 |
| WO | 2015/138855 A1 | 9/2015 |
| WO | 2016/004925 A1 | 1/2016 |
| WO | 2016/025131 A2 | 2/2016 |
| WO | 2016/028682 A1 | 2/2016 |
| WO | 2016/049163 A2 | 3/2016 |
| WO | 2016/049258 A2 | 3/2016 |
| WO | 2016/069591 A2 | 5/2016 |
| WO | 2016/073433 A1 | 5/2016 |
| WO | 2016/094867 A1 | 6/2016 |
| WO | 2016/094872 A1 | 6/2016 |
| WO | 2016/094874 A1 | 6/2016 |
| WO | 2016/099887 A1 | 6/2016 |
| WO | 2016/100272 A1 | 6/2016 |
| WO | 2016/100562 A1 | 6/2016 |
| WO | 2016/100568 A1 | 6/2016 |

(56) References Cited

FOREIGN PATENT DOCUMENTS

| | | |
|---|---|---|
| WO | 2016/100571 A1 | 6/2016 |
| WO | 2016/106244 A1 | 6/2016 |
| WO | 2016/094872 A9 | 8/2016 |
| WO | 2016/186745 A1 | 11/2016 |
| WO | 2016/205613 A1 | 12/2016 |
| WO | 2017/019867 A1 | 2/2017 |
| WO | 2017/066175 A1 | 4/2017 |
| WO | 2017/100158 A1 | 6/2017 |
| WO | 2017/105991 A1 | 6/2017 |
| WO | 2017/106414 A1 | 6/2017 |
| WO | 2018/035250 A1 | 2/2018 |
| WO | 2018/035387 A1 | 2/2018 |
| WO | 2018/035388 A1 | 2/2018 |
| WO | 2018/170333 A1 | 9/2018 |
| WO | 2018/204777 A2 | 11/2018 |
| WO | 2019/046636 A1 | 3/2019 |

OTHER PUBLICATIONS

Anderson, et al., "Transcription of the Non-Coding RNA Upperhand Controls Hand2 Expression and Heart Development", Nature, vol. 539, No. 7629, Nov. 17, 2016, 26 pages.

Bhatia, et al., "Present Scenario of Long Non-Coding RNAs in Plants", Non-Coding RNA, vol. 3, No. 2, Jun. 2017, 22 pages.

Cabili, et al., "Integrative Annotation of Human Large Intergenic Noncoding RNAs Reveals Global Properties and Specific Subclasses", Genes & Development, vol. 25, No. 18, Sep. 15, 2011, 1915-1927.

Derrien, et al., "The GENCODE V7 Catalog of Human Long Noncoding Rnas: Analysis of their Gene Structure, Evolution, and Expression", Genome Research, vol. 22, No. 9, Sep. 2012, 1775-1789.

Ding, et al., "A Long Noncoding RNA Regulates Photoperiod-Sensitive Male Sterility, an Essential Component of Hybrid Rice", Proceedings of the National Academy of Sciences, vol. 109, No. 7, Feb. 14, 2012, 2654-2659.

Engreitz, et al., "Local Regulation of Gene Expression by lncRNA Promoters, Transcription and Splicing", Nature, vol. 539, Nov. 17, 2016, 19 pages.

Engreitz, et al., "The Xist Lncrna Exploits Three-Dimensional Genome Architecture to Spread Across the X Chromosome", Science, vol. 341, No. 3147, Aug. 16, 2013, 18 pages.

Fulco, et al., "Systematic Mapping of Functional Enhancer-Promoter Connections with CRISPR Interference", Science, vol. 354, No. 6313, Nov. 11, 2016, 11 pages.

Gilbert, et al., "Genome-Scale CRISPR-Mediated Control of Gene Repression and Activation", Cell, vol. 159, No. 3, Oct. 23, 2014, 647-661.

Guttman, et al., "Chromatin Signature Reveals Over a Thousand Highly Conserved Large Non-Coding Rnas in Mammals", Nature, vol. 458, No. 4235, Mar. 12, 2009, 13 pages.

Guttman, et al., "Modular Regulatory Principles of Large Non-Coding RNAs", Nature, vol. 482, Issue 7385, Feb. 16, 2012, 339-346.

Heo, et al., "Epigenetic Regulation by Long Noncoding RNAs in Plants", Chromosome Research, vol. 21, No. 0, Dec. 2013, 13 pages.

Hsu, et al., "DNA Targeting Specificity of RNA-Guided Cas9 Nucleases", Nature Biotechnology, vol. 31, No. 9, Sep. 2013, 17 pages.

Joung, et al., "Genome-Scale Crispr-Cas9 Knockout and Transcriptional Activation Screening", Nature Protocols, vol. 12, No. 4, Apr. 2017, 71 pages.

Konermann, et al., "Genome-Scale Transcriptional Activation by an Engineered CRISPR-Cas9 Complex", Nature, vol. 517, No. 7536, Dec. 10, 2014, 18 pages.

Kretz, et al., "Control of Somatic Tissue Differentiation by the Long Non-coding RNA TINCR", Nature, vol. 493, No. 7431, Jan. 10, 2013, 16 pages.

Lei, et al., "TAZ Promotes Cell Proliferation and Epithelial-Mesenchymal Transition and is Inhibited by the Hippo Pathway", Molecular and Cellular Biology, vol. 28, No. 7, Apr. 2008, 2426-2436.

Lin, et al., "The Hippo Effector YAP Promotes Resistance to RAF- and Mektargeted Cancer Therapies", Nature Genetics, vol. 47. No. 3, Mar. 2015, 18 pages.

Liu, et al., "Crispri-Based Genome-Scale Identification of Functional Long Non-Coding RNA Loci in Human Cells", Science, vol. 355, No. 6320, Jan. 6, 2017, 19 pages.

Liu, et al., "Long Non-coding RNAs and their Biological Roles in Plants", Genomics Proteomics Bioinformatics, vol. 13, No. 3, Jun. 2015, 137-147.

Mach, et al., "The Long-Noncoding RNA ELENA1 Functions in Plant Immunity", The Plant Cell, vol. 29, No. 5, May 2017, 1 page.

Paralkar, et al., "Unlinking a lncRNA from its associated cis Element", Molecular Cell, vol. 62, No. 1, Apr. 7, 2016, 13 pages.

Praskova, et al., "MOBKL1A/MOBKL1B Phosphorylation by MST1 and MST2 Inhibits Cell Proliferation", Current Biology, vol. 18, No. 5, Mar. 11, 2008, 19 pages.

Qi, et al., "Genome-Wide Annotation of Genes nd Noncoding RNAS of Foxtail Millet in Response to Simulated Drought Stress by Deep Sequencing", Plant Molecular Biology, vol. 83, No. (4-5), Nov. 2013, 15 pages.

Sanjana, et al., "High-Resolution Interrogation of Functional Elements in the Noncoding Genome", Science, vol. 353, No. 6307, Sep. 2016, 1545-1549.

Shalem, et al., "Genome-Scale CRISPR-Cas9 Knockout Screening in Human Cells", Science, vol. 343, No. 6166, Jan. 3, 2014, 10 pages.

Zhu, et al., "Genome-scale deletion screening of human long non-coding RNAs using a paired-guide RNA CRISPR-Cas9 library", Nature Biotechnology, vol. 34, No. 12, Dec. 2016, 10 pages.

Skalska, et al., "Regulatory Feedback from Nascent RNA to Chromatin and Transcription", Nature Reviews Molecular Cell Biology, vol. 18, No. 5, Mar. 8, 2017, 7 pages.

Wang, et al., "A Long Noncoding RNA Maintains Active Chromatin to Coordinate Homeotic Gene Expression", Nature, vol. 472, No. 7341, Mar. 2011, 8 pages.

Xin, et al., "Identification and Characterization of Wheat Long Non-Protein Coding Rnas Responsive to Powdery Mildew Infection and Heat Stress by Using Microarray Analysis and SBS Sequencing", BMC Plant Biology, vol. 11, No. 61, Apr. 7, 2011, 13 pages.

Zhou, et al., "Photoperiod- and Thermo-Sensitive Genic Male Sterility in Rice are Caused by a Point Mutation in a Novel Noncoding RNA that produces a Small RNA", Cell Research, vol. 22, No. 1114, Feb. 21, 2012, 649-660.

The Broad Institute, Inc., "International Search Report for PCT/US2018/031075", dated Nov. 6, 2018, 8 pages.

Joung, et al., "Genome-Scale Activation Screen Identifies a lncRNA Locus Regulating a Gene Neighborhood", Nature, vol. 548, No. 7667, Aug. 9, 2017, pp. 343-346.

Konermann, et al., "Genome-Scale Transcriptional Activation by an Engineered CRISPR-Cas9 Complex", Nature, vol. 517, No. 7536, Dec. 10, 2014, pp. 583-588.

Sanjana et al., "High-Resolution Interrogation of Functional Elements in the Noncoding Genome", Science, vol. 353, No. 6307, Sep. 2016, pp. 1545-1549.

\* cited by examiner

METHODS FOR IDENTIFICATION AND MODIFICATION OF LNCRNA ASSOCIATED WITH TARGET GENOTYPES AND PHENOTYPES

RELATED APPLICATIONS AND INCORPORATION BY REFERENCE

This application is a National Stage Application of International Application No. PCT/US2018/031075 filed May 4, 2018, which claims the benefit of U.S. Provisional Application No. 62/502,064 filed May 5, 2017, and U.S. Provisional Application No. 62/564,102 filed Sep. 27, 2017, each of which is incorporated herein by reference in its entirety.

STATEMENT AS TO FEDERALLY SPONSORED RESEARCH

This invention was made with government support under Grant Nos. MH100706 and MH110049 awarded by the National Institutes of Health. The government has certain rights in the invention.

REFERENCE TO AN ELECTRONIC SEQUENCE LISTING

The contents of the electronic sequence listing ("BROD-0980US_ST25.txt"; Size is 70,000 bytes and it was created on Jun. 7, 2021) is herein incorporated by reference in its entirety.

FIELD OF THE INVENTION

The invention relates to methods and compositions for identification and modification of lncRNAs associated with target genotypes and phenotypes, including diagnosing and treating melanoma resistant to BRAF-inhibitors, such as Vemurafenib. The invention also relates to methods and compositions for identifying lncRNAs associated with drug resistance as well as desirable agricultural traits of interest.

BACKGROUND OF THE INVENTION

Melanoma is a skin cancer derived from melanocytes and is the most dangerous type of skin cancer. About 60% of melanomas have a V600E BRAF mutation (that is, a valine to glutamic acid substitution at amino acid 600 of B-Raf protein). A smaller number have a V600K mutation (similarly, a valine to lysine substitution at amino acid 600 of B-Raf protein).

The V600E and V600K BRAF are targeted by so-called BRAF inhibitors, which include Vemurafenib, Dabrafenib, Sorafenib, GDC-0879, PLX-4720, and LGX818. Vemurafenib and Dabrafenib are approved for the treatment of melanoma. BRAF inhibitors cause programmed cell death in melanoma cell lines by interrupting the V600E/V600K in the B-Raf/MEK step in the B-Raf/MEK/ERK pathway. Clinical trial data demonstrate that resistance to BRAF inhibitors occurs within 6 to 7 months. To overcome this resistance, Dabrafenib is approved for co-treatment with the MEK inhibitor Trametinib, but this is not universally effective.

Three mechanisms of vemurafenib resistance have been discovered: cancer cells begin to overexpress cell surface protein PDGFRB, creating an alternative survival pathway; a second oncogene called NRAS mutates, reactivating the BRAF survival pathway; and stromal cell secretion of hepatocyte growth factor (HGF), which leads to activation of the HGF receptor MET, reactivation of the mitogen-activated protein kinase (MAPK) and phosphatidylinositol-3-OH kinase (PI(3)K)-AKT signaling pathways, and resistance to RAF inhibition. These mechanisms collectively explain 40% of BRAF inhibitor resistance, leaving about 60% of treatment-resistant melanoma without an appropriate therapy or a mechanistic explanation to guide diagnosis or target treatment.

In plants, long noncoding RNAs are believed to be involved in different processes such as the response of plant development based on environmental cues, stress reactions and the regulation of symbiotic interactions with soil bacteria (Bok Heo et al., 2013 Chromosome Res. 21(0): 685-693). While the development of high-throughput sequencing technologies has facilitated their identification, elucidating the roles played by thousands of plant genomic loci that transcribe long noncoding RNAs (lncRNAs) in regulating plant genotypes and phenotypes has remained difficult.

SUMMARY OF THE INVENTION

Preferred statements (features) and embodiments of the invention are set forth herein below. Each statements and embodiments of the invention so defined may be combined with any other statement and/or embodiments unless clearly indicated to the contrary. In particular, any feature indicated as being "preferred" or "advantageous" may be combined with any other feature or features indicated as being preferred or advantageous or otherwise.

In one embodiment, the invention includes a method for identifying a lncRNA locus associated with a desirable genotype or phenotype, comprising: introducing a library of CRISPR guides into a population of cells, the cells either expressing a modified Cas protein that is not catalytically competent or having the modified Cas protein or a coding sequence thereof introduced simultaneously or sequentially with the CRISPR guides, wherein the CRISPR guides target different genomic sequences encoding lncRNA or associated with lncRNA transcription, wherein the CRISPR guides optionally comprise a loop capable of binding a transcriptional activator domain or a transcription repressor domain, and wherein the modified Cas protein is optionally linked to a transcription activator domain or a transcription repressor domain; selecting cells based on the desirable genotype or phenotype; and sequencing CRISPR guides present in the selected cells, wherein the enrichment or depletion of CRISPR guides are quantified and/or ranked to identify a lncRNA locus associated with the desirable genotype or phenotype.

In a related embodiment, the population of cells are plant cells or plant protoplasts. The plant cells or plant protoplasts can be derived from a monocotyledonous plant, such as wheat, turf, turf grass, cereal, maize, rice, oat, wheat, barley, sorghum, orchid, iris, lily, onion, banana, sugarcane, sorghum, palm, and *setaria*. The plant cells or plant protoplasts can be derived from a dicotyledonous plant, such as avocado, potato, tobacco, tomato, eggplant, sugarbeet, broccoli, cassava, sweet potato, pepper, cotton, poinsettia, legumes, alfalfa, soybean, carrot, strawberry, lettuce, oak, maple, walnut, rose, mint, squash, daisy, and *Arabidopsis*.

In a related embodiment, the desirable plant genotype is increased or decreased expression of a gene of interest. In this regard, the method can comprise quantitatively labeling single cells using fluorescence in situ hybridization (FISH) according to expression of an mRNA of interest, and sorting labeled cells into a plurality of bins based on the expression of the mRNA of interest, and determining in each of the bins relative representation of the CRISPR guides present in the labeled cells to identify a lncRNA locus associated with the desirable genotype.

In a related embodiment, the desirable plant phenotype is selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, and a combination thereof. In this regard, the method can comprise exposing the plant cells or plant protoplasts or tissues or plants derived therefrom to a stress condition selected from the group consisting of abiotic stress, drought stress, flood stress, heat stress, cold and frost stress, salt stress, heavy metal stress, low-nitrogen stress, disease stress, pest stress, herbicide stress, or a combination thereof, and selecting plant cells or plant protoplasts or tissues or plants derived therefrom based on increased tolerance or resistance to the stress condition.

In another embodiment, the invention includes a composition comprising a population of at least 500 plant cells or plant protoplasts each comprising (i) a different CRISPR guide targeting a genomic sequence encoding lncRNA or associated with lncRNA transcription and (ii) a modified Cas protein that is not catalytically competent, wherein the CRISPR guides optionally comprise a loop capable of binding a transcriptional activator domain or a transcription repressor domain, and wherein the modified Cas protein is optionally linked to a transcription activator domain or a transcription repressor domain.

In a related embodiment, the modified Cas protein is Cas9, Cpf1, C2c1, or C2c3. The modified Cas protein can be fused to a transcription activator domain or a transcription repressor domain. Alternatively, the CRISPR guides comprise a loop capable of binding a transcriptional activator domain or a transcription repressor domain.

In a related embodiment, one or more CRISPR guides target a cytoplasmic DNA sequence, or a mitochondrial DNA sequence.

In a related embodiment, the population of plant cells or plant protoplasts comprises at least 100, at least 200, at least 500, at least 1,000, at least 2,000, at least 5,000, or at least 10,000 plant cells or plant protoplasts, each comprising a different CRISPR guide targeting a genomic sequence encoding lncRNA or associated with lncRNA transcription.

In one embodiment, the invention includes a method of detecting resistance to a BRAF inhibitor (such as vemurafenib) in a melanoma cell or a patient with melanoma. Such a method includes identifying resistance to a BRAF inhibitor in a melanoma cell comprising measuring the transcriptional expression of at least one lncRNA locus selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873. In particular, the invention relates to the identification of lncRNA loci that are important for vemurafenib resistance. These loci can function as enhancers, through transcription of lncRNAs at the locus, or through the lncRNA transcript itself.

In a related embodiment, the method comprises measuring the expression of a gene regulated through such lncRNA locus. Genes upregulated through TCONS_00015940 include EQTN, MOB3B, IFNK, and C9orf72.

Elevated expression of lncRNA loci or the aforementioned genes which the lncRNA loci regulate are associated with resistance to a BRAF inhibitor. Accordingly, in some embodiments, the invention comprises a method of detecting resistance to a BRAF inhibitor in a melanoma cell, or a patient with melanoma, by detecting upregulated expression of the aforementioned lncRNA loci, or mRNA or protein of the aforementioned genes. Also disclosed is a method of monitoring vemurafenib resistant melanoma in a patient being treated with vemurafenib, comprising identifying melanoma cells resistant to a BRAF inhibitor.

In related embodiments, the invention comprises obtaining a sample from a patient suffering from melanoma, detecting the expression of a lncRNA locus or mRNA or protein of the aforementioned genes, and comparing the expression level of the lncRNA locus or mRNA or protein of the aforementioned genes of the patient to that of a control individual not suffering from a melanoma that is resistant to a BRAF inhibitor, wherein a statistically significant higher expression level of the lncRNA locus or mRNA or protein of the aforementioned genes of the patient is indicative of the presence of melanoma resistant to the BRAF inhibitor. In further embodiments, a patient having BRAF inhibitor-resistant melanoma is to be administered a pharmaceutical composition capable of countering such resistance to the BRAF inhibitor.

The invention also includes a method of inhibiting the resistance to a BRAF inhibitor. In some embodiments, the method comprises inhibiting the transcriptional expression of at least one lncRNA locus selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873. Inhibiting of lncRNA loci comprises mutating, deleting, or inactivating a genomic region encoding the lncRNA or being associated with lncRNA transcription by an RNA-guided DNA binding protein, a zinc finger, a zinc finger nuclease (ZFN), a transcription activator-like effector (TALE), a transcription activator-like effector nuclease (TALEN), or a meganuclease.

In a related embodiment, the method comprises inhibiting a gene regulated through such lncRNA locus. Genes upregulated through TCONS_00015940 include EQTN, MOB3B, IFNK, and C9orf72, preferably MOB3B.

Inhibition of genes comprises mutating, deleting, or inactivating genes (such as MOB3B) by an RNA-guided DNA binding protein, a zinc finger, a zinc finger nuclease (ZFN), a transcription activator-like effector (TALE), a transcription activator-like effector nuclease (TALEN), or a meganuclease. In some embodiments, the inhibition comprises down-regulating an mRNA transcript with an antisense nucleic acid or an RNA-guided RNA binding protein.

Inhibition of protein and protein function may include use of small molecule inhibitors, antibodies, lectins and the like. Accordingly, in some embodiments the invention includes a method of inhibiting a gene (e.g., MOB3B) by administration of a small molecule inhibitor against the polypeptide (e.g., encoded by MOB3B), or an antibody against the polypeptide (e.g. encoded by MOB3B).

Accordingly, in some embodiments, a patient with melanoma is treated by inhibition of the aforementioned pathways.

In further embodiments, the invention comprises a method of drug screening, comprising contacting a melanoma cell comprising transcriptionally activated EMICERI and having BRAF inhibitor resistance, with a compound and optionally a BRAF inhibitor to identify a compound capable of overcoming the BRAF inhibitor resistance. In some embodiments, the melanoma cell comprises a CRISPR-Cas effector, wherein the CRISPR-Cas effector is not catalytically competent. In some embodiments, the CRISPR-Cas effector is fused to a transcriptional activator domain. In some embodiments, the melanoma cell further comprises a guide RNA targeting a genomic region associated with transcription of TCONS_00015940, wherein the guide RNA comprises a loop capable of binding a transcriptional activator domain.

It is an object of the invention to not encompass within the invention any previously known product, process of making the product, or method of using the product. Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed in the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
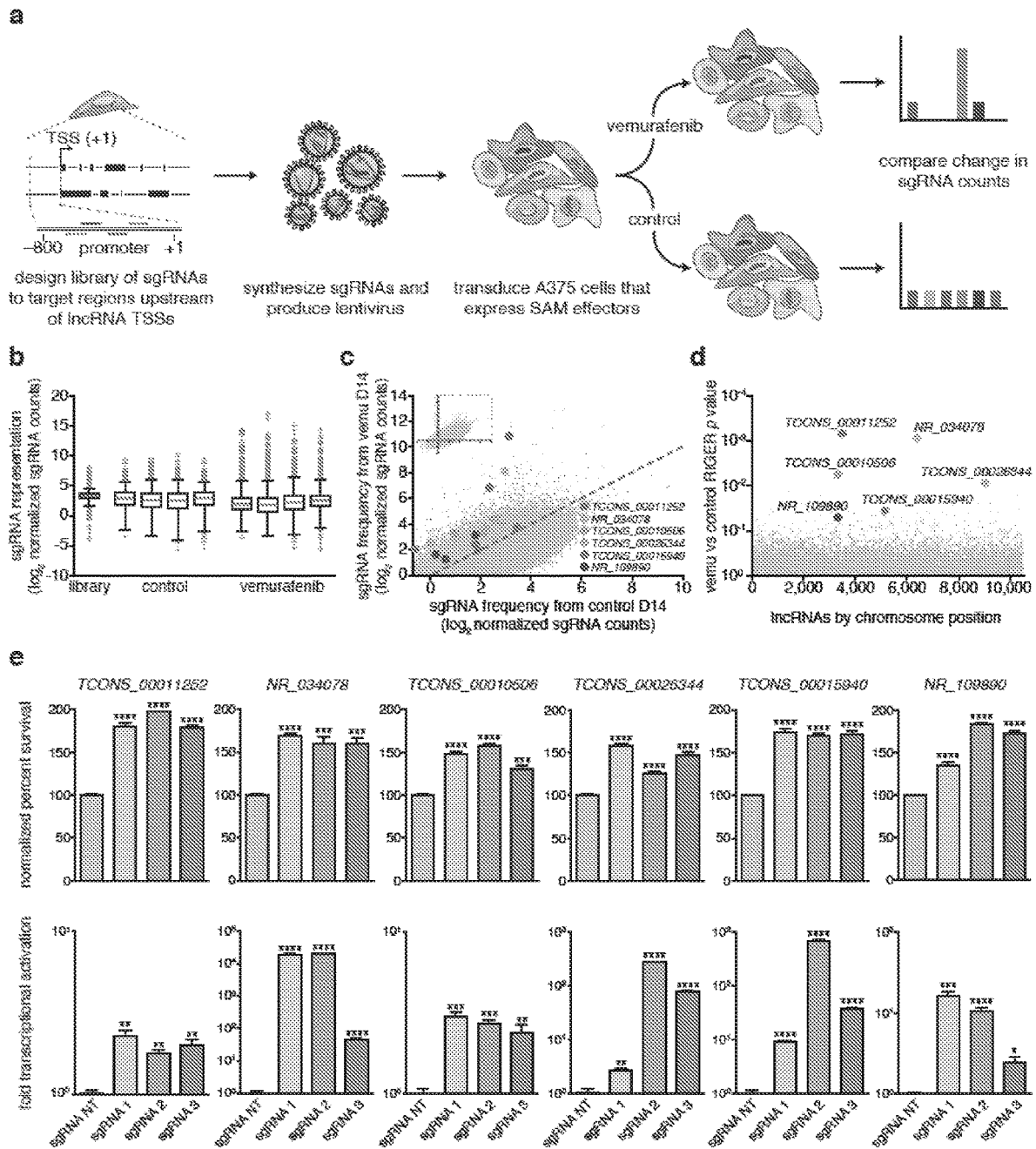
FIG. 1. Genome-scale activation screen identifies lncRNA loci involved in vemurafenib resistance. a, A375 cells expressing SAM effectors are transduced with the pooled sgRNA library targeting >10,000 lncRNA TSSs and treated with BRAF inhibitor vemurafenib or DMSO (control) for 14 days. Deep sequencing identified changes in sgRNA distribution. b, Box plot showing the distribution of sgRNA frequencies after vemurafenib or control treatment from n=4 infection replicates. c, Scatterplot showing enrichment of sgRNAs targeting 6 candidate lncRNA loci. d, RIGER P values of the candidate lncRNA loci. e, Validation of vemurafenib resistance and transcriptional activation in A375 cells expressing individual sgRNAs targeting 6 candidate lncRNA loci or non-targeting (NT) control sgRNA. All values are mean±SEM with n=4. **$P<0.0001$; *$P<0.001$; **$P<0.01$; *$P<0.05$.

In one embodiment, the invention relates to a method of treating vemurafenib resistant melanoma, comprising administering to a patient suffering from melanoma resistant to the BRAF inhibitor an effective amount of a pharmaceutical composition that inhibits a lncRNA locus selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873, or a gene regulated by the lncRNA locus.

In some embodiments, the melanoma is selected from the group consisting of nodular melanoma, lentigo maligna, lentigo maligna melanoma, acral lentiginous melanoma, superficial spreading melanoma, mucosal melanoma, polypoid melanoma, desmoplastic melanoma, amelanotic melanoma, and soft-tissue melanoma. In some embodiments, the BRAF inhibitor is selected from the group consisting of Vemurafenib, Dabrafenib, Sorafenib, GDC-0879, PLX-4720, and LGX818.

In some embodiments, the pharmaceutical composition is adapted to inhibit a lncRNA locus selected from the group consisting of TCONS_00015940, TCONS_00011252, NR_034078, NR_109890, TCONS_00010506, and TCONS_00026344. In some embodiments, the pharmaceutical composition is adapted to inhibit TCONS_00015940 or a gene regulated by TCONS_00015940. In some embodiments, the pharmaceutical composition is adapted to inhibit MOB3B.

In some embodiments, the pharmaceutical composition is adapted to inhibit TCONS_00011252 or a gene regulated by TCONS_00011252. In some embodiments, the pharmaceutical composition is adapted to inhibit PSMG4. In some embodiments, the pharmaceutical composition is adapted to inhibit SLC22A23, SERPINB9, LINC01600, or MYLK4.

In some embodiments, the pharmaceutical composition is adapted to inhibit NR_034078 or a gene regulated by NR_034078. In some embodiments, the pharmaceutical composition is adapted to inhibit CASP4 or PDGFD. In some embodiments, the pharmaceutical composition is adapted to inhibit CARD16, GRIA4, CASP1, or DDI1.

In some embodiments, the pharmaceutical composition is adapted to inhibit NR_109890 or a gene regulated by NR_109890. In some embodiments, the pharmaceutical composition is adapted to inhibit RNF145 or EBF1. In some embodiments, the pharmaceutical composition is adapted to inhibit IL12B.

In some embodiments, the pharmaceutical composition is adapted to inhibit TCONS_00026344 or a gene regulated by TCONS_00026344. In some embodiments, the pharmaceutical composition is adapted to inhibit ALPK2, MALT1, or ZNF532. In some embodiments, the pharmaceutical composition is adapted to inhibit NM_001289967, GRP, RAX, CPLX4, or ATP8B1.

In some embodiments, the pharmaceutical composition is adapted to inhibit TCONS_00010506 or a gene regulated by TCONS_00010506. In some embodiments, the pharmaceutical composition is adapted to inhibit PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, or PCDHB11. In some embodiments, the pharmaceutical composition is adapted to inhibit CD14, PCDHGA8, PCDHGA11, PCDHGA3, PCDHGA12, PSD2, PCDHGC5, PCDHGC4, SLC25A2, PCDHB1, or SLC4A9.

In some embodiments, the pharmaceutical composition is adapted to inhibit TCONS_00009861 or a gene regulated by TCONS_00009861. In some embodiments, the pharmaceutical composition is adapted to inhibit NSUN2 or SRD5A1. In some embodiments, the pharmaceutical composition is adapted to inhibit UBE2QL1 or ADCY2.

In some embodiments, the pharmaceutical composition is adapted to inhibit NR_125939 or a gene regulated by NR_125939. In some embodiments, the pharmaceutical composition is adapted to inhibit RABGGTB or ACADM. In some embodiments, the pharmaceutical composition is adapted to inhibit MSH4, LHX8, or ST6GALNAC5.

In some embodiments, the pharmaceutical composition is adapted to inhibit NR_033834 or a gene regulated by NR_033834. In some embodiments, the pharmaceutical composition is adapted to inhibit RAN. In some embodiments, the pharmaceutical composition is adapted to inhibit TMEM132D, ADGRD1, FZD10, or RIMBP2.

In some embodiments, the pharmaceutical composition is adapted to inhibit NR_026873 or a gene regulated by NR_026873. In some embodiments, the pharmaceutical composition is adapted to inhibit TMEM248.

In some embodiments, the pharmaceutical composition is adapted to inhibit TCONS_00006579 or a gene regulated by TCONS_00006579. In some embodiments, the pharmaceutical composition is adapted to inhibit BBX or CBLB. In some embodiments, the pharmaceutical composition is adapted to inhibit CCDC54.

In some embodiments, the lncRNA locus is inhibited by mutating, deleting, or transcriptionally inactivating the lncRNA locus (e.g., TCONS_00015940), for example, by an RNA-guided DNA binding protein, a zinc finger, a zinc finger nuclease (ZFN), a transcription activator-like effector (TALE), a transcription activator-like effector nuclease (TALEN), or a meganuclease. In some embodiments, the RNA-guided DNA binding protein is a CRISPR-Cas effector. In some embodiments, the CRISPR-Cas effector is a Class II, Type II CRISPR effector. In some embodiments, the CRISPR-Cas effector is Cas9 or orthologs thereof. In some embodiments, the CRISPR-Cas effector is a Class II, Type V CRISPR effector. In some embodiments, the CRISPR-Cas effector is Cpf1 or orthologs thereof. In some embodiments, the CRISPR-Cas effector is catalytically competent. In some embodiments, the CRISPR-Cas effector is catalytically competent and is administered with an HDR template comprising one or more polyadenylation signal (pAS) sequences. In some embodiments, the CRISPR-Cas effector is not catalytically competent. In some embodiments, the CRISPR-Cas effector is not catalytically competent and is fused to a transcriptional repressor domain. In some embodiments, the CRISPR-Cas effector is not catalytically competent and is administered with a guide RNA comprising a loop capable of binding a transcriptional repressor domain.

In some embodiments, the lncRNA locus is inhibited by downregulating the lncRNA transcript (e.g., EMICERI) with an antisense nucleic acid, an interfering RNA, an microRNA, a riboswitch, a ribosome, or an RNA-guided RNA binding protein. In some embodiments, the RNA-guided RNA binding protein is a CRISPR-Cas effector. In some embodiments, the CRISPR-Cas effector is a Class II, Type VI CRISPR effector. In some embodiments, the CRISPR-Cas effector is C2c2 or orthologs thereof. In some embodiments, the CRISPR-Cas effector is Cas13b or orthologs thereof.

In some embodiments, the gene regulated by the lncRNA locus (e.g., MOB3B) is inhibited by mutating, deleting, or transcriptionally or translationally inactivating the gene locus or an mRNA transcript thereof, for example, by an RNA-guided DNA binding protein, a zinc finger, a zinc finger nuclease (ZFN), a transcription activator-like effector (TALE), a transcription activator-like effector nuclease (TALEN), or a meganuclease. In some embodiments, the RNA-guided DNA binding protein is a CRISPR-Cas effector. In some embodiments, the CRISPR-Cas effector is a Class II, Type II CRISPR effector. In some embodiments, the CRISPR-Cas effector is Cas9 or orthologs thereof. In some embodiments, the CRISPR-Cas effector is a Class II, Type V CRISPR effector. In some embodiments, the CRISPR-Cas effector is Cpf1 or orthologs thereof. In some embodiments, the CRISPR-Cas effector is catalytically competent. In some embodiments, the CRISPR-Cas effector is catalytically competent and is administered with an HDR template comprising one or more polyadenylation signal (pAS) sequences. In some embodiments, the CRISPR-Cas effector is not catalytically competent. In some embodiments, the CRISPR-Cas effector is not catalytically competent and is fused to a transcriptional repressor domain. In some embodiments, the CRISPR-Cas effector is not catalytically competent and is administered with a guide RNA comprising a loop capable of binding a transcriptional repressor domain.

In some embodiments, the gene regulated by the lncRNA locus (e.g., MOB3B) is inhibited by downregulating an mRNA transcript thereof with an antisense nucleic acid, an interfering RNA, an microRNA, a riboswitch, a ribosome, or an RNA-guided RNA binding protein. In some embodiments, the RNA-guided RNA binding protein is a CRISPR-Cas effector. In some embodiments, the CRISPR-Cas effector is a Class II, Type VI CRISPR effector. In some embodiments, the CRISPR-Cas effector is C2c2 or orthologs thereof. In some embodiments, the CRISPR-Cas effector is Cas13b or orthologs thereof.

In some embodiments, MOB3B is inhibited by administration of a small molecule inhibitor against the polypeptide encoded by MOB3B. In some embodiments, MOB3B is inhibited by administration of an antibody against the polypeptide encoded by MOB3B.

In a second embodiment, the invention relates to a method of identifying a melanoma cell resistant to a BRAF inhibitor, comprising measuring an expression level of a lncRNA locus or a gene regulated by the lncRNA locus in a biological sample of a patient suffering from melanoma, wherein the lncRNA locus is selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873, and comparing the expression level of the lncRNA locus or the gene regulated by the lncRNA locus of the patient to that of a control individual not suffering from a cancer that is resistant to a BRAF inhibitor, wherein a statistically significant higher expression level of the lncRNA locus or the gene regulated by the lncRNA locus of the patient is indicative of the presence of a melanoma cell resistant to a BRAF inhibitor.

In some embodiments, the melanoma is selected from the group consisting of nodular melanoma, lentigo maligna, lentigo maligna melanoma, acral lentiginous melanoma, superficial spreading melanoma, mucosal melanoma, polypoid melanoma, desmoplastic melanoma, amelanotic melanoma, and soft-tissue melanoma. In some embodiments, the BRAF inhibitor is selected from the group consisting of Vemurafenib, Dabrafenib, Sorafenib, GDC-0879, PLX-4720, and LGX818. In some embodiments, the BRAF inhibitor is vemurafenib.

In some embodiments, the method comprises measuring the expression of a lncRNA locus selected from the group consisting of TCONS_00015940, TCONS_00011252, NR_034078, NR_109890, TCONS_00010506, and TCONS_00026344, or a gene regulated by the lncRNA locus.

In some embodiments, the method comprises measuring the expression of TCONS_00015940. In some embodiments, the method comprises measuring the expression of CAAP1, IFT74, C9orf72, MOB3B, or PLAA. In some embodiments, the method comprises measuring the expression of EQTN, LRRC19, TEK, or IFNK. In some embodiments, the method comprises measuring the expression of MOB3B.

In some embodiments, the method comprises measuring the expression of TCONS_00011252. In some embodiments, the method comprises measuring the expression of PSMG4. In some embodiments, the method comprises measuring the expression of SLC22A23, SERPINB9, LINC01600, or MYLK4.

In some embodiments, the method comprises measuring the expression of NR_034078. In some embodiments, the method comprises measuring the expression of CASP4 or PDGFD. In some embodiments, the method comprises measuring the expression of CARD16, GRIA4, CASP1, or DDI1.

In some embodiments, the method comprises measuring the expression of NR_109890. In some embodiments, the method comprises measuring the expression of RNF145 or EBF1. In some embodiments, the method comprises measuring the expression of IL12B.

In some embodiments, the method comprises measuring the expression of TCONS_00026344. In some embodiments, the method comprises measuring the expression of ALPK2, MALT1, or ZNF532. In some embodiments, the method comprises measuring the expression of NM_001289967, GRP, RAX, CPLX4, or ATP8B1.

In some embodiments, the method comprises measuring the expression of TCONS_00010506. In some embodiments, the method comprises measuring the expression of PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, or PCDHB11. In some embodiments, the method comprises measuring the expression of CD14, PCDHGA8, PCDHGA11, PCDHGA3, PCDHGA12, PSD2, PCDHGC5, PCDHGC4, SLC25A2, PCDHB1, or SLC4A9.

In some embodiments, the method comprises measuring the expression of TCONS_00009861. In some embodiments, the method comprises measuring the expression of NSUN2 or SRD5A1. In some embodiments, the method comprises measuring the expression of UBE2QL1 or ADCY2.

In some embodiments, the method comprises measuring the expression of NR_125939. In some embodiments, the method comprises measuring the expression of RABGGTB or ACADM. In some embodiments, the method comprises measuring the expression of MSH4, LHX8, or ST6GALNAC5.

In some embodiments, the method comprises measuring the expression of NR_033834. In some embodiments, the method comprises measuring the expression of RAN. In some embodiments, the method comprises measuring the expression of TMEM132D, ADGRD1, FZD10, or RIMBP2.

In some embodiments, the method comprises measuring the expression of NR_026873. In some embodiments, the method comprises measuring the expression of TMEM248.

In some embodiments, the method comprises measuring the expression of TCONS_00006579. In some embodiments, the method comprises measuring the expression of BBX or CBLB. In some embodiments, the method comprises measuring the expression of CCDC54.

In some embodiments, the method further comprises diagnosing the patient as having vemurafenib resistant melanoma based on a statistically significant higher expression level of the lncRNA locus or the gene regulated by the lncRNA locus of the patient compared to that of a control individual not suffering from vemurafenib resistant melanoma.

In some embodiments, the method further comprises administering to the patient a pharmaceutical composition comprising an active ingredient different from vemurafenib.

In a third embodiment, the invention relates to a method of monitoring vemurafenib resistant melanoma in a patient being treated with vemurafenib, comprising measuring an expression level of a lncRNA locus or a gene regulated by the lncRNA locus in a biological sample of a patient suffering from melanoma, wherein the lncRNA locus is selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873, and comparing the expression level of the lncRNA locus or the gene regulated by the lncRNA locus of the patient to that of a control individual not suffering from vemurafenib resistant melanoma, wherein a statistically significant higher expression level of the lncRNA locus or the gene regulated by the lncRNA locus of the patient is indicative of the presence of vemurafenib resistant melanoma. In some embodiments, the lncRNA locus is selected from the group consisting of TCONS_00015940, TCONS_00011252, NR_034078, NR_109890, TCONS_00010506, and TCONS_00026344.

In some embodiments, the method comprises measuring the expression of TCONS_00015940. In some embodiments, the method comprises measuring the expression of CAAP1, IFT74, C9orf72, MOB3B, or PLAA. In some embodiments, the method comprises measuring the expression of EQTN, LRRC19, TEK, or IFNK. In some embodiments, the method comprises measuring the expression of MOB3B.

In some embodiments, the method comprises measuring the expression of TCONS_00011252. In some embodiments, the method comprises measuring the expression of PSMG4. In some embodiments, the method comprises measuring the expression of SLC22A23, SERPINB9, LINC01600, or MYLK4.

In some embodiments, the method comprises measuring the expression of NR_034078. In some embodiments, the method comprises measuring the expression of CASP4 or PDGFD. In some embodiments, the method comprises measuring the expression of CARD16, GRIA4, CASP1, or DDI1.

In some embodiments, the method comprises measuring the expression of NR_109890. In some embodiments, the method comprises measuring the expression of RNF145 or EBF1. In some embodiments, the method comprises measuring the expression of IL12B.

In some embodiments, the method comprises measuring the expression of TCONS_00026344. In some embodiments, the method comprises measuring the expression of ALPK2, MALT1, or ZNF532. In some embodiments, the method comprises measuring the expression of NM_001289967, GRP, RAX, CPLX4, or ATP8B1.

In some embodiments, the method comprises measuring the expression of TCONS_00010506. In some embodiments, the method comprises measuring the expression of PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, or PCDHB11. In some embodiments, the method comprises measuring the expression of CD14, PCDHGA8, PCDHGA11, PCDHGA3, PCDHGA12, PSD2, PCDHGC5, PCDHGC4, SLC25A2, PCDHB1, or SLC4A9.

In some embodiments, the method comprises measuring the expression of TCONS_00009861. In some embodiments, the method comprises measuring the expression of NSUN2 or SRD5A1. In some embodiments, the method comprises measuring the expression of UBE2QL1 or ADCY2.

In some embodiments, the method comprises measuring the expression of NR_125939. In some embodiments, the method comprises measuring the expression of RABGGTB or ACADM. In some embodiments, the method comprises measuring the expression of MSH4, LHX8, or ST6GALNAC5.

In some embodiments, the method comprises measuring the expression of NR_033834. In some embodiments, the method comprises measuring the expression of RAN. In some embodiments, the method comprises measuring the expression of TMEM132D, ADGRD1, FZD10, or RIMBP2.

In some embodiments, the method comprises measuring the expression of NR_026873. In some embodiments, the method comprises measuring the expression of TMEM248.

In some embodiments, the method comprises measuring the expression of TCONS_00006579. In some embodiments, the method comprises measuring the expression of BBX or CBLB. In some embodiments, the method comprises measuring the expression of CCDC54.

In a fourth embodiment, the invention relates to a method of drug screening, comprising contacting a melanoma cell comprising a transcriptionally activated lncRNA locus or a transcriptionally activated or over-expressed gene regulated by the lncRNA locus and is resistant to a BRAF inhibitor, with a candidate compound and optionally the BRAF inhibitor, and measuring apoptosis of melanoma cell to identify a compound capable of overcoming resistance to the BRAF inhibitor, wherein the lncRNA locus is selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873. In some embodiments, the lncRNA locus is selected from the group consisting of TCONS_00015940, TCONS_00011252, NR_034078, NR_109890, TCONS_00010506, and TCONS_00026344.

In some embodiments, the melanoma cell comprises transcriptionally activated TCONS_00015940. In some embodiments, the melanoma cell comprises transcriptionally activated or over-expressed MOB3B.

In some embodiments, the melanoma cell comprises transcriptionally activated TCONS_00011252. In some embodiments, the melanoma cell comprises transcriptionally activated or over-expressed PSMG4. In some embodiments, the melanoma cell comprises transcriptionally activated or over-expressed SLC22A23, SERPINB9, LINC01600, or MYLK4.

In some embodiments, the melanoma cell comprises transcriptionally activated NR_034078. In some embodiments, the melanoma cell comprises transcriptionally activated or over-expressed CASP4 or PDGFD. In some embodiments, the melanoma cell comprises transcriptionally activated or over-expressed CARD16, GRIA4, CASP1, or DDI1.

In some embodiments, the melanoma cell comprises transcriptionally activated NR_109890. In some embodiments, the melanoma cell comprises transcriptionally activated or over-expressed RNF145 or EBF1. In some embodiments, the melanoma cell comprises transcriptionally activated or over-expressed IL12B.

In some embodiments, the melanoma cell comprises transcriptionally activated TCONS_00026344. In some embodiments, the melanoma cell comprises transcriptionally activated or over-expressed ALPK2, MALT1, or ZNF532. In some embodiments, the melanoma cell comprises transcriptionally activated or over-expressed NM_001289967, GRP, RAX, CPLX4, or ATP8B1.

In some embodiments, the melanoma cell comprises transcriptionally activated TCONS_00010506. In some embodiments, the melanoma cell comprises transcriptionally activated or over-expressed PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, or PCDHB11. In some embodiments, the melanoma cell comprises transcriptionally activated or over-expressed CD14, PCDHGA8, PCDHGA11, PCDHGA3, PCDHGA12, PSD2, PCDHGC5, PCDHGC4, SLC25A2, PCDHB1, or SLC4A9.

In some embodiments, the melanoma cell comprises transcriptionally activated TCONS_00009861. In some embodiments, the melanoma cell comprises transcriptionally activated or over-expressed NSUN2 or SRD5A1. In some embodiments, the melanoma cell comprises transcriptionally activated or over-expressed UBE2QL1 or ADCY2.

In some embodiments, the melanoma cell comprises transcriptionally activated NR_125939. In some embodiments, the melanoma cell comprises transcriptionally activated or over-expressed RABGGTB or ACADM. In some embodiments, the melanoma cell comprises transcriptionally activated or over-expressed MSH4, LHX8, or ST6GALNAC5.

In some embodiments, the melanoma cell comprises transcriptionally activated NR_033834. In some embodiments, the melanoma cell comprises transcriptionally activated or over-expressed RAN. In some embodiments, the melanoma cell comprises transcriptionally activated or over-expressed TMEM132D, ADGRD1, FZD10, or RIMBP2.

In some embodiments, the melanoma cell comprises transcriptionally activated NR_026873. In some embodiments, the melanoma cell comprises transcriptionally activated or over-expressed TMEM248.

In some embodiments, the melanoma cell comprises transcriptionally activated TCONS_00006579. In some embodiments, the melanoma cell comprises transcriptionally activated or over-expressed BBX or CBLB. In some embodiments, the melanoma cell comprises transcriptionally activated or over-expressed CCDC54.

In some embodiments, the melanoma cell comprises a CRISPR-Cas effector, wherein the CRISPR-Cas effector is not catalytically competent. In some embodiments, the CRISPR-Cas effector is dCas9. In some embodiments, the CRISPR-Cas effector is fused to a transcriptional activator domain. In some embodiments, the CRISPR-Cas effector is fused to VP64.

In some embodiments, the melanoma cell further comprises a guide RNA targeting a genomic sequence encoding TCONS_00015940 or being associated with transcription of TCONS_00015940, wherein the guide RNA comprises a loop capable of binding a transcriptional activator domain. In some embodiments, the guide RNA comprises a MS2 binding loop which is adapted to recruit activation domains p65 and HSF1 to dCas9 fused with a VP64 activation domain.

In a fifth embodiment, the invention relates to a melanoma cell having BRAF inhibitor resistance and comprising (a) a CRISPR-Cas effector that is not catalytically competent, and (b) a guide RNA targeting a genomic sequence encoding a lncRNA locus or a gene regulated by the lncRNA locus, or being associated with transcription of the lncRNA locus or the gene, wherein the guide RNA comprises a loop capable of binding a transcriptional activator domain, and wherein the lncRNA locus is selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873. In some embodiments, the lncRNA locus is selected from the group consisting of TCONS_00015940, TCONS_00011252, NR_034078, NR_109890, TCONS_00010506, and TCONS_00026344.

In some embodiments, the guide RNA targets TCONS_00015940 or transcriptional promoters or enhancers thereof. In some embodiments, the guide RNA targets MOB3B or transcriptional promoters or enhancers thereof.

In some embodiments, the guide RNA targets TCONS_00011252 or transcriptional promoters or enhancers thereof. In some embodiments, the guide RNA targets PSMG4 or transcriptional promoters or enhancers thereof. In some embodiments, the guide RNA targets SLC22A23, SERPINB9, LINC01600, or MYLK4 or transcriptional promoters or enhancers thereof.

In some embodiments, the guide RNA targets NR_034078 or transcriptional promoters or enhancers thereof. In some embodiments, the guide RNA targets CASP4 or PDGFD or transcriptional promoters or enhancers thereof. In some embodiments, the guide RNA targets CARD16, GRIA4, CASP1, or DDI1 or transcriptional promoters or enhancers thereof.

In some embodiments, the guide RNA targets NR_109890 or transcriptional promoters or enhancers thereof. In some embodiments, the guide RNA targets RNF145 or EBF1 or transcriptional promoters or enhancers thereof. In some embodiments, the guide RNA targets IL12B or transcriptional promoters or enhancers thereof.

In some embodiments, the guide RNA targets TCONS_00026344 or transcriptional promoters or enhancers thereof. In some embodiments, the guide RNA targets ALPK2, MALT1, or ZNF532 or transcriptional promoters or enhancers thereof. In some embodiments, the guide RNA targets NM 001289967, GRP, RAX, CPLX4, or ATP8B1 or transcriptional promoters or enhancers thereof.

In some embodiments, the guide RNA targets TCONS_00010506 or transcriptional promoters or enhancers thereof. In some embodiments, the guide RNA targets PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, or PCDHB11, or transcriptional promoters or enhancers thereof. In some embodiments, the guide RNA targets CD14, PCDHGA8, PCDHGA11, PCDHGA3, PCDHGA12, PSD2, PCDHGC5, PCDHGC4, SLC25A2, PCDHB1, or SLC4A9, or transcriptional promoters or enhancers thereof.

In some embodiments, the guide RNA targets TCONS_00009861 or transcriptional promoters or enhancers thereof. In some embodiments, the guide RNA targets NSUN2 or SRD5A1 or transcriptional promoters or enhancers thereof. In some embodiments, the guide RNA targets UBE2QL1 or ADCY2 or transcriptional promoters or enhancers thereof.

In some embodiments, the guide RNA targets NR_125939 or transcriptional promoters or enhancers thereof. In some embodiments, the guide RNA targets RABGGTB or ACADM or transcriptional promoters or enhancers thereof. In some embodiments, the guide RNA targets MSH4, LHX8, or ST6GALNAC5, or transcriptional promoters or enhancers thereof.

In some embodiments, the guide RNA targets NR_033834 or transcriptional promoters or enhancers thereof. In some embodiments, the guide RNA targets RAN or transcriptional promoters or enhancers thereof. In some embodiments, the guide RNA targets TMEM132D, ADGRD1, FZD10, or RIMBP2, or transcriptional promoters or enhancers thereof.

In some embodiments, the guide RNA targets NR_026873 or transcriptional promoters or enhancers thereof. In some embodiments, the guide RNA targets TMEM248 or transcriptional promoters or enhancers thereof.

In some embodiments, the guide RNA targets TCONS_00006579 or transcriptional promoters or enhancers thereof. In some embodiments, the guide RNA targets BBX or CBLB or transcriptional promoters or enhancers thereof. In some embodiments, the guide RNA targets CCDC54 or transcriptional promoters or enhancers thereof.

In a sixth embodiment, the invention relates to a method for identifying a lncRNA locus associated with a phenotype, comprising:

introducing a library of guide RNAs into a population of cells, the cells either expressing an RNA-guided DNA binding protein or having the RNA-guided DNA binding protein or a coding sequence thereof introduced simultaneously or sequentially with the guide RNAs, wherein the guide RNAs target different genomic sequences encoding lncRNA or associated with lncRNA transcription;

selecting cells based on a phenotype; and determining the guide RNAs present in the selected cells, wherein the enrichment or depletion of a guide RNA can correlate the corresponding lncRNA locus with the phenotype.

The lncRNA screen can be applied to phenotypes where the lncRNA locus modulates cell proliferation, cell death, or changes in gene expression, all of which are screenable phenotypes. In some embodiments, the phenotype is a disease phenotype, and the lncRNA locus is associated with the disease phenotype. In some embodiments, the phenotype is drug resistance, and the lncRNA locus is associated with the drug resistance. In some embodiments, the phenotype is resistance to a BRAF inhibitor. In some embodiments, the phenotype is vemurafenib resistance.

In some embodiments where the population of cells are plant cells or plant protoplasts, the phenotype is a desirable plant phenotype, such as increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance, increased biomass production, or a combination thereof.

In some embodiments, the desirable plant phenotype is selected by exposing the plant cells, plant protoplasts, or tissues or plants derived therefrom, to a stress condition selected from the group consisting of abiotic stress, drought stress, flood stress, heat stress, cold and frost stress, salt stress, heavy metal stress, low-nitrogen stress, disease stress, pest stress, herbicide stress, or a combination thereof, and selecting plant cells, plant protoplasts, or tissues or plants derived therefrom based on increased tolerance or resistance to the stress condition.

In some embodiments, the RNA-guided DNA binding protein is a CRISPR effector protein. In some embodiments, the CRISPR effector protein is a modified Cas protein. In some embodiments, the modified Cas protein is a modified Cas9. In some embodiments, the modified Cas protein is not catalytically competent. In some embodiments, the modified Cas protein comprises one or more mutations compared to a wild-type Cas protein.

In some embodiments, the modified Cas is fused to a transcription activation domain. In some embodiments, the modified Cas is fused to a VP64 domain, a P65 domain, a MyoD1 domain, a HSF1 domain, or a Rta domain (see Chavez et al., *Nat Methods*, 2015, 12:326-328, which is incorporated by reference in its entirety).

In some embodiments, the modified Cas is fused to a transcription repression domain. In some embodiments, the modified Cas is fused to a KRAB domain. In some embodiments, the modified Cas is fused to a NuE domain, an NcoR domain, a SID domain, or a SID4X domain.

In some embodiments, at least one of the guide RNAs comprises a loop modified by insertion of at least one distinct aptamer RNA sequence adapted to bind to an adaptor protein. In some embodiments, the aptamer RNA sequence is adapted to bind to an adaptor protein comprising a transcription activation domain. In some embodiments, the aptamer RNA sequence is adapted to bind to an adaptor protein comprising a VP64 domain, a P65 domain, a MyoD1 domain, a HSF1 domain, or a Rta domain.

In some embodiments, the aptamer RNA sequence is adapted to bind to an adaptor protein comprising a transcription repression domain. In some embodiments, the aptamer RNA sequence is adapted to bind to an adaptor protein comprising a KRAB domain. In some embodiments, the aptamer RNA sequence is adapted to bind to an adaptor protein comprising a NuE domain, an NcoR domain, a SID domain, or a SID4X domain.

In some embodiments, the population of cells are introduced with an average of no more than one guide RNA per cell. In some embodiments, the population of cells are introduced with an average of more than one guide RNA per cell.

In some embodiments, a library of guide RNAs are introduced into the population of cells, wherein the library comprises at least 100 guide RNAs targeting at least 100 different genomic sequences encoding lncRNA or associated with lncRNA transcription. In some embodiments, the library introduced into the population of cells comprises at least 1,000 guide RNAs targeting at least 1,000 different genomic sequences encoding lncRNA or associated with lncRNA transcription. In some embodiments, the library introduced into the population of cells comprises at least 10,000 guide RNAs targeting at least 10,000 different genomic sequences encoding lncRNA or associated with lncRNA transcription. In some embodiments, the guide RNAs target at least 100 different lncRNAs. In some embodiments, the guide RNAs target at least 1,000 different lncRNAs. In some embodiments, the guide RNAs target at least 10,000 different lncRNAs.

In some embodiments, the population of cells are eukaryotic cells. In some embodiments, the population of cells are prokaryotic cells. In some embodiments, the eukaryotic cells selected from embryonic stem (ES) cells, neuronal cells, epithelial cells, immune cells, endocrine cells, muscle cells, erythrocytes, lymphocytes, plant cells, and yeast cells. In some embodiments, the eukaryotic cells are cancer cells. In some embodiments, the eukaryotic cells are melanoma cells.

The cells can be selected based on a phenotype such as drug resistance, and the lncRNA locus associated with a change in phenotype are identified based on whether or not they give rise to a change in phenotype in the cells. Typically, the methods involve selecting the cells based on the phenotype and determining the guide RNAs present in the selected cells, and a lncRNA locus associated with the change in phenotype can be determined based on the enrichment or depletion of the corresponding guide RNA. In some embodiments, the phenotype for selecting cells is drug resistance. In some embodiments, the phenotype for selecting/sorting the cells is resistance to a cancer drug.

In a seventh embodiment, the invention relates to a method for identifying a lncRNA locus associated with resistance to a drug, comprising:
  introducing a library of guide RNAs into a population of cells, the cells either expressing a modified Cas protein that is not catalytically competent or having the modified Cas protein or a coding sequence thereof introduced simultaneously or sequentially with the guide RNAs, wherein the guide RNAs target different genomic sequences encoding lncRNA or associated with lncRNA transcription, wherein the guide RNAs optionally comprise a loop capable of binding a transcriptional activator domain or a transcription repressor domain, and wherein the modified Cas protein is optionally fused to a transcription activator domain or a transcription repressor domain;
  exposing the cells to the drug and selecting cells based on resistance to the drug; and
  sequencing guide RNAs present in the selected cells, wherein the enrichment or depletion of guide RNAs are quantified and/or ranked to identify a lncRNA locus associated with the drug resistance.

In an eighth embodiment, the invention relates to a method for identifying a lncRNA locus associated with resistance to a cancer drug, comprising:
  introducing a library of guide RNAs into a population of cancer cells, the cancer cells either expressing a modified Cas protein that is not catalytically competent fused to a transcription activator domain or having the modified Cas protein or a coding sequence thereof introduced simultaneously or sequentially with the guide RNAs, wherein the guide RNAs target different genomic sequences encoding lncRNA or associated with lncRNA transcription, and wherein the guide RNAs comprise a loop capable of binding a transcriptional activator domain;
  exposing the cancer cells to the cancer drug and selecting cancer cells based on resistance to the cancer drug; and
  sequencing guide RNAs present in the selected cells, wherein the enrichment of guide RNAs are quantified and/or ranked to identify a lncRNA locus associated with the resistance to the cancer drug.

In a ninth embodiment, the invention relates to a method for inhibiting or downregulating LATS1/2 expression, comprising transcriptionally activating or overexpressing TCONS_00015940 or MOB3B.

In a tenth embodiment, the invention relates to a method for activating or upregulating Hippo signaling pathway, comprising transcriptionally activating or overexpressing TCONS_00015940 or MOB3B.

In an eleventh embodiment, the invention relates to a method for activating or upregulating LATS1/2 expression, comprising mutating, deleting, or transcriptionally repressing TCONS_00015940 or MOB3B, or downregulating EMICERI or the mRNA or polypeptide encoded by MOB3B.

In a twelfth embodiment, the invention relates to a method for inhibiting or downregulating Hippo signaling pathway, comprising mutating, deleting, or transcriptionally repressing TCONS_00015940 or MOB3B, or downregulating EMICERI or the mRNA or polypeptide encoded by MOB3B.

Certain embodiments of the invention require the use of a DNA binding protein to facilitate modification, deletion, and transcriptional activation or repression of a genomic sequence. In some embodiments, the DNA binding protein is a (endo)nuclease or a variant thereof having altered or modified activity (i.e. a modified nuclease, as described herein elsewhere). In certain embodiments, the nuclease is a targeted or site-specific or homing nuclease or a variant thereof having altered or modified activity. In certain embodiments, the nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, the (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As used herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA binding protein is a (modified) transcription activator-like effector nuclease (TALEN) system. Transcription activator-like effectors (TALEs) can be engineered to bind practically any desired DNA sequence in its entirety. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference.

By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids.

A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary methods for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9 CRISPR/Cas-expressing eukaryotic cells, Cas9 CRISPR/Cas expressing eukaryotes, such as a mouse, reference is made to: U.S. Pat.

Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (application. Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/051830), WO/2016/094867 (PCT/US2015/065385), WO/2016/094872 (PCT/US2015/065393), WO/2016/094874 (PCT/US2015/065396), WO/2016/106244 (PCT/US2015/067177). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYS- TEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference therein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also, with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse);

In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546): 186-91 (2015);

Shalem et al., "High-throughput functional genomics using CRISPR-Cas9," Nature Reviews Genetics 16, 299-311 (May 2015);

Xu et al., "Sequence determinants of improved CRISPR sgRNA design," Genome Research 25, 1147-1157 (August 2015);

Parnas et al., "A Genome-wide CRISPR Screen in Primary Immune Cells to Dissect Regulatory Networks," Cell 162, 675-686 (Jul. 30, 2015);

Ramanan et al., CRISPR/Cas9 cleavage of viral DNA efficiently suppresses hepatitis B virus," Scientific Reports 5:10833. doi: 10.1038/srep10833 (Jun. 2, 2015);

Nishimasu et al., "Crystal Structure of *Staphylococcus aureus* Cas9," Cell 162, 1113-1126 (Aug. 27, 2015);

Zetsche et al. (2015), "Cpf1 is a single RNA-guided endonuclease of a class 2 CRISPR-Cas system," Cell 163, 759-771 (Oct. 22, 2015) doi: 10.1016/j.cell.2015.09.038. Epub Sep. 25, 2015;

Shmakov et al. (2015), "Discovery and Functional Characterization of Diverse Class 2 CRISPR-Cas Systems," Molecular Cell 60, 385-397 (Nov. 5, 2015) doi: 10.1016/j.molcel.2015.10.008. Epub Oct. 22, 2015; and Gao et al, "Engineered Cpf1 Enzymes with Altered PAM Specificities," bioRxiv 091611; doi: dx.doi.org/10.1101/091611 (Dec. 4, 2016);

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

End Edits

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of TLR4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Gao et al. (2016) reported using a structure-guided saturation mutagenesis screen to increase the targeting range of Cpf1. AsCpf1 variants were engineered with the mutations S542R/K607R and S542R/K548V/N552R that can cleave target sites with TYCV/CCCC and TATV PAMs, respectively, with enhanced activities in vitro and in human cells.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of U.S. provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a $C_{1-6}$ alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

Preferred DNA binding proteins are CRISPR/Cas enzymes or variants thereof.

In certain embodiments, the CRISPR/Cas protein is a class 2 CRISPR/Cas protein. In certain embodiments, the CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using the short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In the context of the guide RNA, this may include one or more of, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system). In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence. In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize.

In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In particular embodiments, the DNA binding protein is a catalytically active protein. In these embodiments, the formation of a nucleic acid-targeting complex comprising a guide RNA hybridized to a target sequence results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g., within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

Accordingly, in particular embodiments, the DNA binding protein has nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g., for Cas9, such as SaCas9 or SpCas9). In some embodiments, the cleavage may be staggered (e.g., for Cpf1), i.e., generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of the target polynucleotide thereby modifying the target polynucleotide, wherein the CRISPR complex comprises a CRISPR enzyme complexed with a guide sequence hybridized to a target sequence within the target polynucleotide, wherein the guide sequence is linked to a tracr mate sequence which in turn hybridizes to a tracr sequence. The skilled person will understand that other Cas proteins may be modified analogously.

As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein. In certain embodiments, the nuclease, in particular the Cas protein, may comprise one or more modifications resulting in a nuclease that has reduced or no catalytic activity, or is a split nuclease (see e.g. "A split-Cas9 architecture for inducible genome editing and transcription modulation", Zetsche et al. (2015), Nat Biotechnol. 33(2): 139-42).

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g., RuvC I, RuvC II, and RuvC III or the HNH domain of a Cas9 protein) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As detailed above, in certain embodiments, the nuclease as referred to herein is modified. As used herein, the term "modified" refers to which may or may not have an altered functionality. By means of example, and in particular with reference to Cas proteins, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc., as well as chimeric nucleases (e.g., comprising domains from different orthologues or homologues) or fusion proteins. Fusion proteins may without limitation include for instance fusions with heterologous domains or functional domains (e.g., localization signals, catalytic domains, etc.). Accordingly, in certain embodiments, the modified nuclease may be used as a generic nucleic acid binding protein with fusion to or being operably linked to a functional domain.

In certain embodiments, various different modifications may be combined (e.g., a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g., altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR/Cas system or complex preferably still has the capacity to interact with or bind to the polynucleic acid (e.g. in complex with the gRNA).

By means of further guidance and without limitation, in certain embodiments, the nuclease may be modified as detailed below. As already indicated, more than one of the indicated modifications may be combined. For instance, codon optimization may be combined with NLS or NES fusions, catalytically inactive nuclease modifications or nickase mutants may be combined with fusions to functional (heterologous) domains, etc.

In certain embodiments, the nuclease, and in particular the Cas proteins of prokaryotic origin, may be codon optimized for expression into a particular host (cell). An example of a codon optimized sequence is, in this instance, a sequence optimized for expression in a eukaryote, e.g., humans (i.e., being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells.

The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid.

Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

In certain embodiments, the nuclease, in particular the Cas protein, may comprise one or more modifications resulting in enhanced activity and/or specificity, such as including mutating residues that stabilize the targeted or non-targeted strand (e.g., eCas9; "Rationally engineered Cas9 nucleases with improved specificity", Slaymaker et al. (2016), Science, 351(6268):84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci.

In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g., cleavage or binding properties, activity, or kinetics), such as in case for Cas proteins for instance resulting in a lower tolerance for mismatches between target and gRNA. Other mutations may lead to increased off-target effects (e.g., cleavage or binding properties, activity, or kinetics). Other mutations may lead to increased or decreased on-target effects (e.g., cleavage or binding properties, activity, or kinetics).

In certain embodiments, the mutations result in altered (e.g., increased or decreased) helicase activity, association or formation of the functional nuclease complex (e.g., CRISPR/Cas complex). In certain embodiments, the mutations result in an altered PAM recognition, i.e., a different PAM may be (in addition or in the alternative) be recognized, compared to the unmodified Cas protein (see e.g. "Engineered CRISPR-Cas9 nucleases with altered PAM specificities", Kleinstiver et al. (2015), Nature, 523(7561): 481-485, incorporated herein by reference in its entirety). Particularly preferred mutations include positively charged residues and/or (evolutionary) conserved residues, such as conserved positively charged residues, in order to enhance specificity. In certain embodiments, such residues may be mutated to uncharged residues, such as alanine.

In certain embodiments, the nuclease, in particular the Cas protein, may comprise one or more modifications resulting in a nuclease that has reduced or no catalytic activity, or alternatively (in case of nucleases that target double stranded nucleic acids) resulting in a nuclease that only cleaves one strand, i.e., a nickase. By means of further guidance, and without limitation, for example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As further guidance, where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged.

As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A with reference to the positions in SpCas9. In particular embodiments, the catalytically inactive Cas9 comprises the D10A and H840A mutation.

In certain embodiments, the nuclease is a split nuclease (see e.g. "A split-Cas9 architecture for inducible genome editing and transcription modulation", Zetsche et al. (2015), Nat Biotechnol. 33(2):139-42, incorporated herein by reference in its entirety). In a split nuclease, the activity (which may be a modified activity, as described herein elsewhere), relies on the two halves of the split nuclease to be joined, i.e., each half of the split nuclease does not possess the required activity, until joined. As further guidance, and without limitation, with specific reference to Cas9, a split Cas9 may result from splitting the Cas9 at any one of the following split points, according or with reference to SpCas9: a split position between 202A/203S; a split position between 255F/256D; a split position between 310E/3111; a split position between 534R/535K; a split position between 572E/573C; a split position between 7135/714G; a split position between 1003L/104E; a split position between 1054G/1055E; a split position between 1114N/1115S; a split position between 1152K/1153S; a split position between 1245K/1246G; or a split between 1098 and 1099. Identifying potential split sides is most simply done with the help of a crystal structure.

For Sp mutants, it should be readily apparent what the corresponding position for, for example, a sequence alignment. For non-Sp enzymes one can use the crystal structure of an ortholog if a relatively high degree of homology exists between the ortholog and the intended Cas9. Ideally, the split position should be located within a region or loop. Preferably, the split position occurs where an interruption of the amino acid sequence does not result in the partial or full destruction of a structural feature (e.g., alpha-helixes or beta-sheets). Unstructured regions (regions that did not show up in the crystal structure because these regions are not structured enough to be "frozen" in a crystal) are often preferred options. In certain embodiments, a functional domain may be provided on each of the split halves, thereby allowing the formation of homodimers or heterodimers. The functional domains may be (inducible) interact, thereby joining the split halves, and reconstituting (modified) nuclease activity.

By means of example, an inducer energy source may inducibly allow dimerization of the split halves, through appropriate fusion partners. An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together. The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer. The Cas9 is split in the sense that the two parts of the Cas9 enzyme substantially comprise a functioning Cas9.

That Cas9 may function as a genome editing enzyme (when forming a complex with the target DNA and the guide), such as a nickase or a nuclease (cleaving both strands of the DNA), or it may be a dead Cas9 which is essentially a DNA binding protein with very little or no catalytic activity, due to typically two or more mutations in its catalytic domains as described herein further.

In certain embodiments, the nuclease may comprise one or more additional (heterologous) functional domains, i.e. the modified nuclease is a fusion protein comprising the nuclease itself and one or more additional domains, which may be fused C-terminally or N-terminally to the nuclease, or alternatively inserted at suitable and appropriate sited internally within the nuclease (preferably without perturbing its function, which may be an otherwise modified function, such as including reduced or absent catalytic activity, nickase activity, etc.). any type of functional domain may suitably be used, such as without limitation including functional domains having one or more of the following activities: (DNA or RNA) methyltransferase activity, methylase activity, demethylase activity, DNA hydroxylmethylase domain, histone acetylase domain, histone deacetylases domain, transcription or translation activation activity, transcription or translation repression activity, transcription or translation release factor activity, histone modification activity, nuclease activity, single-strand RNA cleavage activity, double-strand RNA cleavage activity, single-strand DNA cleavage activity, double-strand DNA cleavage activity, nucleic acid binding activity, a protein acetyltransferase, a protein deacetylase, a protein methyltransferase, a protein deaminase, a protein kinase, a protein phosphatase, transposase domain, integrase domain, recombinase domain, resolvase domain, invertase domain, protease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase, histone tail protease, HDACs, histone methyltransferases (HMTs), and histone acetyltransferase (HAT) inhibitors, as well as HDAC and HMT recruiting proteins, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains.

In some embodiments, the functional domain is an epigenetic regulator; see, e.g., Zhang et al., U.S. Pat. No. 8,507,272 (incorporated herein by reference in its entirety). In some embodiments, the functional domain is a transcriptional activation domain, such as VP64, p65, MyoD1, HSF1, RTA, SETT/9 or a histone acetyltransferase. In some embodiments, the functional domain is a transcription repression domain, such as KRAB. In some embodiments, the transcription repression domain is SID, or concatemers of SID (e.g., SID4X), NuE, or NcoR. In some embodiments, the functional domain is an epigenetic modifying domain, such that an epigenetic modifying enzyme is provided. In some embodiments, the functional domain is an activation domain, which may be the P65 activation domain. In some embodiments, the functional domain comprises nuclease activity. In one such embodiment, the functional domain may comprise Fok1. Mention is made of U.S. Pat. Pub. 2014/0356959, U.S. Pat. Pub. 2014/0342456, U.S. Pat. Pub. 2015/0031132, and Mali, P. et al., 2013, Science 339(6121): 823-6, doi: 10.1126/science.1232033, published online 3 Jan. 2013 and through the teachings herein the invention comprehends methods and materials of these documents applied in conjunction with the teachings herein.

It is to be understood that also destabilization domains or localization domains as described herein elsewhere are encompassed by the generic term "functional domain". In certain embodiments, one or more functional domains are associated with the nuclease itself. In some embodiments, one or more functional domains are associated with an adaptor protein, for example as used with the modified guides of Konnerman et al. (Nature 517(7536): 583-588, 2015; incorporated herein by reference in its entirety), and hence form part of a Synergistic activator mediator (SAM) complex. The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb 12r, φCb23r, 7s and PRR1. These adaptor proteins or orthogonal RNA binding proteins can further recruit effector proteins or fusions which comprise one or more functional domains.

In certain embodiments, the nuclease, in particular the Cas protein, may comprise one or more modifications resulting in a destabilized nuclease when expressed in a host (cell). Such may be achieved by fusion of the nuclease with a destabilization domain (DD). Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, A temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment.

A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ESR1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known.

There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield1 ligand; see, e.g., Nature Methods 5, (2008). For instance, a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398—all of which are incorporated herein by reference and may be employed in the practice of the invention in selected a DD to associate with a CRISPR enzyme in the practice of this invention.

As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled—turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to an associated Cas being degraded.

When a new DD is fused to a protein of interest, its instability is conferred to the protein of interest, resulting in the rapid degradation of the entire fusion protein. Peak activity for Cas is sometimes beneficial to reduce off-target effects. Thus, short bursts of high activity are preferred. The invention is able to provide such peaks. In some senses the system is inducible. In some other senses, the system repressed in the absence of stabilizing ligand and de-repressed in the presence of stabilizing ligand. By means of example, and without limitation, in some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT. More than one (the same or different) DD may be present, and may be fused for instance C-terminally, or N-terminally, or even internally at suitable locations. Having two or more DDs which are heterologous may be advantageous as it would provide a greater level of degradation control.

In some embodiments, the fusion protein as described herein may comprise a linker between the nuclease and the fusion partner (e.g., functional domain). In some embodiments, the linker is a GlySer linker. Attachment of a functional domain or fusion protein can be via a linker, e.g., a flexible glycine-serine (GlyGlyGlySer) (SEQ ID NO: 1) or (GGGS)3 (SEQ ID NO: 2) or a rigid alpha-helical linker such as (Ala(GluAlaAlaAlaLys)Ala) (SEQ ID NO: 3). Linkers such as (GGGGS)3 (SEQ ID NO: 4) are preferably used herein to separate protein or peptide domains. (GGGGS)3 (SEQ ID NO: 5) is preferable because it is a relatively long linker (15 amino acids). The glycine residues are the most flexible and the serine residues enhance the chance that the linker is on the outside of the protein. (GGGGS)6 (SEQ ID NO: 6) (GGGGS)9 (SEQ ID NO: 7) or (GGGGS)12 (SEQ ID NO: 8) may preferably be used as alternatives. Other preferred alternatives are (GGGGS)1 (SEQ ID NO: 9), (GGGGS)2 (SEQ ID NO: 10), (GGGGS)4 (SEQ ID NO: 11), (GGGGS)5 (SEQ ID NO: 12), (GGGGS)7 (SEQ ID NO: 13), (GGGGS)8 (SEQ ID NO: 14), (GGGGS)10 (SEQ ID NO: 15), or (GGGGS)11 (SEQ ID NO: 16). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 (SEQ ID NO: 4) linker may be used here (or the 6 (SEQ ID NO: 6), 9 (SEQ ID NO: 7), or 12 (SEQ ID NO: 8) repeat versions therefore) or the NLS of nucleoplasmin can be used as a linker between Cas9 and the functional domain.

In some embodiments, the Cas sequence is fused to one or more nuclear localization sequences (NLSs) or nuclear export signals (NESs), such as about or more than about 1, 2, 3, 4, 5, 6, 7, 8, 9, 10, or more NLSs or NESs. In some embodiments, the Cas comprises about or more than about 1, 2, 3, 4, 5, 6, 7, 8, 9, 10, or more NLSs or NESs at or near the amino-terminus, about or more than about 1, 2, 3, 4, 5, 6, 7, 8, 9, 10, or more NLSs or NESs at or near the carboxy-terminus, or a combination of these (e.g. zero or at least one or more NLS or NES at the amino-terminus and zero or at one or more NLS or NES at the carboxy terminus). When more than one NLS or NES is present, each may be selected independently of the others, such that a single NLS or NES may be present in more than one copy and/or in combination with one or more other NLSs or NESs present in one or more copies. In a preferred embodiment of the invention, the Cas comprises at most 6 NLSs. In some embodiments, an NLS or NES is considered near the N- or C-terminus when the nearest amino acid of the NLS or NES is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 17); the NLS from nucleoplasmin (e.g. the nucleoplasmin bipartite NLS with the sequence KRPAATKKAGQAKKKK) (SEQ ID NO: 18); the c-myc NLS having the amino acid sequence PAAKRVKLD (SEQ ID NO: 19) or RQRRNELKRSP (SEQ ID NO: 20); the hnRNPA1 M9 NLS having the sequence NQSSNFGPMKGGNFGGRSSGPYGGGGQYFAK-PRNQGGY (SEQ ID NO: 21); the sequence RMRIZFKNKGKDTAELRRRRVEVSVELRKAKKD-EQILKRRNV (SEQ ID NO: 22) of the IBB domain from importin-alpha; the sequences VSRKRPRP (SEQ ID NO: 23) and PPKKARED (SEQ ID NO: 24) of the myoma T protein; the sequence PQPKKKPL (SEQ ID NO: 25) of human p53; the sequence SALIKKKKKMAP (SEQ ID NO: 26) of mouse c-abl IV; the sequences DRLRR (SEQ ID NO: 27) and PKQKKRK (SEQ ID NO: 28) of the influenza virus NS1; the sequence RKLKKKIKKL (SEQ ID NO: 29) of the Hepatitis virus delta antigen; the sequence REKKKFLKRR (SEQ ID NO: 30) of the mouse Mx1 protein; the sequence KRKGDEVDGVDEVAKKKSKK (SEQ ID NO: 31) of the human poly(ADP-ribose) polymerase; and the sequence RKCLQAGMNLEARKTKK (SEQ ID NO: 32) of the steroid hormone receptors (human) glucocorticoid. Non-limiting examples of NESs include an NES sequence LYPER-LRRILT (SEQ ID NO: 33) (ctgtaccctgagcggctgcggcggatcctgacc (SEQ ID NO: 34)). In general, the one or more NLSs or NESs are of sufficient strength to drive accumulation of the Cas in a detectable amount in respectively the nucleus or the cytoplasm of a eukaryotic cell. In general, strength of nuclear localization/export activity may derive from the number of NLSs/NESs in the Cas, the particular NLS(s) or NES(s) used, or a combination of these factors. Detection of accumulation in the nucleus/cytoplasm may be performed by any suitable technique. For example, a detectable marker may be fused to the Cas, such that location within a cell may be visualized, such as in combination with a means for detecting the location of the nucleus (e.g., a stain specific for the nucleus such as DAPI) or cytoplasm. Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g., assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs or NESs. In certain embodiments, other localization tags may be fused to the Cas protein, such as without limitation for localizing the Cas to particular sites in a cell, such as organelles, such mitochondria, plastids, chloroplast, vesicles, golgi, (nuclear or cellular) membranes, ribosomes, nucleolus, ER, cytoskeleton, vacuoles, centrosome, nucleosome, granules, centrioles, etc.

In certain aspects the invention involves vectors, e.g., for delivering or introducing in a cell Cas and/or RNA capable of guiding Cas to a target locus (i.e., guide RNA), but also for propagating these components (e.g., in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (www.genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters—especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Orthologs of Cas9

The CRISPR-Cas9 system is described in detail in international patent application no. PCT/US2017/047458, titled "NOVEL CRISPR ENZYMES AND SYSTEMS" and filed Aug. 17, 2017, which is incorporated by reference in its entirety. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

The Cas9 gene is found in several diverse bacterial genomes, typically in the same locus with cas1, cas2, and cas4 genes and a CRISPR cassette. Furthermore, the Cas9 protein contains a readily identifiable C-terminal region that is homologous to the transposon ORF-B and includes an active RuvC-like nuclease, an arginine-rich region.

In particular embodiments, the effector protein is a Cas9 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium*, or *Corynebacterium*.

In particular embodiments, the effector protein is a Cas9 effector protein from an organism from a genus comprising *Carnobacterium, Rhodobacter, Listeria, Paludibacter, Clostridium*, Lachnospiraceae, *Clostridiaridium, Leptotrichia, Francisella, Legionella, Alicyclobacillus, Methanomethylophilus, Porphyromonas, Prevotella*, Bacteroidetes, *Helcococcus, Leptospira, Desulfovibrio, Desulfonatronum*, Opitutaceae, *Tuberibacillus, Bacillus, Brevibacillus, Methylobacterium* or *Acidaminococcus*.

In further particular embodiments, the Cas9 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii*. In particular embodiments, the effector protein is a Cas9 effector protein from an organism from *Streptococcus pyogenes, Staphylococcus aureus*, or *Streptococcus thermophilus* Cas9.

The effector protein may comprise a chimeric effector protein comprising a first fragment from a first effector protein (e.g., a Cas9) ortholog and a second fragment from a second effector (e.g., a Cas9) protein ortholog, and wherein the first and second effector protein orthologs are different. At least one of the first and second effector protein (e.g., a Cas9) orthologs may comprise an effector protein (e.g., a Cas9) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*; e.g., a chimeric effector protein comprising a first fragment and a second fragment wherein each of the first and second fragments is selected from a Cas9 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus* wherein the first and second fragments are not from the same bacteria; for instance a chimeric effector protein comprising a first fragment and a second fragment wherein each of the first and second fragments is selected from a Cas9 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*, wherein the first and second fragments are not from the same bacteria.

In a more preferred embodiment, the Cas9 is derived from a bacterial species selected from *Streptococcus pyogenes, Staphylococcus aureus*, or *Streptococcus thermophilus* Cas9. In certain embodiments, the Cas9p is derived from a bacterial species selected from *Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*. In certain embodiments, the Cas9p is derived from a bacterial species selected from *Acidaminococcus* sp. BV3L6, *Lachnospiraceae bacterium* MA2020. In certain embodiments, the effector protein is derived from a subspecies of *Francisella tularensis* 1, including but not limited to *Francisella tularensis* subsp. *Novicida*.

The nucleic acid-targeting system may be derived advantageously from a Type VI CRISPR system. In some embodiments, one or more elements of a nucleic acid-targeting system is derived from a particular organism comprising an endogenous RNA-targeting system. In particular embodiments, the Type VI RNA-targeting Cas enzyme is C2c2. In an embodiment of the invention, there is provided a effector protein which comprises an amino acid sequence having at least 80% sequence homology to the wild-type sequence of any of *Leptotrichia shahii* C2c2, *Lachnospiraceae bacterium* MA2020 C2c2, *Lachnospiraceae bacterium* NK4A179 C2c2, *Clostridium aminophilum* (DSM 10710) C2c2, *Carnobacterium gallinarum* (DSM 4847) C2c2, *Paludibacter propionicigenes* (WB4) C2c2, *Listeria weihenstephanensis* (FSL R9-0317) C2c2, *Listeriaceae bacterium* (FSL M6-0635) C2c2, *Listeria newyorkensis* (FSL M6-0635) C2c2, *Leptotrichia wadei* (F0279) C2c2, *Rhodobacter capsulatus* (SB 1003) C2c2, *Rhodobacter capsulatus* (R121) C2c2, *Rhodobacter capsulatus* (DE442) C2c2, *Leptotrichia wadei* (Lw2) C2c2, or *Listeria seeligeri* C2c2.

In particular embodiments, the homologue or orthologue of Cas9 as referred to herein has a sequence homology or identity of at least 80%, more preferably at least 85%, even more preferably at least 90%, such as for instance at least 95% with Cas9. In further embodiments, the homologue or orthologue of Cas9 as referred to herein has a sequence identity of at least 80%, more preferably at least 85%, even more preferably at least 90%, such as for instance at least 95% with the wild type Cas9. Where the Cas9 has one or more mutations (mutated), the homologue or orthologue of said Cas9 as referred to herein has a sequence identity of at least 80%, more preferably at least 85%, even more preferably at least 90%, such as for instance at least 95% with the mutated Cas9.

In an embodiment, the Cas9 protein may be an ortholog of an organism of a genus which includes, but is not limited to *Streptococcus* sp. or *Staphylococcus* sp.; in particular embodiments, Cas9 protein may be an ortholog of an organism of a species which includes, but is not limited to *Streptococcus pyogenes*, *Staphylococcus aureus*, or *Streptococcus thermophilus* Cas9. In particular embodiments, the homologue or orthologue of Cas9p as referred to herein has a sequence homology or identity of at least 80%, more preferably at least 85%, even more preferably at least 90%, such as for instance at least 95% with one or more of the Cas9 sequences disclosed herein. In further embodiments, the homologue or orthologue of Cas9 as referred to herein has a sequence identity of at least 80%, more preferably at least 85%, even more preferably at least 90%, such as for instance at least 95% with the wild type SpCas9, SaCas9 or StCas9.

In particular embodiments, the Cas9 protein of the invention has a sequence homology or identity of at least 60%, more particularly at least 70, such as at least 80%, more preferably at least 85%, even more preferably at least 90%, such as for instance at least 95% with SpCas9, SaCas9 or StCas9. In further embodiments, the Cas9 protein as referred to herein has a sequence identity of at least 60%, such as at least 70%, more particularly at least 80%, more preferably at least 85%, even more preferably at least 90%, such as for instance at least 95% with the wild type SpCas9, SaCas9 or StCas9. The skilled person will understand that this includes truncated forms of the Cas9 protein whereby the sequence identity is determined over the length of the truncated form.

In an embodiment of the invention, the effector protein comprises at least one HEPN domain, including but not limited to HEPN domains described herein, HEPN domains known in the art, and domains recognized to be HEPN domains by comparison to consensus sequences and motifs.

Determination of Cas9 PAM

Determination of PAM can be ensured as follows. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target. Two *E. coli* strains are used in this assay. One carries a plasmid that encodes the endogenous effector protein locus from the bacterial strain. The other strain carries an empty plasmid (e.g., pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has an 8 random bp 5' of the proto-spacer (e.g. total of 65536 different PAM sequences=complexity). The other library has 7 random bp 3' of the proto-spacer (e.g., total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransformed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

Codon Optimized Cas9

Where the effector protein is to be administered as a nucleic acid, the application envisages the use of codon-optimized Cas9 sequences. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cas9) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or *Codon selection in yeast*, Bennetzen and Hall, J Biol Chem. 1982 Mar. 25; 257(6):3026-31. As to codon usage in plants including algae, reference is made to *Codon usage in higher plants, green algae, and cyanobacteria*, Campbell and Gowri, Plant Physiol. 1990 January; 92(1): 1-11.; as well as *Codon usage in plant genes*, Murray et al, Nucleic Acids Res. 1989 Jan. 25; 17(2):477-98; or *Selection on the codon bias of chloroplast and cyanelle genes in different plant and algal lineages*, Morton B R, J Mol Evol. 1998 April; 46(4):449-59.

Modified Cas9 Protein

In particular embodiments, it is of interest to make an engineered Cas9 protein as defined herein, such as Cas9, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cas9 protein, and wherein the CRISPR complex comprising the modified protein has altered activity as compared to the complex comprising the unmodified Cas9 protein. It is to be understood that when referring herein to CRISPR "protein", the Cas9 protein preferably is a modified CRISPR enzyme (e.g., having increased or decreased (or no) enzymatic activity, such as without limitation including Cas9). The term "CRISPR protein" may be used interchangeably with "CRISPR enzyme", irrespective of whether the CRISPR protein has altered, such as increased or decreased (or no), enzymatic activity, compared to the wild type CRISPR protein.

Several small stretches of unstructured regions are predicted within the Cas9 primary structure. Unstructured regions, which are exposed to the solvent and not conserved within different Cas9 orthologs, are preferred sides for splits and insertions of small protein sequences. In addition, these sides can be used to generate chimeric proteins between Cas9 orthologs.

Based on the above information, mutants can be generated which lead to inactivation of the enzyme or which modify the double strand nuclease to nickase activity. In alternative embodiments, this information is used to develop enzymes with reduced off-target effects (described elsewhere herein). In certain example embodiments, the information is used to develop enzymes with altered editing preferences as compared to wild type.

In one example embodiment, a modified Cas9 protein comprises at least one modification that alters editing preference as composed to wild type. In certain example embodiments, the editing preference is for a specific insert or deletion within the target region. In certain example embodiments, the at least one modification increases formation of one or more specific indels. In one example embodiment, the at least on modification is in the binding region including the targeting region and/or the PAM interacting region. In another example embodiment, the at least one modification is not in the binding region including the targeting region and/or the PAM interacting region. In one example embodiment, the one or more modification are located in or proximate to a RuvC domain. In another example embodiment, the one or more modification are located in or proximate to a HNH or Nuc domain. In another example embodiment, the one or more modification are in or proximate to a bridge helix. In another example embodiment, the one or more modifications are in or proximate to a recognition lobe. In another example embodiment, the at least one modification is present or proximate to a D10 active site residue. In another example embodiment, the at least one modification is present in or proximate to a linker region. The linker region may form a linker from a RuVc domain to the bridge helix. In certain example embodiments, the one or more modifications are located at residues 6-19, 51-60, 690-696, 698-700, 725-734, 764-786, 802-811, 837-871, 902-929, 976-982, 998-1007, or a combination thereof, of SpCas9 or a residue in an ortholog corresponding or functionally equivalent thereto.

In certain example embodiments, the at least one modification increases formation of one or more specific insertions. In certain example embodiments, the at least one modification results in an insertion of an A adjacent to an A, T, G, or C in the target region. In another example embodiment, the at least one modification results in insertion of a T adjacent to an A, T, G, or C in the target region. In another example embodiment, the at least one modification results in insertion of a G adjacent to an A, T, G, or C in the target region. In another example embodiment, the at least one modification results in insertion of a C adjacent to an A, T, C, or G in the target region. The insertion may be 5' or 3' to the adjacent nucleotide. In one example embodiment, the one or more modification direct insertion of a T adjacent to an existing T. In certain example embodiments, the existing T corresponds to the $4^{th}$ position in the binding region of a guide sequence. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutations in diseases caused by small deletions, more particularly where HDR is not possible. For example, correction of the F508del mutation in CFTR via delivery of three sRNA directing insertion of three T's, which is the most common genotype of cystic fibrosis, or correction of Alia Jafar's single nucleotide deletion in CDKL5 in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity and/or decrease off-target effects.

In certain example embodiments, the engineered CRISPR-cas effector comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph.

Suitable Cas9 enzyme modifications which enhance specificity in particular by reducing off-target effects, are described for instance in PCT/US2016/038034, which is incorporated herein by reference in its entirety. In particular embodiments, a reduction of off-target cleavage is ensured by destabilizing strand separation, more particularly by introducing mutations in the Cas9 enzyme decreasing the positive charge in the DNA interacting regions (as described herein and further exemplified for Cas9 by Slaymaker et al. 2016 (Science, 1; 351(6268):84-8)). In further embodiments, a reduction of off-target cleavage is ensured by introducing mutations into Cas9 enzyme which affect the interaction between the target strand and the guide RNA sequence, more particularly disrupting interactions between Cas9 and the phosphate backbone of the target DNA strand in such a way as to retain target specific activity but reduce off-target activity (as described for Cas9 by Kleinstiver et al. 2016, Nature, 28; 529(7587):490-5). In particular embodiments, the off-target activity is reduced by way of a modified Cas9 wherein both interaction with target strand and non-target strand are modified compared to wild-type Cas9.

The methods and mutations which can be employed in various combinations to increase or decrease activity and/or specificity of on-target vs. off-target activity, or increase or decrease binding and/or specificity of on-target vs. off-target binding, can be used to compensate or enhance mutations or modifications made to promote other effects. Such mutations or modifications made to promote other effects include mutations or modification to the Cas9 effector protein and/or mutation or modification made to a guide RNA.

With a similar strategy used to improve Cas9 specificity (Slaymaker et al. 2015 "Rationally engineered Cas9 nucleases with improved specificity"), specificity of Cas9 can be further improved by mutating residues that stabilize the non-targeted DNA strand. This may be accomplished without a crystal structure by using linear structure alignments to predict 1) which domain of Cas9 binds to which strand of DNA and 2) which residues within these domains contact DNA.

However, this approach may be limited due to poor conservation of Cas9 with known proteins. Thus, it may be desirable to probe the function of all likely DNA interacting amino acids (lysine, histidine and arginine).

Without being bound by theory, in an aspect of the invention, the methods and mutations described provide for enhancing conformational rearrangement of Cas9 domains to positions that results in cleavage at on-target sits and avoidance of those conformational states at off-target sites. Cas9 cleaves target DNA in a series of coordinated steps. First, the PAM-interacting domain recognizes the PAM sequence 5' of the target DNA. After PAM binding, the first 10-12 nucleotides of the target sequence (seed sequence) are sampled for sgRNA:DNA complementarity, a process dependent on DNA duplex separation. If the seed sequence nucleotides complement the sgRNA, the remainder of DNA is unwound and the full length of sgRNA hybridizes with the target DNA strand. The nt-groove between the RuvC and HNH domains stabilizes the non-targeted DNA strand and facilitates unwinding through non-specific interactions with positive charges of the DNA phosphate backbone. RNA:cDNA and Cas9:ncDNA interactions drive DNA unwinding in competition against cDNA:ncDNA rehybridization. Other cas9 domains affect the conformation of nuclease domains as well, for example linkers connecting HNH with RuvCII and RuvCIII. Accordingly, the methods and mutations provided encompass, without limitation, RuvCI, RuvCIII, RuvCIII and HNH domains and linkers. Conformational changes in Cas9 brought about by target DNA binding, including seed sequence interaction, and interactions with the target and non-target DNA strand determine whether the domains are positioned to trigger nuclease activity. Thus, the mutations and methods provided herein demonstrate and enable modifications that go beyond PAM recognition and RNA-DNA base pairing. In an aspect, the invention provides Cas9 nucleases that comprise an improved equilibrium towards conformations associated with cleavage activity when involved in on-target interactions and/or improved equilibrium away from conformations associated with cleavage activity when involved in off-target interactions. In one aspect, the invention provides Cas9 nucleases with improved proof-reading function, i.e., a Cas9 nuclease which adopts a conformation comprising nuclease activity at an on-target site, and which conformation has increased unfavorability at an off-target site. Sternberg et al., Nature 527(7576):110-3, doi: 10.1038/nature15544, published online 28 Oct. 2015. Epub 2015 Oct. 28, used Förster resonance energy transfer (FRET) experiments to detect relative orientations of the Cas9 catalytic domains when associated with on- and off-target DNA.

For SpCas9, the single and combination mutants listed herein including in the foregoing Examples are presently considered advantageous as having demonstrated preferred specificity enhancement SpCas9 and SaCas9 mutants, including those tested and those otherwise within this disclosure are listed below in Tables 1-7.

TABLE 1

List of SpCas9 quadruple mutants

| Mutant | Residue | Residue | Residue | Residue |
|---|---|---|---|---|
| QM1 | R63A | K855A | R1060A | E610G |
| QM2 | R63A | H982A | K1003A | K1129E |
| QM3 | R63A | K810A | K1003A | R1060A |

TABLE 2

List of SpCas9 single mutants

| Mutant | Residue and substitution |
|---|---|
| 1 | R63A |
| 2 | H415A |
| 3 | H447A |
| 4 | R778A |
| 5 | R780A |
| 6 | R783A |
| 7 | Q807A |
| 8 | K810A |
| 9 | R832A |
| 10 | K848A |
| 11 | K855A |
| 12 | K968A |
| 13 | R976A |
| 14 | H982A |
| 15 | K1000A |
| 16 | K1003A |
| 17 | K1047A |
| 18 | R1060A |
| 19 | K1107A |
| 20 | R1114A |
| 21 | K1118A |
| 22 | R403A |
| 23 | K1200A |

TABLE 3

List of SpCas9 double and triple mutants

| Mutant | Residue and substitution | | |
|---|---|---|---|
| 1 | R780A | R1060A | |
| 2 | R780A | K1003A | |
| 3 | K810A | K848A | |
| 4 | K810A | K855A | |
| 5 | K848A | K855A | |
| 6 | K855A | R1060A | |
| 7 | R780A | K1003A | R1060A |
| 8 | K855A | K1003A | R1060A |
| 9 | H982A | K1003A | K1129E |
| 10 | K810A | K1003A | R1060A |

TABLE 4

List of SaCas9 single mutants

| Mutant | Residue |
|---|---|
| 1 | H700 |
| 2 | R694 |
| 3 | K692 |
| 4 | R686 |
| 5 | K687 |
| 6 | K751 |
| 7 | R561 |
| 8 | H557 |
| 9 | K572 |
| 10 | K523 |
| 11 | K518 |
| 12 | K525 |

TABLE 5

List of SaCas9 single mutants

| Mutant | Residue |
|---|---|
| 2 | R245 |
| 3 | R480 |
| 4 | R497 |

TABLE 5-continued

List of SaCas9 single mutants

| Mutant | Residue |
|---|---|
| 5 | R499 |
| 6 | R617 |
| 7 | R630 |
| 8 | R634 |
| 9 | R644 |
| 10 | R650 |
| 11 | R654 |
| 12 | K736 |

Representative examples of SpCas9 mutants are listed in Table 6 below.

TABLE 6

List of SpCas9 single mutants

| Mutant | Residue and substitution |
|---|---|
| 1 | N14K |
| 2 | N776L |
| 3 | E781L |
| 4 | E809K |
| 5 | L813R |
| 6 | S845K |
| 7 | L847R |
| 8 | D849A |
| 9 | I852K |
| 10 | D859A |
| 11 | S964K |
| 12 | V975K |
| 13 | E977K |
| 14 | N978K |

Table 7, below, provides exemplary mutants within this disclosure, including those exemplified.

Representative Mutants Within This Disclosure

Single Mutants

| Mutant | Residue | Region |
|---|---|---|
| SM1 | K775A | Groove |
| SM2 | R780A | Groove |
| SM3 | R780A | Groove |
| SM4 | K810A | Groove |
| SM5 | R832A | Groove |
| SM6 | K848A | Groove |
| SM7 | K855A | Groove |
| SM8 | R859A | Groove |
| SM9 | K862A | Groove |
| SM10 | K866A | Groove |
| SM11 | K961A | Groove |
| SM12 | K968A | Groove |
| SM13 | K974A | Groove |
| SM14 | R976A | Groove |
| SM15 | H982A | Groove |
| SM16 | H983A | Groove |
| SM17 | K1014A | Groove |
| SM18 | K1047A | Groove |
| SM19 | K1059A | Groove |
| SM20 | R1060A | Groove |
| SM21 | K1003A | Groove |
| SM22 | H1240A | Groove |
| SM23 | K1244A | Groove |
| SM24 | K1289A | Groove |
| SM25 | K1296A | Groove |
| SM26 | H1297A | Groove |
| SM27 | R1298A | Groove |
| SM28 | K1300A | Groove |
| SM29 | R1303A | Groove |

| Representative Mutants Within This Disclosure | | |
|---|---|---|
| SM30 | H1311A | Groove |
| SM31 | K1325A | Groove |
| SM32 | K1107A | PL |
| SM33 | E1108A | PL |
| SM34 | S1109A | PL |
| SM35 | ΔK1107 | PL |
| SM36 | ΔE1108 | PL |
| SM37 | ΔS1109 | PL |
| SM38 | ES_G | PL |
| SM39 | KES_GG | PL |
| SM40 | R778A | DNA |
| SM41 | K782A | DNA |
| SM42 | R783A | DNA |
| SM43 | K789A | DNA |
| SM44 | K797A | DNA |
| SM45 | K890A | DNA |
| SM46 | R1114A | cDNA |
| SM47 | K1118A | cDNA |
| SM48 | K1200A | cDNA |
| SM49 | R63A | cDNA |
| SM50 | K163A | sgRNA |
| SM51 | R165A | sgRNA |
| SM52 | R403A | sgRNA |
| SM53 | H415A | sgRNA |
| SM54 | R447A | sgRNA |
| SM55 | K1000A | Groove |

| Double Mutants | | | | | |
|---|---|---|---|---|---|
| Mutant# | Residue | Residue | Mutant | Residue | Residue |
| DM1 | R780A | K810A | DM21 | K855A | K1003A |
| DM2 | R780A | K848A | DM22 | R780A | R1060A |
| DM3 | R780A | K855A | DM23 | K810A | R1060A |
| DM4 | R780A | R976A | DM24 | K848A | R1060A |
| DM5 | K810A | K848A | DM25 | K855A | R1060A |
| DM6 | K810A | K855A | DM26 | R63A | R780A |
| DM7 | K810A | R976A | DM27 | R63A | K810A |
| DM8 | K848A | K855A | DM28 | R63A | K848A |
| DM9 | K848A | R976A | DM29 | R63A | K855A |
| DM10 | K855A | R976A | DM30 | R63A | H982A |
| DM11 | H982A | R1060A | DM31 | R63A | R1060A |
| DM12 | H982A | K1003A | DM32 | H415A | R780A |
| DM13 | K1003A | R1060A | DM33 | H415A | K848A |
| DM14 | R780A | H982A | DM34 | R1114A | R780A |
| DM15 | K810A | H982A | DM35 | R1114A | K848A |
| DM16 | K848A | H982A | DM36 | K1107A | R780A |
| DM17 | K855A | H982A | DM37 | K1107A | K848A |
| DM18 | R780A | K1003A | DM38 | E1108A | R780A |
| DM19 | K810A | K1003A | DM39 | E1108A | K848A |
| DM20 | K848A | K1003A | | | |

| Triple Mutants | | | |
|---|---|---|---|
| TM1 | R780A | K810A | K848A |
| TM2 | R780A | K810A | K855A |
| TM3 | R780A | K810A | R976A |
| TM4 | R780A | K848A | K855A |
| TM5 | R780A | K848A | R976A |
| TM6 | R780A | K855A | R976A |
| TM7 | K810A | K848A | K855A |
| TM8 | K810A | K848A | R976A |
| TM9 | K810A | K855A | R976A |
| TM10 | K848A | K855A | R976A |
| TM11 | H982A | K1003A | R1060A |
| TM12 | H982A | K1003A | K1129E |
| TM13 | R780A | K1003A | R1060A |
| TM14 | K810A | K1003A | R1060A |
| TM15 | K848A | K1003A | R1060A |
| TM16 | K855A | K1003A | R1060A |
| TM17 | R63A | H982A | R1060A |
| TM18 | R63A | K1003A | R1060A |
| TM19 | R63A | K848A | R1060A |

| Multiple Mutants | | | | | |
|---|---|---|---|---|---|
| 6x | R780A | K810A | K848A | K855A | R976A H982A |
| QM1 | R63A | K855A | R1060A | E610G | |
| QM2 | R63A | H982A | K1003A | K1129E | |
| QM3 | R63A | K810A | K1003A | R1060A | |

In certain embodiments, the modification or mutation comprises a mutation in a RuvCI, RuvCIII, RuvCIII or HNH domain. In certain embodiments, the modification or mutation comprises an amino acid substitution at one or more of positions 12, 13, 63, 415, 610, 775, 779, 780, 810, 832, 848, 855, 861, 862, 866, 961, 968, 974, 976, 982, 983, 1000, 1003, 1014, 1047, 1060, 1107, 1108, 1109, 1114, 1129, 1240, 1289, 1296, 1297, 1300, 1311, and 1325; preferably 855; 810, 1003, and 1060; or 848, 1003 with reference to amino acid position numbering of SpCas9. In certain embodiments, the modification or mutation at position 63, 415, 775, 779, 780, 810, 832, 848, 855, 861, 862, 866, 961, 968, 974, 976, 982, 983, 1000, 1003, 1014, 1047, 1060, 1107, 1108, 1109, 1114, 1129, 1240, 1289, 1296, 1297, 1300, 1311, or 1325; preferably 855; 810, 1003, and 1060; 848, 1003, and 1060; or 497, 661, 695, and 926 comprises an alanine substitution. In certain embodiments, the modification comprises K855A; K810A, K1003A, and R1060A; or K848A, K1003A (with reference to SpCas9), and R1060A. In certain embodiments, in certain embodiments, the modification comprises N497A, R661A, Q695A, and Q926A (with reference to SpCas9).

Other mutations may include N692A, M694A, Q695A, H698A or combinations thereof and as otherwise described in Kleinstiver et al. "High-fidelity CRISP-Cas9 nucleases with no detectable genome-wide off-target effects" Nature 529, 590-607 (2016). In addition, mutations and/or modifications within the REC3 domain (with reference to SpCas9-HF1 and eSpCas9(1.1)) may also be targeted for increased target specificity and as further described in Chen et al. "Enhanced proofreading governs CRISPR-Cas9 targeting accuracy" bioRxiv Jul. 6, 2017 doi: dx.doi.org/10.1101/160036. Other mutations may be located in an HNH nuclease domain as further described in Sternberg et al. Nature 2015 doi:10.1038/nature15544.

In some embodiments, a vector encodes a Cas that is mutated to with respect to a corresponding wild-type enzyme such that the mutated Cas lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, aD10A mutation is combined with one or more of H840A, N854A, or N863A mutations to produce a Cas9 enzyme substantially lacking all DNA cleavage activity.

In certain of the above-described Cas9 enzymes, the enzyme is modified by mutation of one or more residues including but not limited to positions D10, E762, H840, N854, N863, or D986 according to SpCas9 protein or any corresponding ortholog. In an aspect the invention provides a herein-discussed composition wherein the Cas9 enzyme is an inactivated enzyme which comprises one or more mutations selected from the group consisting of D10A, E762A, H840A, N854A, N863A and/or D986A as to SpCas9 or corresponding positions in a Cas9 ortholog. In an aspect the invention provides a herein-discussed composition, wherein the CRISPR enzyme comprises H840A, or D10A and H840A, or D10A and N863A, according to SpCas9 protein or a corresponding position in a Cas9 ortholog.

Deactivated/Inactivated Cas9 Protein

Where the Cas9 protein has nuclease activity, the Cas9 protein may be modified to have diminished nuclease activity e.g., nuclease inactivation of at least 70%, at least 80%, at least 90%, at least 95%, at least 97%, or 100% as compared with the wild type enzyme; or to put in another way, a Cas9 enzyme having advantageously about 0% of the nuclease activity of the non-mutated or wild type Cas9 enzyme or CRISPR enzyme, or no more than about 3% or about 5% or about 10% of the nuclease activity of the non-mutated or wild type Cas9 enzyme. This is possible by introducing mutations into the nuclease domains of the Cas9 and orthologs thereof.

In certain embodiments, the CRISPR enzyme is engineered and can comprise one or more mutations that reduce or eliminate a nuclease activity. When the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10, E762, H840, N854, N863, or D986; as well as conservative substitution for any of the replacement amino acids is also envisaged. The point mutations to be generated to substantially reduce nuclease activity include but are not limited to D10A, E762A, H840A, N854A, N863A and/or D986A. In an aspect the invention provides a herein-discussed composition, wherein the CRISPR enzyme comprises two or more mutations wherein two or more of D10, E762, H840, N854, N863, or D986 according to SpCas9 protein or any corresponding or N580 according to SaCas9 protein ortholog are mutated, or the CRISPR enzyme comprises at least one mutation wherein at least H840 is mutated. In an aspect the invention provides a herein-discussed composition wherein the CRISPR enzyme comprises two or more mutations comprising D10A, E762A, H840A, N854A, N863A or D986A according to SpCas9 protein or any corresponding ortholog, or N580A according to SaCas9 protein, or at least one mutation comprising H840A, or, optionally wherein the CRISPR enzyme comprises: N580A according to SaCas9 protein or any corresponding ortholog; or D10A according to SpCas9 protein, or any corresponding ortholog, and N580A according to SaCas9 protein. In an aspect the invention provides a herein-discussed composition, wherein the CRISPR enzyme comprises H840A, or D10A and H840A, or D10A and N863A, according to SpCas9 protein or any corresponding ortholog.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain. In some embodiments, two Cas9 variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In preferred embodiments the Cas9 effector protein cleaves sequences associated with or at a target locus of interest as a homodimer comprising two Cas9 effector protein molecules. In a preferred embodiment the homodimer may comprise two Cas9 effector protein molecules comprising a different mutation in their respective RuvC domains.

The inactivated Cas9 CRISPR enzyme may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that gRNAs are designed to provide proper spacing for functional use (Fok1) as specifically described in Tsai et al. Nature Biotechnology, Vol. 32, Number 6, June 2014. The adaptor protein may utilize known linkers to attach such functional domains. In some cases, it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated Cas9 enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

Chemically-Modified Cas9 Guide

In certain embodiments, the Cas9 guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotide comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'-phosphorothioate (MS), S-constrained ethyl(cEt), or 2'-O-methyl 3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target DNA and one or more deoxyribonucleotides and/or nucleotide analogs in a region that binds to Cas9. In an embodiment of the invention, deoxyribonucleotides and/or nucleotide analogs are incorporated in engineered guide structures, such as, without limitation, stem-loop regions, and the seed region. In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3'-phosphorothioate (MS), S-constrained ethyl(cEt), or 2'-O-methyl 3'-thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS*, E7110-E7111). In an embodiment of the invention, a guide is modified to comprise a chemical moiety at its 3' and/or 5' end. Such moieties include, but are not limited to, amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife*, 2017, 6:e25312, DOI:10.7554). In certain embodiments, a guide comprises ribonucleotides in a region that binds to a target DNA and one or more deoxyribonucleotides and/or nucleotide analogs in a region that binds Cas9. In an embodiment of the invention, deoxyribonucleotides and/or nucleotide analogs are incorporated in engineered guide structures, such as, without limitation, stem-loop regions.

In some embodiments, the guide molecule comprises a tracr sequence and a tracr mate sequence that are chemically linked or conjugated via a non-phosphodiester bond. In one aspect, the guide comprises a tracr sequence and a tracr mate sequence that are chemically linked or conjugated via a non-nucleotide loop. In some embodiments, the tracr and tracr mate sequences are joined via a non-phosphodiester covalent linker. Examples of the covalent linker include but are not limited to a chemical moiety selected from the group consisting of carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, the tracr or tracr mate sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl ally, propargyl, diene, alkyne, and azide. Once the tracr and the tracr mate sequences are functionalized, a covalent chemical bond or linkage can be formed between the two oligonucleotides. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, the tracr and tracr mate sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In some embodiments, the tracr and tracr mate sequences can be covalently linked using various bioconjugation reactions, loops, bridges, and non-nucleotide links via modifications of sugar, internucleotide phosphodiester bonds, purine and pyrimidine residues. Sletten et al., Angew. Chem. Int. Ed. (2009) 48:6974-6998; Manoharan, M. Curr. Opin. Chem. Biol. (2004) 8: 570-9; Behlke et al., Oligonucleotides (2008) 18: 305-19; Watts, et al., Drug. Discov. Today (2008) 13: 842-55; Shukla, et al., ChemMedChem (2010) 5: 328-49.

In some embodiments, the tracr and tracr mate sequences can be covalently linked using click chemistry. In some embodiments, the tracr and tracr mate sequences can be covalently linked using a triazole linker. In some embodiments, the tracr and tracr mate sequences can be covalently linked using Huisgen 1,3-dipolar cycloaddition reaction involving an alkyne and azide to yield a highly stable triazole linker (He et al., ChemBioChem (2015) 17: 1809-1812; WO 2016/186745). In some embodiments, the tracr and tracr mate sequences are covalently linked by ligating a 5'-hexyne tracrRNA and a 3'-azide crRNA. In some embodiments, either or both of the 5'-hexyne tracrRNA and a 3'-azide crRNA can be protected with 2'-acetoxyethyl orthoester (2'-ACE) group, which can be subsequently removed using Dharmacon protocol (Scaringe et al., J. Am. Chem. Soc. (1998) 120: 11820-11821; Scaringe, Methods Enzymol. (2000) 317: 3-18).

In some embodiments, the tracr and tracr mate sequences can be covalently linked via a linker (e.g., a non-nucleotide loop) that comprises a moiety such as spacers, attachments, bioconjugates, chromophores, reporter groups, dye labeled RNAs, and non-naturally occurring nucleotide analogues. More specifically, suitable spacers for purposes of this invention include, but are not limited to, polyethers (e.g., polyethylene glycols, polyalcohols, polypropylene glycol or mixtures of ethylene and propylene glycols), polyamines group (e.g., spennine, spermidine and polymeric derivatives thereof), polyesters (e.g., poly(ethyl acrylate)), polyphosphodiesters, alkylenes, and combinations thereof. Suitable attachments include any moiety that can be added to the linker to add additional properties to the linker, such as but not limited to, fluorescent labels. Suitable bioconjugates include, but are not limited to, peptides, glycosides, lipids, cholesterol, phospholipids, diacyl glycerols and dialkyl glycerols, fatty acids, hydrocarbons, enzyme substrates, steroids, biotin, digoxigenin, carbohydrates, polysaccharides. Suitable chromophores, reporter groups, and dye-labeled RNAs include, but are not limited to, fluorescent dyes such as fluorescein and rhodamine, chemiluminescent, electrochemiluminescent, and bioluminescent marker compounds. The design of example linkers conjugating two RNA components are also described in WO 2004/015075.

The linker (e.g., a non-nucleotide loop) can be of any length. In some embodiments, the linker has a length equivalent to about 0-16 nucleotides. In some embodiments, the linker has a length equivalent to about 0-8 nucleotides. In some embodiments, the linker has a length equivalent to about 0-4 nucleotides. In some embodiments, the linker has a length equivalent to about 2 nucleotides. Example linker design is also described in WO2011/008730.

In certain embodiments, the Cas9 protein uses of a tracrRNA, the guide sequence, tracr mate, and tracr sequence may reside in a single RNA, i.e., an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR-Cas9 complex to the target sequence. A typical Type II Cas9 sgRNA comprises (in 5' to 3' direction): a guide sequence, a poly U tract, a first complimentary stretch (the "repeat"), a loop (tetraloop), a second complimentary stretch (the "anti-repeat" being complimentary to the repeat), a stem, and further stem loops and stems and a poly A (often poly U in RNA) tail (terminator). In preferred embodiments, certain aspects of guide architecture are retained, certain aspect of guide architecture cam be modified, for example by addition, subtraction, or substitution of features, whereas certain other aspects of guide architecture are maintained. Preferred locations for engineered sgRNA modifications, including but not limited to insertions, deletions, and substitutions include guide termini and regions of the sgRNA that are exposed when complexed with CRISPR protein and/or target, for example the tetraloop and/or loop2.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In particular embodiments, such as where the CRISPR-Cas protein is a Cas9 protein, the "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and guide sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferrably more than 17 nts, and has more than one stem loops or optimized secondary structures. In particular embodiments the guide molecule comprises or consists of the guide sequence linked to all or part of the natural direct repeat sequence. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with CRISPR protein and/or target, for example the tetraloop and/or loop2.

The repeat:anti repeat duplex will be apparent from the secondary structure of the sgRNA. It may be typically a first complimentary stretch after (in 5' to 3' direction) the poly U tract and before the tetraloop; and a second complimentary stretch after (in 5' to 3' direction) the tetraloop and before the poly A tract. The first complimentary stretch (the "repeat") is complimentary to the second complimentary stretch (the "anti-repeat"). As such, they Watson-Crick base pair to form a duplex of dsRNA when folded back on one another. As such, the anti-repeat sequence is the complimentary sequence of the repeat and in terms to A-U or C-G base pairing, but also in terms of the fact that the anti-repeat is in the reverse orientation due to the tetraloop.

In an embodiment of the invention, modification of guide architecture comprises replacing bases in stemloop 2. For example, in some embodiments, "actt" ("acuu" in RNA) and "aagt" ("aagu" in RNA) bases in stemloop2 are replaced with "cgcc" and "gcgg". In some embodiments, "actt" and "aagt" bases in stemloop2 are replaced with complimentary GC-rich regions of 4 nucleotides. In some embodiments, the complimentary GC-rich regions of 4 nucleotides are "cgcc" and "gcgg" (both in 5' to 3' direction). In some embodiments, the complimentary GC-rich regions of 4 nucleotides are "gcgg" and "cgcc" (both in 5' to 3' direction). Other combination of C and G in the complimentary GC-rich regions of 4 nucleotides will be apparent including CCCC and GGGG.

In one aspect, the stemloop 2, e.g., "ACTTgtttAAGT" (SEQ ID NO: 35) can be replaced by any "XXXXgtttYYYY" (SEQ ID NO: 36), e.g., where XXXX and YYYY represent any complementary sets of nucleotides that together will base pair to each other to create a stem.

In one aspect, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-12 and Y2-12 (wherein X and Y represent any complementary set of nucleotides) may be contemplated. In one aspect, the stem made of the X and Y nucleotides, together with the "gttt," will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire sgRNA is preserved.

In one aspect, the stem can be a form of X:Y basepairing that does not disrupt the secondary structure of the whole sgRNA in that it has a DR:tracr duplex, and 3 stemloops. In one aspect, the "gttt" tetraloop that connects ACTT and AAGT (or any alternative stem made of X:Y basepairs) can be any sequence of the same length (e.g., 4 basepair) or longer that does not interrupt the overall secondary structure of the sgRNA. In one aspect, the stemloop can be something that further lengthens stemloop2, e.g. can be MS2 aptamer. In one aspect, the stemloop3 "GGCACCGagtCGGTGC" (SEQ ID NO: 37) can likewise take on a "XXXXXXX-agtYYYYYYY" (SEQ ID NO: 38) form, e.g., wherein X7 and Y7 represent any complementary sets of nucleotides that together will base pair to each other to create a stem. In one aspect, the stem comprises about 7 bp comprising complementary X and Y sequences, although stems of more or fewer basepairs are also contemplated. In one aspect, the stem made of the X and Y nucleotides, together with the "agt", will form a complete hairpin in the overall secondary structure. In one aspect, any complementary X:Y basepairing sequence is tolerated, so long as the secondary structure of the entire sgRNA is preserved. In one aspect, the stem can be a form of X:Y basepairing that doesn't disrupt the secondary structure of the whole sgRNA in that it has a DR:tracr duplex, and 3 stemloops. In one aspect, the "agt" sequence of the stemloop 3 can be extended or be replaced by an aptamer, e.g., a MS2 aptamer or sequence that otherwise generally preserves the architecture of stemloop3. In one aspect for alternative Stemloops 2 and/or 3, each X and Y pair can refer to any basepair. In one aspect, non-Watson Crick basepairing is contemplated, where such pairing otherwise generally preserves the architecture of the stemloop at that position.

In one aspect, the DR:tracrRNA duplex can be replaced with the form: gYYYYag(N)NNNNxxxxNNNN(AAN)uuRRRRu (SEQ ID NO: 39) (using standard IUPAC nomenclature for nucleotides), wherein (N) and (AAN) represent part of the bulge in the duplex, and "xxxx" represents a linker sequence. NNNN on the direct repeat can be anything so long as it basepairs with the corresponding NNNN portion of the tracrRNA. In one aspect, the DR:tracrRNA duplex can be connected by a linker of any length (xxxx . . . ), any base composition, as long as it doesn't alter the overall structure.

In one aspect, the sgRNA structural requirement is to have a duplex and 3 stemloops. In most aspects, the actual sequence requirement for many of the particular base requirements are lax, in that the architecture of the DR:tracrRNA duplex should be preserved, but the sequence that creates the architecture, i.e., the stems, loops, bulges, etc., may be alterred.

Orthologs of Cpf1

The CRISPR-Cas9 system is described in detail in international patent application no. PCT/US2017/047459, titled "NOVEL CRISPR ENZYMES AND SYSTEMS" and filed Aug. 17, 2017, which is incorporated by reference in its entirety. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. Doi: 10.1002/pro.2225.). See also Shmakov et al. (2015) for application in the field of CRISPR-Cas loci. Homologous proteins may but need not be structurally related, or are only partially structurally related.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2c1p which does not have an identical domain structure and is hence denoted to be in subtype V-B.

In particular embodiments, the effector protein is a Cpf1 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*.

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii*.

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. Tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*, wherein the first and second fragments are not from the same bacteria.

In a more preferred embodiment, the Cpf1p is derived from a bacterial species selected from *Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae*. In certain embodiments, the Cpf1p is derived from a bacterial species selected from *Acidaminococcus* sp. BV3L6, *Lachnospiraceae bacterium* MA2020. In certain embodiments, the effector protein is derived from a subspecies of *Francisella tularensis* 1, including but not limited to *Francisella tularensis* subsp. *Novicida*.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to *Acidaminococcus* sp, *Lachnospiraceae bacterium* or *Moraxella* bovoculi; in particular embodiments, the type V Cas protein may be an ortholog of an organism of a species which includes, but is not limited to *Acidaminococcus* sp. BV3L6; *Lachnospiraceae bacterium* ND2006 (LbCpf1) or *Moraxella* bovoculi 237. In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form.

In an embodiment of the invention, the effector protein comprises at least one HEPN domain, including but not limited to HEPN domains described herein, HEPN domains known in the art, and domains recognized to be HEPN domains by comparison to consensus sequences and motifs.

Determination of Cpf1 PAM

Determination of PAM can be ensured as follows. This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target. Two *E. coli* strains are used in this assay. One carries a plasmid that encodes the endogenous effector protein locus from the bacterial strain. The other strain carries an empty plasmid (e.g., pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has an 8 random bp 5' of the proto-spacer (e.g., total of 65536 different PAM sequences=complexity). The other library has 7 random bp 3' of the proto-spacer (e.g., total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransformed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

For the Cpf1 orthologues identified to date, the following PAMs have been identified: the *Acidaminococcus* sp. BV3L6 Cpf1 (AsCpf1) and *Lachnospiraceae bacterium* ND2006 Cpf1 (LbCpf1) can cleave target sites preceded by a TTTV PAM, FnCpf1p, can cleave sites preceded by TTN, where N is A/C/G or T.

Codon Optimized Cpf1 Sequences

Where the effector protein is to be administered as a nucleic acid, the application envisages the use of codon-optimized Cpf1 sequences. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cpf1) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11.; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

Modified Cpf1 Enzymes

In particular embodiments, it is of interest to make us of an engineered Cpf1 protein as defined herein, such as Cpf1, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cpf1 protein, and wherein the CRISPR complex comprising the modified protein has altered activity as compared to the complex comprising the unmodified Cpf1 protein. It is to be understood that when referring herein to CRISPR "protein", the Cpf1 protein preferably is a modified CRISPR enzyme (e.g., having increased or decreased (or no) enzymatic activity, such as without limitation including Cpf1). The term "CRISPR protein" may be used interchangeably with "CRISPR enzyme", irrespective of whether the CRISPR protein has altered, such as increased or decreased (or no) enzymatic activity, compared to the wild type CRISPR protein.

Computational analysis of the primary structure of Cpf1 nucleases reveals three distinct regions. First a C-terminal RuvC like domain, which is the only functional characterized domain. Second a N-terminal alpha-helical region and third a mixed alpha and beta region, located between the RuvC like domain and the alpha-helical region.

Several small stretches of unstructured regions are predicted within the Cpf1 primary structure. Unstructured regions, which are exposed to the solvent and not conserved within different Cpf1 orthologs, are preferred sides for splits and insertions of small protein sequences. In addition, these sides can be used to generate chimeric proteins between Cpf1 orthologs.

In certain example embodiments, a modified Cpf1 protein comprises at least one modification that alters editing preference as compared to wild type. In certain example embodiments, the editing preference is for a specific insert or deletion within the target region. In certain example embodiments, the at least one modification increases formation of one or more specific indels. In certain example embodiments, the at least one modification is in a C-terminal RuvC like domain, the N-terminal alpha-helical region, the mixed alpha and beta region, or a combination thereof. In certain example embodiments the altered editing preference is indel formation. In certain example embodiments, the at least one modification increases formation of one or more specific insertions.

In certain example embodiments, the at least one modification increases formation of one or more specific insertions. In certain example embodiments, the at least one modification results in an insertion of an A adjacent to an A, T, G, or C in the target region. In another example embodiment, the at least one modification results in insertion of a T adjacent to an A, T, G, or C in the target region. In another example embodiment, the at least one modification results in insertion of a G adjacent to an A, T, G, or C in the target region. In another example embodiment, the at least one modification results in insertion of a C adjacent to an A, T, C, or G in the target region. The insertion may be 5' or 3' to the adjacent nucleotide. In one example embodiment, the one or more modification direct insertion of a T adjacent to an existing T. In certain example embodiments, the existing T corresponds to the 4th position in the binding region of a guide sequence. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutations in diseases caused by small deletions, more particularly where HDR is not possible. For example, correction of the F508del mutation in CFTR via delivery of three sRNA directing insertion of three T's, which is the most common genotype of cystic fibrosis, or correction of Alia Jafar's single nucleotide deletion in CDKL5 in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity and/or decrease off-target effects.

In certain example embodiments, the engineered CRISPR-cas effector comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph. Based on the above information, mutants can be generated which lead to inactivation of the enzyme or which modify the double strand nuclease to nickase activity. In alternative embodiments, this information is used to develop enzymes with reduced off-target effects (described elsewhere herein).

In certain of the above-described Cpf1 enzymes, the enzyme is modified by mutation of one or more residues including but not limited to positions D917, E1006, E1028, D1227, D1255A, N1257, according to FnCpf1 protein or any corresponding ortholog. In an aspect the invention provides a herein-discussed composition wherein the Cpf1 enzyme is an inactivated enzyme which comprises one or more mutations selected from the group consisting of D917A, E1006A, E1028A, D1227A, D1255A, N1257A, D917A, E1006A, E1028A, D1227A, D1255A and N1257A according to FnCpf1 protein or corresponding positions in a Cpf1 ortholog. In an aspect the invention provides a herein-discussed composition, wherein the CRISPR enzyme comprises D917, or E1006 and D917, or D917 and D1255, according to FnCpf1 protein or a corresponding position in a Cpf1 ortholog.

In certain of the above-described Cpf1 enzymes, the enzyme is modified by mutation of one or more residues (in the RuvC domain) including but not limited to positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (Acidaminococcus sp. BV3L6).

In certain of the above-described non-naturally-occurring CRISPR enzymes, the enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (Acidaminococcus sp. BV3L6).

In certain of the Cpf1 enzymes, the enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (Acidaminococcus sp. BV3L6).

In certain embodiments, the Cpf1 enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (Lachnospiraceae bacterium ND2006).

In certain embodiments, the Cpf1 enzyme is modified by mutation of one or more residues including but not limited positions K15, R18, K26, Q34, R43, K48, K51, R56, R84, K85, K87, N93, R103, N104, T118, K123, K134, R176, K177, R192, K200, K226, K273, K275, T291, R301, K307, K369, S404, V409, K414, K436, K438, K468, D482, K516, R518, K524, K530, K532, K548, K559, K570, R574, K592, D596, K603, K607, K613, C647, R681, K686, H720, K739, K748, K757, T766, K780, R790, P791, K796, K809, K815, T816, K860, R862, R863, K868, K897, R909, R912, T923, R947, K949, R951, R955, K965, K968, K1000, R1003, K1009, K1017, K1022, K1029, A1053, K1072, K1086, F1103, S1209, R1226, R1252, K1273, K1282, and/or K1288 with reference to amino acid position numbering of AsCpf1 (Acidaminococcus sp. BV3L6).

In certain embodiments, the enzyme is modified by mutation of one or more residues including but not limited positions K15, R18, K26, R34, R43, K48, K51, K56, K87, K88, D90, K96, K106, K107, K120, Q125, K143, R186, K187, R202, K210, K235, K296, K298, K314, K320, K326, K397, K444, K449, E454, A483, E491, K527, K541, K581, R583, K589, K595, K597, K613, K624, K635, K639, K656, K660, K667, K671, K677, K719, K725, K730, K763, K782, K791, R800, K809, K823, R833, K834, K839, K852, K858, K859, K869, K871, R872, K877, K905, R918, R921, K932, I960, K962, R964, R968, K978, K981, K1013, R1016, K1021, K1029, K1034, K1041, K1065, K1084, and/or K1098 with reference to amino acid position numbering of FnCpf1 (Francisella novicida U112).

In certain embodiments, the enzyme is modified by mutation of one or more residues including but not limited positions K15, R18, K26, K34, R43, K48, K51, R56, K83, K84, R86, K92, R102, K103, K116, K121, R158, E159, R174, R182, K206, K251, K253, K269, K271, K278, P342, K380, R385, K390, K415, K421, K457, K471, A506, R508, K514, K520, K522, K538, Y548, K560, K564, K580, K584, K591, K595, K601, K634, K640, R645, K679, K689, K707, T716, K725, R737, R747, R748, K753, K768, K774, K775, K785, K787, R788, Q793, K821, R833, R836, R847, K879, K881, R883, R887, K897, K900, K932, R935, K940, K948, K953, K960, K984, K1003, K1017, R1033, K1121, R1138, R1165, K1190, K1199, and/or K1208 with reference to amino acid position numbering of LbCpf1 (Lachnospiraceae bacterium ND2006).

In certain embodiments, the enzyme is modified by mutation of one or more residues including but not limited positions K14, R17, R25, K33, M42, Q47, K50, D55, K85, N86, K88, K94, R104, K105, K118, K123, K131, R174, K175, R190, R198, I221, K267, Q269, K285, K291, K297, K357, K403, K409, K414, K448, K460, K501, K515, K550, R552, K558, K564, K566, K582, K593, K604, K608, K623, K627, K633, K637, E643, K780, Y787, K792, K830, Q846, K858, K867, K876, K890, R900, K901, M906, K921, K927, K928, K937, K939, R940, K945, Q975, R987, R990, K1001, R1034, I1036, R1038, R1042, K1052, K1055, K1087, R1090, K1095, N1103, K1108, K1115, K1139, K1158, R1172, K1188, K1276, R1293, A1319, K1340, K1349, and/or K1356 with reference to amino acid position numbering of MbCpf1 (Moraxella bovoculi 237).

Recently a method was described for the generation of Cas9 orthologs with enhanced specificity (Slaymaker et al. 2015). This strategy can be used to enhance the specificity of Cpf1 orthologs. The following modifications are presently considered to provide enhanced Cpf1 specificity.

TABLE 8

Conserved Lysine and Arginine residues within RuvC.

| AsCpf1 | LbCpf1 |
|---|---|
| R912 | R833 |
| T923 | R836 |
| R947 | K847 |
| K949 | K879 |
| R951 | K881 |
| R955 | R883 |
| K965 | R887 |
| K968 | K897 |
| K1000 | K900 |
| R1003 | K932 |
| K1009 | R935 |
| K1017 | K940 |
| K1022 | K948 |
| K1029 | K953 |
| K1072 | K960 |
| K1086 | K984 |
| F1103 | K1003 |
| R1226 | K1017 |
| R1252 | R1033 |
|  | R1138 |
|  | R1165 |

Additional candidates are positive charged residues that are conserved between different orthologs (Table B2).

TABLE 9

Conserved Lysine and Arginine residues

| Residue | AsCpf1 | FnCpf1 | LbCpf1 | MbCpf1 |
|---|---|---|---|---|
| Lys | K15 | K15 | K15 | K14 |
| Arg | R18 | R18 | R18 | R17 |
| Lys/Arg | K26 | K26 | K26 | R25 |
| Lys/Arg | Q34 | R34 | K34 | K33 |
| Arg | R43 | R43 | R43 | M42 |
| Lys | K48 | K48 | K48 | Q47 |
| Lys | K51 | K51 | K51 | K50 |
| Lys/Arg | R56 | K56 | R56 | D55 |
| Lys/Arg | R84 | K87 | K83 | K85 |
| Lys/Arg | K85 | K88 | K84 | N86 |
| Lys/Arg | K87 | D90 | R86 | K88 |
| Arg | N93 | K96 | K92 | K94 |
| Lys/Arg | R103 | K106 | R102 | R104 |
| Lys | N104 | K107 | K103 | K105 |
| Lys | T118 | K120 | K116 | K118 |
| Lys/Arg | K123 | Q125 | K121 | K123 |
| Lys | K134 | K143 | — | K131 |
| Arg | R176 | R186 | R158 | R174 |
| Lys | K177 | K187 | E159 | K175 |
| Arg | R192 | R202 | R174 | R190 |
| Lys/Arg | K200 | R210 | R182 | R198 |
| Lys | K226 | K235 | K206 | I221 |
| Lys | K273 | K296 | K251 | K267 |
| Lys | K275 | K298 | K253 | Q269 |
| Lys | T291 | K314 | K269 | K285 |
| Lys/Arg | R301 | K320 | R271 | K291 |
| Lys | K307 | K326 | K278 | K297 |
| Lys | K369 | K397 | P342 | K357 |
| Lys | S404 | K444 | K380 | K403 |
| Lys/Arg | V409 | K449 | R385 | K409 |
| Lys | K414 | E454 | K390 | K414 |
| Lys | K436 | A483 | K415 | K448 |
| Lys | K438 | E491 | K421 | K460 |
| Lys | K468 | K527 | K457 | K501 |
| Lys | D482 | K541 | K471 | K515 |
| Lys | K516 | K581 | A506 | K550 |
| Arg | R518 | R583 | R508 | R552 |
| Lys | K524 | K589 | K514 | K558 |
| Lys | K530 | K595 | K520 | K564 |
| Lys | K532 | K597 | K522 | K566 |
| Lys | K548 | K613 | K538 | K582 |
| Lys | K559 | K624 | Y548 | K593 |
| Lys | K570 | K635 | K560 | K604 |
| Lys/Arg | R574 | R639 | K564 | K608 |
| Lys | K592 | K656 | K580 | K623 |
| Lys | D596 | K660 | K584 | K627 |
| Lys | K603 | K667 | K591 | K633 |
| Lys | K607 | K671 | K595 | K637 |
| Lys | K613 | K677 | K601 | E643 |
| Lys | C647 | K719 | K634 | K780 |
| Lys/Arg | R681 | K725 | K640 | Y787 |
| Lys/Arg | R686 | K730 | R645 | K792 |
| Lys | H720 | K763 | K679 | K830 |
| Lys | K739 | K782 | K689 | Q846 |
| Lys | K748 | K791 | K707 | K858 |
| Lys/Arg | K757 | R800 | T716 | K867 |
| Lys/Arg | T766 | K809 | K725 | K876 |
| Lys/Arg | K780 | K823 | R737 | K890 |
| Arg | R790 | R833 | R747 | R900 |
| Lys/Arg | P791 | K834 | R748 | K901 |
| Lys | K796 | K839 | K753 | M906 |
| Lys | K809 | K852 | K768 | K921 |
| Lys | K815 | K858 | K774 | K927 |
| Lys | T816 | K859 | K775 | K928 |
| Lys | K860 | K869 | K785 | K937 |
| Lys/Arg | R862 | K871 | K787 | K939 |
| Arg | R863 | K872 | R788 | K940 |
| Lys | K868 | K877 | Q793 | K945 |
| Lys | K897 | K905 | K821 | Q975 |
| Arg | R909 | R918 | R833 | R987 |
| Arg | R912 | R921 | R836 | R990 |
| Lys | T923 | K932 | K847 | K1001 |
| Lys/Arg | R947 | I960 | K879 | R1034 |
| Lys | K949 | K962 | K881 | I1036 |
| Arg | R951 | R964 | R883 | R1038 |
| Arg | R955 | R968 | R887 | R1042 |

TABLE 9-continued

Conserved Lysine and Arginine residues

| Residue | AsCpf1 | FnCpf1 | LbCpf1 | MbCpf1 |
|---|---|---|---|---|
| Lys | K965 | K978 | K897 | K1052 |
| Lys | K968 | K981 | K900 | K1055 |
| Lys | K1000 | K1013 | K932 | K1087 |
| Arg | R1003 | R1016 | R935 | R1090 |
| Lys | K1009 | K1021 | K940 | K1095 |
| Lys | K1017 | K1029 | K948 | N1103 |
| Lys | K1022 | K1034 | K953 | K1108 |
| Lys | K1029 | K1041 | K960 | K1115 |
| Lys | A1053 | K1065 | K984 | K1139 |
| Lys | K1072 | K1084 | K1003 | K1158 |
| Lys/Arg | K1086 | K1098 | K1017 | R1172 |
| Lys/Arg | F1103 | K1114 | R1033 | K1188 |
| Lys | S1209 | K1201 | K1121 | K1276 |
| Arg | R1226 | R1218 | R1138 | R1293 |
| Arg | R1252 | R1244 | R1165 | A1319 |
| Lys | K1273 | K1265 | K1190 | K1340 |
| Lys | K1282 | K1274 | K1199 | K1349 |
| Lys | K1288 | K1281 | K1208 | K1356 |

Table 9 provides the positions of conserved Lysine and Arginine residues in an alignment of Cpf1 nuclease from Francisella novicida U112 (FnCpf1), Acidaminococcus sp. BV3L6 (AsCpf1), Lachnospiraceae bacterium ND2006 (LbCpf1) and Moraxella bovoculi 237 (MbCpf1). These can be used to generate Cpf1 mutants with enhanced specificity.

With a similar strategy used to improve Cas9 specificity, specificity of Cpf1 can be improved by mutating residues that stabilize the non-targeted DNA strand. This may be accomplished without a crystal structure by using linear structure alignments to predict 1) which domain of Cpf1 binds to which strand of DNA and 2) which residues within these domains contact DNA.

However, this approach may be limited due to poor conservation of Cpf1 with known proteins. Thus, it may be desirable to probe the function of all likely DNA interacting amino acids (lysine, histidine and arginine).

Positively charged residues in the RuvC domain are more conserved throughout Cpf1s than those in the Rad50 domain indicating that RuvC residues are less evolutionarily flexible. This suggests that rigid control of nucleic acid binding is needed in this domain (relative to the Rad50 domain). Therefore, it is possible this domain cuts the targeted DNA strand because of the requirement for RNA:DNA duplex stabilization (precedent in Cas9). Furthermore, more arginines are present in the RuvC domain (5% of RuvC residues 904 to 1307 vs 3.8% in the proposed Rad50 domains) suggesting again that RuvC targets the DNA strand complexed with the guide RNA. Arginines are more involved in binding nucleic acid major and minor grooves (Rohs et al. Nature (2009): Vol 461: 1248-1254). Major/minor grooves would only be present in a duplex (such as DNA:RNA targeting duplex), further suggesting that RuvC cuts the "targeted strand".

From these specific observations about AsCpf1 we can identify similar residues in Cpf1 from other species by sequence alignments. Example includes alignment of AsCpf1 and FnCpf1, identifying Rad50 binding domains and the Arginines and Lysines within.

Crystal structures of two similar domains as those found in Cpf1 (RuvC holiday junction resolvase and Rad50 DNA repair protein) are available. Based on these structures, it can be deduced what the relevant domains look like in Cpf1, and infer which regions and residues may contact DNA. In each structure residues are highlighted that contact DNA. In the alignments the regions of AsCpf1 that correspond to these DNA binding regions can be annotated. The list of residues in Table B4 are those found in the two binding domains.

TABLE 10 list of probabl DNA interacting residues

| RuvC domain probable DNA interacting residues: | Rad50 domain probable DNA interacting residues: |
|---|---|
| AsCpf1 | AsCpf1 |
| R909 | K324 |
| R912 | K335 |
| R930 | K337 |
| R947 | R331 |
| K949 | K369 |
| R951 | K370 |
| R955 | R386 |
| K965 | R392 |
| K968 | R393 |
| K1000 | K400 |
| K1002 | K404 |
| R1003 | K406 |
| K1009 | K408 |
| K1017 | K414 |
| K1022 | K429 |
| K1029 | K436 |
| K1035 | K438 |
| K1054 | K459 |
| K1072 | K460 |
| K1086 | K464 |
| R1094 | R670 |
| K1095 | K675 |
| K1109 | R681 |
| K1118 | K686 |
| K1142 | K689 |
| K1150 | R699 |
| K1158 | K705 |
| K1159 | R725 |
| R1220 | K729 |
| R1226 | K739 |
| R1242 | K748 |
| R1252 | K752 |
|  | R670 |

Deactivated/Inactivated Cpf1 Protein

Where the Cpf1 protein has nuclease activity, the Cpf1 protein may be modified to have diminished nuclease activity e.g., nuclease inactivation of at least 70%, at least 80%, at least 90%, at least 95%, at least 97%, or 100% as compared with the wild type enzyme; or to put in another way, a Cpf1 enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme, e.g. of the non-mutated or wild type *Francisella novicida* U112 (FnCpf1), *Acidaminococcus* sp. BV3L6 (AsCpf1), *Lachnospiraceae bacterium* ND2006 (LbCpf1) or *Moraxella bovoculi* 237 (MbCpf1) Cpf1 enzyme or CRISPR enzyme. This is possible by introducing mutations into the nuclease domains of the Cpf1 and orthologs thereof.

In certain embodiments, the CRISPR enzyme is engineered and can comprise one or more mutations that reduce or eliminate a nuclease activity. The amino acid positions in the FnCpf1p RuvC domain include but are not limited to D917A, E1006A, E1028A, D1227A, D1255A, N1257A, D917A, E1006A, E1028A, D1227A, D1255A and N1257A. Applicants have also identified a putative second nuclease domain which is most similar to PD-(D/E)XK (SEQ ID NO: 165) nuclease superfamily and HincII endonuclease like. The point mutations to be generated in this putative nuclease domain to substantially reduce nuclease activity include but are not limited to N580A, N584A, T587A, W609A, D610A, K613A, E614A, D616A, K624A, D625A, K627A and Y629A. In a preferred embodiment, the mutation in the FnCpf1p RuvC domain is D917A or E1006A, wherein the D917A or E1006A mutation completely inactivates the DNA cleavage activity of the FnCpf1 effector protein. In another embodiment, the mutation in the FnCpf1p RuvC domain is D1255A, wherein the mutated FnCpf1 effector protein has significantly reduced nucleolytic activity.

More particularly, the inactivated Cpf1 enzymes include enzymes mutated in amino acid positions As908, As993, As1263 of AsCpf1 or corresponding positions in Cpf1 orthologs. Additionally, the inactivated Cpf1 enzymes include enzymes mutated in amino acid position Lb832, 925, 947 or 1180 of LbCpf1 or corresponding positions in Cpf1 orthologs. More particularly, the inactivated Cpf1 enzymes include enzymes comprising one or more of mutations AsD908A, AsE993A, AsD1263A of AsCpf1 or corresponding mutations in Cpf1 orthologs. Additionally, the inactivated Cpf1 enzymes include enzymes comprising one or more of mutations LbD832A, E925A, D947A or D1180A of LbCpf1 or corresponding mutations in Cpf1 orthologs.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain. In some embodiments, two FnCpf1, AsCpf1 or LbCpf1 variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In preferred embodiments the Cpf1 effector protein cleaves sequences associated with or at a target locus of interest as a homodimer comprising two Cpf1 effector protein molecules. In a preferred embodiment the homodimer may comprise two Cpf1 effector protein molecules comprising a different mutation in their respective RuvC domains.

The inactivated Cpf1 CRISPR enzyme may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that gRNAs are designed to provide proper spacing for functional use (Fok1) as specifically described in Tsai et al. Nature Biotechnology, Vol. 32, Number 6, June 2014. The adaptor protein may utilize known linkers to attach such functional domains. In some cases, it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated Cpf1 enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

Chemically-Modified Cpf1 Guide

In certain embodiments, the Cpf1 guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotide comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'-phosphorothioate (MS), S-constrained ethyl(cEt), or 2'-O-methyl 3'-thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi: 10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.,* 2012, 3:154; Deng et al., *PNAS,* 2015, 112:11870-11875; Sharma et al., *MedChemComm.,* 2014, 5:1454-1471; Hendel et al., *Nat. Biotechnol.* (2015) 33(9): 985-989; Li et al., *Nature Biomedical Engineering,* 2017, 1, 0066 DOI:10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target DNA and one or more deoxyribonucletides and/or nucleotide analogs in a region that binds to Cpf1. In an embodiment of the invention, deoxyribonucleotides and/or nucleotide analogs are incorporated in engineered guide structures, such as, without limitation, stem-loop regions, and the seed region. For Cpf1 guide, in certain embodiments, the modification is not in the 5'-handle of the stem-loop regions. Chemical modification in the 5'-handle of the stem-loop region of a guide may abolish its function (see Li, et al., *Nature Biomedical Engineering,* 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3'-phosphorothioate (MS), S-constrained ethyl(cEt), or 2'-O-methyl 3'-thioPACE (MSP). Such modification can enhance genome editing efficiency (see Hendel et al., *Nat. Biotechnol.* (2015) 33(9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemically modified with 2'-O-Me, 2'-F or S-constrained ethyl(cEt). Such chemically modified guide can mediate enhanced levels of gene disruption (see Ragdarm et al., 0215, *PNAS*, E7110-E7111). In an embodiment of the invention, a guide is modified to comprise a chemical moiety at its 3' and/or 5' end. Such moieties include, but are not limited to, amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6:e25312, DOI:10.7554). In certain embodiments, a guide comprises ribonucleotides in a region that binds to a target DNA and one or more deoxyribonucleotides and/or nucleotide analogs in a region that binds Cpf1. In an embodiment of the invention, deoxyribonucleotides and/or nucleotide analogs are incorporated in engineered guide structures, such as, without limitation, stem-loop regions.

In some embodiments, the guide comprises a modified Cpf1 crRNA, having a 5'-handle and a guide segment further comprising a seed region and a 3'-terminus. In some embodiments, the modified guide can be used with a Cpf1 of any one of *Acidaminococcus* sp. BV3L6 Cpf1 (AsCpf1); *Francisella tularensis* subsp. *Novicida* U112 Cpf1 (FnCpf1); *L. bacterium* MC2017 Cpf1 (Lb3Cpf1); *Butyrivibrio proteoclasticus* Cpf1 (BpCpf1); *Parcubacteria bacterium*_GWC2011_GWC2_44_17 Cpf1 (PbCpf1); *Peregrinibacteria bacterium* GW2011_GWA_33_10 Cpf1 (PeCpf1); *Leptospira inadai* Cpf1 (LiCpf1); *Smithella* sp. SC_K08D17 Cpf1 (SsCpf1); *L. bacterium* MA2020 Cpf1 (Lb2Cpf1); *Porphyromonas crevioricanis* Cpf1 (PcCpf1); *Porphyromonas macacae* Cpf1 (PmCpf1); *Candidatus Methanoplasma termitum* Cpf1 (CMtCpf1); *Eubacterium eligens* Cpf1 (EeCpf1); *Moraxella bovoculi* 237 Cpf1 (MbCpf1); *Prevotella disiens* Cpf1 (PdCpf1); or *L. bacterium* ND2006 Cpf1 (LbCpf1).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (melΨ), 5-methoxyuridine(5moU), inosine, 7-methylguanosine, 2'-O-methyl 3'-phosphorothioate (MS), S-constrained ethyl(cEt), phosphorothioate (PS), or 2'-O-methyl 3'-thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cpf1 CrRNA may improve Cpf1 activity (see Li, et al., Nature Biomedical Engineering, 2017, 1:0066). In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrozide, semicarbazide, thio semicarbazide, thiol, maleimide, haloalkyl, sulfonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrozone, disulfides, thioethers, thioesters, phosphorothioates, phosphorodithioates, sulfonamides, sulfonates, fulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule (capable of guiding Cpf1 to a target locus) comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e., the sequence essential critical for recognition and/or hybridization to the sequence at the target locus) of the Cpf1 guide sequence is approximately within the first 10 nucleotides of the guide sequence. In particular embodiments, the Cpf1 is FnCpf1 and the seed sequence is approximately within the first 5 nt on the 5' end of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferrably more than 17 nts, and has more than one stem loops or optimized secondary structures. In particular embodiments the guide molecule comprises or consists of the guide sequence linked to all or part of the natural direct repeat sequence. A typical Type V Cpf1 guide molecule comprises (in 3' to 5' direction): a guide sequence a first complimentary stretch (the "repeat"), a loop (which is typically 4 or 5 nucleotides long), a second complimentary stretch (the "anti-repeat" being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the Cpf1 protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X:Y basepairing sequence (e.g., as to length) is tolerated, so long as the secondary structure of the entire guide molecule is preserved. In one aspect, the loop that connects the stem made of X:Y basepairs can be any sequence of the same length (e.g., 4 or 5 nucleotides) or longer that does not interrupt the overall secondary structure of the guide molecule. In one aspect, the stemloop can further comprise, e.g., an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

C2c2 and Cas13b Nucleases

The CRISPR-Cas13a/C2c2 system is described in detail in U.S. provisional patent application No. 62/484,786, titled "NOVEL TYPE VI CRISPR ORTHOLOGS AND SYSTEMS" and filed Apr. 12, 2017, which is incorporated by reference in its entirety.

In some embodiments, the Cas13a/C2c2 effector protein is derived from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*. In some embodiments, C2c2 effector protein may comprise a chimeric effector protein comprising a first fragment from a first effector protein ortholog and a second fragment from a second effector protein ortholog, and wherein the first and second effector protein orthologs are different. At least one of the first and second effector protein orthologs may comprise an effector protein from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacterium, Carnobacterium, Rhodobacter, Listeria, Paludibacter, Clostridium, Lachnospiraceae, Clostridiaridium, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*.

In certain embodiments, the effector protein, particularly a Type VI loci effector protein, more particularly a C2c2p, may originate from, may be isolated from, or may be derived from a bacterial species belonging to the taxa alpha-proteobacteria, Bacilli, Clostridia, Fusobacteria and Bacteroidetes. In certain embodiments, the effector protein, particularly a Type VI loci effector protein, more particularly a C2c2p, may originate from, may be isolated from, or may be derived from a bacterial species belonging to a genus selected from the group consisting of Lachnospiraceae, *Clostridium, Carnobacterium, Paludibacter, Listeria, Leptotrichia*, and *Rhodobacter*. In certain embodiments, the effector protein, particularly a Type VI loci effector protein, more particularly a C2c2p may originate from, may be isolated from or may be derived from a bacterial species selected from the group consisting of *Lachnospiraceae bacterium MA2020, Lachnospiraceae bacterium NK4A179, Clostridium aminophilum* (e.g., DSM 10710), *Lachnospiraceae bacterium NK4A144, Carnobacterium gallinarum* (e.g., DSM 4847 strain MT44), *Paludibacter propionicigenes* (e.g., WB4), *Listeria seeligeri* (e.g., serovar ½b str. SLCC3954), *Listeria weihenstephanensis* (e.g., FSL R9-0317 c4), *Listeria newyorkensis* (e.g., strain FSL M6-0635: also "LbFSL"), *Leptotrichia wadei* (e.g., F0279: also "Lw" or "Lw2"), *Leptotrichia buccalis* (e.g., DSM 1135), *Leptotrichia* sp. Oral taxon 225 (e.g., str. F0581), *Leptotrichia* sp. Oral taxon 879 (e.g., strain F0557), *Leptotrichia shahii* (e.g., DSM 19757), *Rhodobacter capsulatus* (e.g., SB 1003, R121, or DE442). In certain preferred embodiments, the C2c2 effector protein originates from Listeriaceae bacterium (e.g. FSL M6-0635: also "LbFSL"), *Lachnospiraceae bacterium MA2020, Lachnospiraceae bacterium NK4A179, Clostridium aminophilum* (e.g., DSM 10710), *Carnobacterium gallinarum* (e.g., DSM 4847), *Paludibacter propionicigenes* (e.g., WB4), *Listeria seeligeri* (e.g., serovar ½b str. SLCC3954), *Listeria weihenstephanensis* (e.g., FSL R9-0317 c4), *Leptotrichia wadei* (e.g., F0279: also "Lw" or "Lw2"), *Leptotrichia shahii* (e.g., DSM 19757), *Rhodobacter capsulatus* (e.g., SB 1003, R121, or DE442); preferably Listeriaceae bacterium FSL M6-0635 (i.e. *Listeria newyorkensis* FSL M6-0635) or *Leptotrichia wadei* F0279 (also "Lw" or "Lw2").

In some embodiments, in order to overcome resistance to a drug, the lncRNA transcript which has been identified as contributing to the drug resistance can be downregulated by a C2c2 nuclease. The activity of C2c2 depends on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild-type form, cutting RNA, then it is preferred that the C2c2 effector protein has RNase function. It may also, or alternatively, have DNase function.

The CRISPR-Cas13b system is described in detail in U.S. provisional patent application No. 62/484,791, titled "NOVEL TYPE VI CRISPR ORTHOLOGS AND SYSTEMS" and filed Apr. 12, 2017, which is incorporated by reference in its entirety.

In some embodiments, the Cas13b effector protein is derived from a prokaryotic organism selected from the group consisting of *Porphyromonas, Prevotella, Bacteroides, Riemerella, Bergeyella, Alistipes, Myroides, Capnocytophaga*, and *Flavobacterium*. In some embodiments, the Cas13b effector protein is derived from a prokaryotic organism selected from the group consisting of *Porphyromonas gulae, Prevotella* sp., *Porphyromonas gingivalis, Bacteroides pyogenes, Riemerella anatipestifer, Bergeyella zoohekum, Prevotella intermedia, Prevotella buccae, Alistipes* sp., *Prevotella aurantiaca, Myroides odoratimimus, Capnocytophaga canimorsus, Flavobacterium branchiophilum*, and *Flavobacterium columnare*. In preferred embodiments, the Cas13b effector protein is *Porphyromonas* gulae Cas13b (accession number WP 039434803), *Prevotella* sp. P5-125 Cas13b (accession number WP 044065294), *Porphyromonas gingivalis* Cas13b (accession number WP_053444417), *Porphyromonas* sp. COT-052 OH4946 Cas13b (accession number WP_039428968), *Bacteroides pyogenes* Cas13b (accession number WP_034542281), or *Riemerella anatipestifer* Cas13b (accession number WP_004919755). In more preferred embodiments, the Cas13b effector protein is *Porphyromonas* gulae Cas13b (accession number WP_039434803), *Prevotella* sp. P5-125 Cas13b (accession number WP_044065294), *Porphyromonas gingivalis* Cas13b (accession number WP_053444417), or *Porphyromonas* sp. COT-052 OH4946 Cas13b (accession number WP_039428968). In most I preferred embodiments, the Cas13b effector protein is *Porphyromonas* gulae Cas13b (accession number WP_039434803) or *Prevotella* sp. P5-125 Cas13b (accession number WP_044065294).

In some embodiments, in order to overcome resistance to a drug, the lncRNA transcript which has been identified as contributing to the drug resistance can be downregulated by a Cas13b nuclease. The activity of Cas13b depends on the presence of two HEPN domains. These have been shown to be RNase domains, i.e. nuclease (in particular an endonuclease) cutting RNA. Cas13b HEPN may also target DNA, or potentially DNA and/or RNA. On the basis that the HEPN domains of Cas13b are at least capable of binding to and, in their wild-type form, cutting RNA, then it is preferred that the Cas13b effector protein has RNase function. It may also, or alternatively, have DNase function. DNase function, the ability to bind and, potentially cut or nick, DNA is discussed in detail herein.

Thus, in some embodiments, the effector protein may be a RNA-binding protein, such as a dead-Cas type effector protein, which may be optionally functionalised as described herein for instance with an transcriptional activator or repressor domain, NLS or other functional domain. In some embodiments, the effector protein may be a RNA-binding protein that cleaves a single strand of RNA. If the RNA bound is ssRNA, then the ssRNA is fully cleaved. In some embodiments, the effector protein may be a RNA-binding protein that cleaves a double strand of RNA, for example if it comprises two RNase domains. If the RNA bound is dsRNA, then the dsRNA is fully cleaved.

RNase function in CRISPR systems is known, for example mRNA targeting has been reported for certain type III CRISPR-Cas systems (Hale et al., 2014, Genes Dev, vol. 28, 2432-2443; Hale et al., 2009, Cell, vol. 139, 945-956; Peng et al., 2015, Nucleic acids research, vol. 43, 406-417) and provides significant advantages. In the *Staphylococcus epidermis* type III-A system, transcription across targets results in cleavage of the target DNA and its transcripts, mediated by independent active sites within the Cas10-Csm ribonucleoprotein effector complex (see, Samai et al., 2015, Cell, vol. 151, 1164-1174). A CRISPR-Cas system, composition or method targeting RNA via the present effector proteins is thus provided.

The target RNA, i.e., the RNA of interest, is the lncRNA transcript to be targeted by the present invention leading to the recruitment to, and the binding of the effector protein at, the target site of interest on the target lncRNA transcript.
Interfering RNA (RNAi) and microRNA (miRNA)

In some embodiments, in order to overcome resistance to a drug, the lncRNA transcript which has been identified as contributing to the drug resistance can be downregulated by interfering RNA, i.e., RNA involved in an RNA interference pathway, such as shRNA, siRNA and so forth. In other embodiments, in order to overcome resistance to a drug, the lncRNA transcript which has been identified as contributing to the drug resistance can be downregulated by microRNA (miRNA).
Riboswitches A riboswitch (also known as an aptozyme) is a regulatory segment of a messenger RNA molecule that binds a small molecule. This typically results in a change in production of the proteins encoded by the mRNA. In some embodiments, in order to overcome resistance to a drug, the lncRNA transcript which has been identified as contributing to the drug resistance can be downregulated by a riboswitch.
Ribozymes Ribozymes are RNA molecules having catalytic properties, analogous to enzymes (which are of course proteins). In some embodiments, in order to overcome resistance to a drug, the lncRNA transcript which has been identified as contributing to the drug resistance can be downregulated by a ribozyme.
Additional Guide Modifications With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g., also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867 (PROTECTED GUIDE RNAS (PGRNAS)); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

By means of further guidance, and without limitation, in certain embodiments, the gRNA is a dead gRNA (dgRNA), which are guide sequences which are modified in a manner which allows for formation of the CRISPR complex and successful binding to the target, while at the same time, not allowing for successful nuclease activity (i.e., without nuclease activity/without indel activity). These dead guides or dead guide sequences can be thought of as catalytically inactive or conformationally inactive with regard to nuclease activity. Several structural parameters allow for a proper framework to arrive at such dead guides. Dead guide sequences are shorter than respective guide sequences which result in active Cas-specific indel formation. Dead guides are 5%, 10%, 20%, 30%, 40%, 50%, shorter than respective guides directed to the same Cas protein leading to active Cas-specific indel formation. Guide RNA comprising a dead guide may be modified to further include elements in a manner which allow for activation or repression of gene activity, in particular protein adaptors (e.g., aptamers) as described herein elsewhere allowing for functional placement of gene effectors (e.g., activators or repressors of gene activity).

One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g., an activator or repressor; dimerized MS2 bacteriophage coat proteins as fusion proteins with an activator or repressor), or a protein which itself binds an effector (e.g., activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

By means of further guidance, and without limitation, in certain embodiments, the gRNA is an escorted gRNA (egRNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The escorted Cpf1 CRISPR-Cas systems or complexes have a gRNA with a functional structure designed to improve gRNA structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and Hicke B J, Stephens A W. "Escort aptamers: a delivery service for diagnosis and therapy." J Clin Invest 2000, 106:923-928.).

Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

By means of further guidance, and without limitation, in certain embodiments, the gRNA is a protected guide. Protected guides are designed to enhance the specificity of a Cas protein given individual guide RNAs through thermodynamic tuning of the binding specificity of the guide RNA to target nucleic acid. This is a general approach of introducing mismatches, elongation or truncation of the guide sequence to increase/decrease the number of complimentary bases vs. mismatched bases shared between a target and its potential off-target loci, in order to give thermodynamic advantage to targeted genomic loci over genomic off-targets. In certain embodiments, the guide sequence is modified by secondary structure to increase the specificity of the CRISPR-Cas system and whereby the secondary structure can protect against exonuclease activity and allow for 3' additions to the guide sequence. In certain embodiments, a "protector RNA" is hybridized to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target binding to the mismatched basepairs at the 3' end.

In certain embodiments, additional sequences comprising an extended length may also be present. Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region.

Thermodynamic prediction can be used to predict completely matching or partially matching guide extensions that result in protected gRNA states. This extends the concept of protected gRNAs to interaction between X and Z, where X will generally be of length 17-20 nt and Z is of length 1-30 nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended. An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length.

In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

Aspects of the invention also relate to synthesizing different unique 20 bp spacer or guide RNA sequences with which different genomic locations, in particular those associated with lncRNA transcription, can be targeted. It is this easy programmability that makes CRISPR an attractive targeted screening system. Array oligonucleotide synthesis technologies allow for parallel synthesis of thousands of targeting sequences that can be cloned en masse into a vector, e.g., a viral vector such as an AAV vector or a lentiviral vector, and produced as virus in a pool. This allows for targeting of the RNA-guided DNA binding protein by modification of a 20 nt RNA guide sequence and genetic perturbation on the level of the genome itself.

In one aspect, the invention provides a library comprising a plurality of unique CRISPR-Cas system guide sequences that are capable of targeting a plurality of target sequences in one or more given genomic regions associated with lncRNA transcription. In particular embodiments, the library is a tilled library spanning a given intergenic region. Aspects of the invention, including libraries, methods and kits also expressly include the library and guide sequences as described in "Genome-scale CRISPR-Cas9 knockout screening in human cells", Shalem O, Sanjana N E, Hartenian E, Shi X, Scott D A, Mikkelsen T S, Heckl D, Ebert B L, Root D E, Doench J G, Zhang F., Science. 2014 Jan. 3; 343(6166):84-7, including all and any disclosure thereof and all and any disclosure from the corresponding Supplementary materials available from the publisher, including Supplementary materials made available online.

In one aspect, the invention provides a CRISPR library for use in a method of perturbing in parallel different sequences in the genome. In one aspect, the library or libraries consist of specific gRNA sequences for perturbing specified genomic regions associated with lncRNA transcription.

In one aspect, the library is packaged in a viral vector. In one aspect, the library is packaged in a lentivirus vector. In one aspect, the packaged library is transduced at an MOI (multiplicity of infection) of about 10, of about 5, of about 3, of about 1 or of about less than 1, about less than 0.75, about less than 0.5, about less than 0.4, about less than 0.3, about less than 0.2 or about less than 0.1. In a further embodiment the cell is transduced with a multiplicity of infection (MOI) of 0.3-0.75, preferably, the MOI has a value close to 0.4, more preferably the MOI is 0.3 or 0.4. In one aspect, the MOI is about 0.3 or 0.4, thereby creating a panel of cells comprising about 1 CRISPR-Cas system guide RNAs per cell, after appropriate selection for successfully transfected/transduced cells, thereby providing a panel of cells comprising a cellular library with parallel knock outs of the different target sequences.

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA targeting a non-coding genomic sequence. In particular embodiments, the vector comprises two or more guide RNAs. The two or more guide RNAs may target a different target (so as to ensure multiplex targeting) or the same target, in which case two different guide RNAs are used which target different sequences within the same target sequence or targeted non-coding genomic sequences. In particular embodiments, where deletion of a target sequence is envisaged, the guide RNAs used have target sequences which are less than 500 nts apart, more particularly less than 200 nts apart, such as less than 100 nts apart. Where provided in a vector the different guide RNAs may be under common control of the same promoter, or may be each be under control of the same or different promoters, generating separate expression cassettes for each guide RNA.

In particular embodiments, the vector comprises two expression cassettes for RNAs in tandem, wherein the first guide RNA under the control of a first promoter and the second guide RNA is under the control of a second promoter. In particular embodiments, the first and second promoter are selected from a U6 and an 7SK promoter. In particular embodiments both the first and the second promoter are the U6 promoter. In particular embodiments, each of the expression cassettes comprises a transcription termination signal, such as a Polymerase II terminator. In particular embodiments, the first and second expression cassette are separated by a buffer sequence. Such a sequence is typically between 10-500 nucleotides, such as between 100-200 nucleotides.

The application provides methods of screening for genomic sites associated with a change in a phenotype. The change in phenotype can be detectable at one or more levels including at DNA, RNA, protein and/or functional level of the cell. In particular embodiments, the change is detectable as a change in gene expression in the cell, which is associated with expression of a lncRNA.

The methods of screening for genomic sites associated with a change in phenotype comprise introducing the library of guide RNAs targeting genomic regions associated with lncRNA expression as envisaged herein into a population of cells. Typically, the cells are adapted to contain a Cas protein. However, in particular embodiments, the Cas protein may also be introduced simultaneously with the guide RNA. In some embodiments, the introduction of the library into the cell population in the methods envisage herein is such that each cell of the population contains no more than one guide RNA. Hereafter, the cells are typically selected based on a phenotype such as drug resistance, and the lncRNAs associate with a change in phenotype are identified based on whether or not their expression give rise to a change in phenotype in the cells. Typically, the methods involve selected cells based on the phenotype and determining the guide RNAs present in the selected cells, and a lncRNA associated with the change in phenotype can be determined based on enrichment or depletion of the corresponding guide RNA.

The methods provided herein may additionally comprise further validating the identified genomic site by specifically altering the genomic site encoding lncRNA or associated with lncRNA expression and checking whether the phenotypic change is confirmed. Specific alteration of a genomic site can be achieved by different methods such as by CRISPR/Cas system mediated DNA targeting.

Delivery of the CRISPR Effector Protein Complex or Components Thereof

Through this disclosure and the knowledge in the art, TALEs, CRISPR-Cas systems, or components thereof or nucleic acid molecules thereof or nucleic acid molecules encoding or providing components thereof may be delivered by a delivery system herein described both generally and in detail.

Vector delivery, e.g., plasmid, viral delivery: The CRISPR enzyme (e.g., a Type-II CRISPR effector protein such as Cas9, a Type-V CRISPR effector protein such as Cpf1, or a Type-VI CRISPR effector protein such as C2c2 and Cas13b), and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Effector proteins and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^9$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a nucleic acid-targeting CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539:

111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver nucleic acid-targeting Cas proteinCas9 and guide RNAgRNA (and, for instance, HR repair template) into cells using liposomes or particles. Thus, delivery of the nucleic acid-targeting Cas protein/CRISPR enzyme, such as a CasCas9 and/or delivery of the guide RNAs of the invention may be in RNA form and via microvesicles, liposomes or particles. For example, Cas mRNA and guide RNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the RNA-targeting system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with nucleic acid-targeting Cas protein and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or TocsiBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of nucleic acid-targeting effector protein conjugated to $\alpha$-tocopherol and co-administered with HDL targeted to the brain may be contemplated for humans in the present invention, for example, about 3 nmol to about 3 $\mu$mol of nucleic acid-targeting effector protein targeted to the brain may be contemplated. Zou et al. (HUMAN GENE THERAPY 22:465-475 (April 2011)) describes a method of lentiviral-mediated delivery of short-hairpin RNAs targeting PKC$\gamma$ for in vivo gene silencing in the spinal cord of rats. Zou et al. administered about 10 $\mu$l of a recombinant lentivirus having a titer of $1 \times 10^9$ transducing units (TU)/ml by an intrathecal catheter. A similar dosage of nucleic acid-targeting effector protein expressed in a lentiviral vector targeted to the brain may be contemplated for humans in the present invention, for example, about 10-50 ml of nucleic acid-targeting effector protein targeted to the brain in a lentivirus having a titer of $1 \times 10^9$ transducing units (TU)/ml may be contemplated.

In terms of local delivery to the brain, this can be achieved in various ways. For instance, material can be delivered intrastriatally e.g., by injection. Injection can be performed stereotactically via a craniotomy.

Packaging and Promoters Generally

Ways to package nucleic acid-targeting effector coding nucleic acid molecules, e.g., DNA, into vectors, e.g., viral vectors, to mediate genome modification in vivo include:
To achieve NHEJ-mediated gene knockout:
Single Virus Vector:
Vector containing two or more expression cassettes:
Promoter-nucleic acid-targeting effector protein coding nucleic acid molecule-terminator
Promoter-guide RNA1-terminator
Promoter-guide RNA (N)-terminator (up to size limit of vector)
Double Virus Vector:
Vector 1 containing one expression cassette for driving the expression of nucleic acid-targeting effector protein
Promoter-nucleic acid-targeting effector protein coding nucleic acid molecule-terminator
Vector 2 containing one more expression cassettes for driving the expression of one or more guideRNAs
Promoter-guide RNA1-terminator
Promoter-guide RNA1 (N)-terminator (up to size limit of vector)
To mediate homology-directed repair.
In addition to the single and double virus vector approaches described above, an additional vector is used to deliver a homology-direct repair template.

The promoter used to drive nucleic acid-targeting effector protein coding nucleic acid molecule expression can include:
AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of nucleic acid-targeting effector protein.
For ubiquitous expression, can use promoters: CMV, CAG, CBh, PGK, SV40, Ferritin heavy or light chains, etc.
For brain or other CNS expression, can use promoters: SynapsinI for all neurons, CaMKIIalpha for excitatory neurons, GAD67 or GAD65 or VGAT for GABAergic neurons, etc.
For liver expression, can use Albumin promoter.
For lung expression, can use SP-B.
For endothelial cells, can use ICAM.
For hematopoietic cells can use IFNbeta or CD45.
For Osteoblasts can use OG-2.
The promoter used to drive guide RNA can include:
Pol III promoters such as U6 or H1
Use of Pol II promoter and intronic cassettes to express guide RNA
Adeno Associated Virus (AAV)
nucleic acid-targeting effector protein and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g., a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome/transcriptome modification, the expression of nucleic acid-targeting effector protein can be driven by a cell-type specific promoter. For example, liver-specific expression might use the Albumin promoter and neuron-specific expression (e.g., for targeting CNS disorders) might use the Synapsin I promoter.

In terms of in vivo delivery, AAV is advantageous over other viral vectors for a couple of reasons:
- Low toxicity (this may be due to the purification method not requiring ultra centrifugation of cell particles that can activate the immune response) and
- Low probability of causing insertional mutagenesis because it doesn't integrate into the host genome.

AAV has a packaging limit of 4.5 or 4.75 Kb. This means that nucleic acid-targeting effector protein (e.g., a Type-II CRISPR effector protein such as Cas9, a Type-V CRISPR effector protein such as Cpf1, or a Type-VI CRISPR effector protein such as C2c2 and Cas13b) as well as a promoter and transcription terminator have to be all fit into the same viral vector. Therefore embodiments of the invention include utilizing homologs of nucleic acid-targeting effector protein that are shorter.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 11

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in an ultracentrifuge for 2 hours at 24,000 rpm. Viral pellets were resuspended in 50 ul of DMEM overnight at 4° C. They were then aliquotted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the nucleic acid-targeting system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the nucleic acid-targeting system of the present invention. A minimum of $2.5 \times 10^6$ CD34+ cells per kilogram patient weight may be collected and prestimulated for 16 to 20 hours in X-VIVO 15 medium (Lonza) containing 2 μmon-glutamine, stem cell factor (100 ng/ml), Flt-3 ligand (Flt-3L) (100 ng/ml), and thrombopoietin (10 ng/ml) (Cell-Genix) at a density of $2 \times 10^6$ cells/ml. Prestimulated cells may be transduced with lentiviral at a multiplicity of infection of 5 for 16 to 24 hours in 75-cm' tissue culture flasks coated with fibronectin (25 mg/cm$^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The nucleic acid-targeting Cas protein (e.g., a Type-II CRISPR effector protein such as Cas9, a Type-V CRISPR effector protein such as Cpf1, or a Type-VI CRISPR effector protein such as C2c2 and Cas13b), and/or guide RNA, can also be delivered in the form of RNA. Nucleic acid-targeting Cas protein (e.g., a Type-II CRISPR effector protein such as Cas9, a Type-V CRISPR effector protein such as Cpf1, or a Type-VI CRISPR effector protein such as C2c2 and Cas13b) mRNA can be generated using in vitro transcription. For example, nucleic acid-targeting effector protein (e.g., a Type-II CRISPR effector protein such as Cas9, a Type-V CRISPR effector protein such as Cpf1, or a Type-VI CRISPR effector protein such as C2c2 and Cas13b) mRNA can be synthesized using a PCR cassette containing the following elements: T7_promoter-kozak sequence (GCCACC)-effector protein-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the nucleic acid-targeting effector protein-coding sequence and/or the guide RNA can be modified to include one or more modified nucleoside e.g., using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g., diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particle delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes.

Nucleic acid-targeting effector proteins (e.g., a Type-II CRISPR effector protein such as Cas9, a Type-V CRISPR effector protein such as Cpf1, or a Type-VI CRISPR effector protein such as C2c2 and Cas13b) mRNA and guide RNA may be delivered simultaneously using particles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured particles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self-assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver RNA to a cancer cell to stop tumor growth developed by Dan Anderson's lab at MIT may be used/and or adapted to the nucleic acid-targeting system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the nucleic acid-targeting system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the nucleic acid-targeting system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the nucleic acid-targeting system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding nucleic acid-targeting effector protein to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinKDMA), and 1,2-dilinoleyl-4-(2-dimethylaminoethyl)[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and CRISPR-Cas encapsulation may be used/and or adapted from Rosin et al, Molecular Therapy, vol. 19, no. 12, pages 1286-2200, December 2011. The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG)), and R-3-[(ω-methoxy-poly(ethylene glycol)2000) carbamoyl]-1,2-dimyristyloxypropyl-3-amine (PEG-C-DOMG) may be provided by Tekmira Pharmaceuticals (Vancouver, Canada) or synthesized. Cholesterol may be purchased from Sigma (St Louis, Mo.). The specific nucleic acid-targeting complex (CRISPR-Cas) RNA may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore poly-carbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a nucleic acid-targeting system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano Z S, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at a RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other particles (particularly gold particles) are also contemplated as a means to delivery nucleic acid-targeting system to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of nucleic acid-targeting complex RNA is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinimide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles comprise, consist essentially of, or consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the nucleic acid-targeting system of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

In terms of this invention, it is preferred to have one or more components of nucleic acid-targeting complex, e.g., nucleic acid-targeting effector protein or mRNA, or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, particles of the invention have a greatest dimension of 100 nm or less. In other preferred embodiments, nanoparticles of the invention have a greatest dimension ranging between 35 nm and 60 nm.

Particles encompassed in the present invention may be provided in different forms, e.g., as solid particles (e.g., metal such as silver, gold, iron, titanium), non-metal, lipid-based solids, polymers, suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such methods and materials of herein-cited documents, e.g., conjugated lipomers can be used in the context of the nucleic acid-targeting system to achieve in vitro, ex vivo and in vivo genomic perturbations to modify gene expression, including modulation of protein expression.

In one embodiment, the particle may be epoxide-modified lipid-polymer, advantageously 7C$_1$ (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the nucleic acid-targeting system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (PTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, $P<0.05$, versus 62%, $P<0.01$) in both siRNA-RVG-9R-treated and siRNA-RVG exosome-treated mice was observed, resulting from a significant decrease in BACE1 mRNA levels (66% [+ or −] 15%, $P<0.001$ and 61% [+ or −] 13% respectively, $P<0.01$). Moreover, Applicants demonstrated a significant decrease (55%, $P<0.05$) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the nucleic acid-targeting system of the present invention to therapeutic targets, especially neurodegenerative diseases. A dosage of about 100 to 1000 mg of nucleic acid-targeting system encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of nucleic acid-targeting system into exosomes may be conducted similarly to siRNA. The exosomes may be co-cultured with monocytes and lymphocytes isolated from the peripheral blood of healthy donors. Therefore, it may be contemplated that exosomes containing nucleic acid-targeting system may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshl-p.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the nucleic acid-targeting system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific nucleic acid-targeting system targeted in a SNALP are contemplated. The daily treatment may be over about three days and then weekly for about five weeks. In another embodiment, a specific nucleic acid-targeting system encapsulated (SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(w-methoxy poly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-[(w-methoxy poly(ethylene glycol) 2000)carbamoyl]-1,2-dimyri styloxypropylamine, and cationic 1,2-dilinoleyloxy-3-N,N-dimethylaminopropane (see, e.g., Geisbert et al., Lancet 2010; 375: 1896-905). A dosage of about 2 mg/kg total nucleic acid-targeting system per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 µm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the nucleic acid-targeting system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate nucleic acid-targeting system or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the nucleic acid-targeting system of the present invention or component(s) thereof or nucleic acid molecule(s) coding therefor to form lipid nanoparticles (LNPs). Lipids include, but are not limited to, DLin-KC2-DMA, C12-200 and colipids distearoylphosphatidyl choline, cholesterol, and PEG-DMG may be formulated with RNA-targeting system instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/distearoylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The nucleic acid-targeting system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to, PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid-based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery.

Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of nucleic acid-targeting system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of nucleic acid-targeting system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1 \times 10^5$ cells per well in a 48-well plate.

(2) On the day of treatment, dilute purified +36 GFP protein in serumfree media to a final concentration 200 nM. Add RNA to a final concentration of 50 nM. Vortex to mix and incubate at room temperature for 10 min.

(3) During incubation, aspirate media from cells and wash once with PBS.

(4) Following incubation of +36 GFP and RNA, add the protein-RNA complexes to cells.

(5) Incubate cells with complexes at 37° C. for 4 h.

(6) Following incubation, aspirate the media and wash three times with 20 U/mL heparin PBS. Incubate cells with serum-containing media for a further 48 h or longer depending upon the assay for activity.

(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1 \times 10^5$ per well in a 48-well plate.

(2) On the day of treatment, dilute purified þ 36 GFP protein in serumfree media to a final concentration 2 mM. Add 1 mg of plasmid DNA. Vortex to mix and incubate at room temperature for 10 min.

(3) During incubation, aspirate media from cells and wash once with PBS.

(4) Following incubation of þ 36 GFP and plasmid DNA, gently add the protein-DNA complexes to cells.

(5) Incubate cells with complexes at 37 C for 4 h.

(6) Following incubation, aspirate the media and wash with PBS. Incubate cells in serum-containing media and incubate for a further 24-48 h.

(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the nucleic acid-targeting system of the present invention. These systems of Dr. Lui and documents herein in conjunction with herein teachings can be employed in the delivery of nucleic acid-targeting system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles including nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs is to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MM contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951 provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the nucleic acid-targeting system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the nucleic acid-targeting system of the present invention. The modes of implantation in some embodiments are existing implantation procedures that are developed and used today for other treatments, including brachytherapy and needle biopsy. In such cases the dimensions of the new implant described in this invention are similar to the original implant. Typically, a few devices are implanted during the same treatment procedure.

US Patent Publication 20110195123 provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m³ to 1000 mm³, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example, the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the nucleic acid-targeting system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the nucleic acid-targeting system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the nucleic acid-targeting system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the nucleic acid-targeting system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, CRISPR-Cas system or components thereof or nucleic acid molecules thereof or encoding or providing components may be delivered via an implantable device.

CRISPR Effector Protein mRNA and Guide RNA

CRISPR effector protein mRNA and guide RNA might also be delivered separately. CRISPR effector protein mRNA can be delivered prior to the guide RNA to give time for CRISPR effector protein to be expressed. CRISPR effector protein mRNA might be administered 1-12 hours (preferably around 2-6 hours) prior to the administration of guide RNA.

Alternatively, CRISPR effector protein mRNA and guide RNA can be administered together. Advantageously, a second booster dose of guide RNA can be administered 1-12 hours (preferably around 2-6 hours) after the initial administration of CRISPR effector protein mRNA+guide RNA.

The CRISPR effector protein of the present invention is sometimes referred to herein as a CRISPR Enzyme. However, it will also be appreciated that the effector protein may, as required in some embodiments, have DNA or RNA binding, but not necessarily cutting or nicking, activity, including a dead-Cas effector protein function.

Additional administrations of CRISPR effector protein mRNA and/or guide RNA might be useful to achieve the most efficient levels of genome modification. In some embodiments, phenotypic alteration is preferably the result of genome modification when a genetic disease is targeted, especially in methods of therapy and preferably where a repair template is provided to correct or alter the phenotype.

In some embodiments diseases or conditioned that may be targeted include those concerned with drug resistance (e.g., resistance to a BRAF inhibitor such as Vemurafenib, Dabrafenib, Sorafenib, GDC-0879, PLX-4720, and LGX818), particularly those associated with upregulation of one or more lncRNAs.

For minimization of toxicity and off-target effect, it will be important to control the concentration of CRISPR effector protein mRNA and guide RNA delivered. Optimal concentrations of CRISPR effector protein mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 40) in the EMX1 gene of the human genome, deep sequencing can be used to assess the level of modification at the following two off-target loci, 1: 5'-GAGTCCTAGCAG-GAGAAGAA-3' (SEQ ID NO: 41) and 2: 5'-GAGTCTAAGCAGAAGAAGAA-3' (SEQ ID NO: 42). The concentration that gives the highest level of on-target modification while minimizing the level of off-target modification should be chosen for in vivo delivery.

Inducible Systems

In some embodiments, a CRISPR effector protein may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR effector protein may be a part of a Light Inducible Transcriptional Effector (LITE) to direct changes in transcriptional activity in a sequence-specific manner. The components of a light may include a CRISPR effector protein, a light-responsive cytochrome heterodimer (e.g., from *Arabidopsis thaliana*), and a transcriptional activation/repression domain. Further examples of inducible DNA binding proteins and methods for their use are provided in U.S. 61/736,465 and U.S. 61/721,283 and WO 2014018423 A2 which is hereby incorporated by reference in its entirety.

Application of CRISPR-Cas Systems to Plants and Yeast

An overview of plant lncRNA characterization studies in provided by Bhatia et al. (2017, Non-coding RNA,3:16). Long ncRNAs in plants have been shown to be involved in the reaction of plants to stress, such as caused by microbial infections or extreme temperatures or drought (Xin et al. 2011, BMC Plant Biol, 11:61; Qi et al. 2013, Plant Mol Biol, 83 (2013), pp. 459-473). Accordingly, in particular embodiments, the desirable phenotype is increased stress resistance. In rice, lncRNAs have been found to play a role in male sterility (Zhou et al., 2012, Cell Res, 22 (2012), pp. 649-660; Ding et al. 2012, Proc Natl Acad Sci USA, 109 (2012), pp. 2654-2659), more particularly in the development of male sterility in reaction to light and temperature changes. Generally, lncRNAs have been found to be involved in the photomorphogenesis, i.e., the influence of light on processes of growth and development (Liu et al. 2015, Gen Proteom & Bioinform, 13(3):137-147). Accordingly, in particular embodiments, the methods of the invention are of interest to identify increased or reduced sensitivity to light. More recently, lncRNA ELENA1 has been found to be involved in plant immunity, whereby overexpression of ELENA1 increased the expression of a number of genes involved in defense responses (Mach, 2017, Plant Cell, Vol. 29(5):916).

In particular embodiments, the methods of the invention relate to identifying a lncRNA locus associated with a desirable genotype or phenotype, comprising introducing a library of CRISPR guides into a population of cells, the cells either expressing a modified Cas protein that is not catalytically competent or having the modified Cas protein or a coding sequence thereof introduced simultaneously or sequentially with the CRISPR guides, wherein the CRISPR guides target different genomic sequences encoding lncRNA or associated with lncRNA transcription, wherein the CRISPR guides optionally comprise a loop capable of binding a transcriptional activator domain or a transcription repressor domain, and wherein the modified Cas protein is optionally linked to a transcription activator domain or a transcription repressor domain.

The methods of the invention may further be used to identify inhibitors or stimulators of lncRNA expression, directly or indirectly, which allow the generation of a plant phenotype of interest such as those described herein. In particular embodiments, the methods comprise development of said inhibitor or stimulator (including synthesis or production thereof).

In further embodiments, the methods of the invention relate to identifying plant cells having a modified phenotype, which comprise measuring an expression level of a lncRNA locus of interest or a gene regulated by the lncRNA locus of interest and comparing to the expression level of the lncRNA of interest in a control plant cell.

The methods of the invention may further be used in the development of plants with desirable phenotypes as described further herein. In particular embodiments such methods may comprise selecting plants based on the increased or decreased expression of the lncRNA of interest identified in the methods described herein. Additionally, or alternatively, the methods may comprise modifying the expression of one or more lncRNA of interest identified in the methods described herein.

Accordingly, the invention further provides modified plant cells comprising (a) a CRISPR-Cas effector that is not catalytically competent, and (b) a guide RNA targeting a genomic sequence encoding a lncRNA of interest in said plant cell or being associated with transcription of a lncRNA of interest, wherein the guide RNA comprises a loop capable of binding a transcriptional activator domain. The invention further provides plants and plant parts comprising the modified plant cell as described herein.

In certain aspects and embodiments, the CRISPR-Cas systems as referred to herein can be used in plants/algae or yeasts. By means of example, and without limitation, the CRISPR-Cas systems as defined herein can be used in the screening methods as described herein in plants/algae (or plant cells or plant organs) or yeasts, such as the methods for identifying a lncRNA locus associated with a desirable genotype or phenotype. In further aspects and embodiments, the invention relates to methods for altering expression or otherwise modulating a lncRNA in plants/algae (or plant cells or plant organs) or yeasts. In further aspects and embodiments, the invention relates to plants/algae (or plant cells or plant organs) or yeasts obtained or obtainable by such methods.

Engineering of plant genome using CRISPR-Cas9 and CRISPR-Cpf1 systems have been described. See Li et al., Nat. Biotechnol. 31(8): 688-691 (2013); Nekrasov et al., Nat. Biotechnol. 31(8): 691-693 (2013); Bortesi et al., Biotechnology Advances 33(1):41-52 (2015); Belhaj et al., Current Opinion in Biotechnology, 32:76-84 (2015); Endo et al., Scientific Reports 6:38169 (2016); Wang et al., Mol. Plant 10(7):1011-1013 (2017); Xu et al., Plant Biotechnol. J., 16(6):713-717 (2017), and European patent publication no. 2970997A1, each of which is incorporated by reference in its entirety.

In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods as described herein, such as for genome editing or transcriptional modulation using the CRISPR-Cas system as described herein can be used to identify and/or confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., Arabidopsis). Thus, the methods and CRISPR-Cas systems can be used over a broad range of plants, such as for example with dicotyledonous plants belonging to the orders Magnoliales, Illiciales, Laurales, Piperales, Aristolochiales, Nymphaeales, Ranunculales, Papaverales, Sarraceniaceae, Trochodendrales, Hamamelidales, Eucommiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santalales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g those belonging to the orders Pinales, Ginkgoales, Cycadales, Araucariales, Cupressales and Gnetales.

The CRISPR-Cas systems and methods of use described herein can be used over a broad range of plant species, included in the non-limitative list of dicot, monocot or gymnosperm genera hereunder: Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis, and Vigna; and the genera Allium, Andropogon, Eragrostis, Asparagus, Avena, Cynodon, Elaeis, Festuca, Festulolium, Heterocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus, and Pseudotsuga.

The CRISPR-Cas systems and methods of use can also be used over a broad range of "algae" or "algae cells"; including for example algae selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: Amphora, Anabaena, Ankistrodesmus, Botryococcus, Chaetoceros, Chlamydomonas, Chlorella, Chlorococcum, Cyclotella, Cylindrotheca, Dunaliella, Emiliana, Euglena, Hematococcus, Isochrysis, Monochrysis, Monoraphidium, Nannochloris, Nannochloropsis, Navicula, Nephrochloris, Nephroselmis, Nitzschia, Nodularia, Nostoc, Ochromonas, Oocystis, Oscillatoria, Pavlova, Phaeodactylum, Platymonas, Pleurochrysis, Porphyra, Pseudoanabaena, Pyramimonas, Stichococcus, Synechococcus, Synechocystis, Tetraselmis, Thalassiosira, and Trichodesmium.

A part of a plant, i.e., a "plant tissue" may be treated according to the methods of the present invention to produce an improved or modified plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction. In some embodiments, the transgenic plant is male sterile or capable of producing male sterile non-transgenic seeds.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an S. cerervisiae, *Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and Issatchenkia spp. (e.g., Issatchenkia *orientalis*, a.k.a. *Pichia* kudriavzevii and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guideRNA may more often be a rate-limiting component in genome engineering of polyploid cells than in haploid cells, and thus the methods using the CRISPR-Cas CRISPRS system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

Stable Integration of CRISPR-Cas System Components in the Genome of Plants and Plant Cells, or Algae or Yeasts In particular embodiments, it is envisaged that the polynucleotides encoding the components of the CRISPR-Cas system are introduced for stable integration into the genome of a plant cell, algae cell, or yeast cell. In these embodiments, the design of the transformation vector or the expression system can be adjusted depending on for when, where and under what conditions the guide RNA and/or the CRISPR protein gene are expressed.

In particular embodiments, it is envisaged to introduce the components of the CRISPR-Cas system stably into the genomic DNA of a plant cell. Additionally, or alternatively, it is envisaged to introduce the components of the CRISPR-Cas system for stable integration into the DNA of a plant organelle such as, but not limited to a plastid, a mitochondrion or a chloroplast.

The expression system for stable integration into the genome of a plant cell may contain one or more of the following elements: a promoter element that can be used to express the RNA and/or CRISPR-Cas enzyme in a plant cell; a 5' untranslated region to enhance expression; an intron element to further enhance expression in certain cells, such as monocot cells; a multiple-cloning site to provide convenient restriction sites for inserting the guide RNA and/or the CRISPR-Cas gene sequences and other desired elements; and a 3' untranslated region to provide for efficient termination of the expressed transcript.

The elements of the expression system may be on one or more expression constructs which are either circular such as a plasmid or transformation vector, or non-circular such as linear double stranded DNA.

In a particular embodiment, a CRISPR-Cas expression system comprises at least: a nucleotide sequence encoding a guide RNA (gRNA) that hybridizes with a target sequence in a plant, and wherein the guide RNA comprises a guide sequence and a direct repeat sequence, and a nucleotide sequence encoding a CRISPR-Cas protein, wherein components (a) or (b) are located on the same or on different constructs, and whereby the different nucleotide sequences can be under control of the same or a different regulatory element operable in a plant cell. The skilled person will understand that if and when needed a tracr sequence may be included as well.

DNA construct(s) containing the components of the CRISPR-Cas system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993).).

In particular embodiments, the DNA constructs containing components of the CRISPR-Cas system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g., Fraley et al., (1985), Rogers et al., (1987) and U.S. Pat. No. 5,563,055).

Plant Promoters

In order to ensure appropriate expression in a plant cell, the components of the CRISPR-Cas system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the CRISPR-Cas components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the CRISPR-Cas system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include a CRISPR-Cas enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In particular embodiments, transient or inducible expression can be achieved by using, for example, chemical-regulated promotors, i.e., whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-II-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156), can also be used herein.

Translocation to and/or Expression in Specific Plant Organelles

The expression system may comprise elements for translocation to and/or expression in a specific plant organelle.

Chloroplast Targeting

In particular embodiments, it is envisaged that the CRISPR-Cas system is used to specifically modify chloroplast genes or to ensure expression in the chloroplast. For this purpose, use is made of chloroplast transformation methods or compartmentalization of the CRISPR-Cas components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the CRISPR-Cas components to the plant chloroplast. This is achieved by incorporating in the expression construct a sequence encoding a chloroplast transit peptide (CTP) or plastid transit peptide, operably linked to the 5' region of the sequence encoding the CRISPR-Cas protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments it is also desired to target the guide RNA to the plant chloroplast. Methods and constructs which can be used for translocating guide RNA into the chloroplast by means of a chloroplast localization sequence are described, for instance, in US 20040142476, incorporated herein by reference. Such variations of constructs can be incorporated into the expression systems of the invention to efficiently translocate the CRISPR-Cas-guide RNA.

Mitochondrion Targeting

Mitochondrial gene expression has been linked to desirable plant phenotypes such as male sterility. Bosacchi et al., Plant Physiology 169:2129-2137 (2015), which is incorporated by reference in its entirety. In particular embodiments, it is envisaged that the CRISPR-Cas system is used to specifically modify mitochondrial DNA or to ensure expression thereof in the mitochondrion. Jo et al., Biomed Research International 2015:305716 (2015), which is incorporated by reference in its entirety. For this purpose, use is made of mitochondrion transformation methods or compartmentalization of the CRISPR-Cas components to the mitochondrion.

Targeting to plant mitochondria can occur in different ways in nature. The most common is through the presence of an N-terminal presequence, the actual sequence of which varies but which generally has a number of conserved features. The mitochondrial targeting sequences of plants are generally about 40 amino acids in length, they have a net positive charge (rich in arginine and poor in acidic amino acids), contain many aliphatic residues (mainly leucine and alanine), and are particularly rich in serine residues (Peeters et al. 2001, BBA—Mol. Cell Res. 1541: 54-63).

Examples of mitochondrial targeting sequences that have been shown to be suitable for targeting heterologous proteins to the mitochondria include the mitochondrial-targeting sequence derived from atp2-1 (Yang et al. 2010, *BMC Plant Biology* 10:231) and the presequence of the yeast cytochrome C oxidase subunit IV (Chuah et al. 2015, Scientific Reports 5:7751).

Introduction of Polynucleotides Encoding the CRISPR-Cas System in Algal Cells.

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) species) using CRISPR/Cas. Using similar tools, the methods of the CRISPR-Cas system described herein can be applied on *Chlamydomonas* species and other algae. In particular embodiments, CRISPR protein and guide RNA are introduced in algae expressed using a vector that expresses CRISPR protein under the control of a constitutive promoter such as Hsp70A-Rbc S2 or Beta2-tubulin. Guide RNA is optionally delivered using a vector containing T7 promoter. Alternatively, CRISPR protein mRNA and in vitro transcribed guide RNA can be delivered to algal cells. Electroporation protocols are available to the skilled person such as the standard recommended protocol from the GeneArt *Chlamydomonas* Engineering kit.

In particular embodiments, the endonuclease used herein is a Split CRISPR protein. Split CRISPR proteins are preferentially used in Algae for targeted genome modification as has been described for Cas9 in WO 2015086795. Use of the CRISPR protein split system is particularly suitable for an inducible method of genome targeting and avoids the potential toxic effect of the CRISPR protein overexpression within the algae cell. In particular embodiments, said CRISPR protein split domains (e.g., RuvC and HNH domains for Cas9) can be simultaneously or sequentially introduced into the cell such that said split CRISPR protein domain(s) process the target nucleic acid sequence in the algae cell. The reduced size of the split CRISPR protein compared to the wild type CRISPR protein allows other methods of delivery of the CRISPR system to the cells, such as the use of Cell Penetrating Peptides as described herein. This method is of particular interest for generating genetically modified algae.

Introduction of Polynucleotides Encoding CRISPR-Cas Components in Yeast Cells

In particular embodiments, the invention relates to the use of the CRISPR-Cas system for genome editing of yeast cells. Methods for transforming yeast cells which can be used to introduce polynucleotides encoding the CRISPR-Cas system components are well known to the artisan and are reviewed by Kawai et al., 2010, Bioeng Bugs. 2010 November-December; 1(6): 395-403. Non-limiting examples include transformation of yeast cells by lithium acetate treatment (which may further include carrier DNA and PEG treatment), bombardment or by electroporation.

Transient Expression of CRISPR-Cas System Components in Plants and Plant Cell

In particular embodiments, it is envisaged that the guide RNA and/or CRISPR protein gene are transiently expressed in the plant cell. In these embodiments, the CRISPR-Cas system can ensure modification of a target gene only when both the guide RNA and the CRISPR protein is present in a cell, such that genomic modification can further be controlled. As the expression of the CRISPR protein is transient, plants regenerated from such plant cells typically contain no foreign DNA. In particular embodiments the CRISPR protein is stably expressed by the plant cell and the guide sequence is transiently expressed.

In particular embodiments, the CRISPR-Cas system components can be introduced in the plant cells using a plant viral vector (Scholthof et al. 1996, *Annu Rev Phytopathol.* 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of CRISPR-Cas constructs is for instance a pEAQ vector, which is tailored for *Agrobacterium*-mediated transient expression (Sainsbury F. et al., *Plant Biotechnol J.* 2009 September; 7(7):682-93) in the protoplast. Precise targeting of genomic locations was demonstrated using a modified Cabbage Leaf Curl virus (CaLCuV) vector to express gRNAs in stable transgenic plants expressing a CRISPR enzyme (Scientific Reports 5, Article number: 14926 (2015), doi:10.1038/srep14926).

In particular embodiments, double-stranded DNA fragments encoding the guide RNA and/or the CRISPR protein gene can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the CRISPR protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of CRISPR-Cas Components to the Plant Cell

In particular embodiments, it is of interest to deliver one or more components of the CRISPR-Cas system directly to the plant cell. This is of interest, inter alia, for the generation of non-transgenic plants (see below). In particular embodiments, one or more of the components is prepared outside the plant or plant cell and delivered to the cell. For instance, in particular embodiments, the CRISPR protein is prepared in vitro prior to introduction to the plant cell. CRISPR protein can be prepared by various methods known by one of skill in the art and include recombinant production. After expression, the CRISPR protein is isolated, refolded if needed, purified and optionally treated to remove any purification tags, such as a His-tag. Once crude, partially purified, or more completely purified CRISPR protein is obtained, the protein may be introduced to the plant cell.

In particular embodiments, the CRISPR protein is mixed with guide RNA targeting the gene of interest to form a pre-assembled ribonucleoprotein.

The individual components or pre-assembled ribonucleoprotein can be introduced into the plant cell via electroporation, by bombardment with CRISPR protein-associated gene product coated particles, by chemical transfection or by some other means of transport across a cell membrane. For instance, transfection of a plant protoplast with a pre-assembled CRISPR ribonucleoprotein has been demonstrated to ensure targeted modification of the plant genome (as described by Woo et al. *Nature Biotechnology,* 2015; DOI: 10.1038/nbt.3389).

In particular embodiments, the CRISPR-Cas system components are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In particular, embodiments of the invention comprise nanoparticles uploaded with or packed with DNA molecule(s) encoding the CRISPR protein, DNA molecules encoding the guide RNA and/or isolated guide RNA as described in WO2015089419.

Further means of introducing one or more components of the CRISPR-Cas system to the plant cell is by using cell penetrating peptides (CPP). Accordingly, in particular, embodiments the invention comprises compositions comprising a cell penetrating peptide linked to the CRISPR protein. In particular embodiments of the present invention, the CRISPR protein and/or guide RNA is coupled to one or more CPPs to effectively transport them inside plant protoplasts; see also Ramakrishna (2014 *Genome Res.* 2014 June; 24(6):1020-7 for Cas9 in human cells). In other embodiments, the CRISPR protein gene and/or guide RNA are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and antimicrobial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type 1, penetratin, Kaposi fibroblast growth factor (FGF) signal peptide sequence, integrin (33 signal peptide sequence; polyarginine peptide Args sequence, Guanine rich-molecular transporters, sweet arrow peptide, etc.

Use of the CRISPR-Cas System to Make Genetically Modified Non-Transgenic Plants

In particular embodiments, the methods described herein are used to modify endogenous genes or to modify their expression without the permanent introduction into the genome of the plant of any foreign gene, including those encoding CRISPR components, so as to avoid the presence of foreign DNA in the genome of the plant. This can be of interest as the regulatory requirements for non-transgenic plants are less rigorous.

In particular embodiments, this is ensured by transient expression of the CRISPR-Cas components. In particular embodiments one or more of the CRISPR components are expressed on one or more viral vectors which produce sufficient CRISPR protein and guide RNA to consistently steadily ensure modification of a gene of interest according to a method described herein.

In particular embodiments, transient expression of CRISPR-Cas constructs is ensured in plant protoplasts and thus not integrated into the genome. The limited window of expression can be sufficient to allow the CRISPR-Cas system to ensure modification of a target gene as described herein.

In particular embodiments, the different components of the CRISPR-Cas system are introduced in the plant cell, protoplast or plant tissue either separately or in mixture, with the aid of particulate delivering molecules such as nanoparticles or CPP molecules as described herein above.

The expression of the CRISPR-Cas components can induce targeted modification of the genome, either by direct activity of the CRISPR protein nuclease and optionally introduction of template DNA or by modification of genes targeted using the CRISPR-Cas system as described herein. The different strategies described herein above allow CRISPR protein-mediated targeted genome editing without requiring the introduction of the CRISPR-Cas components into the plant genome. Components which are transiently introduced into the plant cell are typically removed upon crossing.

Detecting Modifications in the Plant Genome-Selectable Markers

In particular embodiments, where the method involves detection/identification and/or modification of an endogenous target gene of the plant genome, any suitable method can be used to determine, after the plant, plant part or plant cell is infected or transfected with the CRISPR-Cas system, whether gene targeting or targeted mutagenesis has occurred at the target site. Where the method involves introduction of a transgene, a transformed plant cell, callus, tissue or plant may be identified and isolated by selecting or screening the engineered plant material for the presence of the transgene or for traits encoded by the transgene. Physical and biochemical methods may be used to identify plant or plant cell transformants containing inserted gene constructs or an endogenous DNA modification. These methods include but are not limited to: 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art.

Additionally (or alternatively), the expression system encoding the CRISPR-Cas components is typically designed to comprise one or more selectable or detectable markers that provide a means to isolate or efficiently select cells that contain and/or have been modified by the CRISPR-Cas system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system).

For particle bombardment or with protoplast transformation, the expression system can comprise one or more isolated linear fragments or may be part of a larger construct that might contain bacterial replication elements, bacterial selectable markers or other detectable elements. The expression cassette(s) comprising the polynucleotides encoding the guide and/or CRISPR protein may be physically linked to a marker cassette or may be mixed with a second nucleic acid molecule encoding a marker cassette. The marker cassette is comprised of necessary elements to express a detectable or selectable marker that allows for efficient selection of transformed cells.

The selection procedure for the cells based on the selectable marker will depend on the nature of the marker gene. In particular embodiments, use is made of a selectable marker, i.e., a marker which allows a direct selection of the cells based on the expression of the marker. A selectable marker can confer positive or negative selection and is conditional or non-conditional on the presence of external substrates (Miki et al. 2004, 107(3): 193-232). Most commonly, antibiotic or herbicide resistance genes are used as a marker, whereby selection is be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptII), and genes that confer resistance to herbicides, such as phosphinothricin (bar) and chlorsulfuron (als).

Transformed plants and plant cells may also be identified by screening for the activities of a visible marker, typically an enzyme capable of processing a colored substrate (e.g., the β-glucuronidase, luciferase, B or C1 genes). Such selection and screening methodologies are well known to those skilled in the art.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the Cas9 or Cfp1 enzyme whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, Calif., 50-98 (1960)).

Generation or Identification of Plants with Enhanced Agronomic Traits

The CRISPR protein based CRISPR systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the CRISPR-Cas system as described herein is used to detect and/or introduce targeted double-strand breaks (DSB) in an endogenous DNA sequence. The DSB activates cellular DNA repair pathways, which can be harnessed to achieve desired DNA sequence modifications near the break site. This is of interest where the inactivation of endogenous genes can confer or contribute to a desired trait. In particular embodiments, homologous recombination with a template sequence is promoted at the site of the DSB, in order to introduce a gene of interest.

In particular embodiments, the CRISPR-Cas system may be used as a generic nucleic acid binding protein with fusion to or being operably linked to a functional domain for activation and/or repression of endogenous plant genes. Exemplary functional domains may include but are not limited to translational initiator, translational activator, translational repressor, nucleases, in particular ribonucleases, a spliceosome, beads, a light inducible/controllable domain or a chemically inducible/controllable domain. Typically, in these embodiments, the CRISPR protein comprises at least one mutation, such that it has no more than 5% of the activity of the CRISPR protein not having the at least one mutation; the guide RNA comprises a guide sequence capable of hybridizing to a target sequence.

The methods described herein generally result in the generation of "improved plants" in that they have one or more desirable traits compared to the wildtype plant. In particular embodiments, the plants, plant cells or plant parts obtained are transgenic plants, comprising an exogenous DNA sequence incorporated into the genome of all or part of the cells of the plant. In particular embodiments, non-transgenic genetically modified plants, plant parts or cells are obtained, in that no exogenous DNA sequence is incorporated into the genome of any of the plant cells of the plant. In such embodiments, the improved plants are non-transgenic. Where only the modification of an endogenous gene is ensured and no foreign genes are introduced or maintained in the plant genome, the resulting genetically modified crops contain no foreign genes and can thus basically be considered non-transgenic. The different applications of the CRISPR-Cas system for plant genome editing are described more in detail below:

a) Introduction of One or More Foreign Genes to Identify or Confer an Agricultural Trait of Interest The invention provides methods of genome editing or modifying sequences associated with or at a target locus of interest wherein the method comprises introducing a CRISPR effector protein complex into a plant cell, whereby the CRISPR effector protein complex effectively functions to integrate a DNA insert, e.g., encoding a foreign gene of interest, into the genome of the plant cell. In preferred embodiments the integration of the DNA insert is facilitated by HR with an exogenously introduced DNA template or repair template. Typically, the exogenously introduced DNA template or repair template is delivered together with the CRISPR effector protein complex or one component or a polynucleotide vector for expression of a component of the complex.

The CRISPR-Cas systems provided herein allow for targeted gene delivery. It has become increasingly clear that the efficiency of expressing a gene of interest is to a great extent determined by the location of integration into the genome. The present methods allow for targeted integration of the foreign gene into a desired location in the genome. The location can be selected based on information of previously generated events or can be selected by methods disclosed elsewhere herein.

In particular embodiments, the methods provided herein include (a) introducing into the cell a CRISPR-Cas complex comprising a guide RNA, comprising a direct repeat and a guide sequence, wherein the guide sequence hybridizes to a target sequence that is endogenous to the plant cell; (b) introducing into the plant cell a CRISPR effector molecule which complexes with the guide RNA when the guide sequence hybridizes to the target sequence and induces a double strand break at or near the sequence to which the guide sequence is targeted; and (c) introducing into the cell a nucleotide sequence encoding an HDR repair template which encodes the gene of interest and which is introduced into the location of the DS break as a result of HDR. In particular embodiments, the step of introducing can include delivering to the plant cell one or more polynucleotides encoding CRISPR effector protein, the guide RNA and the repair template. In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the CRISPR effector protein, the guide RNA and the repair template, where the delivering is via *Agrobacterium*. The nucleic acid sequence encoding the CRISPR effector protein can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the repair template i.e., the gene of interest has been introduced. In particular embodiments, the methods include the step of regenerating a plant from the plant cell. In further embodiments, the methods include cross breeding the plant to obtain a genetically desired plant lineage. Examples of foreign genes encoding a trait of interest are listed below.

b) Editing of Endogenous Genes to Identify or Confer an Agricultural Trait of Interest The invention provides methods of genome editing or modifying sequences associated with or at a target locus of interest wherein the method comprises introducing a CRISPR effector protein complex into a plant cell, whereby the CRISPR-Cas complex modifies the expression of an endogenous gene of the plant. This can be achieved in different ways. In particular embodiments, the elimination of expression of an endogenous gene is desirable and the CRISPR-Cas complex is used to target and cleave an endogenous gene so as to modify gene expression. In these embodiments, the methods provided herein include (a) introducing into the plant cell a CRISPR-Cas complex comprising a guide RNA, comprising a direct repeat and a guide sequence, wherein the guide sequence hybridizes to a target sequence within a gene of interest in the genome of the plant cell; and (b) introducing into the cell a CRISPR effector protein, which upon binding to the guide RNA comprises a guide sequence that is hybridized to the target sequence, ensures a double strand break at or near the sequence to which the guide sequence is targeted; In particular embodiments, the step of introducing can include delivering to the plant cell one or more polynucleotides encoding CRISPR effector protein and the guide RNA.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the CRISPR effector protein and the guide RNA, where the delivering is via *Agrobacterium*. The polynucleotide sequence encoding the components of the CRISPR-Cas system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

In particular embodiments of the methods described above, disease resistant crops are obtained by targeted mutation of disease susceptibility genes or genes encoding negative regulators (e.g., Mlo gene) of plant defense genes. In a particular embodiment, herbicide-tolerant crops are generated by targeted substitution of specific nucleotides in plant genes such as those encoding acetolactate synthase (ALS) and protoporphyrinogen oxidase (PPO). In particular embodiments, drought and salt tolerant crops by targeted mutation of genes encoding negative regulators of abiotic stress tolerance, low amylose grains by targeted mutation of Waxy gene, rice or other grains with reduced rancidity by targeted mutation of major lipase genes in aleurone layer, etc. In particular embodiments, a more extensive list of endogenous genes encoding a trait of interest are listed below.

c) Modulating of Endogenous Genes by the CRISPR-Cas System to Identify or Confer an Agricultural Trait of Interest Also provided herein are methods for modulating (i.e., activating or repressing) endogenous gene expression using the CRISPR protein provided herein. Such methods make use of distinct RNA sequence(s) which are targeted to the plant genome by the CRISPR-Cas complex. More particularly the distinct RNA sequence(s) bind to two or more adaptor proteins (e.g. aptamers) whereby each adaptor protein is associated with one or more functional domains and wherein at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity; The functional domains are used to modulate expression of an endogenous plant gene so as to obtain the desired trait. Typically, in these embodiments, the CRISPR effector protein has one or more mutations such that it has no more than 5% of the nuclease activity of the CRISPR effector protein not having the at least one mutation.

In particular embodiments, the methods provided herein include the steps of (a) introducing into the cell a CRISPR-Cas complex comprising a guide RNA, comprising a direct repeat and a guide sequence, wherein the guide sequence hybridizes to a target sequence that is endogenous to the plant cell; (b) introducing into the plant cell a CRISPR effector molecule which complexes with the guide RNA when the guide sequence hybridizes to the target sequence; and wherein either the guide RNA is modified to comprise a distinct RNA sequence (aptamer) binding to a functional domain and/or the CRISPR effector protein is modified in that it is linked to a functional domain. In particular embodiments, the step of introducing can include delivering to the plant cell one or more polynucleotides encoding the (modified) CRISPR effector protein and the (modified) guide RNA. The details the components of the CRISPR-Cas system for use in these methods are described elsewhere herein.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the CRISPR effector protein and the guide RNA, where the delivering is via *Agrobacterium*. The nucleic acid sequence encoding the one or more components of the CRISPR-Cas system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage. A more extensive list of endogenous genes encoding a trait of interest are listed below.

Use of CRISPR/Cas to Identify or Modify Polyploid Plants

Many plants are polyploid, which means they carry duplicate copies of their genomes—sometimes as many as six, as in wheat. The methods according to the present invention, which make use of the CRISPR-Cas effector protein can be "multiplexed" to affect all copies of a gene, or to target dozens of genes at once. For instance, in particular embodiments, the methods of the present invention are used to simultaneously ensure a loss of function mutation in different genes responsible for suppressing defences against a disease. In particular embodiments, the methods of the present invention are used to simultaneously suppress the expression of the TaMLO-A1, TaMLO-B1 and TaMLO-D1 nucleic acid sequence in a wheat plant cell and regenerating a wheat plant therefrom, in order to ensure that the wheat plant is resistant to powdery mildew (see also WO2015109752).

Exemplary Genes Conferring Agronomic Traits

In particular embodiments relating to screening and identification of lncRNA loci associated with desirable plant genotypes or phenotypes, said desirable plant genotypes or phenotypes can be or can be linked to increased or decreased expression level of one of the protein-coding genes discussed below:

1. Genes that Confer Resistance to Pests or Diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (*Arabidopsis* be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: doi.org/10.1101/064824 Epub. Jul. 23, 2016 (tomato plants with deletions in the S1DMR6-1 which is normally upregulated during pathogen infection).

Genes conferring resistance to a pest, such as soybean cyst nematode. See e.g., PCT Application WO 96/30517; PCT Application WO 93/19181.

*Bacillus thuringiensis* proteins see, e.g., Geiser et al., Gene 48:109 (1986).

Lectins, see, for example, Van Damme et al., Plant Molec. Biol. 24:25 (1994).

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example, Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulate signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will cause tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Using methods and components of the CRISP-Cas system, a new tool now exists to induce specific mutations in anticipation hereon. Accordingly, one can analyze the genome of sources of resistance genes, and in plants having desired characteristics or traits, use the method and components of the CRISPR-Cas system to induce the rise of resistance genes. The present systems can do so with more precision than previous mutagenic agents and hence accelerate and improve plant breeding programs.

2. Genes Involved in Plant Diseases, Such as Those Listed in WO 2013046247:

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeaemaydis, Rhizoctonia solani;*

Citrus diseases: *Diaporthe citri, Elsinoe fawcetti, Penicillium digitatum, P. italicum, Phytophthora parasitica, Phytophthora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophtora cactorum*;

Pear diseases: *Venturia nashicola, V. pirina, Alternaria alternata* Japanese pear pathotype, *Gymnosporangium haraeanum, Phytophthora cactorum*;

Peach diseases: *Monilinia fructicola, Cladosporium carpophilum, Phomopsis* sp.;

Grape diseases: *Elsinoe ampelina, Glomerella cingulata, Uncinula necator, Phakopsora ampelopsidis, Guignardia bidwellii, Plasmopara viticola*;

Persimmon diseases: *Gloeosporium kaki, Cercospora kaki, Mycosphaerella nawae*;

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans; Pseudomonas syringae* pv. Tomato; *Phytophthora capsici; Xanthomonas*;

Eggplant diseases: *Phomopsis vexans, Erysiphe cichoracearum*; Brassicaceous vegetable diseases: *Alternaria japonica, Cercosporella brassicae, Plasmodiophora brassicae, Peronospora parasitica*;

Welsh onion diseases: *Puccinia allii, Peronospora destructor*;

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora cassiicola, Sclerotinia sclerotiorum*;

Kidney bean diseases: *Colletotrichum lindemuthianum*;

Peanut diseases: *Cercospora personata, Cercospora arachidicola, Sclerotium rolfsii*;

Pea diseases pea: *Erysiphe pisi*;

Potato diseases: *Alternaria solani, Phytophthora infestans, Phytophthora erythroseptica*, Spongospora subterranean, f. sp. Subterranean;

Strawberry diseases: *Sphaerotheca humuli, Glomerella cingulata*;

Tea diseases: *Exobasidium reticulatum, Elsinoe leucospila, Pestalotiopsis* sp., *Colletotrichum* theae-*sinensis*;

Tobacco diseases: *Alternaria longipes, Erysiphe cichoracearum, Colletotrichum tabacum, Peronospora tabacina, Phytophthora nicotianae*;

Rapeseed diseases: *Sclerotinia sclerotiorum, Rhizoctonia solani*;

Cotton diseases: *Rhizoctonia solani*;

Beet diseases: *Cercospora beticola, Thanatephorus cucumeris, Thanatephorus cucumeris, Aphanomyces cochlioides*;

Rose diseases: *Diplocarpon rosae, Sphaerotheca pannosa, Peronospora sparsa*;

Diseases of *chrysanthemum* and asteraceae: *Bremia lactuca, Septoria chrysanthemi-indici, Puccinia horiana*;

Diseases of various plants: *Pythium aphanidermatum, Pythium debaryanum, Pythium graminicola, Pythium irregulare, Pythium ultimum, Botrytis cinerea, Sclerotinia sclerotiorum*;

Radish diseases: *Alternaria brassicicola*;

Zoysia diseases: *Sclerotinia homeocarpa, Rhizoctonia solani*;

Banana diseases: *Mycosphaerella fijiensis, Mycosphaerella musicola*;

Sunflower diseases: *Plasmopara halstedii*;

Seed diseases or diseases in the initial stage of growth of various plants caused by *Aspergillus* spp., *Penicillium* spp., *Fusarium* spp., *Gibberella* spp., *Trichoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymyxa* spp., *Olpidium* spp., or the like.

3. Examples of Genes that Confer Resistance to Herbicides:

Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridochromogenes*), and to pyridinoxy or phenoxy propionic acids and cyclohexanones by ACCase inhibitor-encoding genes. See, for example, U.S. Pat. Nos. 4,940,835 and 6,248,876, 4,769,061, EP No. 0333033 and U.S. Pat. No. 4,975,374. See also EP No. 0242246, DeGreef et al., Bio/Technology 7:61 (1989), Marshall et al., Theor. Appl. Genet. 83:435 (1992), WO 2005012515 to Castle et. al. and WO 2005107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g., U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenase (HPPD) inhibitors, i.e., naturally occurring HPPD resistant enzymes, or genes encoding a mutated or chimeric HPPD enzyme as described in WO 96/38567, WO 99/24585, and WO 99/24586, WO 2009/144079, WO 2002/046387, or U.S. Pat. No. 6,768,044.

4. Examples of Genes Involved in Abiotic Stress Tolerance:

Transgene capable of reducing the expression and/or the activity of poly(ADP-ribose) polymerase (PARP) gene in the plant cells or plants as described in WO 00/04173 or, WO/2006/045633.

Transgenes capable of reducing the expression and/or the activity of the PARG encoding genes of the plants or plants cells, as described e.g., in WO 2004/090140.

Transgenes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g., in EP 04077624.7, WO 2006/133827, PCT/EP07/002,433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013122472 discloses that the absence or reduced level of functional Ubiquitin Protein Ligase protein (UPL) protein, more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/08391 1 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield etc. A few specific non-limiting examples are provided hereinbelow.

In addition to targeted mutation of single genes, CRISPR/Cas complexes can be designed to allow targeted mutation of multiple genes, deletion of chromosomal fragment, site-specific integration of transgene, site-directed mutagenesis in vivo, and precise gene replacement or allele swapping in plants. Therefore, the methods described herein have broad applications in gene discovery and validation, mutational and cisgenic breeding, and hybrid breeding. These applications facilitate the production of a new generation of genetically modified crops with various improved agronomic traits such as herbicide resistance, disease resistance, abiotic stress tolerance, high yield, and superior quality.

Use of CRISPR/Cas to Identify or Create Male Sterile Plants

Hybrid plants typically have advantageous agronomic traits compared to inbred plants. However, for self-pollinating plants, the generation of hybrids can be challenging. In different plant types, genes have been identified which are important for plant fertility, more particularly male fertility. For instance, in maize, at least two genes have been identified which are important in fertility (Amitabh Mohanty International Conference on New Plant Breeding Molecular Technologies Technology Development And Regulation, Oct. 9-10, 2014, Jaipur, India; Svitashev et al. *Plant Physiol.* 2015 October; 169(2):931-45; Djukanovic et al. *Plant J.* 2013 December; 76(5):888-99). The methods provided herein can be used to screen and identification of lncRNA loci associated with desirable plant genotypes or phenotypes, such as expression of target genes required for male fertility so as to generate male sterile plants which can easily be crossed to generate hybrids. In particular embodiments, the CRISPR-Cas system provided herein is used for targeted modulation of lncRNA loci regulating expression of the cytochrome P450-like gene (MS26) or the meganuclease gene (MS45) thereby conferring male sterility to the maize plant. Maize plants which are as such genetically altered can be used in hybrid breeding programs.

Increasing the Fertility Stage in Plants

In particular embodiments, the methods provided herein are used to prolong the fertility stage of a plant such as of a rice plant or to identify genes involved in such process. For instance, a rice fertility stage gene such as Ehd3 or lncRNAs regulating said gene can be targeted in order to modulate expression in the gene and plantlets can be selected for a prolonged regeneration plant fertility stage (as described in CN 104004782).

Use of CRISPR/Cas to Identify or Generate Genetic Variation in a Crop of Interest The availability of wild germplasm and genetic variations in crop plants is the key to crop improvement programs, but the available diversity in germplasms from crop plants is limited. The present invention envisages methods for generating a diversity of genetic variations in a germplasm of interest. In this application of the CRISPR-Cas system a library of guide RNAs targeting different locations in the plant genome is provided and is introduced into plant cells together with the CRISPR effector protein. In this way a collection of genome-scale transcriptional modulation, point mutations and gene knock-outs can be generated. In particular embodiments, the methods comprise generating a plant part or plant from the cells so obtained and screening the cells for a trait of interest. The target genes can include both coding and non-coding regions (e.g., protein-coding genes and lncRNA genes). In particular embodiments, the trait is stress tolerance and the method is a method for the generation of stress-tolerant crop varieties.

Use of CRISPR/Cas to Affect or Identify Genes Involved in Fruit-Ripening

Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus, in particular embodiments, the methods comprise the use of the CRISPR-Cas system to identify or ensure one or more modifications of the genome of a plant cell such as described above, and regenerating a plant therefrom. In particular embodiments, the plant is a tomato plant.

Increasing Storage Life of Plants

In particular embodiments, the methods of the present invention are used to identify or modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the CRISPR-Cas System to Identify or Ensure a Value Added Trait

In particular embodiments the CRISPR-Cas system is used to identify or produce nutritionally improved agricultural crops. In particular embodiments, the methods provided herein are adapted to generate "functional foods", i.e., a modified food or food ingredient that may provide a health benefit beyond the traditional nutrients it contains and/or "nutraceutical", i.e., substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

Modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; Li et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A);

Essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 GM crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204);

Oils and Fatty acids such as for Canola (Dehesh et al. (1996)) Plant J 9 167-172 [PubMed]; Del Vecchio (1996) INFORM International News on Fats, Oils and Related Materials 7 230-243; Roesler et al. (1997) Plant Physiol 113 75-81 [PMC free article] [PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); cotton (Chapman et al. (2001)). J Am Oil Chem Soc 78 941-947; Liu et al. (2002) J Am Coll Nutr 21 205S-211S [PubMed]; O'Neill (2007) Australian Life Scientist. www.biotechnews.com.au/index.php/id; 866694817; fp; 4; fpid; 2 (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008);

Carbohydrates, such as Fructans described for Chicory (Smeekens (1997) Trends Plant Sci 2 286-287, Sprenger et al. (1997) FEBS Lett 400 355-358, Sévenier et al. (1998) Nat Biotechnol 16 843-846), Maize (Caimi et al. (1996) Plant Physiol 110 355-363), Potato (Hellwege et al.,1997

Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143);

Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustard seed (Shewmaker et al. (1999)) Plant J 20 401-412, Potato (Ducreux et al., 2005, J Exp Bot 56 81-89), Rice (Ye et al. (2000)) Science 287 303-305, Strawberry (Agius et al. (2003), Nat Biotechnol 21 177-181), Tomato (Rosati et al. (2000)) Plant J 24 413-419, Fraser et al. (2001) J Sci Food Agric 81 822-827, Mehta et al. (2002) Nat Biotechnol 20 613-618, Díaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676;

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999) www.molecularfarming.com/nonmedical.html), Lettuce (iron, Goto et al. (2000) Theor Appl Genet 100 658-664), Rice (iron, Lucca et al. (2002) J Am Coll Nutr 21 184S-190S), Maize, Soybean and wheat (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which neutralizes free radicals that may cause damage to cells or β-Carotene present in various fruits and vegetables which neutralizes free radicals;

Lutein present in green vegetables which contributes to maintenance of healthy vision;

Lycopene present in tomato and tomato products, which is believed to reduce the risk of prostate cancer;

Zeaxanthin, present in citrus and maize, which contributes to maintenance of healthy vision;

Dietary fiber such as insoluble fiber present in wheat bran which may reduce the risk of breast and/or colon cancer and β-Glucan present in oat, soluble fiber present in Psyllium and whole cereal grains which may reduce the risk of cardiovascular disease (CVD);

Fatty acids, such as ω-3 fatty acids which may reduce the risk of CVD and improve mental and visual functions, Conjugated linoleic acid, which may improve body composition, may decrease risk of certain cancers and GLA which may reduce inflammation risk of cancer and CVD, may improve body composition;

Flavonoids such as Hydroxycinnamates, present in wheat which have Antioxidant-like activities, may reduce risk of degenerative diseases, flavonols, catechins and tannins present in fruits and vegetables which neutralize free radicals and may reduce risk of cancer;

Glucosinolates, indoles, isothiocyanates, such as Sulforaphane, present in Cruciferous vegetables (broccoli, kale), horseradish, which neutralize free radicals, may reduce risk of cancer;

Phenolics, such as stilbenes present in grape which may reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease;

Plant stanols/sterols present in maize, soy, wheat and wooden oils which may reduce risk of coronary heart disease by lowering blood cholesterol levels;

Fructans, inulins, fructo-oligosaccharides present in Jerusalem artichoke, shallot, onion powder which may improve gastrointestinal health;

Saponins present in soybean, which may lower LDL cholesterol;

Soybean protein present in soybean which may reduce risk of heart disease;

Phytoestrogens such as isoflavones present in soybean which may reduce menopause symptoms, such as hot flashes, may reduce osteoporosis and CVD and lignans present in flax, rye and vegetables, which May protect against heart disease and some cancers, may lower LDL cholesterol, total cholesterol;

Sulfides and thiols such as diallyl sulphide present in onion, garlic, olive, leek and scallion and Allyl methyl trisulfide, dithiolthiones present in cruciferous vegetables which may lower LDL cholesterol, helps to maintain healthy immune system; and Tannins, such as proanthocyanidins, present in cranberry, cocoa, which may improve urinary tract health, may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for identifying or producing plants with nutritional added value, said methods comprising modulating expression of or introducing into a plant cell a gene encoding an enzyme involved in the production of a component of added nutritional value, or a lncRNA regulating expression of said gene, using the CRISPR-Cas system as described herein and regenerating a plant from said plant cell, said plant characterized in an increase expression of said component of added nutritional value. In particular embodiments, the CRISPR-Cas system is used to modify the endogenous synthesis of these compounds indirectly, e.g. by modifying one or more transcription factors that controls the metabolism of this compound. Methods for introducing a gene of interest into a plant cell and/or modifying an endogenous gene using the CRISPR-Cas system are described herein above.

Some specific examples of modifications in plants that have been modified to confer value-added traits are: plants with modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992). Another example involves decreasing phytate content, for example by cloning and then reintroducing DNA associated with the single allele which may be responsible for maize mutants characterized by low levels of phytic acid. See Raboy et al, Maydica 35:383 (1990).

Similarly, expression of the maize (Zea mays) Tfs C1 and R, which regulate the production of flavonoids in maize aleurone layers under the control of a strong promoter, resulted in a high accumulation rate of anthocyanins in Arabidopsis (Arabidopsis thaliana), presumably by activating the entire pathway (Bruce et al., 2000, Plant Cell 12:65-80). DellaPenna (Welsch et al., 2007 Annu Rev Plant Biol 57: 711-738) found that Tf RAP2.2 and its interacting partner SINAT2 increased carotenogenesis in Arabidopsis leaves. Expressing the Tf Dof1 induced the up-regulation of genes encoding enzymes for carbon skeleton production, a marked increase of amino acid content, and a reduction of the Glc level in transgenic Arabidopsis (Yanagisawa, 2004 Plant Cell Physiol 45: 386-391), and the DOF Tf AtDof1.1 (OBP2) up-regulated all steps in the glucosinolate biosynthetic pathway in Arabidopsis (Skirycz et al., 2006 Plant J 47: 10-24).

Reducing Allergen in Plants

In particular embodiments the methods provided herein are used to identify or generate plants with a reduced level of allergens, making them safer for the consumer. In particular embodiments, the methods comprise modifying expression of one or more genes responsible for the production of plant allergens or lncRNAs regulating said genes. For instance, in particular embodiments, the methods comprise down-regulating expression of a Lol p5 gene in a plant cell, such as a ryegrass plant cell and regenerating a plant therefrom so as to reduce allergenicity of the pollen of said plant (Bhalla et al. 1999, Proc. Natl. Acad. Sci. USA Vol. 96: 11676-11680).

Peanut allergies and allergies to legumes generally are a real and serious health concern. The CRISPR effector protein system of the present invention can be used to identify and then edit or silence genes encoding allergenic proteins of such legumes or encoding lncRNAs regulating expression of said protein-coding genes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222.

Screening Methods for Endogenous Genes of Interest

The methods provided herein further allow the identification of genes of value, in particular lncRNAs, involved in the production of a component of added nutritional value or generally genes affecting agronomic traits of interest, across species, phyla, and plant kingdom. By selectively targeting e.g., genes encoding enzymes of metabolic pathways in plants using the CRISPR-Cas system as described herein, the genes responsible for certain nutritional aspects of a plant can be identified. Similarly, by selectively targeting genes which may affect a desirable agronomic trait, the relevant genes can be identified. Accordingly, the present invention encompasses screening methods for genes involved in the production of compounds with a particular nutritional value and/or agronomic traits.

Use of CRISPR-Cas System in Biofuel Production

The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation. The CRISPR system described herein can be used to identify lncRNAs associated with desirable genotypes or phenotypes linked to increased biofuel production in plant or yeast.

Enhancing Plant Properties for Biofuel Production

In particular embodiments, the methods using the CRISPR-Cas system as described herein are used to alter the properties of the cell wall in order to facilitate access by key hydrolysing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

In particular embodiments, the methods described herein are used to produce plant mass that produces lower levels of acetic acid during fermentation (see also WO 2010096488). More particularly, the methods disclosed herein are used to generate mutations in homologs to Cas1L to reduce polysaccharide acetylation.

Modifying Yeast for Biofuel Production

In particular embodiments, the CRISPR protein provided herein is used for bioethanol production by recombinant micro-organisms. For instance, CRISPR protein can be used to engineer micro-organisms, such as yeast, to generate biofuel or biopolymers from fermentable sugars and optionally to be able to degrade plant-derived lignocellulose derived from agricultural waste as a source of fermentable sugars. More particularly, the invention provides methods whereby the CRISPR-Cas complex is used to introduce foreign genes required for biofuel production into micro-organisms and/or to modify endogenous genes why may interfere with the biofuel synthesis. More particularly the methods involve introducing into a micro-organism such as a yeast one or more nucleotide sequence encoding enzymes involved in the conversion of pyruvate to ethanol or another product of interest. In particular embodiments the methods ensure the introduction of one or more enzymes which allows the micro-organism to degrade cellulose, such as a cellulase. In yet further embodiments, the CRISPR-Cas complex is used to modify endogenous metabolic pathways which compete with the biofuel production pathway.

Accordingly, in more particular embodiments, the methods described herein are used to modify a micro-organism as follows:

to introduce at least one heterologous nucleic acid or increase expression of at least one endogenous nucleic acid encoding a plant cell wall degrading enzyme, such that said micro-organism is capable of expressing said nucleic acid and of producing and secreting said plant cell wall degrading enzyme;

to introduce at least one heterologous nucleic acid or increase expression of at least one endogenous nucleic acid encoding an enzyme that converts pyruvate to acetaldehyde optionally combined with at least one heterologous nucleic acid encoding an enzyme that converts acetaldehyde to ethanol such that said host cell is capable of expressing said nucleic acid; and/or to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

Modifying Algae and Plants for Production of Vegetable Oils or Biofuels

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

According to particular embodiments of the invention, the CRISPR-Cas system is used to generate lipid-rich diatoms which are useful in biofuel production.

In particular embodiments it is envisaged to specifically modify genes that are involved in the modification of the quantity of lipids and/or the quality of the lipids produced by the algal cell. Examples of genes encoding enzymes involved in the pathways of fatty acid synthesis can encode proteins having for instance acetyl-CoA carboxylase, fatty acid synthase, 3-ketoacyl-acyl-carrier protein synthase III, glycerol-3-phosphate dehydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid:diacylglycerol acyltransferase, phosphatidate phosphatase, fatty acid thioesterase such as palmitoyl protein thioesterase, or malic enzyme activities. In further embodiments it is envisaged to generate diatoms that have increased lipid accumulation. This can be achieved by targeting genes that decrease lipid catabolisation. Of particular interest for use in the methods of the present invention are genes involved in the activation of both triacylglycerol and free fatty acids, as well as genes directly involved in β-oxidation of fatty acids, such as acyl-CoA synthetase, 3-ketoacyl-CoA thiolase, acyl-CoA oxidase activity and phosphoglucomutase. The CRISPR-Cas system and methods described herein can be used to specifically activate such genes in diatoms as to increase their lipid content.

Organisms such as microalgae are widely used for synthetic biology. Stovicek et al. (Metab. Eng. Comm., 2015; 2:13) describes genome editing of industrial yeast, for example, Saccharomyces cerevisae, to efficiently produce robust strains for industrial production. Stovicek used a CRISPR-Cas system codon-optimized for yeast to simultaneously disrupt both alleles of an endogenous gene and knock in a heterologous gene. CRISPR protein and gRNA were expressed from genomic or episomal 2μ-based vector locations. The authors also showed that gene disruption efficiency could be improved by optimization of the levels of CRISPR protein and gRNA expression. Hlavová et al. (Biotechnol. Adv. 2015) discusses development of species or strains of microalgae using techniques such as CRISPR to target nuclear and chloroplast genes for insertional mutagenesis and screening. The methods of Stovicek and Hlavová may be applied to the CRISPR effector protein system of the present invention.

U.S. Pat. No. 8,945,839 describes a method for engineering Micro-Algae (*Chlamydomonas reinhardtii* cells) species using Cas9. Using similar tools, the methods of the CRISPR-Cas system described herein can be applied on *Chlamydomonas* species and other algae. In particular embodiments, CRISPR protein and guide RNA are introduced in algae expressed using a vector that expresses CRISPR protein under the control of a constitutive promoter such as Hsp70A-Rbc S2 or Beta2-tubulin. Guide RNA will be delivered using a vector containing T7 promoter. Alternatively, CRISPR protein mRNA and in vitro transcribed guide RNA can be delivered to algal cells. Electroporation protocol follows standard recommended protocol from the GeneArt *Chlamydomonas* Engineering kit.

The Use of CRISPR/Cas in the Generation of Micro-Organisms Capable of Fatty Acid Production In particular embodiments, the methods of the invention are used for the generation of genetically engineered microorganisms capable of the production of fatty esters, such as fatty acid methyl esters ("FAME") and fatty acid ethyl esters ("FAEE").

Typically, host cells can be engineered to produce fatty esters from a carbon source, such as an alcohol, present in the medium, by expression or overexpression of a gene encoding a thioesterase, a gene encoding an acyl-CoA synthase, and a gene encoding an ester synthase. Accordingly, the methods provided herein are used to modify a micro-organisms so as to overexpress or introduce a thioesterase gene, a gene encoding an acyl-CoA synthase, and a gene encoding an ester synthase. In particular embodiments, the thioesterase gene is selected from tesA, 'tesA, tesB, fatB, fatB2, fatB3, fatA1, or fatA. In particular embodiments, the gene encoding an acyl-CoA synthase is selected from fadDJadK, BH3103, pfl-4354, EAV15023, fadD1, fadD2, RPC_4074, fadDD35, fadDD22, faa39, or an identified gene encoding an enzyme having the same properties. In particular embodiments, the gene encoding an ester synthase is a gene encoding a synthase/acyl-CoA: diacylglycerol acyltransferase from *Simmondsia chinensis, Acinetobacter* sp. ADP, *Alcanivorax borkumensis, Pseudomonas aeruginosa, Fundibacter jadensis, Arabidopsis thaliana*, or *Alcaligenes eutrophus*, or a variant thereof. Additionally, or alternatively, the methods provided herein are used to decrease expression in said micro-organism of at least one of a gene encoding an acyl-CoA dehydrogenase, a gene encoding an outer membrane protein receptor, and a gene encoding a transcriptional regulator of fatty acid biosynthesis. In particular embodiments one or more of these genes is inactivated, such as by introduction of a mutation. In particular embodiments, the gene encoding an acyl-CoA dehydrogenase is fadE. In particular embodiments, the gene encoding a transcriptional regulator of fatty acid biosynthesis encodes a DNA transcription repressor, for example, fabR.

Additionally, or alternatively, said micro-organism is modified to reduce expression of at least one of a gene encoding a pyruvate formate lyase, a gene encoding a lactate dehydrogenase, or both. In particular embodiments, the gene encoding a pyruvate formate lyase is pflB. In particular embodiments, the gene encoding a lactate dehydrogenase is ldhA. In particular embodiments one or more of these genes is inactivated, such as by introduction of a mutation therein.

In particular embodiments, the micro-organism is selected from the genus *Escherichia, Bacillus, Lactobacillus, Rhodococcus, Synechococcus, Synechocystis, Pseudomonas, Aspergillus, Trichoderma, Neurospora, Fusarium, Humicola, Rhizomucor, Kluyveromyces, Pichia, Mucor, Myceliophthora, Penicillium, Phanerochaete, Pleurotus, Trametes, Chrysosporium, Saccharomyces, Stenotrophomonas, Schizosaccharomyces, Yarrowia*, or *Streptomyces*.

The Use of CRISPR-Cas in the Generation of Micro-Organisms Capable of Organic Acid Production The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase. In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally, or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The Use of CRISPR/Cas in the Generation of Improved Xylose or Cellobiose Utilizing Yeasts Strains In particular embodiments, the CRISPR-Cas system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc. Natl. Acad. Sci. USA 108(2):504-9 and Galazka, J. M., et al. (2010) Science 330(6000):84-6. Resulting libraries of double-stranded DNA molecules, each comprising a random mutation in such a selected gene could be co-transformed with the components of the CRISPR-Cas system into a yeast strain (for instance S288C) and strains can be selected with enhanced xylose or cellobiose utilization capacity, as described in WO2015138855.

The Use of CRISPR/Cas in the Generation of Improved Yeasts Strains for Use in Isoprenoid Biosynthesis Tadas Jakočiūnas et al. described the successful application of a multiplex CRISPR/Cas system for genome engineering of up to 5 different genomic loci in one transformation step in baker's yeast *Saccharomyces cerevisiae* (Metabolic Engineering Volume 28, March 2015, Pages 213-222) resulting in strains with high mevalonate production, a key intermediate for the industrially important isoprenoid biosynthesis pathway. In particular embodiments, the CRISPR-Cas system may be applied in a multiplex genome engineering method as described herein for identifying additional high producing yeast strains for use in isoprenoid synthesis.

The Use of CRISPR/Cas in the Generation of Lactic Acid Producing Yeasts Strains

In another embodiment, successful application of a multiplex CRISPR-Cas system is encompassed. In analogy with Vratislav Stovicek et al. (Metabolic Engineering Communications, Volume 2, December 2015, Pages 13-22), improved lactic acid-producing strains can be designed and obtained in a single transformation event. In a particular embodiment, the CRISPR-Cas system is used for simultaneously inserting the heterologous lactate dehydrogenase gene and disruption of two endogenous genes PDC1 and PDC5 genes.

Further Applications of the CRISPR-Cas System in Plants

In particular embodiments, the CRISPR system, and preferably the CRISPR-Cas system described herein, can be used for visualization of genetic element dynamics. For example, CRISPR imaging can visualize either repetitive or non-repetitive genomic sequences, report telomere length change and telomere movements and monitor the dynamics of gene loci throughout the cell cycle (Chen et al., Cell, 2013). These methods may also be applied to plants.

Other applications of the CRISPR system, and preferably the CRISPR-Cas system described herein, is the targeted gene disruption positive-selection screening in vitro and in vivo (Malina et al., *Genes and Development*, 2013). These methods may also be applied to plants.

In particular embodiments, fusion of inactive CRISPR protein endonucleases with histone-modifying enzymes can introduce custom changes in the complex epigenome (Rusk et al., *Nature Methods*, 2014). These methods may also be applied to plants.

In particular embodiments, the CRISPR system, and preferably the CRISPR-Cas system described herein, can be used to purify a specific portion of the chromatin and identify the associated proteins, thus elucidating their regulatory roles in transcription (Waldrip et al., *Epigenetics*, 2014). These methods may also be applied to plants.

In particular embodiments, present invention can be used as a therapy for virus removal in plant systems as it is able to cleave both viral DNA and RNA. Previous studies in human systems have demonstrated the success of utilizing CRISPR in targeting the single strand RNA virus, hepatitis C (A. Price, et al., Proc. Natl. Acad. Sci, 2015) as well as the double stranded DNA virus, hepatitis B (V. Ramanan, et al., Sci. Rep, 2015). These methods may also be adapted for using the CRISPR-Cas system in plants.

In particular embodiments, present invention could be used to alter genome complexity. In further particular embodiment, the CRISPR system, and preferably the CRISPR-Cas system described herein, can be used to disrupt or alter chromosome number and generate haploid plants, which only contain chromosomes from one parent. Such plants can be induced to undergo chromosome duplication and converted into diploid plants containing only homozygous alleles (Karimi-Ashtiyani et al., PNAS, 2015; Anton et al., Nucleus, 2014). These methods may also be applied to plants.

In particular embodiments, the CRISPR-Cas system described herein, can be used for self-cleavage. In these embodiments, the promotor of the CRISPR protein and gRNA can be a constitutive promotor and a second gRNA is introduced in the same transformation cassette, but controlled by an inducible promoter. This second gRNA can be designated to induce site-specific cleavage in the CRISPR protein gene in order to create a non-functional CRISPR protein. In a further particular embodiment, the second gRNA induces cleavage on both ends of the transformation cassette, resulting in the removal of the cassette from the host genome. This system offers a controlled duration of cellular exposure to the Cas enzyme and further minimizes off-target editing. Furthermore, cleavage of both ends of a CRISPR/Cas cassette can be used to generate transgene-free T0 plants with biallelic mutations (as described for Cas9 e.g. Moore et al., Nucleic Acids Research, 2014; Schaeffer et al., Plant Science, 2015). The methods of Moore et al. may be applied to the CRISPR-Cas systems described herein.

Sugano et al. (Plant Cell Physiol. 2014 March; 55(3):475-81. doi: 10.1093/pcp/pcu014. Epub 2014 Jan. 18) reports the application of CRISPR-Cas9 to targeted mutagenesis in the liverwort *Marchantia polymorpha* L., which has emerged as a model species for studying land plant evolution. The U6 promoter of *M. polymorpha* was identified and cloned to express the gRNA. The target sequence of the gRNA was designed to disrupt the gene encoding auxin response factor 1 (ARF1) in *M. polymorpha*. Using *Agrobacterium*-mediated transformation, Sugano et al. isolated stable mutants in the gametophyte generation of *M. polymorpha*. CRISPR-Cas-based site-directed mutagenesis in vivo was achieved using either the Cauliflower mosaic virus 35S or *M. polymorpha* EF1α promoter to express CRISPR protein. Isolated mutant individuals showing an auxin-resistant phenotype were not chimeric. Moreover, stable mutants were produced by asexual reproduction of T1 plants. Multiple arf1 alleles were easily established using CRISPR-Cas-based targeted mutagenesis. The methods of Sugano et al. may be applied to the CRISPR effector protein system of the present invention.

Kabadi et al. (Nucleic Acids Res. 2014 Oct. 29; 42(19): e147. doi: 10.1093/nar/gku749. Epub 2014 Aug. 13) developed a single lentiviral system to express a Cas9 variant, a reporter gene and up to four sgRNAs from independent RNA polymerase III promoters that are incorporated into the vector by a convenient Golden Gate cloning method. Each sgRNA was efficiently expressed and can mediate multiplex gene editing and sustained transcriptional activation in immortalized and primary human cells. The methods of Kabadi et al. may be applied to the CRISPR effector protein system of the present invention.

Ling et al. (BMC Plant Biology 2014, 14:327) developed a CRISPR-Cas9 binary vector set based on the pGreen or pCAMBIA backbone, as well as a gRNA This toolkit requires no restriction enzymes besides BsaI to generate final constructs harboring maize-codon optimized CRISPR protein and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the T1 generation. Moreover, the multiple-gene mutations could be inherited by the next generation (guide RNA) module vector set, as a toolkit for multiplex genome editing in plants. The toolbox of Lin et al. may be applied to the CRISPR effector protein system of the present invention.

Protocols for targeted plant genome editing via CRISPR-Cas are also available based on those disclosed for the CRISPR-Cas9 system in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR-Cas system to generating targeted genome modifications in whole plants are also discussed. The protocols described in the chapter may be applied to the CRISPR effector protein system of the present invention.

Ma et al. (Mol Plant. 2015 Aug. 3; 8(8):1274-84. doi: 10.1016/j.molp.2015.04.007) reports robust CRISPR-Cas9 vector system, utilizing a plant codon optimized Cas9 gene, for convenient and high-efficiency multiplex genome editing in monocot and dicot plants. Ma et al. designed PCR-based procedures to rapidly generate multiple sgRNA expression cassettes, which can be assembled into the binary CRISPR-Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in T0 rice and T1*Arabidopsis* plants by simultaneous targeting of multiple (up to eight) members of a gene family, multiple genes in a biosynthetic pathway, or multiple sites in a single gene. The methods of Ma et al. may be applied to the CRISPR effector protein system of the present invention.

Lowder et al. (Plant Physiol. 2015 Aug. 21. pii: pp. 00636.2015) also developed a CRISPR-Cas9 toolbox enables multiplex genome editing and transcriptional regulation of expressed, silenced or non-coding genes in plants. This toolbox provides researchers with a protocol and reagents to quickly and efficiently assemble functional CRISPR-Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cas9 (WT, nickase or dCas9) and gRNA(s) into a T-DNA destination-vector of interest. The assembly method is based on both Golden Gate assembly and MultiSite Gateway recombination. Three modules are required for assembly. The first module is a Cas9 entry vector, which contains promoterless Cas9 or its derivative genes flanked by attL1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cas9 expression. The toolbox of Lowder et al. may be applied to the CRISPR effector protein system of the present invention.

Wang et al. (bioRxiv 051342; doi: doi.org/10.1101/051342; Epub. May 12, 2016) demonstrate editing of homoeologous copies of four genes affecting important agronomic traits in hexaploid wheat using a multiplexed gene editing construct with several gRNA-tRNA units under the control of a single promoter.

In an advantageous embodiment, the plant may be a tree. The present invention may also utilize the herein disclosed CRISPR Cas system for herbaceous systems (see, e.g., Belhaj et al., Plant Methods 9: 39 and Harrison et al., Genes & Development 28: 1859-1872). In a particularly advantageous embodiment, the CRISPR Cas system of the present invention may target single nucleotide polymorphisms (SNPs) in trees (see, e.g., Zhou et al., New Phytologist, Volume 208, Issue 2, pages 298-301, October 2015). In the Zhou et al. study, the authors applied a CRISPR Cas system in the woody perennial *Populus* using the 4-coumarate:CoA ligase (4CL) gene family as a case study and achieved 100% mutational efficiency for two 4CL genes targeted, with every transformant examined carrying biallelic modifications. In the Zhou et al., study, the CRISPR-Cas9 system was highly sensitive to single nucleotide polymorphisms (SNPs), as cleavage for a third 4CL gene was abolished due to SNPs in the target sequence. These methods may be applied to the CRISPR effector protein system of the present invention.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR-Cas editing. The *Populus tremula* x alba clone 717-1B4 routinely used for transformation is divergent from the genome-sequenced *Populus trichocarpa*. Therefore, the 4CL1 and 4CL2 gRNAs designed from the reference genome are interrogated with in-house 717 RNA-Seq data to ensure the absence of SNPs which could limit Cas efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the *Medicago* U6.6 promoter, along with a human codon-optimized Cas under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases. These methods may be applied to the CRISPR effector protein system of the present invention.

In plants, pathogens are often host-specific. For example, *Fusarium oxysporum* f. sp. *lycopersici* causes tomato wilt but attacks only tomato, and *F. oxysporum* f *dianthi Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to conduct genome-wide screening of lncRNAs. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

The following table provides additional references and related fields for which the CRISPR-Cas complexes, modified effector proteins, systems, and methods of optimization may be used to improve bioproduction.

TABLE 12

| | | |
|---|---|---|
| Feb. 17, 2014 | PCT/US15/63434 (WO2016/099887) | Compositions and methods for efficient gene editing in *E. coli* using guide RNA/Cas endonuclease systems in combination with circular polynucleotide modification templates. |
| Aug. 13, 2014 | PCT/US15/41256 (WO2016/025131) | Genetic targeting in non-conventional yeast using an RNA-guided endonuclease. |
| Nov. 6, 2014 | PCT/US15/58760 (WO2016/073433) | Peptide-mediated delivery of RNA-guided endonuclease into cells. |
| Oct. 12, 2015 | PCT/US16/56404 (WO2017/066175) | Protected DNA templates for gene modification and increased homologous recombination in cells and methods of use. |
| Dec. 11, 2015 | PCT/US16/65070 (WO2017/100158) | Methods and compositions for enhanced nuclease-mediated genome modification and reduced off-target site effects. |
| Dec. 18, 2015 | PCT/US16/65537 (WO2017/105991) | Methods and compositions for T-RNA based guide RNA expression. |
| Dec. 18, 2015 | PCT/US16/66772 (WO2017/106414) | Methods and compositions for polymerase II (Pol-II) based guide RNA expression. |
| Dec. 16, 2014 | PCT/US15/65693 (WO2016/100272) | Fungal genome modification systems and methods of use. |
| Dec. 16, 2014 | PCT/US15/66195 (WO2016/100571) | Fungal genome modification systems and methods of use |
| Dec. 16, 2014 | PCT/US15/66192 (WO 2016/100568) | Fungal genome modification systems and methods of use. |
| Dec. 16, 2014 | PCT/US15/66178 (WO 2016/100562) | Use of a helper strain with silenced NHEJ to improve homologous integration of targeted DNA cassettes in *Trichoderma reesei*. |
| Jul. 28, 2015 | PCT/US16/44489 (WO 2017/019867) | Genome editing systems and methods of use. |

Improved Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc. In some embodiments, the improved plants and yeast cells comprise one or more lncRNA genes or protein-coding genes regulated by said lncRNAs mutated, knocked-out, or knocked-down.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the CRISPR system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc of any foreign gene, including those encoding CRISPR components, so as to avoid the presence of foreign DNA in the genome of the plant. This can be of interest as the regulatory requirements for non-transgenic plants are less rigorous.

The CRISPR systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the identification and/or generation of "improved plants, algae, fungi, yeast, etc" in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the CRISPR-Cas system for plant, algae, fungi, yeast, etc. genome editing include, but are not limited to: introduction of one or more foreign genes to confer an agricultural trait of interest; editing of endogenous genes to confer an agricultural trait of interest; modulating of endogenous genes by the CRISPR-Cas system to confer an agricultural trait of interest. Exemplary genes conferring agronomic traits include, but are not limited to, genes that confer resistance to pests or diseases; genes involved in plant diseases, such as those listed in WO 2013046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc; generate genetic variation in a crop of interest; affect fruit-ripening; increasing storage life of plants/algae etc; reducing allergen in plants/algae etc; ensure a value added trait (e.g. nutritional improvement); Screening methods for endogenous genes of interest; biofuel, fatty acid, organic acid, etc. production.

Although the invention and its advantages have been described in detail, it should be understood that various changes, substitutions and alterations can be made herein without departing from the spirit and scope of the invention as defined in the appended claims.

The invention will be further illustrated in the following Examples which are given for illustration purposes only and are not intended to limit the invention in any way.

ADDITIONAL EMBODIMENTS

Embodiment 1. A method of treating melanoma resistant to a BRAF inhibitor, comprising administering to a patient suffering from melanoma resistant to the BRAF inhibitor an effective amount of a pharmaceutical composition that inhibits a lncRNA locus selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873, or a gene regulated by the lncRNA locus.

Embodiment 2. The method of Embodiment 1, wherein the melanoma is selected from the group consisting of nodular melanoma, lentigo maligna, lentigo maligna melanoma, acral lentiginous melanoma, superficial spreading melanoma, mucosal melanoma, polypoid melanoma, desmoplastic melanoma, amelanotic melanoma, and soft-tissue melanoma.

Embodiment 3. The method of Embodiment 1, wherein the BRAF inhibitor is selected from the group consisting of Vemurafenib, Dabrafenib, Sorafenib, GDC-0879, PLX-4720, and LGX818.

Embodiment 4. The method of Embodiment 1, wherein the pharmaceutical composition inhibits TCONS_00015940 or a gene regulated by TCONS_00015940.

Embodiment 5. The method of Embodiment 4, wherein the pharmaceutical composition inhibits MOB3B.

Embodiment 6. The method of Embodiment 4 or 5, wherein TCONS_00015940 or MOB3B is inhibited by mutating, deleting, or transcriptionally inactivating TCONS_00015940 or MOB3B by an RNA-guided DNA binding protein, a zinc finger, a zinc finger nuclease (ZFN), a transcription activator-like effector (TALE), a transcription activator-like effector nuclease (TALEN), or a meganuclease.

Embodiment 7. The method of Embodiment 6, wherein the RNA-guided DNA binding protein is a Type-II or Type-V CRISPR-Cas effector.

Embodiment 8. The method of Embodiment 7, wherein TCONS_00015940 or MOB3B is inhibited by mutating, deleting, or transcriptionally inactivating TCONS_00015940 or MOB3B with a non-naturally occurring or engineered composition comprising: (i) a Type-II or Type-V CRISPR-Cas effector protein or a DNA or mRNA encoding said Type-II or Type-V CRISPR-Cas effector protein, and (ii) a guide RNA targeting TCONS_00015940 or MOB3B, or a DNA encoding the guide RNA, wherein the Type-II or Type V CRISPR-Cas effector protein is capable of forming a complex with the guide RNA, and the guide RNA is capable of directing sequence-specific binding of the complex to the target sequence.

Embodiment 9. The method of Embodiment 4 or 5, wherein TCONS_00015940 or MOB3B is inhibited by downregulating EMICERI or an mRNA transcript of MOB3B with an antisense nucleic acid, an interfering RNA, a microRNA, a riboswitch, a ribosome or catalytic RNA, or an RNA-guided RNA binding protein.

Embodiment 10. The method of Embodiment 9, wherein the RNA-guided RNA binding protein is a Type-VI CRISPR-Cas effector.

Embodiment 11. The method of Embodiment 10, wherein TCONS_00015940 or MOB3B is inhibited by downregulating EMICERI or an mRNA transcript of MOB3B with a non-naturally occurring or engineered compositions comprising: (i) a Type-VI CRISPR-Cas effector protein or a DNA or mRNA encoding said Type-VI CRISPR-Cas effector protein, and (ii) a guide RNA targeting EMICERI or an mRNA transcript of MOB3B, or a DNA encoding the guide RNA, wherein the Type-VI CRISPR-Cas effector protein is capable of forming a complex with the guide RNA, and the guide RNA is capable of directing sequence-specific binding of the complex to the target sequence.

Embodiment 12. The method of Embodiment 5, wherein MOB3B is inhibited by administration of a small molecule inhibitor against the polypeptide encoded by MOB3B.

Embodiment 13. The method of Embodiment 5, wherein MOB3B is inhibited by administration of an antibody against the polypeptide encoded by MOB3B.

Embodiment 14. A method of identifying a melanoma cell resistant to a BRAF inhibitor, comprising measuring an expression level of a lncRNA locus or a gene regulated by the lncRNA locus in a biological sample of a patient suffering from melanoma, wherein the lncRNA locus is selected from the group consisting of TCONS_00011252, NR_034078, TCONS_00010506, TCONS_00026344, TCONS_00015940, TCONS_00028298, TCONS_00026380, TCONS_00009861, TCONS_00026521, TCONS_00016127, NR_125939, NR_033834, TCONS_00021026, TCONS_00006579, NR_109890, and NR_026873, and comparing the expression level of the lncRNA locus or the gene regulated by the lncRNA locus of the patient to that of a control individual not suffering from a cancer that is resistant to a BRAF inhibitor, wherein a statistically significant higher expression level of the lncRNA locus or the gene regulated by the lncRNA locus of the patient is indicative of the presence of a melanoma cell resistant to a BRAF inhibitor.

Embodiment 15. The method of Embodiment 14, wherein the melanoma is selected from the group consisting of nodular melanoma, lentigo maligna, lentigo maligna melanoma, acral lentiginous melanoma, superficial spreading melanoma, mucosal melanoma, polypoid melanoma, desmoplastic melanoma, amelanotic melanoma, and soft-tissue melanoma.

Embodiment 16. The method of Embodiment 14, wherein the BRAF inhibitor is selected from the group consisting of Vemurafenib, Dabrafenib, Sorafenib, GDC-0879, PLX-4720, and LGX818.

Embodiment 17. The method of Embodiment 14, wherein the BRAF inhibitor is vemurafenib.

Embodiment 18. The method of Embodiment 14, wherein the method comprising measuring the expression level of at least one lncRNA locus selected from the group consisting of TCONS_00011252, NR_034078, TCONS_00010506, TCONS_00026344, and TCONS_00015940.

Embodiment 19. The method of Embodiment 14, wherein the method comprising measuring the expression level of at least one gene selected from the group consisting of EQTN, MOB3B, IFNK, and C9orf72.

Embodiment 20. The method of Embodiment 14, wherein the method comprising measuring the expression level of TCONS_00015940.

Embodiment 21. The method of Embodiment 14, wherein the method comprising measuring the expression level of MOB3B Embodiment 22. The method of Embodiment 17, further comprising diagnosing the patient as having vemurafenib resistant melanoma based on a statistically significant higher expression level of the lncRNA locus or the gene regulated by the lncRNA locus of the patient compared to that of a control individual not suffering from vemurafenib resistant melanoma.

Embodiment 23. The method of Embodiment 22, further comprising administering to the patient a pharmaceutical composition comprising an active ingredient different from vemurafenib.

Embodiment 24. A method of drug screening, comprising contacting a melanoma cell comprising transcriptionally activated EMICERI and is resistant to a BRAF inhibitor, with a candidate compound and optionally the BRAF inhibitor, and measuring apoptosis of melanoma cell to identify a compound capable of overcoming resistance to the BRAF inhibitor.

Embodiment 25. The method of Embodiment 24, wherein the melanoma cell comprises a CRISPR-Cas effector, wherein the CRISPR-Cas effector is not catalytically competent.

Embodiment 26. The method of Embodiment 25, wherein the CRISPR-Cas effector is fused to a transcriptional activator domain.

Embodiment 27. The method of Embodiment 25, wherein the melanoma cell further comprises a guide RNA targeting a genomic sequence encoding TCONS_00015940 or being associated with transcription of TCONS_00015940, wherein the guide RNA comprises a loop capable of binding a transcriptional activator domain.

Embodiment 28. A melanoma cell having BRAF inhibitor resistance and comprising (a) a CRISPR-Cas effector that is not catalytically competent, and (b) a guide RNA targeting a genomic sequence encoding TCONS_00015940 or being associated with transcription of TCONS_00015940, wherein the guide RNA comprises a loop capable of binding a transcriptional activator domain.

Embodiment 29. A method for identifying a lncRNA locus associated with resistance to a drug, comprising: introducing a library of guide RNAs into a population of cells, the cells either expressing a modified Cas protein that is not catalytically competent or having the modified Cas protein or a coding sequence thereof introduced simultaneously or sequentially with the guide RNAs, wherein the guide RNAs target different genomic sequences encoding lncRNA or associated with lncRNA transcription, wherein the guide RNAs optionally comprise a loop capable of binding a transcriptional activator domain or a transcription repressor domain, and wherein the modified Cas protein is optionally fused to a transcription activator domain or a transcription repressor domain; exposing the cells to the drug and selecting cells based on resistance to the drug; and sequencing guide RNAs present in the selected cells, wherein the enrichment or depletion of guide RNAs are quantified and/or ranked to identify a lncRNA locus associated with the drug resistance.

Embodiment 30. A method for identifying a lncRNA locus associated with resistance to a cancer drug, comprising: introducing a library of guide RNAs into a population of cancer cells, the cancer cells either expressing a modified Cas protein that is not catalytically competent fused to a transcription activator domain or having the modified Cas protein or a coding sequence thereof introduced simultaneously or sequentially with the guide RNAs, wherein the guide RNAs target different genomic sequences encoding lncRNA or associated with lncRNA transcription, and wherein the guide RNAs comprise a loop capable of binding a transcriptional activator domain; exposing the cancer cells to the cancer drug and selecting cancer cells based on resistance to the cancer drug; and sequencing guide RNAs present in the selected cells, wherein the enrichment of guide RNAs are quantified and/or ranked to identify a lncRNA locus associated with the resistance to the cancer drug.

Embodiment 31. The method of Embodiment 8, wherein the CRISPR-Cas effector protein is Cas9 or Cpf1.

Embodiment 32. The method of Embodiment 11, wherein the CRISPR-Cas effector protein is C2c2 or Cas13b.

Embodiment 33. The method of any of Embodiments 8, 11 and 31-32, wherein the CRISPR-Cas effector protein is a nuclease.

Embodiment 34. The method of any of Embodiments 8, 11 and 31-32, wherein the CRISPR-Cas effector protein is a nickase.

Embodiment 35. The method of any of Embodiments 8, 11 and 31-32, wherein the CRISPR-Cas effector protein is not catalytically competent.

Embodiment 36. The method of any of Embodiments 35, wherein the CRISPR-Cas effector protein is fused to a transcriptional repressor domain.

Embodiment 37. The method of any of Embodiments 8, 11 and 31-36, wherein the naturally occurring or engineered composition comprising (i) and (ii) is delivered by a viral vector.

Embodiment 38. The method of any of Embodiments 8, 11 and 31-36, wherein the naturally occurring or engineered composition comprising (i) and (ii) is delivered by a lipid nanoparticle.

Embodiment 39. A pharmaceutical composition for reducing or overcoming drug resistance, comprising: (i) a CRISPR-Cas effector protein or a DNA or mRNA encoding said CRISPR-Cas effector protein, and (ii) a guide RNA targeting a genomic sequence encoding a lncRNA locus or regulating transcription of the lncRNA locus, or transcript of the lncRNA locus, wherein the lncRNA locus is associated with resistance to a drug, or a DNA encoding the guide RNA, wherein the CRISPR-Cas effector protein is capable of forming a complex with the guide RNA, and the guide RNA is capable of directing sequence-specific binding to the target sequence.

Embodiment 40. A pharmaceutical composition for reducing or overcoming Vemurafenib resistance, comprising: (i) a CRISPR-Cas effector protein or a DNA or mRNA encoding said CRISPR-Cas effector protein, and (ii) a guide RNA targeting TCONS_00015940, EMICERI, MOB3B or an mRNA transcript of MOB3B, or a DNA encoding the guide RNA, wherein the CRISPR-Cas effector protein is capable of forming a complex with the guide RNA, and the guide RNA is capable of directing sequence-specific binding to the target sequence.

Embodiment 41. The pharmaceutical composition of Embodiment 39 or 40, wherein the CRISPR-Cas effector protein is a Type-II or Type-V CRISPR-Cas effector protein.

Embodiment 42. The pharmaceutical composition of Embodiment 41, wherein the CRISPR-Cas effector protein is Cas9 or Cpf1.

Embodiment 43. The pharmaceutical composition of Embodiment 39 or 40, wherein the CRISPR-Cas effector protein is a Type-VI CRISPR-Cas effector protein.

Embodiment 44. The pharmaceutical composition of Embodiment 43, wherein the CRISPR-Cas effector protein is C2c2 or Cas13b.

Embodiment 45. The pharmaceutical composition of any of Embodiments 39-44, wherein the CRISPR-Cas effector protein is a nuclease.

Embodiment 46. The pharmaceutical composition of any of Embodiments 39-44, wherein the CRISPR-Cas effector protein is a nickase.

Embodiment 47. The pharmaceutical composition of any of Embodiments 39-44, wherein the CRISPR-Cas effector protein is not catalytically competent.

Embodiment 48. The pharmaceutical composition of any of Embodiments 47, wherein the CRISPR-Cas effector protein is fused to a transcriptional repressor domain.

Embodiment 49. The pharmaceutical composition of any of Embodiments 39-48, wherein the pharmaceutical composition comprises a viral vector comprising (i) and (ii).

Embodiment 50. The pharmaceutical composition of any of Embodiments 39-48, wherein the pharmaceutical composition comprises a lipid nanoparticle comprising (i) and (ii).

Embodiment 51. A method for identifying a lncRNA locus associated with a desirable genotype or phenotype, comprising: introducing a library of CRISPR guides into a population of cells, the cells either expressing a modified Cas protein that is not catalytically competent or having the modified Cas protein or a coding sequence thereof introduced simultaneously or sequentially with the CRISPR guides, wherein the CRISPR guides target different genomic sequences encoding lncRNA or associated with lncRNA transcription, wherein the CRISPR guides optionally comprise a loop capable of binding a transcriptional activator domain or a transcription repressor domain, and wherein the modified Cas protein is optionally linked to a transcription activator domain or a transcription repressor domain; selecting cells based on the desirable genotype or phenotype; and sequencing CRISPR guides present in the selected cells, wherein the enrichment or depletion of CRISPR guides are quantified and/or ranked to identify a lncRNA locus associated with the desirable genotype or phenotype.

Embodiment 52. The method of Embodiment 51, wherein the population of cells are plant cells or plant protoplasts.

Embodiment 53. The method of Embodiment 52, wherein the plant cells or plant protoplasts are from a monocotyledonous plant.

Embodiment 54. The method of Embodiment 53, wherein the monocotyledonous plant is selected from the group consisting of wheat, turf, turf grass, cereal, maize, rice, oat, wheat, barley, sorghum, orchid, iris, lily, onion, banana, sugarcane, sorghum, palm, and *setaria*.

Embodiment 55. The method of Embodiment 52, wherein the plant cells or plant protoplasts are from a dicotyledonous plant.

Embodiment 56. The method of Embodiment 55, wherein the dicotyledonous plant is selected from the group consisting of avocado, potato, tobacco, tomato, eggplant, sugarbeet, broccoli, cassava, sweet potato, pepper, cotton, poinsettia, legumes, alfalfa, soybean, carrot, strawberry, lettuce, oak, maple, walnut, rose, mint, squash, daisy, and *Arabidopsis*.

Embodiment 57. The method of Embodiment 52, wherein the desirable genotype is increased or decreased expression of a gene of interest.

Embodiment 58. The method of Embodiment 57, wherein the method comprises quantitatively labeling single cells using fluorescence in situ hybridization (FISH) according to expression of an mRNA of interest and sorting labeled cells into a plurality of bins based on the expression of the mRNA of interest, and determining in each of the bins relative representation of the CRISPR guides present in the labeled cells to identify a lncRNA locus associated with the desirable genotype.

Embodiment 59. The method of Embodiment 52, wherein the desirable phenotype is selected from the group consisting of increased yield, increased abiotic stress tolerance, increased drought tolerance, increased flood tolerance, increased heat tolerance, increased cold and frost tolerance, increased salt tolerance, increased heavy metal tolerance, increased low-nitrogen tolerance, increased disease resistance, increased pest resistance, increased herbicide resistance (e.g., increased glyphosate resistance), increased biomass production, male sterility (e.g., cytoplasmic male sterility), and a combination thereof.

Embodiment 60. The method of Embodiment 59, wherein the method comprises exposing the plant cells, plant protoplasts, or tissues or plants derived therefrom to a stress condition selected from the group consisting of abiotic stress, drought stress, flood stress, heat stress, cold and frost stress, salt stress, heavy metal stress, low-nitrogen stress, disease stress, pest stress, herbicide stress, or a combination thereof, and selecting plant cells, plant protoplasts, or tissues or plants derived therefrom based on increased tolerance or resistance to the stress condition.

Embodiment 61. A composition comprising a population of at least 500 plant cells or plant protoplasts each comprising (i) a different CRISPR guide targeting a genomic sequence encoding lncRNA or associated with lncRNA transcription and (ii) a modified Cas protein that is not catalytically competent, wherein the CRISPR guides optionally comprise a loop capable of binding a transcriptional activator domain or a transcription repressor domain, and wherein the modified Cas protein is optionally linked to a transcription activator domain or a transcription repressor domain.

Embodiment 62. The method of Embodiment 52 or the composition of Embodiment 61, wherein the modified Cas protein is Cas9, Cpf1, C2c1, or C2c3.

Embodiment 63. The method of Embodiment 52 or the composition of Embodiment 61, wherein the modified Cas protein is fused to a transcription activator domain.

Embodiment 64. The method of Embodiment 52 or the composition of Embodiment 61, wherein the modified Cas protein is fused to a transcription repressor domain.

Embodiment 65. The method of Embodiment 52 or the composition of Embodiment 61, wherein the CRISPR guides comprise a loop capable of binding a transcriptional activator domain.

Embodiment 66. The method of Embodiment 52 or the composition of Embodiment 61, wherein the CRISPR guides comprise a loop capable of binding a transcription repressor domain.

Embodiment 67. The method of Embodiment 52 or the composition of Embodiment 61, wherein one or more CRISPR guides target a cytoplasmic DNA sequence.

Embodiment 68. The method of Embodiment 52 or the composition of Embodiment 61, wherein one or more CRISPR guides target a mitochondrial DNA sequence.

Embodiment 69. The method of Embodiment 52 or the composition of Embodiment 61, wherein the population of plant cells or plant protoplasts comprises at least 2,000 plant cells or plant protoplasts, each comprising a different CRISPR guide targeting a genomic sequence encoding lncRNA or associated with lncRNA transcription.

Embodiment 70. The method of Embodiment 52 or the composition of Embodiment 61, wherein the population of plant cells or plant protoplasts comprises at least 10,000 plant cells or plant protoplasts, each comprising a different CRISPR guide targeting a genomic sequence encoding lncRNA or associated with lncRNA transcription.

WORKING EXAMPLES

Example 1: Methods

Design and Cloning of SAM lncRNA Library

RefSeq noncoding RNAs (Release 69) were filtered for lncRNA transcripts that were longer than 200 bp and not overlapping with RefSeq coding gene isoforms. The RefSeq lncRNA catalog was combined with the Cabili lncRNA catalog and filtered for unique lncRNA transcriptional start sites (TSSs) defined as TSSs that were >50 bp apart. This resulted in 10,504 unique lncRNA TSSs that were targeted with ~10 single guide RNAs (sgRNAs) each for a total library of 95,958 sgRNAs. sgRNAs were designed to target the first 800 bp upstream of each TSS and subsequently filtered for GC content >25%, minimal overlap of the target sequence, and homopolymer stretch <4 bp. After filtering, the remaining sgRNAs were scored according to predicted off-target matches as described previously, and 6 sgRNAs with the best off-target scores were selected in the first 200 bp region upstream of the TSS, 1 in the 200-300 bp region, 1 in the 300-400 bp region, 1 in the 400-600 bp region, and 1 in the 600-800 bp region. In regions with an insufficient number of possible sgRNAs, sgRNAs were selected from the neighboring region closer to the TSS. An additional 500 non-targeting sgRNAs from the GeCKO library were included as controls. Cloning of the SAM sgRNA libraries was performed as previously described with a minimum representation of 100 transformed colonies per sgRNA followed by next-generation sequencing (NGS) validation.

Lentivirus Production and Transduction

For transduction, plasmids were packaged into lentivirus via transfection of library plasmid with appropriate packaging plasmids (psPAX2: Addgene 12260; pMD2.G: Addgene 12259) using Lipofectamine 2000 (Thermo Fisher 11668019) and Plus reagent (Thermo Fisher 11514015) in HEK293FT (Thermo Fisher R70007) as described previously. Human melanoma A375 cells (Sigma-Aldrich 88113005) were cultured in R10 media: RPMI 1640 (Thermo Fisher 61870) supplemented with 10% FBS (VWR 97068-085) and 1% penicillin/streptomycin (Thermo Fisher 15140122). Cells were passaged every other day at a 1:5 ratio. Concentrations for selection agents were determined using a kill curve: 300 μg/mL Zeocin (Thermo Fisher R25001), 10 μg/mL Blasticidin (Thermo Fisher A1113903), and 300 μg/mL Hygromycin (Thermo Fisher 10687010). Cells were transduced via spinfection and selected with the appropriate antibiotic as described previously. During selection, media was refreshed when cells were passaged every 3 days. The duration of selection was 7 days for Zeocin and 5 days for Hygromycin and Blasticidin. Lentiviral titers were calculated by spinfecting cells with 5 different volumes of lentivirus and determining viability after a complete selection of 3 days.

Vemurafenib Resistance Screen

The vemurafenib resistance screen was conducted as a genome-scale SAM coding gene screen. A375 stably integrated with dCas9-VP64 (Addgene 61425) and MS2-P65-HSF1 (Addgene 61426) were transduced with the pooled sgRNA library (Addgene 61427) as described above at an MOI of 0.3 for a total of 4 infection replicates, with a minimal representation of 500 transduced cells per sgRNA in each replicate. Cells were maintained at >500 cells per sgRNA during subsequent passaging. After 7 days of Zeocin selection and 2 days of no antibiotic selection, cells were split into control (DMSO) and vemurafenib (2 μM PLX-4720 dissolved in DMSO, Selleckchem S1152) conditions. Cells were passaged every 2 days for a total of 14 days of control or vemurafenib treatment. At the end of the screening selection, >500 cells per sgRNA in each condition were harvested for gDNA extraction and amplification of the virally integrated sgRNAs. Resulting libraries were deep-sequenced on Illumina MiSeq or NextSeq platforms with a coverage of >25 million reads passing filter per library.

NGS and Screen Hits Analysis

NGS data was de-multiplexed using unique index reads. sgRNA counts were determined based on perfectly matched sequencing reads only. For each condition, a pseudocount of 1 was added to the sgRNA count and the counts were normalized to the total number of counts in the condition. The sgRNA fold change as a result of screening selection was calculated by dividing the normalized sgRNA counts in the vemurafenib condition by the control and taking the base 2 logarithm. RIGER analysis was performed using GENE-E based on the normalized $\log_2$ ratios for each infection replicate. Since a low percentage of functional sgRNAs was expected for each lncRNA, the weighted sum method was used. To determine the empirical false discovery rate (FDR) of lncRNA screening hits, the weighted sum for 10 randomly selected non-targeting sgRNAs in the sgRNA library was used to estimate the P value for each lncRNA and a threshold based on a FDR of 0.05 (Benjamini-Hochberg) was selected that corresponded to a P value of 0.031. 7 candidate lncRNAs were selected based on the average ranking between infection replicates 1 and 2, and 9 candidate lncRNAs were selected based on the average ranking in all 4 infection replicates. All candidate lncRNAs had P value $<10^{-5}$.

Vemurafenib Resistance Assay

A375 cells stably integrated with dCas9-VP64 and MS2-P65-HSF1 were transduced with individual sgRNAs targeting the 16 top candidate lncRNAs from the vemurafenib resistance screen (3 sgRNAs with the highest enrichment per lncRNA; Table 3) or with control non-targeting sgRNA at an MOI of <0.5 and selected with Zeocin for 5 days as described above. For cDNA overexpression, A375 cells or additional melanoma cell lines (A2058, ATCC CRL-11147; COL0679, Sigma-Aldrich 87061210; UACC62, AddexBio C0020003) cultured in R10 media were transduced with cDNA (Table 4) or control GFP at an MOI of <0.5 and selected with Hygromycin for 4 days. At 5 days post transduction, cells were replated at low density ($3\times10^3$ cells per well in a 96-well plate). 2 μM vemurafenib or control DMSO was added 3 h after plating and refreshed every 2 days for 4 days before cell viability was measured using CellTiter-Glo Luminescent Cell Viability Assay (Promega G7571). Significance testing was performed using Student's t-test. For primary patient tumor-derived melanoma cell lines, cells were plated at low density ($2\times10^3$ cells per well in a 96-well plate) and vemurafenib was added 24 h after plating. Cells were treated for 3 days before cell viability was measured. For vemurafenib dose response curves, the indicated concentrations of vemurafenib were added and the normalized percent survival values were fitted with a non-linear curve (log(inhibitor) vs normalized response; Prism 6). Significant differences in log IC50 values was determined using the extra sum-of-squares F test.

qPCR Quantification of Transcript Expression

A375 cells stably integrated with SAM components were transduced with individual sgRNAs targeting top candidate lncRNAs (Table 3), perturbing the EMICERI locus (Table 5), or non-targeting control at an MOI of <0.5 and selected with Zeocin for 5 days as described above. For cDNA overexpression, A375 cells were transduced with cDNA (Table 4) or control GFP at an MOI of <0.5 and selected with Hygromycin for 4 days. Cells were plated at 5 days post transduction at 70% confluency ($3\times10^4$ cells per well in a 96-well plate) and harvested for RNA 24 h after plating. For transcripts that this method could not detect, cells transduced with the respective sgRNAs were plated at 5 days post transduction ($1.8\times10^5$ cells per well in a 24-well plate). RNA was harvested using the RNeasy Plus Mini Kit (Qiagen 74134) and 1 μg of RNA was used for reverse transcription with the qScript Flex cDNA Kit (VWR 95049) and lncRNA-specific primers (Table 6). After reverse transcription, TaqMan qPCR was performed with custom or readymade probes as described previously (Tables 4 and 5). Significance testing was performed using Student's t-test.

RNA Sequencing and Data Analysis

A375 cells transduced with individual sgRNAs targeting validation lncRNAs or with control non-targeting sgRNAs (Table 3) were plated 5 days post transduction at $9\times10^4$ cells per well or $1.8\times10^5$ cells per well respectively in a 24-well plate. For cDNA overexpression, A375 cells were transduced with cDNA (Table 4) or control GFP at an MOI of <0.5 and selected with Hygromycin for 4 days. Cells were treated with 2 μM vemurafenib for 3 days before RNA was harvested as described above. LncRNA activation samples were prepped with TruSeq Stranded Total RNA Sample Prep Kit with Ribo-Zero Gold (Illumina RS-122-2302) and MOB3B activation samples were prepped with NEBNext Ultra RNA Library Prep Kit for Illumina (NEB E7530S) and NEBNext Poly(A) mRNA Magnetic Isolation Module (NEB E7490S). Libraries were deep-sequenced on the Illumina NextSeq platform (>9 million reads per condition). Bowtie index was created based on the human hg19 UCSC genome and known gene and lncRNA transcriptome constructed as described above. Paired-end reads were aligned directly to this index using Bowtie with command line options "-q--phred33-quals-n 2-e 99999999-1 25-I 1-X 1000--chunkmbs 512-p 1-a-m 200-S". Next, RSEM v1.2.22 was run with default parameters on the alignments created by Bowtie to estimate expression levels.

RSEM's TPM estimates for each transcript were transformed to log-space by taking $\log_2(TPM+1)$. Transcripts were considered detected if their transformed expression level was equal to or above 1 (in $\log_2(TPM+1)$ scale). All genes detected in at least one library (out of three libraries per condition) were used to find differentially expressed genes. For lncRNA activation, the Student's t-test was performed on each of the 3 replicates for each targeting sgRNA against both non-targeting sgRNAs. For MOB3B cDNA overexpression, the t-test was performed on the cDNA overexpression against GFP control. Only genes that were significant (p-value pass 0.05 FDR correction) were reported. For lncRNA activation, the genes overlapping all 3 targeting sgRNAs were reported as differentially expressed as a result of lncRNA loci activation. Power analysis for two-sided t-test were performed on each targeting sgRNA against both non-targeting sgRNAs to determine the probability of correctly identifying a gene as differentially expressed.

For annotating EMICERI, TopHat was used to align RNA-seq reads from A375 transduced with sgRNA 2 or sgRNA 3 (Table 5) with command line options "--solexa-quals--num-threads 8--library-type fr-firststrand--transcriptome-max-hits 1--prefilter-multihits--keep-fasta-order". To further investigate the mechanism for MOB3B overexpression, Ingenuity Pathway Analysis was applied to all genes differentially expressed with at least 1.2-fold change or less than 0.7-fold change and the most likely upstream regulator was reported.

Hi-C and chromatin immunoprecipitation with sequencing (ChIP-seq) in GM12878

In situ Hi-C data for GM12878 was obtained and visualized using 2.5 kb-resolution KL-normalized observed matrix. Hi-C data from 7 cell lines suggested similar topological domain annotations as GM12878 (Rao et al. *Cell* 2014), suggesting that the TAD present in GM12878 is consistent across cell types. CTCF ChIP-seq for GM12878 and hg19 generated by the ENCODE Project Consortium was downloaded from UCSC Genome Browser. CTCF motifs were identified using FIMO to search for the "V_CTCF_01" and "V_CTCF_02" position weight matrices from TRANSFAC.

Assay for Transposable and Accessible Chromatin Sequencing (ATAC-Seq)

ATAC-seq samples were prepared as described previously. A375 cells were cultured in R10 as described above and $5\times10^4$ cells in log-phase growth were harvested using an existing ATAC library preparation protocol with minor modifications. Library was sequenced using the Illumina NextSeq platform at ~136 million paired-end reads. Samples were aligned to the human hg19 UCSC genome using Bowtie with command line options "--chunkmbs 256-p 24-S-m 1-X 2000". For quality control, the duplicate read rate was measured using Picard-Tools Mark Duplicates (10-30%) and the mitochondrial read rate (<5%).

PhastCons Sequence Conservation

PhastCons data for primates (n=10 animals), placental mammals (n=33), and vertebrates (n=46) for hg19 were downloaded from UCSC Genome Browser and aligned to the EMICERI locus.

ChIP-Seq for Histone Modifications

ChIP samples were prepared as described previously. Briefly, A375 cells were plated in T-225 flasks and grown to 70-90% confluence. Formaldehyde was added directly to the growth media for a final concentration of 1% for 10 mins at 37° C. to initiate chromatin fixation. The entire two-day ChIP procedure was performed using the EZ-Magna ChIP HiSens Chromatin Immunoprecipitation Kit (Millipore 1710460) according to the manufacturer's protocol. Samples were pulse sonicated with 2 rounds of 10 mins (30s on-off cycles, high frequency) in a rotating water bath sonicator (Diagenode Bioruptor) with 5 mins on ice between each round. To detect histone modifications, antibodies (H3K4me2: Millipore 17-677, H3K4me3: Millipore 04-745, H3K27ac: Millipore 17-683) were optimized individually for each antibody to be 0.5 μL for 1 million cells. 1 μL of IgG (Millipore 12-370) was used for negative control.

After verifying that the IgG ChIP had minimal background, ChIP samples were prepped with NEBNext Ultra II DNA Library Prep Kit for Illumina (NEB E7645S) and deep-sequenced on the Illumina NextSeq platform (>60 million reads per condition). Bowtie was used to align paired-end reads to the human hg19 UCSC genome with command line options "-q-X 500--sam--chunkmbs 512". Next, Model-based analysis of ChIP-seq (MACS) was run with command line options "-g hs-B-S--call-subpeaks" to identify histone modifications.

Western Blot

A375 cells transduced with MOB3B cDNA or GFP control were plated 5 days post transduction at $1.8\times10^5$ cells per well in a 24-well plate. Cells were treated with 2 μM vemurafenib for 6, 12, 24, or 48 h before protein lysates were harvested with RIPA lysis buffer (Cell Signaling Technologies 9806S) containing protease inhibitor (Roche 05892791001) and phosphatase inhibitor (Cell Signaling Technologies 5870S) cocktails. Samples standardized for protein concentration with the Pierce BCA protein assay (Thermo Fisher 23227) were incubated at 70° C. for 10 mins under reducing conditions. After denaturation, samples were separated by Bolt 4-12% Bis-Tris Plus Gels (Thermo Fisher NW04120BOX) and transferred onto a polyvinylidene difluoride membrane using iBlot Transfer Stacks (Thermo Fisher IB401001). Blots were blocked with Odyssey Blocking Buffer (TB S; LiCOr 927-50000) and probed with different primary antibodies [anti-pERK (Cell Signaling Technologies 4370, 1:2000 dilution), anti-ERK (Cell Signaling Technologies 4695, 1:1000 dilution), anti-pAKT (Ser473, Cell Signaling Technologies 4060, 1:1000 dilution), anti-AKT (Cell Signaling Technologies 4691, 1:1000 dilution), anti-ACTB (Sigma A5441, 1:5000 dilution)] overnight at 4° C. Blots were then incubated with secondary antibodies IRDye 680RD Donkey anti-Mouse IgG (LiCOr 925-68072) and IRDye 800CW Donkey anti-Rabbit IgG (LiCOr 925-32213) at 1:20,000 dilution in Odyssey Blocking Buffer for 1 hr at room temperature. p-ERK and p-AKT blots were stripped with Restore PLUS Western Blot Stripping Buffer (Thermo Fisher 46430) before probing for ERK and AKT respectively. Blots were imaged using the Odyssey CLx (LiCOr).

Primary Patient Melanoma-Derived Cell Lines

CLF_SKCM_001_T and CLF_SKCM_004_T melanoma tumor tissues were obtained from Dana-Farber Cancer Institute hospital with informed consent and the cancer cell model line generation was approved by the ethical committee. Tumor tissues were dissected into tiny pieces by scalpers around 100 times. Dissected tissues were dissociated in the collagenase/hyaluronidase (STEMCELL technologies 07912) medium for 1 hour. The red blood cells were further depleted by adding the Ammonium Chloride Solution (STEMCELL technologies 07800). The dissociated cells were plated with the smooth muscle growing medium-2 (Lonza CC-3181) in the six well plate and split when the well confluency reached to 80%. Cells were passaged for 5 times with 1:4 splitting ratio for a sequencing verification. The confirmed BRAF V600E melanoma cell models were be propagated for another 7-15 passages and cryovial preserved. Passage 12 cells were used for this study. All cells were refed every 3-4 days.

Gene Expression and Pharmacological Validation Analysis

Gene expression data (CCLE, TCGA) and pharmacological data (CCLE) were analyzed to better understand the biological relevance of MOB3B. Transcript expression in TCGA and CCLE samples was quantified as follows: 1) FASTQ files were generated from available BAM files using SamToFastq in Picard Tools (broadinstitute.github.io/picard/); 2) reads were aligned with STAR v2.5.2b using parameters from the GTEx Consortium pipeline (github.com/broadinstitute/gtex-pipeline) and genome indexes generated for read lengths of 48 bp (TCGA) and 101 bp (CCLE) (--sjdbOverhang option); 3) expression was quantified using RSEM v1.2.22. For the alignment and quantification steps, annotations for TCONS_00011252, NR_034078, TCONS_00010506, TCONS_00026344, TCONS_00015940_1, TCONS_00015940_2, and NR_109890 were appended to the GENCODE 19 GTF (www.gencodegenes.org/releases/19.html). Gene-level quantifications were also calculated with RNA-SeQC to validate the RSEM results.

Gene expression (RNA-sequencing) and genotyping data were collected from 113 BRAF$^{V600}$-mutant primary and metastatic patient tumors from The Cancer Genome Atlas (TCGA: tcga-data.nci.nih.gov/tcga/). Because pharmacological data was not available for the TCGA melanoma samples, signature gene sets, including some from the Molecular Signature Database (MSigDB), were used to fully map the transcriptional BRAF-inhibitor resistant/sensitive states in TCGA as previously described. The TCGA dataset was used for determining the association between resistance and the expression of EMICERI neighboring genes. Additionally, we sought a more robust scoring system independent of any single gene. Gene expression signatures were generated based on the genes that were differentially expressed as a result of MOB3B overexpression identified from RNA-seq. Using single-sample Gene Set Enrichment Analysis (ssGSEA), a score was generated for each sample that represents the enrichment of the MOB3B gene expression signature in that sample and the extent to which those genes are coordinately up- or down-regulated. Patient tumors were also sorted by EMICERI expression to determine correlation between expression of EMICERI and its neighboring genes.

In the CCLE dataset, gene expression data (RNA-sequencing, GCHub: cghub.ucsc.edu/datasets/ccle.html) and pharmacological data (activity area for MAPK pathway inhibitors) from BRAF$^{V600}$ mutant melanoma cell lines were used to compute the association between PLX-4720 resistance and the gene expression of EMICERI neighboring genes. Similar to the TCGA analysis, the MOB3B overexpression gene signature was determined using ssGSEA projected onto the CCLE RNA-sequencing dataset. Cell lines were also sorted by EMICERI expression to determine correlation between expression of EMICERI and its neighboring genes.

To measure correlations between different features (signature scores, gene expression, or drug-resistance data) in the external cancer datasets, an information-theoretic approach (Information Coefficient; IC) was used and significance was measured using a permutation test (n=10,000), as previously described. The IC was calculated between the feature used to sort the samples (columns) in each dataset and each of the features plotted in the heat map (pharmacological data, gene expression, and signature scores).

Antisense Oligonucleotide (ASO) Knockdown

ASOs targeting EMICERI/II were custom designed using Exiqon's Antisense LNA GapmeR designer (Table 8) and a non-targeting ASO (Exiqon 300610) was included for control. ASOs were resuspended in water to a final concentration of 100 μM. A375 stably expressing SAM components dCas9-VP64 and MS2-p65-HSF1 were nucleofected with 500 ng sgRNA (Table 5; Addgene 73795) and 100 pmol ASO using the SF Cell Line 4D-Nucleofector X Kit S (Lonza V4XC-2032) according to the manufacturer's instructions. Cells were then seeded at $3\times10^4$ cells per well in a 96-well plate. 24 h after nucleofection, cells were selected for the sgRNA plasmid with 1 μg/mL Puromycin (Thermo Fisher A1113803) for 2 days and changes in transcript expression were determined by qPCR as described above.

Polyadenylation Signal Sequence (Poly(A)) Insertion

To truncate EMICERI, the following poly(A) sequences were inserted consecutively 103, 156, and 198 bp downstream of each copy of EMICERI's TSS:

```
Synthetic poly(A):                        (SEQ ID NO: 43)
AATAAAAGATCTTTATTTTCATTAGATCTGTGTGTTGGTTTTTTGTGTG SV40 poly(A):                             (SEQ ID NO: 44)
GTTTATTGCAGCTTATAATGGTTACAAATAAAGCAATAGCATCACAAATT
TCACAAATAAAGCATTTTTTTCACTGCATTCTAGTTGTGGTTTGTCCAAA
CTCATCAATGTATCTTATCATGTCT PGK poly (A):                             (SEQ ID NO: 45)
AAATTGATGATCTATTAAACAATAAAGATGTCCACTAAAATGGAAGTTTT
TTCCTGTCATACTTTGTTAAGAAGGGTGAGAACAGAGTACCTACATTTTG
AATGGAAGGATTGGAGCTACGGGGGTGGGGGTGGGGTGGGATTAGATAAA
TGCCTGCTCTTTACTGAAGGCTCTTTACTATTGCTTTATGATAATGTTTC
ATAGTTGGATATCATAATTTAAACAAGCAAAACCAAATTAAGGGCCAGCT
CATTCCTCCACTCACGATCTATA
```

Poly(A) clones were generated using CRISPR-Cas9 mediated homology-directed repair (HDR). 3 different sgRNAs targeting 103, 156, and 198 bp downstream of EMICERI (HDR sgRNA 1-3, Table 9) and corresponding poly(A) HDR plasmids were used for inserting poly(A) into each of the 3 copies of EMICERI in A375. To construct the Poly(A) HDR plasmids, for each sgRNA the HDR templates that consisted of the 850-900 bp genomic regions flanking the sgRNA cleave site were PCR amplified from A375 genomic DNA using KAPA HiFi HotStart Readymix (KAPA Biosystems KK2602). Then 3 poly(A) sequences (in the order listed above) flanked by the HDR templates were cloned into pUC19 (Addgene 50005). To insert poly(A) downstream of EMICERI's TSS, 3 rounds of HDR were performed with a different sgRNA and respective poly(A) HDR plasmid at each round such that selected clones contained poly(A) sequences in 1 copy of EMICERI in the first round, 2 copies in the second round, and 3 copies in the third round. At each round of HDR, A375 cells were nucleofected with 4 μg of sgRNA and Cas9 plasmid (Addgene 52961) and 2.5 μg of poly(A) HDR plasmid using SF Cell Line 4D-Nucleofector X Kit L (Lonza V4XC-2024) according to the manufacturer's instructions. Cells were then seeded sparsely ($5 \times 10^4$ cells per 10-cm Petri dish) to form single-cell clones. After 24 h, cells were selected for Cas9 expression with 1 μg/mL Puromycin for 2 days and expanded until colonies can be picked (~5 days).

To pick colonies, cells were detached by replacing the media with PBS and incubating at room temperature for 15 mins. Each cell colony was removed from the Petri dish using a 200 μL pipette tip and transferred a well in a 96-well plate for expansion. Clones with poly(A) insertions were identified by 2-round PCR amplification (Table 9), first with primers amplifying outside of the HDR template (HDR primer F1 and HDR primer R, 15 cycles) and then with primers amplifying the region of insertion (HDR primer F2 and HDR primer R, 15 cycles) to avoid detecting the HDR template plasmid as a false positive. Products were run on a gel to identify insertions and Sanger sequencing confirmed that the poly(A) sequences had been inserted at the appropriate site. During each round of HDR, 3 clones with poly(A) insertions and 1 clone without poly(A) insertion were selected for further expansion and characterization. The wild-type clone controls for potential on- and off-target indels.

Table 13. Average RIGER P values for 16 candidate lncRNAs. List of 16 candidate lncRNAs identified using RIGER analysis of sgRNAs in the vemurafenib-treated condition compared to control. The weighted sum method for scoring lncRNAs in RIGER selects for lncRNAs with multiple enriched sgRNAs. P values were averaged across bioreps.

TABLE 13

| LncRNA | Average RIGER P value |
| --- | --- |
| TCONS_00011252 | 0.0006772 |
| NR_034078 | 0.0008635 |
| TCONS_00028298 | 0.003087 |
| TCONS_00026380 | 0.0045605 |
| TCONS_00009861 | 0.00544545 |
| TCONS_00010506 | 0.0056025 |
| TCONS_00026344 | 0.0085145 |
| TCONS_00015940 | 0.0376155 |
| TCONS_00026521 | 0.04021 |
| NR_125939 | 0.04611425 |
| TCONS_00021026 | 0.05726945 |
| NR_109890 | 0.072690275 |
| TCONS_00016127 | 0.0811585 |
| NR_033834 | 0.082505 |
| TCONS_00006579 | 0.08525 |
| NR_026873 | 0.0868275 |

Table 14. Candidate lncRNAs and possible mechanisms. Eleven candidate lncRNAs that conferred strong vemurafenib resistance (at least 2 sgRNAs with >150% normalized percent survival) and corresponding possible mechanisms of action based on data from this study. LncRNA loci with significant transcript upregulation detected by qPCR upon targeting with SAM can potentially mediate resistance through a lncRNA-mediated mechanism, either through a non-local lncRNA function or a local function of the lncRNA or its transcription (column 2). To distinguish between local and non-local functions, lncRNAs in these loci were overexpressed in trans using random lentiviral integration and measured vemurafenib resistance (FIG. 7b, column 4). LncRNA loci that do not mediate resistance in this overexpression system do not have a non-local effect on resistance. Of the 5 lncRNA loci without detectable upregulation, 4 were not expressed in A375 cells. For all lncRNA loci except for EMICERI, it is possible that SAM is mediating resistance by targeting an endogenous, putative enhancer associated with vemurafenib resistance, or possibly by directly activating a nearby promoter in close three-dimensional proximity to the targeted genomic sequence (column 3). RNA-seq were performed for activation of each lncRNA locus to identify nearby genes within 1 Mb of the targeted sites that could potentially contribute to vemurafenib resistance and suggest a local mechanism of the lncRNA locus in regulating a nearby gene (column 5). Two lncRNA TSSs are located in close proximity (<1 kb) to protein-coding genes that have been shown to confer vemurafenib resistance.

TABLE 14

| LncRNA | Mechanism may involve lncRNA or its transcription | Mechanism may involve putative enhancer or direct effect of SAM | Mechanism involves non-local function of lncRNA transcript | Number of nearby genes with significant differential expression |
| --- | --- | --- | --- | --- |
| TCONS_00011252 | Yes | Yes | No | 1 |
| NR_034078 | Yes | Yes | No | See Example 2, Supplementary Discussion. |
| TCONS_00009861 | No | Yes | Not tested | 2 |
| TCONS_00010506 | Yes | Yes | No | 8 |
| TCONS_00026344 | Yes | Yes | No | 3 |
| TCONS_00015940 | Yes | No | No | 7; MOB3B mediates resistance |
| NR_125939 | No | Yes | Not tested | 2 |
| NR_109890 | Yes | Yes | Not tested | 2; EBF1 has previously been shown to mediate vemurafenib resistance in A375 cells upon over-expression |

TABLE 14-continued

| LncRNA | Mechanism may involve lncRNA or its transcription | Mechanism may involve putative enhancer or direct effect of SAM | Mechanism involves non-local function of lncRNA transcript | Number of nearby genes with significant differential expression |
|---|---|---|---|---|
| NR_033834 | No | Yes | Not tested | 1 |
| TCONS_00006579 | No | Yes | Not tested | See Example 2, Supplementary Discussion. |
| NR_026873 | No | Yes | Not tested | 1 |

Table 15. List of validation sgRNAs and corresponding lncRNA targets for validating the screening hits.

TABLE 15

| Name | sgRNA target sequence (5' to 3') | LncRNA target |
|---|---|---|
| V01 | ACGTTGTGTGAGGTTCCTAG (SEQ ID NO: 46) | TCONS_00011252 |
| V02 | GATTCCTTTGGATATATACC (SEQ ID NO: 47) | TCONS_00011252 |
| V03 | AAGAGGATTGCTGGATAACG (SEQ ID NO: 48) | TCONS_00011252 |
| V04 | GACTGCTGCTTAGAAATTCT (SEQ ID NO: 49) | NR_034078 |
| V05 | CCGTGGGAAGAAACAAAGAA (SEQ ID NO: 50) | NR_034078 |
| V06 | CCAGAAGAATAGTTAGTAAA (SEQ ID NO: 51) | NR_034078 |
| V07 | ATGCTATTGTCAGGAAAGAA (SEQ ID NO: 52) | TCONS_00028298 |
| V08 | GACAGGCATTACAAGAACAC (SEQ ID NO: 53) | TCONS_00028298 |
| V09 | GCCCAATAGCAATAACTTTC (SEQ ID NO: 54) | TCONS_00028298 |
| V10 | CAAGATTTCGTTGGCACTGT (SEQ ID NO: 55) | TCONS_00026380 |
| V11 | TGCTGGAGAAGAGATTTCTC (SEQ ID NO: 56) | TCONS_00026380 |
| V12 | TACTGTGCCTTCTCTAATTG (SEQ ID NO: 57) | TCONS_00026380 |
| V13 | AAGTAGCAAGGGAGATTCTT (SEQ ID NO: 58) | TCONS_00009861 |
| V14 | TGCAAAGAAGTCACATTCAC (SEQ ID NO: 59) | TCONS_00009861 |
| V15 | TTATCAACTCAAAGTTCTGG (SEQ ID NO: 60) | TCONS_00009861 |
| V16 | GCGAGAAGATACAAGTATAC (SEQ ID NO: 61) | TCONS_00010506 |
| V17 | TACATATCGAAAGGAAACCT (SEQ ID NO: 62) | TCONS_00010506 |
| V18 | TAATAACTGGTATTGAGGAA (SEQ ID NO: 63) | TCONS_00010506 |
| V19 | ATATGATCAAAGACTACCTG (SEQ ID NO: 64) | TCONS_00026344 |

TABLE 15-continued

| Name | sgRNA target sequence (5' to 3') | LncRNA target |
|---|---|---|
| V20 | CGTGGACTGGATGTTCTCTG (SEQ ID NO: 65) | TCONS_00026344 |
| V21 | CTGTAGACACATTTAAACAG (SEQ ID NO: 66) | TCONS_00026344 |
| V22 | CCACGGTGCTGCCATACCGC (SEQ ID NO: 67) | TCONS_00015940 |
| V23 | CCCGCGAGACAGTCGAGCCC (SEQ ID NO: 68) | TCONS_00015940 |
| V24 | GCGGGTTCTTACTCACCGTG (SEQ ID NO: 69) | TCONS_00015940 |
| V25 | CATCTCTGTGAAGTTGCTTG (SEQ ID NO: 70) | TCONS_00026521 |
| V26 | CACAGCATGAACTTGGAGGT (SEQ ID NO: 71) | TCONS_00026521 |
| V27 | CATAGCTTGGAGAGCTCTAG (SEQ ID NO: 72) | TCONS_00026521 |
| V28 | GAGACTCCAGCATAGCCACA (SEQ ID NO: 73) | NR_125939 |
| V29 | GACAGTTGGCCACATTTGAT (SEQ ID NO: 74) | NR_125939 |
| V30 | ATGGAATTGTAAACAGACTG (SEQ ID NO: 75) | NR_125939 |
| V31 | GATGAATTATAAGCTCACAT (SEQ ID NO: 76) | TCONS_00021026 |
| V32 | TGACCAGGATAGCATAACTA (SEQ ID NO: 77) | TCONS_00021026 |
| V33 | TGAAGTTCACAACTTATCAG (SEQ ID NO: 78) | TCONS_00021026 |
| V34 | GCCAATCGCGGCCCGGGAGC (SEQ ID NO: 79) | NR_109890 |
| V35 | AGTGTGCCTGTGTTTAGCTC (SEQ ID NO: 80) | NR_109890 |
| V36 | AAACAGAATCTCCATCCAGC (SEQ ID NO: 81) | NR_109890 |
| V37 | GCAACTGAACTGAGTACATT (SEQ ID NO: 82) | TCONS_00016127 |
| V38 | GTTTGAAACTGCTTATCTTC (SEQ ID NO: 83) | TCONS_00016127 |
| V39 | TTGTCAAGCATCCATCCTCC (SEQ ID NO: 84) | TCONS_00016127 |
| V40 | CCTCCTCGGAGCCCGGAGCC (SEQ ID NO: 85) | NR_033834 |
| V41 | ACAAGCAAGGGCCTACTTTA (SEQ ID NO: 86) | NR_033834 |
| V42 | GGGCGCTTTCAAAGGGAGGT (SEQ ID NO: 87) | NR_033834 |
| V43 | GCATTTGGCTCACTAGAACA (SEQ ID NO: 88) | TCONSv00006579 |
| V44 | CCTTACCTAAATGGTTCAAA (SEQ ID NO: 89) | TCONS_00006579 |
| V45 | CATAATGATTTCTCAATGGT (SEQ ID NO: 90) | TCONS_00006579 |

TABLE 15-continued

| Name | sgRNA target sequence (5' to 3') | LncRNA target |
|---|---|---|
| V46 | TGCTCCAGCCTGGGCAACAC (SEQ ID NO: 91) | NR_026873 |
| V47 | GGGTTCTCATGATAATGTTA (SEQ ID NO: 92) | NR_026873 |
| V48 | CCCTGTGGATACAAGAAATA (SEQ ID NO: 93) | NR_026873 |
| sgRNA NT1 or sgRNA NT | CTGAAAAAGGAAGGAGTTGA (SEQ ID NO: 94) | Non-targeting |
| sgRNA NT2 | AAGATGAAAGGAAAGGCGTT (SEQ ID NO: 95) | Non-targeting |

Table 16. RefSeq isoforms and TaqMan qPCR probe ID's from Thermo Fisher for overexpressing genes neighboring EMICERI or positive controls.

TABLE 16

| cDNA | RefSeq isoform(s) | Probe ID |
|---|---|---|
| MOB3B | NM_024761 | Hs01557152_m1 |
| IFNK | NM_020124 | Hs00737883_m1 |
| EQTN | NM_020641 | Hs00294888_m1 |
| C9orf72 | NM_018325, NM_001256054 | Hs00376619_m1 |
| LPAR1 | NM_001401, NM_057159 | Hs00173500_m1 |
| GPR35 | NM_005301 | Hs00271114_s1 |

Table 17. sgRNAs for perturbing the EMICERI locus. sgRNA names, target sequences, and target genes used to functionally dissect the EMICERI locus. T1-T16 refer to sgRNAs for tiling SAM across the EMICERI and MOB3B TSSs.

TABLE 18

| Name | sgRNA target sequence (5' to 3') | Target |
|---|---|---|
| sgRNA 1 (T14) | CCACGGTGCTGCCATACCGC (SEQ ID NO: 96) | EMICERI |
| sgRNA2 (T15) | CCCGCGAGACAGTCGAGCCC (SEQ ID NO: 97) | EMICERI |
| sgRNA 3 (T16) | GCGGGTTCTTACTCACCGTG (SEQ ID NO: 98) | EMICERI |
| sgRNA NT | CTGAAAAAGGAAGGAGTTGA (SEQ ID NO: 99) | non-targeting |
| MOB3B sgRNA 1 | GGCTGGAAGCCCCCTTAGAC (SEQ ID NO: 100) | MOB3B |
| MOB3B sgRNA 2 | GATGATCTCTGGGTCCACAA (SEQ ID NO: 101) | MOB3B |
| IFNK sgRNA 1 | AAGGAAAGGGGCCGCAACCT (SEQ ID NO: 102) | IFNK |
| IFNK sgRNA 2 | TCGGGTGACTATGCCGACTT (SEQ ID NO: 103) | IFNK |
| EQTN sgRNA 1 | TCTGAAGACTGCTTTATCTC (SEQ ID NO: 104) | EQTN |
| EQTN sgRNA 2 | GACTGAGTCACAAAGCTGTT (SEQ ID NO: 105) | EQTN |
| C9orf72 sgRNA 1 | CCAGAGCTTGCTACAGGCTG (SEQ ID NO: 106) | C9orf72 |
| C9orf72 sgRNA 2 | GCTCTCACAGTACTCGCTGA (SEQ ID NO: 107) | C9orf72 |
| T01 | CGCTCCCGATCTCGCCCGGG (SEQ ID NO: 108) | MOB3B/EMICERI |

TABLE 18-continued

| Name | sgRNA target sequence (5' to 3') | Target |
|---|---|---|
| T02 | CTCACCATTTTCTTTCGCGC (SEQ ID NO: 109) | MOB3B/EMICERI |
| T03 | GTCGCTTGCCAATCCACGCA (SEQ ID NO: 110) | MOB3B/EMICERI |
| T04 | CCGTCCGCCGGTTGGCTCGC (SEQ ID NO: 111) | MOB3B/EMICERI |
| T05 | GGTGCATGAGGGGGCTGCTC (SEQ ID NO: 112) | MOB3B/EMICERI |
| T06 | CTTTGGGATCATCTTCCCTC (SEQ ID NO: 113) | MOB3B/EMICERI |
| T07 | GGCTGGAAGCCCCCTTAGAC (SEQ ID NO: 114) | MOB3B/EMICERI |
| T08 | TGACACCTTCTTCACTGCCC (SEQ ID NO: 115) | MOB3B/EMICERI |
| T09 | GATGATCTCTGGGTCCACAA (SEQ ID NO: 116) | MOB3B/EMICERI |
| T10 | CAATCAGAAAATCCTGGGGA (SEQ ID NO: 117) | MOB3B/EMICERI |
| T11 | CAGAGCGGAGCATAAATCAT (SEQ ID NO: 118) | MOB3B/EMICERI |
| T12 | CTGGGAGTCATGGATGAACC (SEQ ID NO: 119) | MOB3B/EMICERI |
| T13 | ACTCTCTACTTGTGTGGTCT (SEQ ID NO: 120) | MOB3B/EMICERI |
| sgRNA 4 | TGCAGAAAAGACACTGGGCC (SEQ ID NO: 121) | EMICERI |
| sgRNA 5 | AAGAAGGTGTCAGATCAGAA (SEQ ID NO: 122) | EMICERI |
| sgRNA 6 | CCCGCGAGACAGTCGAGCCC (SEQ ID NO: 123) | MOB3B |
| sgRNA 7 | CGCGGCGCGCTGGGTGCATG (SEQ ID NO: 124) | MOB3B |

Table 19. Custom TaqMan qPCR probes and gene specific primers for detecting lncRNA transcript upregulation.

TABLE 19

| Target transcript | Primer type | Sequence (5' to 3') |
|---|---|---|
| TCONS_00011252 | Forward | GCCTAGACAGTATGTGAATGAGTAT (SEQ ID NO: 125) |
| TCONS_00011252 | Probe | /56FAM/AAAGCAGCT/ZEN/CACGGCCACAC/3IABKFQ/ (SEQ ID NO: 126) |
| TCONS_00011252 | Reverse | AAGCAAGTTCCTCTGGGAAG (SEQ ID NO: 127) |
| TCONS_00011252 | Gene specific | TTTTGGAAAGAGAGAAAAGA (SEQ ID NO: 128) |

TABLE 19-continued

| Target transcript | Primer type | Sequence (5' to 3') |
|---|---|---|
| NR_034078 | Forward | CATCGCATGCTTCCAGAGATA (SEQ ID NO: 129) |
| NR_034078 | Probe | /56FAM/AAATACTTC/ZEN/CTCTAGGTGGCAGCGC/3IABkFQ/ (SEQ ID NO: 130) |
| NR_034078 | Reverse | CTATGGTGGGCATTTGGACT (SEQ ID NO: 131) |
| NR_034078 | Gene specific | TTCATTTATTTCATACACCAC (SEQ ID NO: 132) |
| TCONS_00010506 | Forward | AAGGACGI AGCCTTTCCIAATC (SEQ ID NO: 133) |
| TCONS_00010506 | Probe | /56FAM/ACTCTGAAG/ZEN/GGCAATTCCAGCAGA/3IABkFQ/ (SEQ ID NO: 134) |
| TCONS_00010506 | Reverse | GTCCCAGATGTCATGGAATGTA (SEQ ID NO: 135) |
| TCONS_00010506 | Gene specific | CTGTAGGTACTGGTATTATC (SEQ ID NO: 136) |
| TCONS_00026344 | Forward | AGAGTO TGCTAAAC TOXCTCTA (SEQ ID NO: 137) |
| TCONS_00026344 | Probe | /56FAM/TCCCAGAGG/ZEN/ACTGAGAACAGGT CA/3IABkFQ/ (SEQ ID NO: 138) |
| TCONS_00026344 | Reverse | CTTCCAGATCCTGACTCCATTC (SEQ ID NO: 139) |
| TCONS_00026344 | Gene specific | TTATAAAGATTTCAGCAGA TG (SEQ ID NO: 140) |
| TCONS_00015940 (EMICERI) | Forward | GACACAGAGCGGAGCATAAA (SEQ ID NO: 141) |
| TCONS_00015940 (EMICERI) | Probe | /56FAM/AACACACTG/ZEN/GGAGTCATGGATGAAC C/3IABkFQ/ (SEQ ID NO: 142) |
| TCONS_00015940 (EMICERI) | Reverse | GACCAAGACCACACAAGTAGAG (SEQ ID NO: 143) |
| TCONS_00015940 (EMICERI, only Fig. 4I) | Forward | CTGTTCATCACCGAGGAATCTC (SEQ ID NO: 144) |
| TCONS_00015940 (EMICERI, only Fig. 4I) | Probe | /56FAM/ACCAGAGTC/ZEN/AGACAGACCCATAGCA/3IABkFQ/ (SEQ ID NO: 145) |
| TCONS_00015940 (EMICERI, only Fig. 4I) | Reverse | ACAGAGCTTCAGAAAGGTT AGAC (SEQ ID NO: 146) |
| EMICERII | Forward | CATCAACCACAGGTAGCAAGTA (SEQ ID NO: 147) |
| EMICERII | Probe | /56FAM/AAAGCAGAC/ZEN/AGTAGAGGTCGTGGC/3IABkFQ/ (SEQ ID NO: 148) |
| EMICERII | Reverse | TCACCAAGACAAGGCAAGAG (SEQ ID NO: 149) |

Table 20. RNA-seq analysis of neighboring genes in 11 candidate lncRNA loci. For each lncRNA, a neighboring gene in the lncRNA locus (<1 Mb from the annotated lncRNA TSS) was considered differentially expressed if gene expression significantly differed for each of the 3 sgRNAs targeting SAM to the lncRNA locus compared to 2 non-targeting sgRNAs. Lowly expressed genes refer to neighboring genes that were detected (0-1 transcript per million), but not considered differentially expressed by the above criteria. To avoid missing genes that were differentially expressed but excluded by the stringent criteria for identifying differentially expressed genes, for each locus manually examined the lowly expressed genes to identify any genes that exhibited dosage-dependent upregulation relative to the lncRNA target. For TCONS_00015940, it was found that IFNK and EQTN exhibited dosage-dependent upregulation but were not considered differentially expressed because both genes were not detected in 1 of the 3 targeting sgRNA conditions. Undetected genes refer to neighboring genes that were not detected (0 reads for all 3 bioreps) at the sequencing depth of >9 million reads per sample.

TABLE 20

| LncRNA | Differentially expressed genes | Lowly expressed genes that are not significantly differentially expressed | Undetected genes |
|---|---|---|---|
| TCONS_00011252 | PSMG4 | SLC22A23, SERPINB9, LINC01600, MYLK4 | |
| NR_034078 | (CASP4, PDGFD) | CARD16, GRIA4, CASP1, DDI1 | CASP5, CARD17, CARD18, CASP12 |
| TCONS_00009861 | NSUN2, SRD5A1 | UBE2QL1, ADCY2 | C5orf49 |
| TCONS_00010506 | PCDHGC3, PCDHB7, PCDHB9, DIAPH1, PCDHB16, IGIP, PCDHGB5, PCDHGA7, PCDHGB1, PCDHA9, PCDHGA10, HARS, PFDN1, HBEGF, PCDHB14, PCDHB15, PCDHB11 | CD14, PCDHGA8, PCDHGA11, PCDHGA3, PCDHGA12, PSD2, PCDHGC5, PCDHGC4, SLC25A2, PCDHB1, SLC4A9 | |
| TCONS_00026344 | ALPK2, MALT1, ZNF532 | NM_001289967, GRP, RAX, CPLX4, ATP8B1 | |
| TCONS_00015940 | CAAP1, IFT74, C9orf72, MOB3B, PLAA | EQTN, LRRC19, TEK, IFNK | |
| NR_125939 | RABGGTB, ACADM | MSH4, LHX8, ST6GALNAC5 | ASB17 |
| NR_109890 | RNF145, EBF1 | IL12B | |
| NR_033834 | RAN | TMEM132D, ADGRD1, FZD10, RIMBP2 | PIWIL1 |
| TCONS_00006579 | (BBX, CBLB) | CCDC54 | |

Table 21. Antisense oligonucleotide sequences for knocking down EMICERI expression.

TABLE 21

| Name | Sequence (5' to 3') | Target |
|---|---|---|
| ASO NT1 | AACACGTCTATACGC (SEQ ID NO: 150) | Control |
| ASO NT2 | TCAAGACTGATAGATA (SEQ ID NO: 151) | Control, EMICERII |
| ASO 1 | CGCCAATTTACGGAGG (SEQ ID NO: 152) | EMICERI |
| ASO 2 | TCGTAGTTAGTTGCAG (SEQ ID NO: 153) | EMICERI |
| ASO 3 | ACACAGAATTAGAGTC (SEQ ID NO: 154) | EMICERI |
| ASO 4 | CGAAAGAAGGACGATC (SEQ ID NO: 155) | MOB3B Intron 1 |
| ASO 5 | CAAAGTTAAGCGCGAT (SEQ ID NO: 156) | MOB3B Intron 1 |
| ASO 6 | CCGAGAGATTTAGAGT (SEQ ID NO: 157) | MOB3B Intron 1 |
| ASO 7 | TCAGGAAAGAGCGCGA (SEQ ID NO: 158) | MOB3B Intron 1 |

Table 22. Primers and sgRNAs for generating poly(A) clones. sgRNA target sequences and respective target sites relative to the EMICERI TSS for inserting poly(A) sequences through homology-directed repair with Cas9. Primers were used to amplify the target region for genotyping clones.

TABLE 22

| Name | Sequence (5' to 3') | 3' target site position relative to EMICERITSS (bp) |
|---|---|---|
| HDR sgRNA 1 | GATGATCTCTGGGTCCACAA (SEQ ID NO: 159) | 106 |
| HDR sgRNA 2 | TCAACAATCAGAAAATCCTG (SEQ ID NO: 160) | 153 |
| HDR sgRNA 3 | ATGAACTGCCTGACACAGAG (SEQ ID NO: 161) | 201 |
| HDR primer F1 | CTCCGTGAGGCATCGTCAG (SEQ ID NO: 162) | -888 |
| HDR primer F2 | ATGACCAGTCTAAGGGGCT (SEQ ID NO: 163) | 27 |
| HDR primer R | CACAAGTAGAGAGTGGCGGG (SEQ ID NO: 164) | 299 |

Example 2

The mammalian genome contains thousands of loci that transcribe long noncoding RNAs (lncRNAs), some of which are known to play critical roles in diverse cellular processes. LncRNA loci can contribute to cellular regulation through a variety of mechanisms: while some encode RNAs that act non-locally (in trans), emerging evidence indicates that many lncRNA loci act locally (in cis)—for example, through functions of the lncRNA promoter, the process of lncRNA transcription, or the lncRNA transcript itself in regulating the expression of nearby genes. Despite their potentially important roles, it remains challenging to identify functional lncRNA loci and distinguish among these and other mechanisms. To address these challenges, a genome-scale CRISPR-Cas9 activation screen targeting more than 10,000 lncRNA transcriptional start sites was developed to identify noncoding loci that influence a phenotype of interest. 11 novel lncRNA loci were found that, upon recruitment of an activator, each mediate BRAF inhibitor resistance in melanoma. Potential local and non-local mechanisms at these candidate loci were investigated, and most appear to regulate nearby genes. Detailed analysis of one candidate, termed EMICERI, revealed that its transcriptional activation results in dosage-dependent activation of four neighboring protein-coding genes, one of which confers the resistance phenotype. The screening and characterization approach provides a CRISPR toolkit to systematically discover functions of noncoding loci and elucidate their diverse roles in gene regulation and cellular function.

Figure 5:
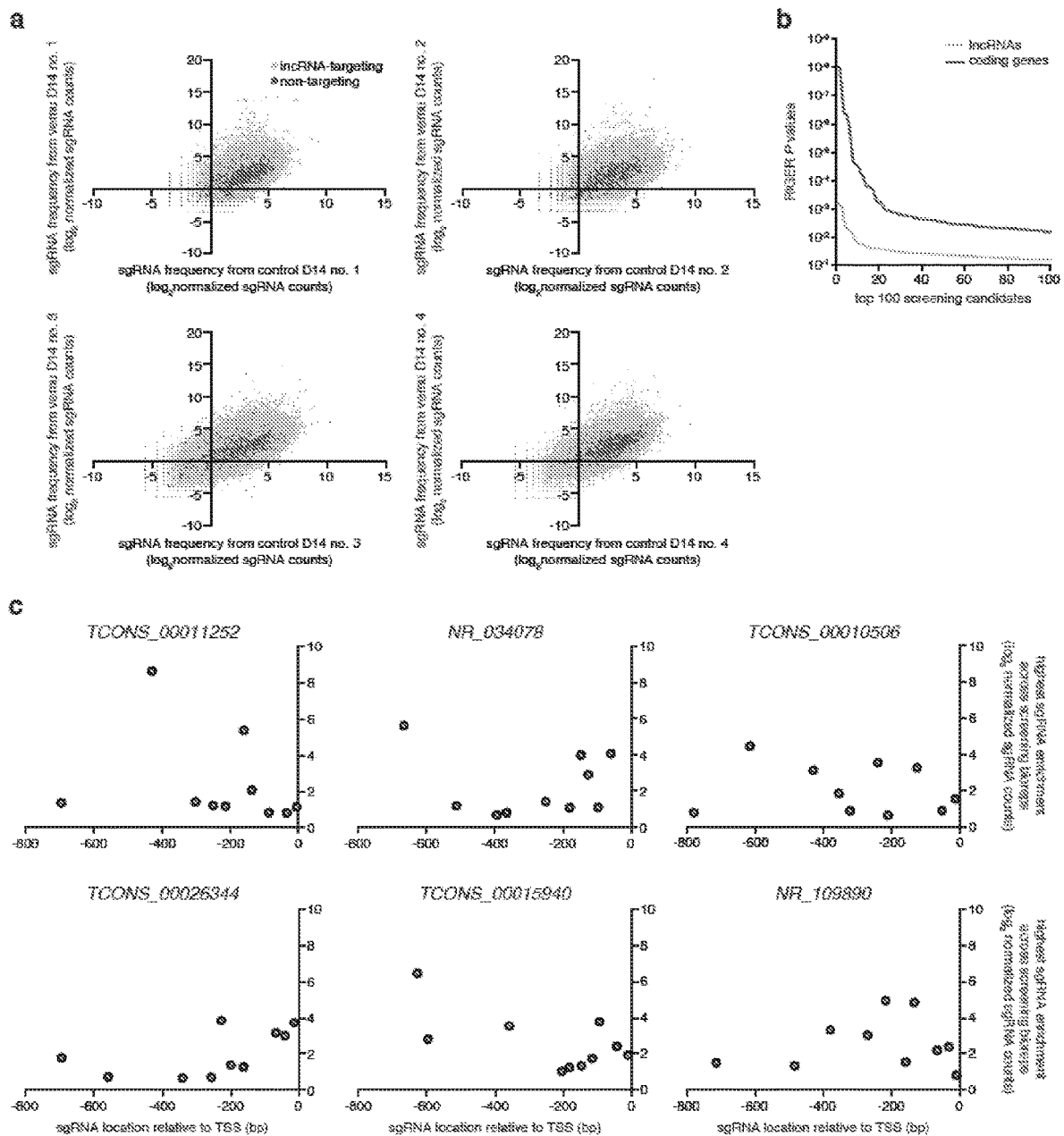
FIG. 5. Genome-scale activation screen for lncRNA loci involved in BRAF inhibitor resistance. a, Scatterplots showing lncRNA-targeting and non-targeting sgRNA frequencies after vemurafenib (vemu) or control treatment from n=4 infection replicates. b, RIGER P values for the top 100 hits from the previous SAM protein-coding gene screen [12] compared to the SAM lncRNA loci screen. c, For each candidate lncRNA locus, 10 sgRNAs were designed to target the proximal promoter region (800 bp upstream of the TSS). The relationship between the highest sgRNA enrichment in vemurafenib-treated compared to control condition across screening bioreps (n=4) and respective spacer position suggests that sgRNAs targeting closer to the annotated TSS are not necessarily more effective, consistent with previous results [12].

Previously Cas9 Synergistic Activation Mediator (SAM) had been used to screen for protein-coding genes that confer resistance to the BRAF inhibitor vemurafenib in melanoma cells, making this an ideal phenotype for high-throughput screening of functional lncRNA loci. A genome-scale sgRNA library targeting 10,504 unique intergenic lncRNA TSSs (>50 bp apart) was designed. A375 (BRAF(V600E)) melanoma cells were transduced with the sgRNA library, cultured in 2 µM vemurafenib or control (dimethyl sulfoxide, DMSO), and sequenced for the distribution of sgRNAs after 14 days of drug treatment (FIG. 1a-b and FIG. 5a). RIGER analysis identified 16 significantly enriched candidate loci (FDR <0.05, FIG. 1c,d, FIG. 5b,c, and Table 1), none of which had been previously functionally characterized.

Figure 6:
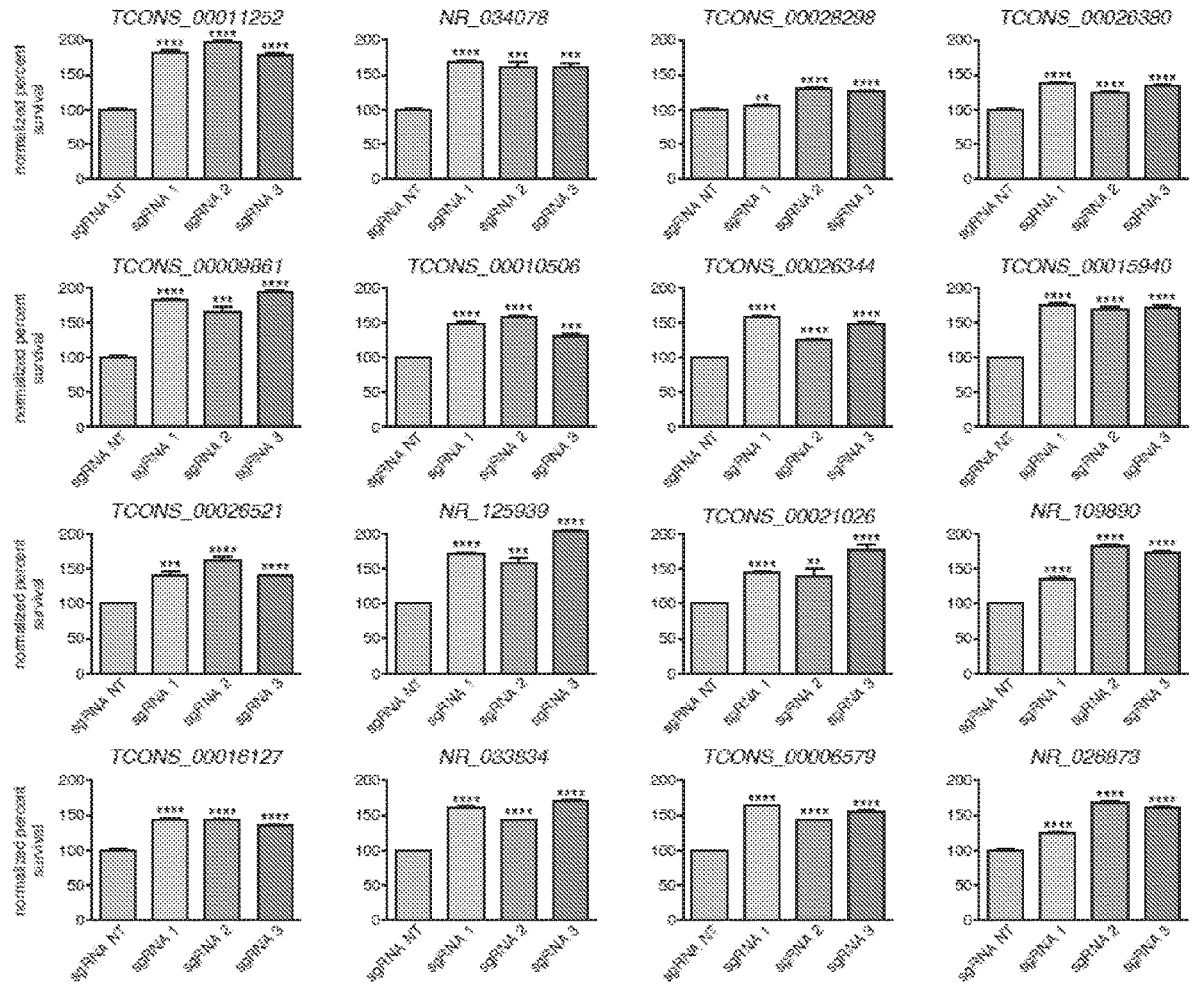
FIG. 6. Validation of candidate lncRNA loci for vemurafenib resistance. Vemurafenib resistance for A375 transduced with SAM and individual sgRNAs targeting the top 16 candidate lncRNA loci normalized to a non-targeting (NT) sgRNA. All values are mean±SEM with n=4. **P<0.0001; *P<0.001; **P<0.01.

To validate the screening results, the 3 most enriched sgRNAs targeting each of the top 16 candidate lncRNA loci were individually expressed in A375 cells. In all 16 cases, the sgRNAs conferred significant vemurafenib resistance (FIG. 6), verifying the robustness of the screening approach. RNA sequencing was performed upon activation of each of the 11 loci with the strongest effects (FIG. 6, Table 2), and global changes in gene expression consistent with vemurafenib resistance were found, supporting the functional relevance of these loci to the screening phenotype (FIG. 7a).

Next, the mechanisms by which activation of these loci might lead to resistance were studied, which could include (i) a non-local function of the lncRNA transcript, (ii) a local function of the lncRNA transcript or its transcription; (iii) a local function of a DNA element in the lncRNA locus; and (iv) a local function of SAM, for example activating a nearby promoter. To focus on loci where the mechanism might require the lncRNA or its transcription (i and ii above), we activated each locus and detected a robust lncRNA transcript upregulation for 6 of these 11 loci (FIG. 1e, Table 2). The remaining 5 loci may function through a mechanism other than activation of the lncRNA transcript (e.g., iii and iv above, Table 7).

Figure 2:
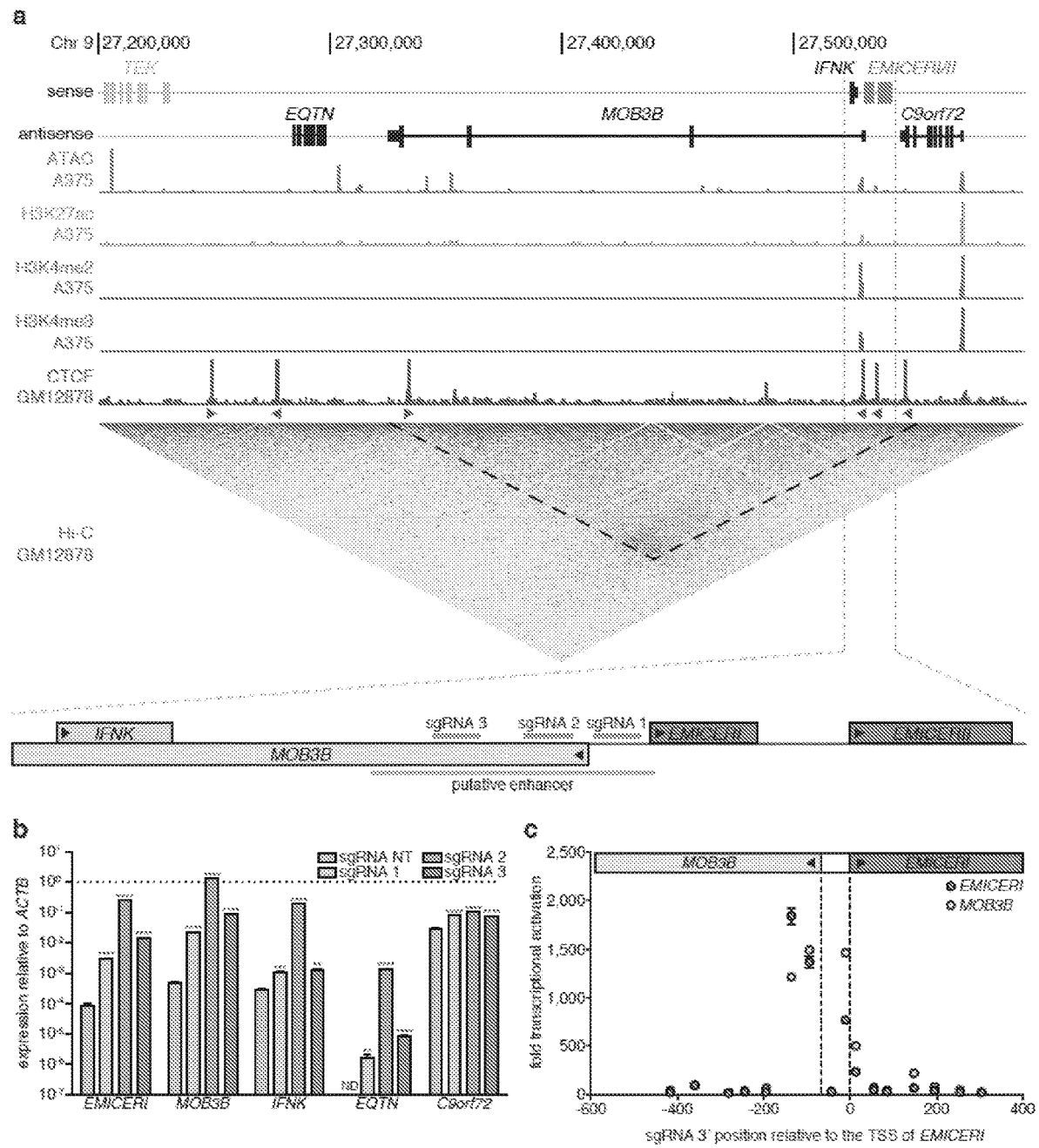
FIG. 2. Activation of the EMICERI promoter produces dosage-dependent upregulation of neighboring genes. a, Genomic locus of EMICERI contains four neighboring genes (EQTN, MOB3B, IFNK, and C9orf72) and a putative enhancer. b, Expression of EMICERI and its neighboring genes after transduction with non-targeting (NT) or EMICERI-targeting sgRNAs and SAM. ND=not detected. c, Expression of EMICERI and MOB3B after transduction with sgRNAs tiling SAM across the EMICERI locus normalized to a NT sgRNA. All values are mean±SEM with n=4. **$P<0.0001$; *$P<0.001$; **$P<0.01$.

Whether activating each of these 6 lncRNA loci might affect vemurafenib resistance through non-local (i above) or local (ii and iii above) functions were explored. To test whether candidate lncRNAs contribute to vemurafenib resistance via non-local functions, cDNAs encoding each lncRNA were overexpressed through random lentiviral integration and did not find any that affected drug resistance (FIG. 7b), suggesting that these loci likely do not act through non-local functions (Table 2). To determine if the phenotype might result instead from local functions of the lncRNA loci in regulating a nearby gene, the expression of all genes within 1 Mb of the targeted sites were examined. At 5 of the 6 loci, SAM targeting led to differential expression of between 1 and 8 nearby protein-coding genes (Table 7). For example, activation of NR_109890 upregulated its neighboring gene EBF1 (FIG. 7c), and activation of TCONS_00015940 led to dosage-dependent upregulation of 4 neighboring protein-coding genes (FIG. 2a,b). Together, these analyses indicate that none of the lncRNA loci appear to confer vemurafenib resistance by producing trans-acting RNAs; rather, the loci may regulate the expression of one or more nearby genes.

Figure 8:
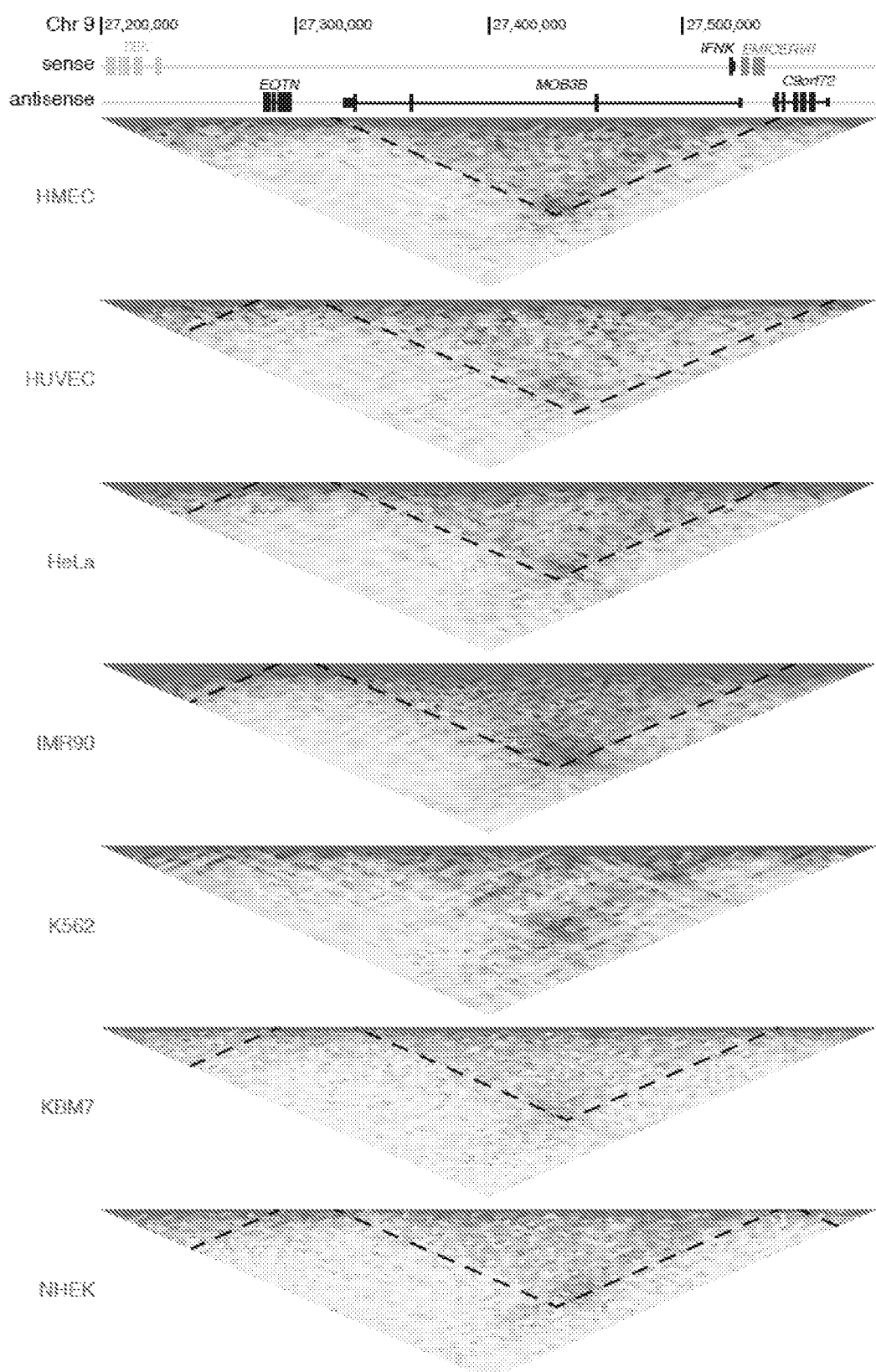
FIG. 8. Topological domain in the EMICERI locus is consistent across cell types Hi-C data and topological domain annotations (dotted lines) in the EMICERI locus from 7 cell lines [31]. Heat map shows KR-normalized contact matrix at 5-kb resolution. Domain annotations for chromosome 9 were not available in K562, but the same topological domain structure is evident.
Figure 9:
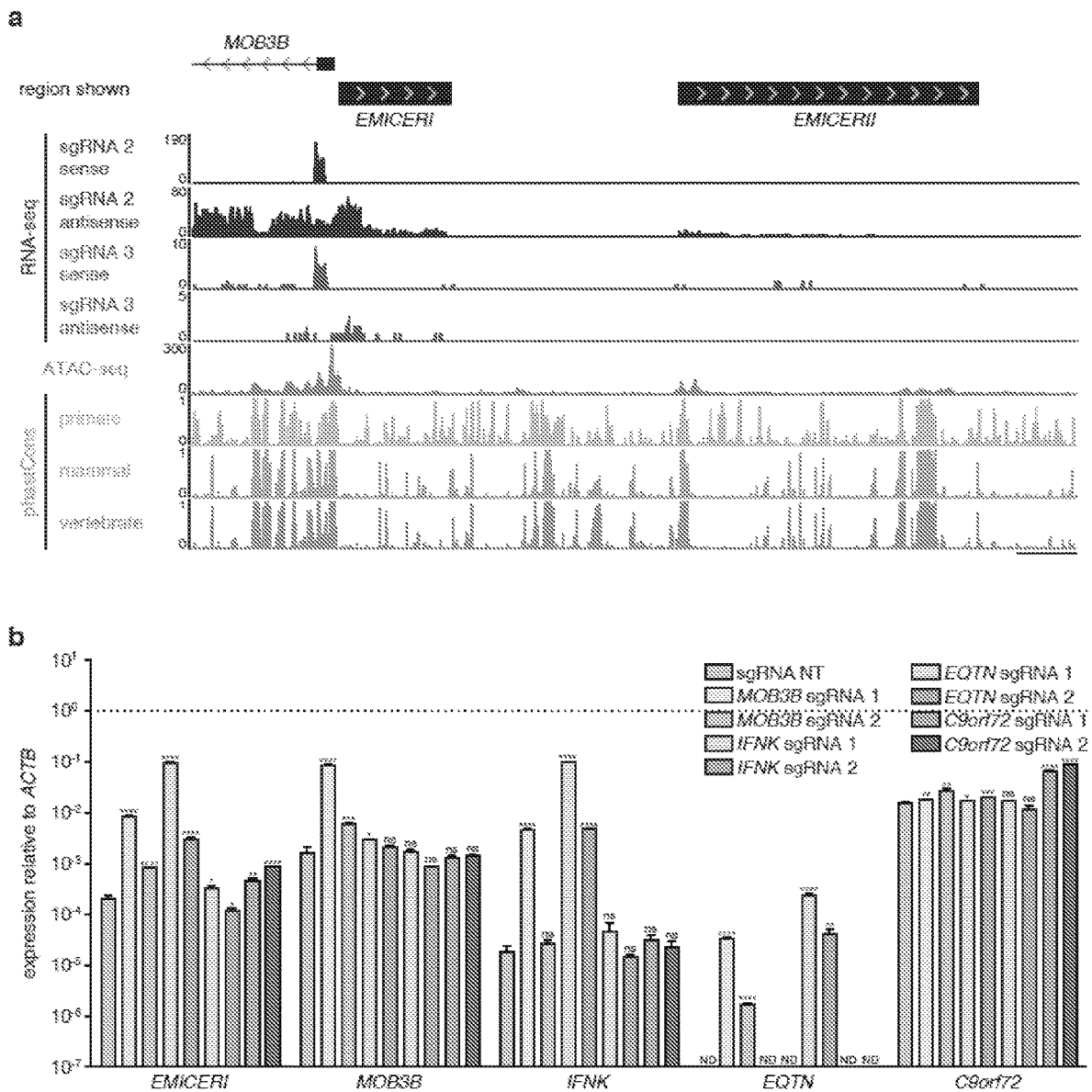
FIG. 9. Dosage-dependent upregulation of the EMICERI locus is specific to activation of EMICERI at its conserved regulatory element. a, TopHat alignment of RNA-seq paired-end reads suggests that EMICERI is located at chr9: 27,529,917-27,531,782 and EMICERII at chr9:27,535,711-27,540,711 (UCSC hg19). A375 ATAC-seq and phastCons conservation scores for primates, placental mammals, and vertebrates at the EMICERI locus. Scale bar, 1 kb. b, Expression of EMICERI and its neighboring genes MOB3B, IFNK, EQTN, and C9orf72 after transduction with sgRNAs targeting SAM to the promoters of neighboring genes. All values are mean±SEM with n=4. **P<0.0001; *P<0.001; **P<0.01; *P<0.05. ns=not significant. ND=not detected.

To further dissect the mechanism for one of these candidate local regulators, the experiments focused on TCONS_00015940, which, when targeted, led to a remarkable dosage-dependent activation of the 4 closest nearby genes (EQTN, MOB3B, IFNK, and C9orf72) (FIG. 2a,b). The targeted site is proximal to the boundary of a topological domain (FIG. 2a and FIG. 8). Upon examining this locus, we found that TCONS_00015940 is actually comprised of two separate transcripts (FIG. 9a), which were named "EQTN MOB3B IFNK C9orf72 enhancer RNA I", or EMICERI, and EMICERII. The EMICERI promoter, targeted in the screen, is actually the promoter for two genes, which are transcribed divergently and initiate ~66 bp apart: EMICERI and MOB3B, a protein-coding gene (FIG. 2a). Tiling SAM across this region indicated that targeting a ~200 bp region activated both of these genes (FIG. 2a,c). In contrast, targeting SAM to the promoters of the other three nearby genes did not produce coordinated transcriptional activation in the region, although targeting the promoter of C9orf72 led to a slight activation of EMICERI alone (FIG. 9b). Together, these results demonstrate that the EMICERI/MOB3B promoter influences gene expression in a ~300 kb gene neighborhood.

Figure 3:
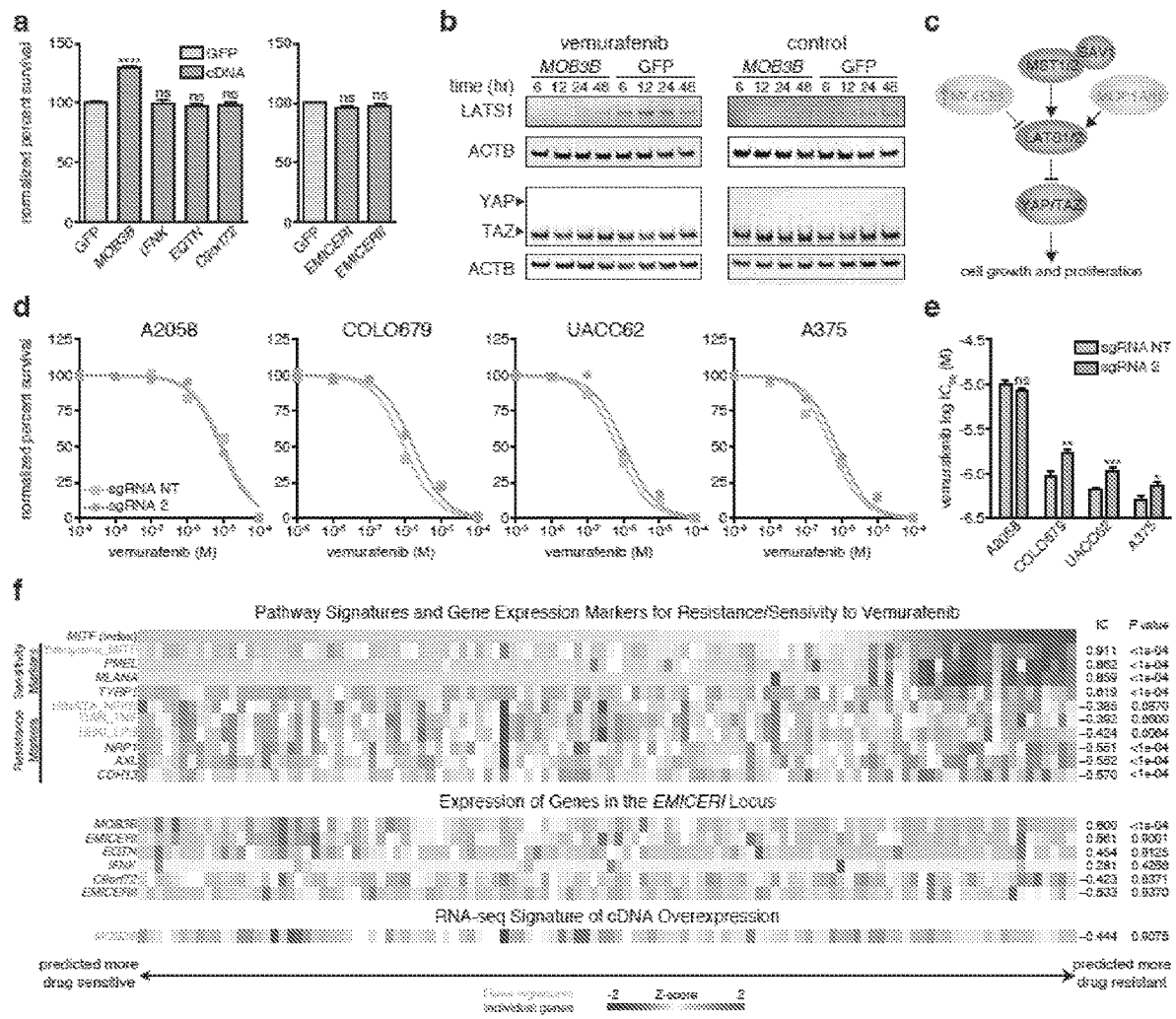
FIG. 3. MOB3B mediates vemurafenib resistance through the Hippo signaling pathway in melanoma models. a, Vemurafenib resistance of A375 cells overexpressing each neighboring gene or lncRNA cDNA normalized to GFP. b, Western blots of LATS1, YAP, and TAZ in A375 stably overexpressing MOB3B cDNA or GFP after vemurafenib or control (DMSO) treatment. c, Schematic of MOB3B mechanism in the Hippo signaling pathway. d, Vemurafenib dose response curves for EMICERI activation in different melanoma cell lines. e, Vemurafenib half maximal inhibitory concentration (IC50) for the same conditions in (d). f, Heat map showing expression of gene/signature markers for BRAF inhibitor sensitivity (top), expression of genes in the EMICERI locus (middle), and MOB3B overexpression RNA-seq signature scores (bottom) in 113 different BRAF (V600) patient melanoma samples (primary or metastatic) from The Cancer Genome Atlas. All associations are measured using the information coefficient (IC) between the index and each of the features and P values are determined using a permutation test. Panels show Z scores. All values are mean±SEM with n=4. **$P<0.0001$; *$P<0.001$; **$P<0.01$. *$P<0.05$. ns=not significant.
Figure 7:
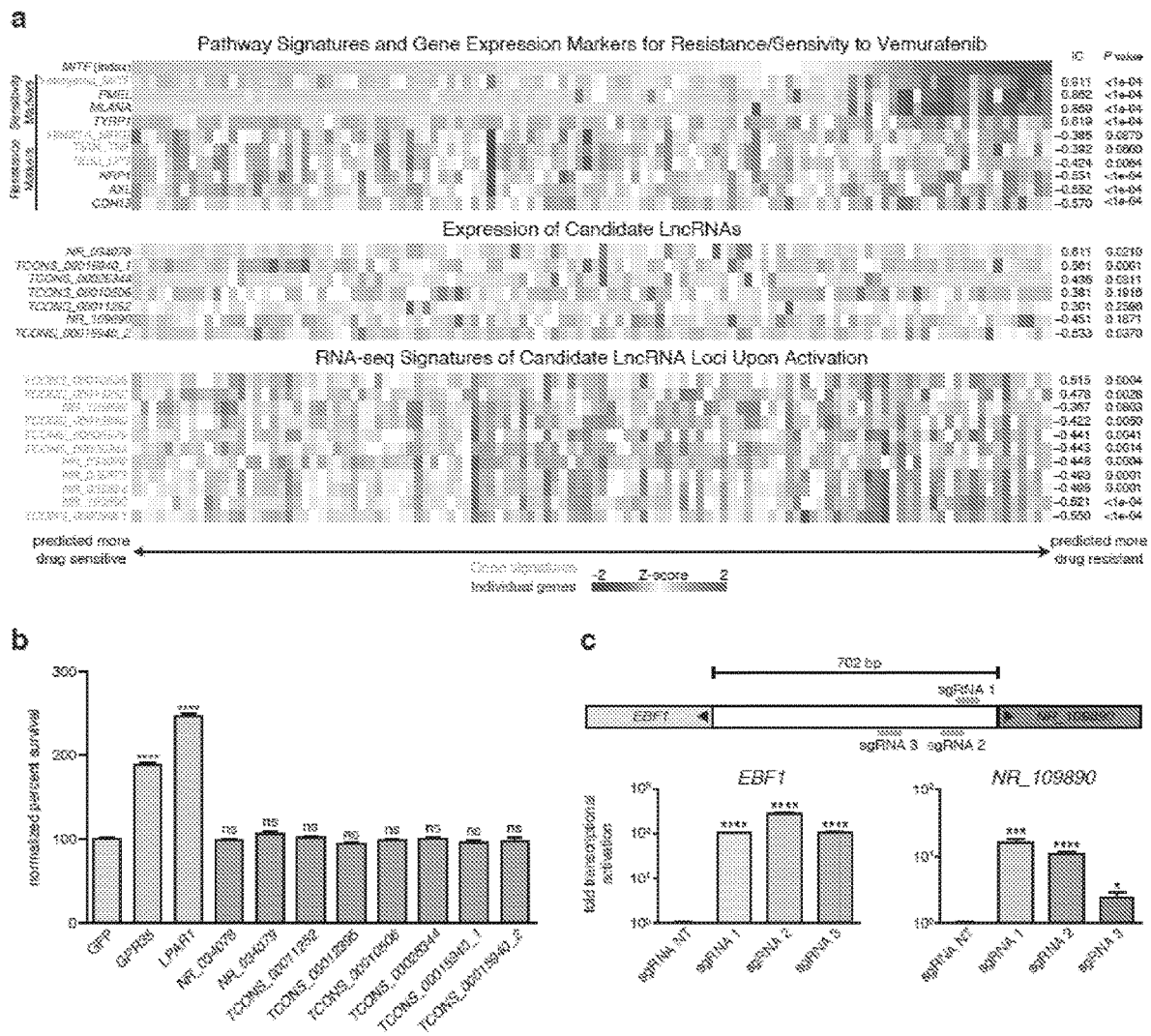
FIG. 7. Activation of candidate lncRNA loci mediate vemurafenib resistance by potentially acting locally to regulate expression of nearby genes. a, Heat map showing expression of gene/signature markers for BRAF inhibitor sensitivity (top), expression of candidate lncRNA loci (middle), and RNA-seq signature of gene expression changes upon activation of candidate lncRNA loci (bottom) in 113 different BRAF (V600) patient melanoma samples (primary or metastatic) from The Cancer Genome Atlas. All associations are measured using the information coefficient (IC) between the index and each of the features and P values are determined using a permutation test. Panels show Z scores. b, Vemurafenib resistance of A375 cells overexpressing each candidate lncRNA cDNA or protein-coding gene normalized to GFP. GPR35 and LPAR1 are positive controls identified previously [12]. The same set of sgRNAs targeted TCONS_00012395 and TCONS_00011252; NR_034078 and NR_034079; TCONS_00015940/and TCONS_00015940_2. c, Expression of NR_109890 and its neighboring gene EBF1 after SAM activation of NR_109890. All values are mean±SEM with n=4. **P<0.0001; *P<0.001; *P<0.05. ns=not significant.
Figure 10:
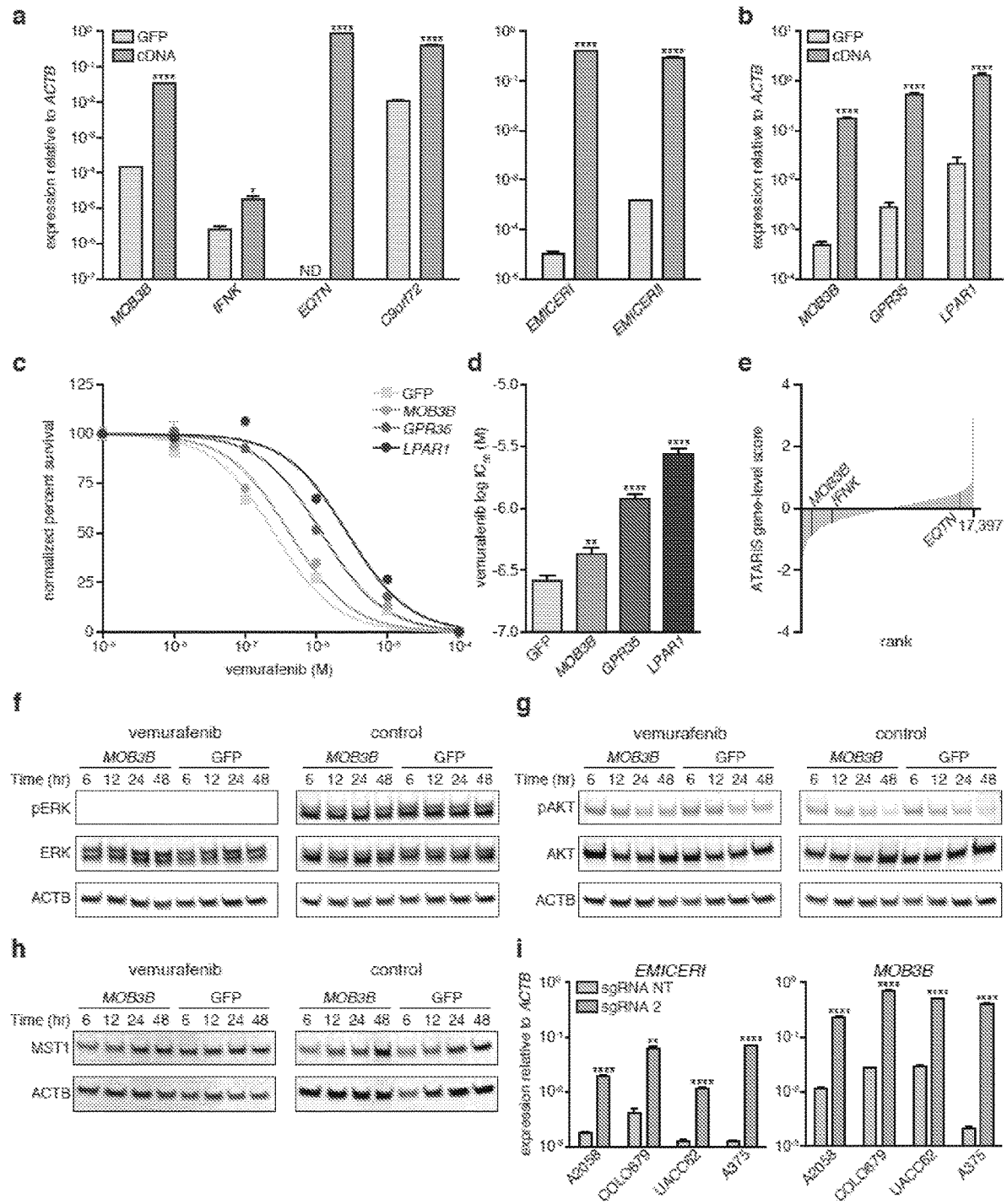
FIG. 10. Activation of EMICERI mediates vemurafenib resistance through MOB3B. a, Expression of the neighboring genes or EMICERI/II after cDNA overexpression compared to GFP control. b, cDNA overexpression of top hits from the SAM protein-coding gene screen for vemurafenib resistance (GPR35 and LPAR1) [12] or MOB3B compared to GFP control. c, Vemurafenib dose response curves for A375 cells overexpressing cDNA or GFP control. d, Vemurafenib half maximal inhibitory concentration (IC50) for the same conditions in (c). e, ATARiS gene-level scores from the Achilles Project that reflect genetic vulnerabilities of A375. Lower ATARiS gene-level scores indicate stronger dependency on the gene. Rank of MOB3B, 1,084; IFNK, 3,078; EQTN, 15,939. f to h, Western blots of A375 stably overexpressing MOB3B cDNA or GFP control after vemurafenib or control (DMSO) treatment. i, Expression of EMICERI and MOB3B after SAM activation in different melanoma cell lines. All values are mean±SEM with n=4. **P<0.0001; P<0.01; *P<0.05. ND=not detected.
Figure 11:
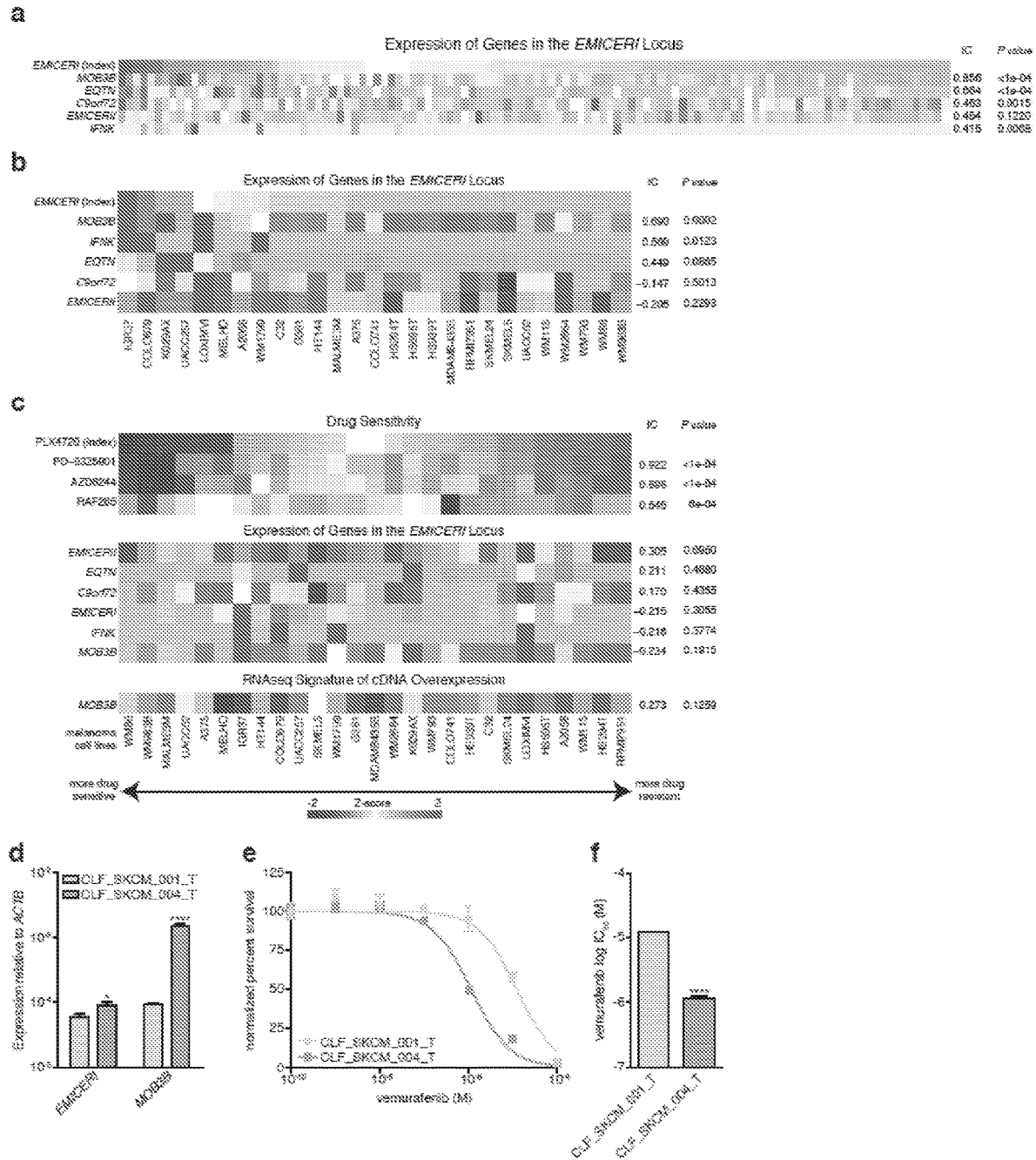
FIG. 11. EMICERI expression is strongly correlated with MOB3B expression and vemurafenib sensitivity in melanoma cell lines and patient samples. a, Heat map showing expression of genes in the EMICERI locus in 113 different BRAF (V600) patient melanoma samples (primary or metastatic) from The Cancer Genome Atlas. Samples are sorted by EMICERI expression. b, Heat map showing expression of genes in the EMICERI locus in melanoma cell lines from the Cancer Cell Line Encyclopedia (CCLE) sorted by EMICERI expression. c, Heat map showing sensitivity to different drugs (top), expression of genes in the EMICERI locus (middle), and MOB3B cDNA overexpression RNA-seq signature (bottom) in melanoma cell lines from CCLE. Drug sensitivities are measured as Activity Areas. The melanoma cell lines are sorted by PLX-4720 (vemurafenib) drug sensitivity. RAF inhibitors: PLX-4720 and RAF265; MEK inhibitors: AZD6244 and PD-0325901. d, Expression of EMICERI and MOB3B in two primary patient-derived BRAF(V600E) melanoma cell lines. e, Vemurafenib dose response curves for the same cell lines. f, Vemurafenib half maximal inhibitory concentration (IC50) for the same conditions as (e). All associations are measured using the information coefficient (IC) between the index and each of the features and P values are determined using a permutation test. Heat maps show Z scores. All values are mean±SEM with n=4. ****P<0.0001; *P<0.05.

To determine how coordinated upregulation of the EMICERI gene neighborhood led to vemurafenib resistance, the cDNA for each of the 4 protein-coding genes as well as EMICERI or II lncRNAs were overexpressed from randomly integrated lentivirus. Only MOB3B overexpression led to vemurafenib resistance (FIG. 3a and FIG. 10a), indicating that although activation of the EMICERI/MOB3B promoter leads to transcriptional upregulation of 4 protein-coding genes and two lncRNA genes, overexpression of only one of these genes is sufficient for the resistance phenotype. Notably, MOB3B, a novel kinase activator of unknown function, is a paralog of MOB1A/B, known components of the Hippo signaling pathway, whose activation has been shown to confer vemurafenib resistance. MOB3B overexpression downregulates LATS1 to activate the Hippo signaling pathway (FIG. 3b,c, FIG. 10f-h). Activation of EMICERI and MOB3B conferred vemurafenib resistance in two additional sensitive melanoma cell lines (FIG. 3d,e, FIG. 10i) and correlated with a gene-expression signature of vemurafenib resistance in melanoma patients from The Cancer Genome Atlas (FIG. 3f, FIGS. 7 and 11). Together, these results indicate that activation of the EMICERI locus confers vemurafenib resistance via upregulation of MOB3B and subsequent activation of the Hippo signaling pathway.

As an aside, it was explored why MOB3B had not been identified in our previous SAM screen for protein-coding genes. The explanation appears to be that the previous sgRNA library targeted MOB3B upstream of its TSS, whereas the optimal position for activation is downstream (FIG. 2c), and because resistance conferred by MOB3B activation is weaker than for the top candidate genes in the previous screen (FIG. 10b-e).

Figure 4:
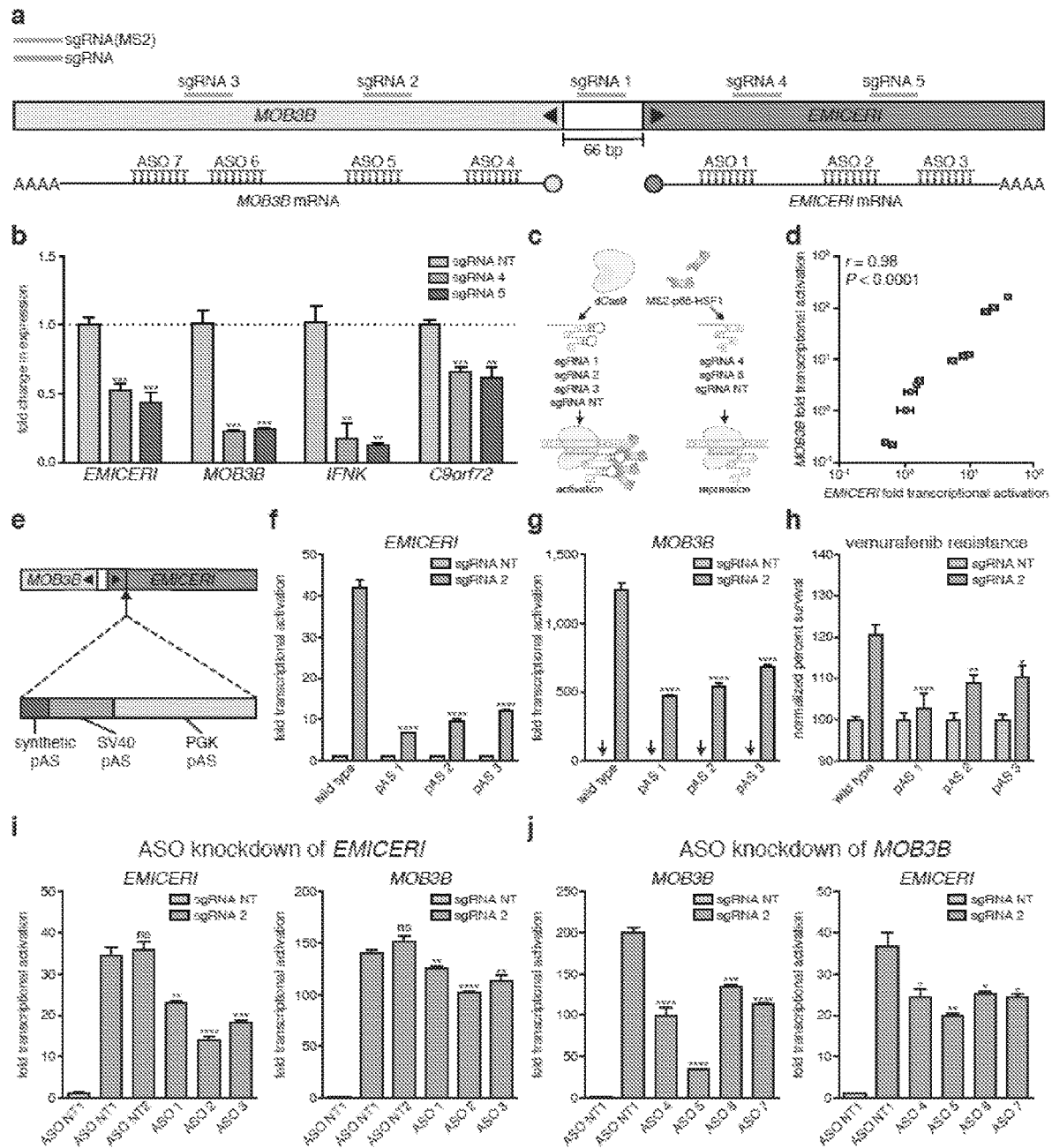
FIG. 4. Transcription of EMICERI modulates MOB3B expression. a, Targeting positions of sgRNAs and antisense oligonucleotides (ASOs) in the EMICERI and MOB3B locus. b, Expression of EMICERI and its neighboring genes in A375 cells transduced with non-targeting (NT) or EMICERI-targeting sgRNAs and dCas9. c, Schematic for bimodal perturbation of EMICERI transcription. sgRNAs 1-3 use MS2 loops to recruit MS2-P65-HSF1 to dCas9 to activate EMICERI, whereas sgRNAs 4-5 recruit only dCas9 to repress d, Correlation between MOB3B and EMICERI expression produced by different combinations of sgRNAs with and without MS2 loops. e, Schematic for inserting polyadenylation signals (pAS) downstream of the EMICERI TSS. SV40, Simian virus 40; PGK, phosphoglycerate kinase. f, EMICERI expression after SAM activation of EMICERI for the wild type and pAS clones. g, MOB3B expression after the same perturbations as (f). h, Vemurafenib resistance after SAM activation of EMICERI. i, Expression of EMICERI and MOB3B after ASO knockdown of EMICERI in the context of SAM activation. j, Expression of MOB3B and EMICERI after ASO knockdown of MOB3B in the context of SAM activation. All values are mean±SEM with n=4. **$P<0.0001$; *$P<0.001$; **$P<0.01$; *$P<0.05$. ns=not significant.

Next it was explored whether transcriptional activation of EMICERI is required for full MOB3B upregulation. Alternatively, it is possible that targeting SAM to the shared EMICERI/MOB3B promoter may confer resistance only through direct activation of MOB3B. Accordingly, three perturbation methods were used to interfere with EMICERI transcription and observed effects on MOB3B:

To block transcription of EMICERI, dCas9 targeted downstream of the EMICERI TSS. This intervention reduced the expression not only of EMICERI, but also of MOB3B and the other neighboring genes (FIG. 4a,b). Then a bimodal perturbation system was used that uses an sgRNA without the SAM-recruitment sequences to target dCas9 to block EMICERI transcription and an sgRNA with the SAM-recruitment sequences was used to activate the promoter region (FIG. 4a, c). Different combinations of repression and activation sgRNAs targeting the EMICERI locus demonstrated that the transcriptional levels of EMICERI and MOB3B are tightly coupled across several orders of magnitude (correlation coefficient r=0.98, P<0.0001) (FIG. 4d).

Figure 12:
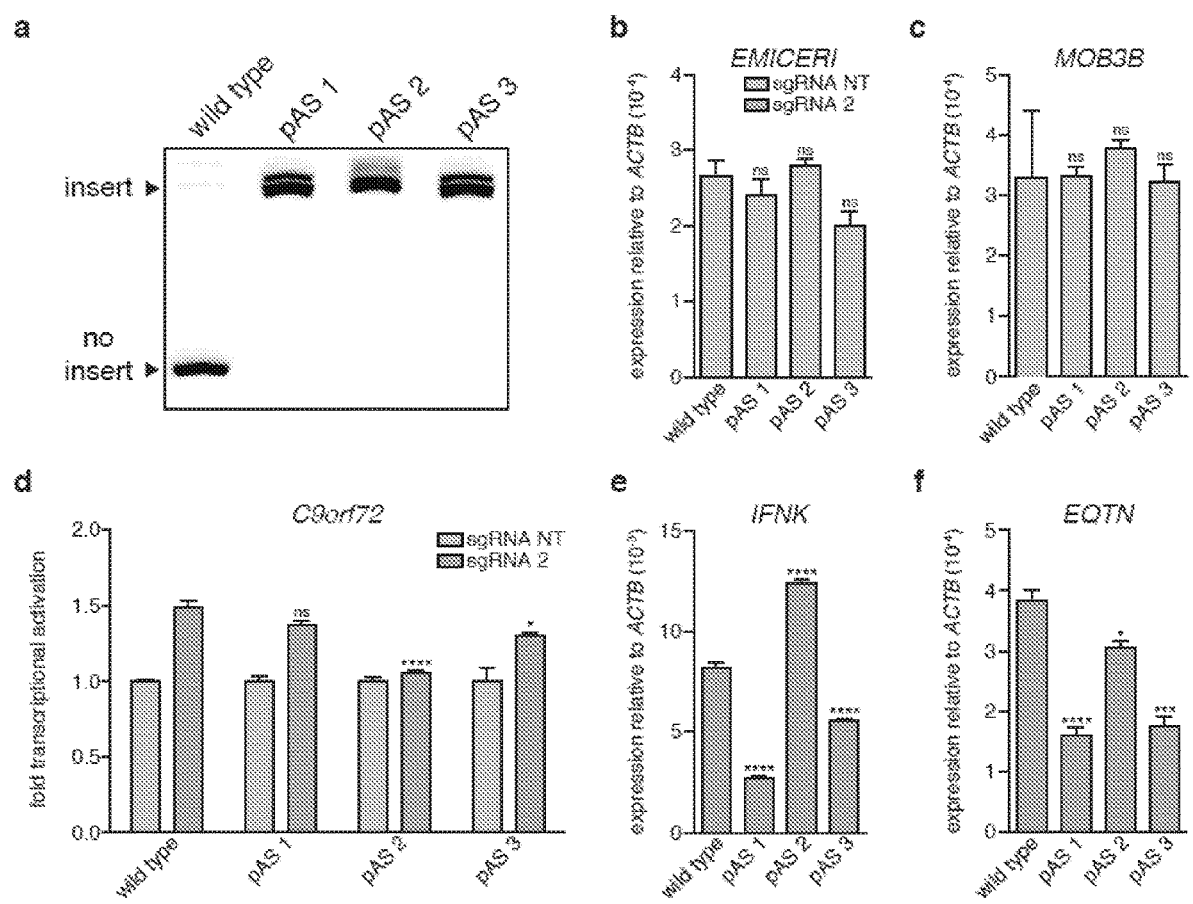
FIG. 12. Transcriptional activation of EMICERI modulates expression of neighboring genes. a, Gel confirming polyadenylation signal (pAS) insertion into all 3 copies of EMICERI for each pAS clone. b to c, Basal expression of EMICERI and MOB3B for the wild type and pAS clones. d to f, Expression of C9orf72, IFNK, and EQTN after targeting SAM to EMICERI for the wild type and pAS clones. All values are mean±SEM with n=4. **P<0.0001; *P<0.001; *P<0.05. ns=not significant.
Figure 13:
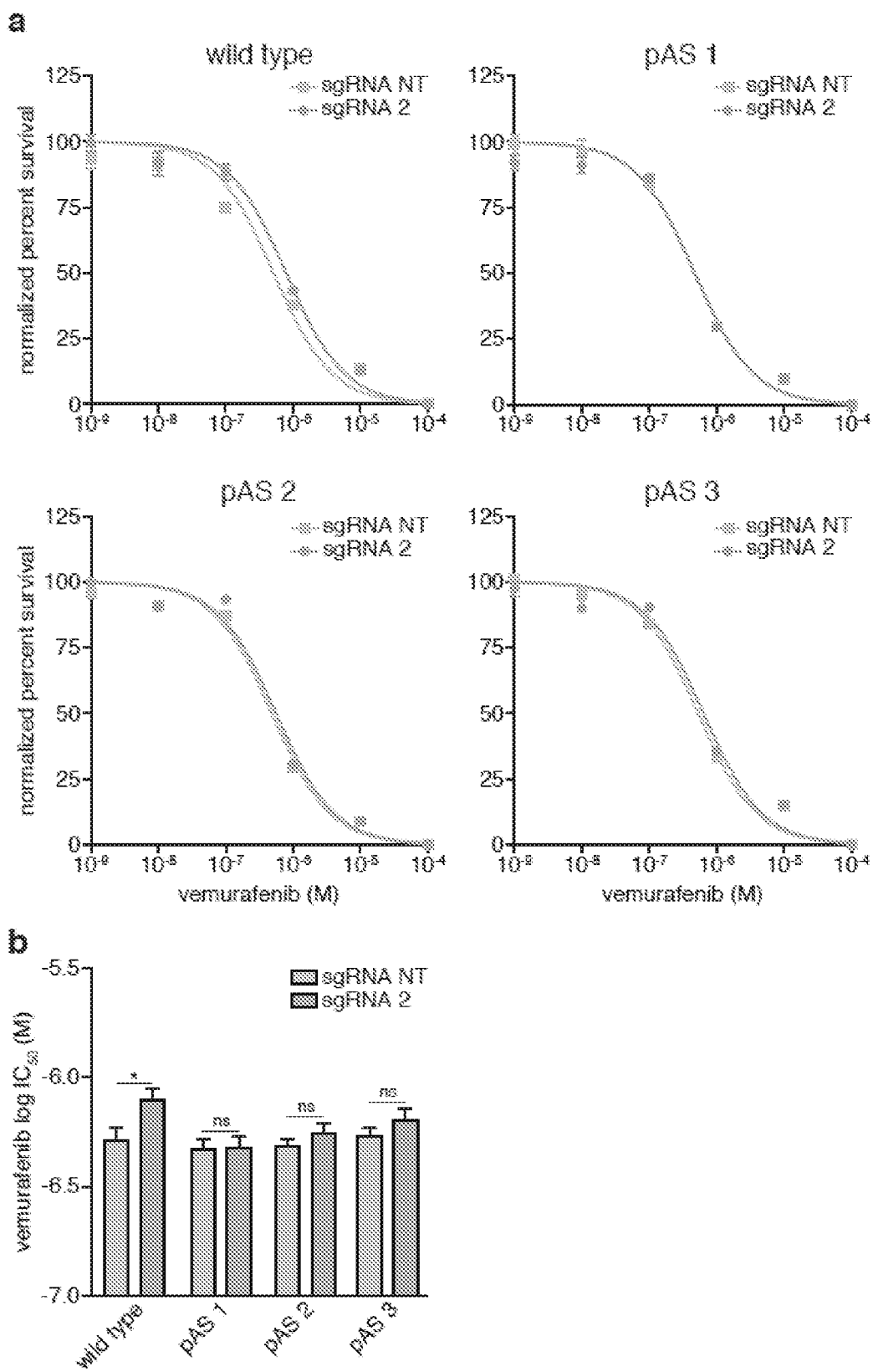
FIG. 13. Transcriptional activation of EMICERI confers vemurafenib resistance. a, Vemurafenib dose response curves for wild type and polyadenylation signal (pAS) clones transduced with SAM and EMICERI-targeting or non-targeting (NT) sgRNAs. b, Vemurafenib half maximal inhibitory concentration (IC50) for the same conditions as (a). All values are mean±SEM with n=4. *P<0.05. ns=not significant.

Clonal A375 cell lines were generated carrying insertions of 3 tandem polyadenylation signals (pAS) downstream of the EMICERI TSS, which eliminated production of most of the EMICERI RNA without disrupting the promoter sequence (FIG. 4e, FIG. 12a-c). Upon SAM activation, the pAS-insertion clones showed significantly reduced expression of EMICERI, MOB3B, and the three other nearby genes compared to wild type clones (FIG. 4f, g and FIG. 12d-f), and, as expected, reduced vemurafenib resistance (FIG. 4h and FIG. 13). This provides genetic evidence that transcription of EMICERI is involved in MOB3B activation.

The EMICERI transcript was knocked down by transient transfection with antisense oligonucleotides (ASOs), which can lead to RNase H-mediated cleavage of nascent transcripts and transcriptional termination of EMICERI (FIG. 4a). These experiments were performed in the context of activating EMICERI by targeting SAM to the promoter. ASOs targeting EMICERI reduced expression of both EMICERI and MOB3B in a dosage-dependent manner (FIG. 4i and FIG. 14a), consistent with the dCas9 and pAS insertion results.

These EMICERI perturbation experiments demonstrate that transcription of EMICERI is required for full activation of MOB3B, confirming that EMICERI is a functional noncoding locus that activates four neighboring protein-coding genes and contributes to the screening phenotype.

Figure 14:
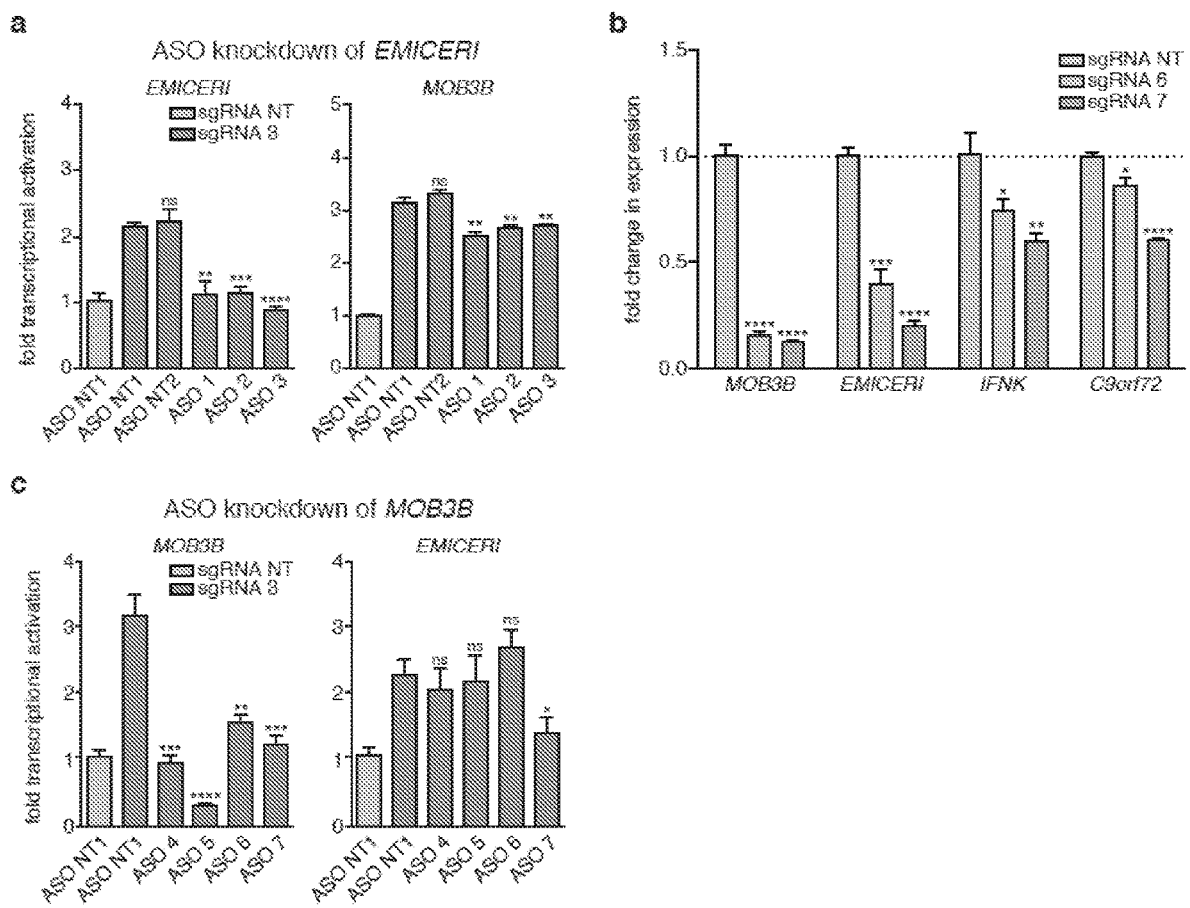
FIG. 14. EMICERI and MOB3B act reciprocally to regulate each other through the process of transcription. a, Expression of EMICERI and MOB3B after antisense oligonucleotide (ASO) knockdown of EMICERI in the context of SAM activation. b, Expression of MOB3B and neighboring genes in A375 cells transduced with non-targeting (NT) or MOB3B-targeting sgRNAs and dCas9. c, Expression of MOB3B and EMICERI after ASO knockdown of MOB3B in the context of SAM activation. c, All values are mean±SEM with n=4. **P<0.0001; *P<0.001; **P<0.01; *P<0.05. ns=not significant.

Although the experiments above demonstrate that EMICERI transcription is required for MOB3B activation, the precise mechanism may involve either a function of the EMICERI transcript itself or the process of its transcription (e.g., recruitment of transcriptional co-activators). In the latter case, MOB3B transcription might reciprocally regulate EMICERI expression. Indeed, targeting dCas9 downstream of the MOB3B TSS successfully blocked MOB3B transcription and reduced expression of EMICERI and other neighboring genes (FIG. 4b); and similarly, in the context of SAM activation, ASOs targeting MOB3B introns reduced the activation of both MOB3B and EMICERI (FIG. 4j and FIG. 14c). Together, the EMICERI and MOB3B perturbation experiments suggested that transcription of both the lncRNA (EMICERI) and the mRNA (MOB3B) regulate one another in a positive feedback mechanism that then activates a broader gene neighborhood, potentially through general processes associated with transcription.

A major challenge in understanding the regulatory logic of the genome has been to identify functional lncRNA loci and characterize their mechanisms. Here it has been demonstrated that genome-scale activation screens enable systematic identification of many lncRNA loci that influence a specific cellular process, facilitating efforts to understand the functions and mechanisms of these key loci. Through a series of functional experiments, a method for distinguishing categories of regulatory mechanisms has been provided, including non-local (trans) functions as well as a diverse array of possible local regulatory mechanisms. Interestingly, the candidate lncRNA loci identified appear to involve largely local, rather than non-local, regulation of gene expression (Table 2), including a remarkable case involving coordinated activation of 4 nearby genes. Further application of this noncoding gain-of-function screening approach in other contexts, together with loss-of-function screening methods and characterization strategy, will help elucidate the complex roles of these poorly understood players in development and disease.

Supplementary Discussion.

Vemurafenib resistance. Cellular response was used to vemurafenib in culture as a convenient screenable assay to identify lncRNAs with important cellular functions. LncRNAs that confer vemurafenib resistance are those that increase cell survival in the presence of the drug in culture.

Local function of SAM. It was noted that it is possible that targeting SAM to a genomic sequence in close three-dimensional proximity to a gene promoter might lead to gene activation through a direct function of the epigenetic regulatory proteins recruited by SAM. In this case, gene activation would not reflect a local or non-local function of the lncRNA locus itself, but rather a direct function of SAM. This is not a likely explanation for the strong activation observed at many of the candidate loci from the screen, as previous studies using CRISPR activators have found that sgRNAs targeting regions close to gene promoters can fail to activate gene expression. Nevertheless, further functional characterization of these loci is required to determine if they indeed have local functions through their promoters, transcription, or RNA transcripts, pursued in detail for the EMICERI locus.

Potential for local functions of lncRNA loci where SAM activation did not lead to transcript up-regulation. For the 5 candidate lncRNA loci with undetectable transcriptional upregulation, targeting of SAM to these loci may confer vemurafenib resistance through a mechanism that does not involve activation of the lncRNA transcript. For instance, SAM targeting can activate an endogenous enhancer or promoter of a nearby gene within 1 Mb that is associated with vemurafenib resistance. To further investigate the mechanism at these loci, RNA sequencing was performed for activation of each of these 5 loci to examine the expression of all genes within 1 Mb of the targeted sites. At 4 of the 5 loci, SAM activation led to differential expression of 1 or 2 neighboring protein-coding genes that may contribute to resistance (Table 7). At the remaining locus TCONS_00006579, differential expression for two of the neighboring genes (BBX and CBLB) and their contribution to resistance could not be statistically excluded, and SAM activation of the TCONS_00006579 locus could be mediating resistance through subtle effects on the expression of a neighboring gene. These analyses provide a candidate list of genes that may be locally regulated by these lncRNA loci through a function that does not involve activating the lncRNA transcript, although direct activation by SAM is also a possibility for the mechanism of resistance at these loci.

Potential non-local functions of candidate lncRNA loci. To test whether candidate lncRNAs contribute to vemurafenib resistance via non-local functions, cDNAs encoding each lncRNA were overexpressed through random lentiviral integration, and none of them were found to have affected drug resistance (FIG. 7b), suggesting that these loci likely do not act through non-local functions to confer vemurafenib resistance. However, this does not rule out the possibility that these lncRNAs could have a different non-local function other than contributing to vemurafenib resistance.

Potential for local function of NR_034078. The NR_034078 locus was further investigated because a function upon cDNA over-expression of the lncRNA transcript (FIG. 7b) was not observe, and yet changes in gene expression within 1 Mb of the lncRNA locus was also not observed. NR_034078 is a pseudogene of CASP4, and therefore sgRNAs targeting NR_034078 may potentially target CASP4 because of sequence similarity. However, the sgRNAs used to activate NR_034078 in the validation experiments were highly specific with specificity scores >0.95. Each sgRNA had 5-7 mismatches compared to the most similar spacer sequence targeting CASP4. BLAST of the 800 bp NR_034078 promoter region targeted by the sgRNA library suggested that the promoter region was not similar to other genomic regions, with the most similar genomic sequence having 80% similarity to only 22% of the region.

Because no evidence suggests off-target activity of the sgRNAs targeting the NR_034078 locus, NR_034078 might indeed regulate the expression of a nearby gene, although the RNA-seq experiments lacks sufficient power to detect that change. Differential expression for two of the neighboring genes within 1 Mb from the annotated NR_034078 TSS (CASP4 and PDGFD) and their contribution to resistance could not be statistically excluded. Together, the specificity and power analyses suggest that SAM activation of the NR_034078 locus may act through a local mechanism, perhaps by subtle effects on the expression of a neighboring gene.

High levels of IFNK activation produces IFNK-EMICERI fusion transcripts. Targeting SAM to EMICERI with sgRNA 2 strongly activates IFNK, which is oriented upstream of EMICERI on the same strand. By RNA-seq that this level of activation generated IFNK transcripts initiating from the IFNK TSS and continuing through the EMICERI TSS (IFNK-EMICERI fusion transcripts, FIG. 9a). For this condition (activation with sgRNA 2), qPCR probes intended to detect EMICERI expression would also detect the elongated transcript initiated from the IFNK TSS, and the observations that EMICERI transcription is altered may occur as a result of direct effects on IFNK transcription. To rule out this possibility, key experiments showing that EMICERI transcription is required for MOB3B activation and vemurafenib resistance were also performed using sgRNA 3, which did not strongly activate IFNK and for which IFNK-EMICERI fusion transcripts were not detected (FIG. 9a).

Activation of C9orf72 by SAM slightly upregulates EMICERI. To determine if the coordinated activation effects observed upon targeting the EMICERI/MOB3B promoter were unique to the EMICERI locus, SAM as targeted to the promoters of the other three nearby genes. Targeting SAM to the C9orf72 promoter led to a slight activation (~3-fold) of EMICERI alone. The 3-fold activation observed when targeting SAM to the C9orf72 promoter is much lower than the ~40-, 200-, and 3000-fold activation observed when directly targeting SAM to the EMICERI/MOB3B promoter with sgRNAs 1, 2, and 3.

MOB3B mediates resistance in multiple melanoma models. Transcriptional activation of EMICERI mediates vemurafenib resistance via upregulation of MOB3B. MOB3B is a paralog of MOB1A/B, which are components of the Hippo signaling pathway, whose activation is known to confer vemurafenib resistance. Accordingly, exploration of potential changes in expression of LATS1 and TAZ, proteins downstream of MOB1A/B, indicated that MOB3B overexpression downregulates LATS1 expression (FIG. 3b,c and FIG. 10f-h) to produce global gene expression changes similar to those observed upon TAZ overexpression. These results suggest that the EMICERI locus mediates resistance by overexpression MOB3B and activating the Hippo signaling pathway.

The observations of EMICERI and MOB3B could extend to other cell lines and patient tumors. Activation of EMICERI with SAM conferred vemurafenib resistance in two additional sensitive melanoma cell lines (FIG. 3d, e and FIG. 10i). Consistent with the observations in A375, expression of EMICERI significantly correlates with its nearby protein-coding genes in patient melanoma from The Cancer Genome Atlas (TCGA) (P<0.01 for all 4 genes; FIG. 11a). Expression of EMICERI and MOB3B are also significantly correlated with previously established gene expression markers of sensitivity to vemurafenib (P=0.0001 and P<0.0001 respectively; FIG. 3f). Conversely, a gene expression signature derived from MOB3B overexpression RNA-seq data was correlated with markers of vemurafenib resistance (P=0.0075; FIG. 3f). Analysis of gene expression and drug resistance data from the Cancer Cell Line Encyclopedia (CCLE) revealed similar correlations (FIG. 11b, c), and a similar trend was observed in two additional primary patient melanoma-derived cell lines (FIG. 11d-f). The analyses and vemurafenib resistance data demonstrate that the EMICERI locus is relevant in multiple melanoma models beyond the initial cell line in which the screen was conducted.

The observations that higher endogenous MOB3B expression is correlated with higher sensitivity to vemurafenib, yet the MOB3B overexpression RNA-seq signature is correlated with higher resistance to vemurafenib are not unusual. Previously identified mediators of vemurafenib resistance exhibit similar correlations: for example, higher endogenous expression of MITF correlates with higher sensitivity to vemurafenib, yet MITF overexpression confers resistance in patient melanoma and melanoma cell lines—identical to the observations for MOB3B. In the case of MITF, higher endogenous expression of MITF indicates higher oncogenic BRAF activity and higher sensitivity to BRAF inhibition by vemurafenib. BRAF inhibition therefore reduces MITF expression. Similarly, RNA-seq for patient melanoma samples pre- and post-RAF/MEK inhibition showed that MOB3B expression decreased after RAF inhibition in 5 out of 6 samples, supporting the potential relevance of MOB3B in vemurafenib resistance.

Insertion of polyadenylation signals (pAS). Although pAS insertion led to decreased expression of EMICERI and MOB3B in the context of SAM activation of the locus, it did not significantly affect the basal expression levels (i.e., without SAM activation) of EMICERI or MOB3B (FIG. 12b, c). To rule out the possibility that the observed differences were caused by off-target activity of the EMICERI qPCR probe, the qPCR probe was validated for detecting EMICERI transcript levels using a control without reverse transcriptase and verified by sequencing the qPCR-amplified product that it matches the desired target fragment. It is possible a decrease in basal expression levels could not be detected because there is high biological variability between clones have been cultured independently for 4 months and/or because MOB3B is an essential gene in A375 cells (i.e., its knockdown is known to affect cell proliferation of A375 cells (FIG. 10e) and over time A375 cells might compensate to recover MOB3B expression).

Antisense oligonucleotides (ASOs). ASOs have been observed to knock down the expression of the mature transcript when targeted to intronic RNA sequences, and thus it was expected that ASOs will affect not only the levels of the RNA transcripts but also the process of transcription in the targeted RNA locus. ASO targeting nascent transcripts is thought to affect transcription because RNAse H cleavage of the targeted nascent RNA transcript should likely be followed by exonuclease-mediated decay and subsequent transcription termination, similar to the "torpedo model" for natural transcriptional termination in which Xrn2 facilitates RNA Polymerase II release after RNA cleavage near the pAS signal.

REFERENCES

1 Guttman, M. et al. Chromatin signature reveals over a thousand highly conserved large non-coding RNAs in mammals. Nature 458, 223-227, doi:10.1038/nature07672 (2009).
2 Cabili, M. N. et al. Integrative annotation of human large intergenic noncoding RNAs reveals global properties and specific subclasses. Genes Dev 25, 1915-1927, doi: 10.1101/gad.17446611 (2011).
3 Derrien, T. et al. The GENCODE v7 catalog of human long noncoding RNAs: analysis of their gene structure, evolution, and expression. Genome Res 22, 1775-1789, doi: 10.1101/gr.132159.111 (2012).
4 Brown, C. J. et al. The human XIST gene: analysis of a 17 kb inactive X-specific RNA that contains conserved repeats and is highly localized within the nucleus. Cell 71, 527-542 (1992).
5 Engreitz, J. M. et al. The Xist lncRNA exploits three-dimensional genome architecture to spread across the X chromosome. Science 341, 1237973, doi:10.1126/science.1237973 (2013).
6 Kretz, M. et al. Control of somatic tissue differentiation by the long non-coding RNA TINCR. Nature 493, 231-235, doi:10.1038/nature11661 (2013).
7 Wang, K. C. et al. A long noncoding RNA maintains active chromatin to coordinate homeotic gene expression. Nature 472, 120-124, doi:10.1038/nature09819 (2011).
8 Guttman, M. & Rinn, J. L. Modular regulatory principles of large non-coding RNAs. Nature 482, 339-346, doi: 10.1038/nature10887 (2012).
9 Anderson, K. M. et al. Transcription of the non-coding RNA upperhand controls Hand2 expression and heart development. Nature, doi:10.1038/nature20128 (2016).
10 Engreitz, J. M. et al. Local regulation of gene expression by lncRNA promoters, transcription and splicing. Nature, doi:10.1038/nature20149 (2016).
11 Paralkar, V. R. et al. Unlinking an lncRNA from Its Associated cis Element. Mol Cell 62, 104-110, doi: 10.1016/j.molcel.2016.02.029 (2016).
12 Konermann, S. et al. Genome-scale transcriptional activation by an engineered CRISPR-Cas9 complex. Nature 517, 583-588, doi:10.1038/nature14136 (2015).
13 O'Leary, N. A. et al. Reference sequence (RefSeq) database at NCBI: current status, taxonomic expansion, and functional annotation. Nucleic Acids Res 44, D733-745, doi:10.1093/nar/gkv1189 (2016).
14 Konig, R. et al. A probability-based approach for the analysis of large-scale RNAi screens. Nat Methods 4, 847-849, doi:10.1038/nmeth1089 (2007).
15 Johannessen, C. M. et al. A melanocyte lineage program confers resistance to MAP kinase pathway inhibition. Nature 504, 138-142, doi:10.1038/nature12688 (2013).
16 Lei, Q. Y. et al. TAZ promotes cell proliferation and epithelial-mesenchymal transition and is inhibited by the hippo pathway. Mol Cell Biol 28, 2426-2436, doi: 10.1128/MCB.01874-07 (2008).
17 Lin, L. et al. The Hippo effector YAP promotes resistance to RAF- and MEK-targeted cancer therapies. Nat Genet 47, 250-256, doi:10.1038/ng.3218 (2015).
18 Praskova, M., Xia, F. & Avruch, J. MOBKL1A/MOBKL1B phosphorylation by MST1 and MST2 inhibits cell proliferation. Curr Biol 18, 311-321, doi:10.1016/j.cub.2008.02.006 (2008).
19 West, S., Proudfoot, N. J. & Dye, M. J. Molecular dissection of mammalian RNA polymerase II transcriptional termination. Mol Cell 29, 600-610, doi:10.1016/j.molcel.2007.12.019 (2008).
20 Skalska, L., Beltran-Nebot, M., Ule, J. & Jenner, R. G. Regulatory feedback from nascent RNA to chromatin and transcription. Nat Rev Mol Cell Biol, doi:10.1038/nrm.2017.12 (2017).
21 Fulco, C. P. et al. Systematic mapping of functional enhancer-promoter connections with CRISPR interference. Science 354, 769-773, doi:10.1126/science.aag2445 (2016).
22 Liu, S. J. et al. CRISPRi-based genome-scale identification of functional long noncoding RNA loci in human cells. Science 355, doi:10.1126/science.aah7111 (2017).
23 Sanjana, N. E. et al. High-resolution interrogation of functional elements in the noncoding genome. Science 353, 1545-1549, doi:10.1126/science.aaf7613 (2016).
24 Zhu, S. et al. Genome-scale deletion screening of human long non-coding RNAs using a paired-guide RNA CRISPR-Cas9 library. Nat Biotechnol, doi:10.1038/nbt.3715 (2016).
25 Hsu, P. D. et al. DNA targeting specificity of RNA-guided Cas9 nucleases. Nat Biotechnol 31, 827-832, doi:10.1038/nbt.2647 (2013).
26 Shalem, O. et al. Genome-scale CRISPR-Cas9 knockout screening in human cells. Science 343, 84-87, doi: 10.1126/science.1247005 (2014).
27 Joung, J. et al. Genome-scale CRISPR-Cas9 knockout and transcriptional activation screening. Nat Protoc 12, 828-863, doi:10.1038/nprot.2017.016 (2017).
28 Langmead, B., Trapnell, C., Pop, M. & Salzberg, S. L. Ultrafast and memory-efficient alignment of short DNA sequences to the human genome. Genome Biol 10, R25, doi:10.1186/gb-2009-10-3-r25 (2009).
29 Li, B. & Dewey, C. N. RSEM: accurate transcript quantification from RNA-Seq data with or without a reference genome. BMC Bioinformatics 12, 323, doi: 10.1186/1471-2105-12-323 (2011).
30 Trapnell, C., Pachter, L. & Salzberg, S. L. TopHat: discovering splice junctions with RNA-Seq. Bioinformatics 25, 1105-1111, doi:10.1093/bioinformatics/btp120 (2009).
31 Rao, S. S. et al. A 3D map of the human genome at kilobase resolution reveals principles of chromatin looping. Cell 159, 1665-1680, doi:10.1016/j.cell.2014.11.021 (2014).
32 Consortium, E. P. An integrated encyclopedia of DNA elements in the human genome. Nature 489, 57-74, doi: 10.1038/nature11247 (2012).
33 Grant, C. E., Bailey, T. L. & Noble, W. S. FIMO: scanning for occurrences of a given motif. Bioinformatics 27, 1017-1018, doi:10.1093/bioinformatics/btr064 (2011).

34 Matys, V. et al. TRANSFAC and its module TRANS-Compel: transcriptional gene regulation in eukaryotes. *Nucleic Acids Res* 34, D108-110, doi:10.1093/nar/gkj143 (2006).
35 Buenrostro, J. D., Wu, B., Chang, H. Y. & Greenleaf, W. J. ATAC-seq: A Method for Assaying Chromatin Accessibility Genome-Wide. *Curr Protoc Mot Biol* 109, 21 29 21-29, doi:10.1002/0471142727.mb2129s109 (2015).
36 Van der Auwera, G. A. et al. From FastQ data to high confidence variant calls: the Genome Analysis Toolkit best practices pipeline. *Curr Protoc Bioinformatics* 43, 11 10 11-33, doi:10.1002/0471250953.bi1110s43 (2013).
37 Felsenstein, J. & Churchill, G. A. A Hidden Markov Model approach to variation among sites in rate of evolution. *Mot Biol Evol* 13, 93-104 (1996).
38 Feng, J., Liu, T., Qin, B., Zhang, Y. & Liu, X. S. Identifying ChIP-seq enrichment using MACS. *Nat Protoc* 7, 1728-1740, doi:10.1038/nprot.2012.101 (2012).
39 Dobin, A. et al. STAR: ultrafast universal RNA-seq aligner. *Bioinformatics* 29, 15-21, doi:10.1093/bioinformatics/bts635 (2013).
40 DeLuca, D. S. et al. RNA-SeQC: RNA-seq metrics for quality control and process optimization. *Bioinformatics* 28, 1530-1532, doi:10.1093/bioinformatics/bts196 (2012).
41 Liberzon, A. et al. Molecular signatures database (MSigDB) 3.0. *Bioinformatics* 27, 1739-1740, doi: 10.1093/bioinformatics/btr260 (2011).
42 Konieczkowski, D. J. et al. A melanoma cell state distinction influences sensitivity to MAPK pathway inhibitors. *Cancer Discov* 4, 816-827, doi:10.1158/2159-8290.CD-13-0424 (2014).
43 Barbie, D. A. et al. Systematic RNA interference reveals that oncogenic KRAS-driven cancers require TBK1. *Nature* 462, 108-112, doi:10.1038/nature08460 (2009).
44 Barretina, J. et al. The Cancer Cell Line Encyclopedia enables predictive modelling of anticancer drug sensitivity. *Nature* 483, 603-607, doi:10.1038/nature11003 (2012).
45 Gilbert, L. A. et al. Genome-Scale CRISPR-Mediated Control of Gene Repression and Activation. *Cell* 159, 647-661, doi:10.1016/j.cell.2014.09.029 (2014).
46 Altschul, S. F. et al. Gapped BLAST and PSI-BLAST: a new generation of protein database search programs. *Nucleic Acids Res* 25, 3389-3402 (1997).
47 Wilks, C. et al. The Cancer Genomics Hub (CGHub): overcoming cancer through the power of torrential data. *Database (Oxford)* 2014, doi:10.1093/database/bau093 (2014).
48 Garraway, L. A. et al. Integrative genomic analyses identify MITF as a lineage survival oncogene amplified in malignant melanoma. *Nature* 436, 117-122, doi:10.1038/nature03664 (2005).
49 Wellbrock, C. et al. Oncogenic BRAF regulates melanoma proliferation through the lineage specific factor MITF. *PLoS One* 3, e2734, doi:10.1371/journal.pone.0002734 (2008).
50 Wagle, N. et al. MAP kinase pathway alterations in BRAF-mutant melanoma patients with acquired resistance to combined RAF/MEK inhibition. *Cancer Discov* 4, 61-68, doi:10.1158/2159-8290.CD-13-0631 (2014).

Example 3: Generation of lncRNA Upregulation Cell Library

This example demonstrates how to generate a library of cells where each cell has a single lncRNA upregulated transcriptionally:

Applicants make a library of ES cells where each cell has a single lncRNA upregulated transcriptionally, and the entire library of ES cells will have every single lncRNA upregulated transcriptionally. This library is useful for the screening of lncRNA in cellular processes as well as diseases and drug resistance.

To make this cell library, Applicants integrate into the ES cell a dCas9 driven by an inducible promoter (e.g., doxycycline inducible promoter) and MS2-P65-HSF1. In addition, Applicants integrate a single guide RNA having an MS2 loop and targeting a specific lncRNA coding sequence in the ES cell. To make the ES cell library, Applicants simply mix ES cells with a library of guide RNAs targeting each lncRNA in the human genome. Applicants first introduce a single BxB1 attB site into the AAVS1 locus of the human ES cell. Then Applicants use the BxB1 integrase to facilitate the integration of individual guide RNA into the BxB1 attB site in AAVS1 locus. To facilitate integration, each guide RNA is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce dCas9 expression. After induction, dCas9 forms an activation complex with the MS2-P65-HSF1 domains recruited by sgRNA having MS2 loops, and the activation complex upregulates lncRNA transcription specified by the guide RNA. To verify the diversity of this cell library, Applicants carry out whole exome sequencing to ensure that Applicants are able to observe upregulation in every single targeted lncRNA. This cell library can be used for a variety of applications, including who library-based screens, or can be sorted into individual cell clones to facilitate rapid generation of clonal cell lines with individual human lncRNA upregulation.

Example 4: Generation of lncRNA Knockout Cell Library

This example demonstrates how to generate a library of cells where each cell has a single lncRNA knocked out:

Applicants make a library of ES cells where each cell has a single lncRNA knocked out, and the entire library of ES cells will have every single lncRNA knocked out. This library is useful for the screening of lncRNA function in cellular processes as well as diseases and drug resistance.

To make this cell library, Applicants integrate Cas9 driven by an inducible promoter (e.g. doxycycline inducible promoter) into the ES cell. In addition, Applicants integrate a single guide RNA targeting a specific lncRNA in the ES cell. To make the ES cell library, Applicants simply mix ES cells with a library of guide RNAs targeting each lncRNA in the human genome. Applicants first introduce a single BxB1 attB site into the AAVS1 locus of the human ES cell. Then Applicants use the BxB1 integrase to facilitate the integration of individual guide RNA into the BxB1 attB site in AAVS1 locus. To facilitate integration, each guide RNA is contained on a plasmid that carries of a single attP site. This way BxB1 will recombine the attB site in the genome with the attP site on the guide RNA containing plasmid.

To generate the cell library, Applicants take the library of cells that have single guide RNAs integrated and induce Cas9 expression. After induction, Cas9 mediates double strand break at sites specified by the guide RNA. To verify the diversity of this cell library, Applicants carry out whole exome sequencing to ensure that Applicants are able to observe mutations in every single targeted lncRNA. This cell library can be used for a variety of applications, including who library-based screens, or can be sorted into individual cell clones to facilitate rapid generation of clonal cell lines with individual human lncRNA knocked out.

Example 5: Genome Scale Perturbation Screening in Mammalian Cells

Similar to Examples 1 to 4 in which genome scale CRISPR lncRNA upregulation screening was conducted in A375 (BRAF(V600E)) melanoma cells to identify lncRNA associated with Vemurafenib resistance, Applicants further conduct genome scale perturbation screening in other mammalian cells to screen for lncRNA function in cellular processes as well as diseases and drug resistance.

Design and Cloning of SAM lncRNA Library

RefSeq noncoding RNAs (Release 69) were filtered for lncRNA transcripts that were longer than 200 bp and not overlapping with RefSeq coding gene isoforms. The RefSeq lncRNA catalog was combined with the Cabili lncRNA catalog and filtered for unique lncRNA transcriptional start sites (TSSs) defined as TSSs that were >50 bp apart. This resulted in 10,504 unique lncRNA TSSs that were targeted with ~10 single guide RNAs (sgRNAs) each for a total library of 95,958 sgRNAs. sgRNAs were designed to target the first 800 bp upstream of each TSS and subsequently filtered for GC content >25%, minimal overlap of the target sequence, and homopolymer stretch <4 bp. After filtering, the remaining sgRNAs were scored according to predicted off-target matches as described previously, and 6 sgRNAs with the best off-target scores were selected in the first 200 bp region upstream of the TSS, 1 in the 200-300 bp region, 1 in the 300-400 bp region, 1 in the 400-600 bp region, and 1 in the 600-800 bp region. In regions with an insufficient number of possible sgRNAs, sgRNAs were selected from the neighboring region closer to the TSS. An additional 500 non-targeting sgRNAs from the GeCKO library were included as controls. Cloning of the SAM sgRNA libraries was performed as previously described with a minimum representation of 100 transformed colonies per sgRNA followed by next-generation sequencing (NGS) validation.

Lentivirus Production and Transduction

For transduction, plasmids were packaged into lentivirus via transfection of library plasmid with appropriate packaging plasmids (psPAX2: Addgene 12260; pMD2.G: Addgene 12259) using Lipofectamine 2000 (Thermo Fisher 11668019) and Plus reagent (Thermo Fisher 11514015) in HEK293FT (Thermo Fisher R70007) as described previously. Human melanoma A375 cells (Sigma-Aldrich 88113005) were cultured in R10 media: RPMI 1640 (Thermo Fisher 61870) supplemented with 10% FBS (VWR 97068-085) and 1% penicillin/streptomycin (Thermo Fisher 15140122). Cells were passaged every other day at a 1:5 ratio. Concentrations for selection agents were determined using a kill curve: 300 µg/mL Zeocin (Thermo Fisher R25001), 10 µg/mL Blasticidin (Thermo Fisher A1113903), and 300 µg/mL Hygromycin (Thermo Fisher 10687010). Cells were transduced via spinfection and selected with the appropriate antibiotic as described previously. During selection, media was refreshed when cells were passaged every 3 days. The duration of selection was 7 days for Zeocin and 5 days for Hygromycin and Blasticidin. Lentiviral titers were calculated by spinfecting cells with 5 different volumes of lentivirus and determining viability after a complete selection of 3 days.

Perturbation Screening of lncRNA Function in Cellular Processes

Applicants conduct a genome-scale SAM perturbation screening of lncRNAs. Mammalian cells stably integrated with dCas9-VP64 (Addgene 61425) and MS2-P65-HSF1 (Addgene 61426) are transduced with the pooled sgRNA library (Addgene 61427) as described above at an MOI of 0.3 for a total of 4 infection replicates, with a minimal representation of 500 transduced cells per sgRNA in each replicate. The mammalian cells may be selected from cells associated with a disease or a drug resistance condition. The mammalian cells are maintained at >500 cells per sgRNA during subsequent passaging. After 7 days of Zeocin selection and 2 days of no antibiotic selection, cells are split into control (DMSO) and perturbation conditions. Cells are passaged every 2 days for a total of 14 days of control or perturbation treatment. At the end of the screening selection, >500 cells per sgRNA in each condition are harvested for gDNA extraction and amplification of the virally integrated sgRNAs. Resulting libraries are deep-sequenced on Illumina MiSeq or NextSeq platforms with a coverage of >25 million reads passing filter per library.

NGS and Screen Hits Analysis

NGS data are de-multiplexed using unique index reads. sgRNA counts are determined based on perfectly matched sequencing reads only. For each condition, a pseudocount of 1 is added to the sgRNA count and the counts are normalized to the total number of counts in the condition. The sgRNA fold change as a result of screening selection is calculated by dividing the normalized sgRNA counts in the perturbation condition by the control and taking the base 2 logarithm. RIGER analysis is performed using GENE-E based on the normalized $\log_2$ ratios for each infection replicate. Since a low percentage of functional sgRNAs is expected for each lncRNA, the weighted sum method is used. To determine the empirical false discovery rate (FDR) of lncRNA screening hits, the weighted sum for 10 randomly selected non-targeting sgRNAs in the sgRNA library is used to estimate the P value for each lncRNA and a threshold based on a FDR of 0.05 (Benjamini-Hochberg) is selected that corresponded to a P value of 0.031.

Further Testing of lncRNA Function

The mammalian cells stably integrated with dCas9-VP64 and MS2-P65-HSF1 are transduced with individual sgRNAs targeting the top candidate lncRNAs from the perturbation screen (3 sgRNAs with the highest enrichment per lncRNA) or with control non-targeting sgRNA at an MOI of <0.5 and selected with Zeocin for 5 days as described above.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

Citation or identification of any document in this application is not an admission that such document is available as prior art to the present invention.

What is claimed is:

1. A method of treating melanoma resistant to a BRAF inhibitor, comprising administering to a patient suffering from melanoma resistant to the BRAF inhibitor an effective amount of a BRAF inhibitor and a pharmaceutical composition that inhibits TCONS_00015940 (SEQ ID NO: 170) or a gene regulated by TCONS_00015940 (SEQ ID NO: 170) selected from the group consisting of EQTN, MOB3B, IFNK, and C9orf72, wherein:

TCONS_00015940 (SEQ ID NO: 170) or the gene regulated by TCONS_00015940 (SEQ ID NO: 170) is inhibited by mutating, deleting, or transcriptionally inactivating TCONS_00015940 (SEQ ID NO: 170) or the gene regulated by TCONS_00015940 (SEQ ID NO: 170) by an RNA-guided DNA binding protein, a zinc finger, a zinc finger nuclease (ZFN), a transcription activator-like effector (TALE), a transcription activator-like effector nuclease (TALEN), or a meganuclease;

TCONS_00015940 (SEQ ID NO: 170) or the gene regulated by TCONS_00015940 (SEQ ID NO: 170) is inhibited by downregulating EMICERI or an mRNA transcript of the gene regulated by TCONS_00015940 (SEQ ID NO: 170) with an antisense oligonucleotide (ASO), an interfering RNA, a microRNA, a riboswitch, a ribosome or catalytic RNA, or an RNA-guided RNA binding protein; and/or the gene regulated by TCONS_00015940 (SEQ ID NO: 170) is inhibited by administration of a small molecule inhibitor against a polypeptide encoded by the gene regulated by TCONS_00015940 (SEQ ID NO: 170) or an antibody that specifically binds the polypeptide encoded by the gene regulated by TCONS_00015940 (SEQ ID NO: 170).

2. The method of claim 1, wherein the melanoma is selected from the group consisting of nodular melanoma, lentigo maligna, lentigo maligna melanoma, acral lentiginous melanoma, superficial spreading melanoma, mucosal melanoma, polypoid melanoma, desmoplastic melanoma, amelanotic melanoma, and soft-tissue melanoma.

3. The method of claim 1, wherein the BRAF inhibitor is selected from the group consisting of Vemurafenib, Dabrafenib, Sorafenib, GDC-0879, PLX-4720, and LGX818.

4. The method of claim 1, wherein the RNA-guided DNA binding protein is a Type-II or Type-V CRISPR-Cas effector.

5. The method of claim 4, wherein TCONS_00015940 (SEQ ID NO: 170) or the gene regulated by TCONS_00015940 (SEQ ID NO: 170) is inhibited by mutating, deleting, or transcriptionally inactivating TCONS_00015940 (SEQ ID NO: 170) or the gene regulated by TCONS_00015940 (SEQ ID NO: 170) with a non-naturally occurring or engineered composition comprising:

(i) a Type-II or Type-V CRISPR-Cas effector protein or a DNA or mRNA encoding said Type-II or Type-V CRISPR-Cas effector protein, and (ii) a guide RNA targeting TCONS_00015940 (SEQ ID NO: 170) or the gene regulated by TCONS_00015940 (SEQ ID NO: 170), or a DNA encoding the guide RNA, wherein the Type-II or Type V CRISPR-Cas effector protein is capable of forming a complex with the guide RNA, and the guide RNA is capable of directing sequence-specific binding of the complex to the target sequence.

6. The method of claim 1 wherein the RNA-guided RNA binding protein is a Type-VI CRISPR-Cas effector.

7. The method of claim 6, wherein TCONS_00015940 (SEQ ID NO: 170) or the gene regulated by TCONS_00015940 (SEQ ID NO: 170) is inhibited by downregulating EMICERI or an mRNA transcript of the gene regulated by TCONS_00015940 (SEQ ID NO: 170) with a non-naturally occurring or engineered compositions comprising:
- (i) a Type-VI CRISPR-Cas effector protein or a DNA or mRNA encoding said Type-VI CRISPR-Cas effector protein, and
- (ii) a guide RNA targeting EMICERI or an mRNA transcript of the gene regulated by TCONS_00015940 (SEQ ID NO: 170), or a DNA encoding the guide RNA, wherein the Type-VI CRISPR-Cas effector protein is capable of forming a complex with the guide RNA, and the guide RNA is capable of directing sequence-specific binding of the complex to the target sequence.

8. The method of claim 5, wherein the Type-II or Type-V CRISPR-Cas effector protein is not catalytically competent, optionally, the CRISPR-Cas effector is dCas9.

9. The method of claim 5, wherein the Type-II or Type-V CRISPR-Cas effector protein is catalytically competent, and wherein the non-naturally occurring or engineered composition further comprises an HDR template comprising one or more polyadenylation signal (pAS) sequences.

* * * * *

SEQUENCE LISTING

```
<160> NUMBER OF SEQ ID NOS: 181

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Gly Gly Ser
1

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 2

Gly Gly Gly Ser Gly Gly Gly Ser Gly Gly Gly Ser
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 3

Ala Glu Ala Ala Ala Lys Ala
1               5

<210> SEQ ID NO 4
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 4

Gly Gly Gly Gly Ser Gly Gly Gly Ser Gly Gly Gly Gly Ser
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 5

Gly Gly Gly Gly Ser Gly Gly Gly Gly Ser Gly Gly Gly Gly Ser
1               5                   10                  15

<210> SEQ ID NO 6
<211> LENGTH: 30
<212> TYPE: PRT
<213> ORGANISM: Artificial Sequence
<220> FEATURE:
<223> OTHER INFORMATION: Synthetic Peptide
```

<400> SEQUENCE: 6

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 7
<211> LENGTH: 45
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 8
<211> LENGTH: 60
<212> TYPE: PRT
<213> ORGANISM: Artificial Sequence
<220> FEATURE:
<223> OTHER INFORMATION: Synthetic Peptide

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 9

Gly Gly Gly Gly Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 10

Gly Gly Gly Gly Ser Gly Gly Gly Gly Ser
1               5                   10

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Gly Gly Gly Gly Ser Gly Gly Gly Gly Ser Gly Gly Gly Gly Ser Gly
1               5                   10                  15

Gly Gly Gly Ser
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 12

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 13
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 13

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 14
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 14

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 15
<211> LENGTH: 50
<212> TYPE: PRT
<213> ORGANISM: Artificial Sequence
<220> FEATURE:
<223> OTHER INFORMATION: Synthetic Peptide -continued

```
<400> SEQUENCE: 15

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
                20                  25                  30
Gly Gly Ser Gly Gly Gly Gly Ser Gly Gly Gly Gly Ser Gly Gly Gly
            35                  40                  45
Gly Ser
    50

<210> SEQ ID NO 16
<211> LENGTH: 55
<212> TYPE: PRT
<213> ORGANISM: Artificial Sequence
<220> FEATURE:
<223> OTHER INFORMATION: Synthetic Peptide

<400> SEQUENCE: 16

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
                20                  25                  30
Gly Gly Ser Gly Gly Gly Gly Ser Gly Gly Gly Gly Ser Gly Gly Gly
            35                  40                  45
Gly Ser Gly Gly Gly Gly Ser
    50                  55

<210> SEQ ID NO 17
<211> LENGTH: 7
<212> TYPE: PRT
<213> ORGANISM: SV40 virus

<400> SEQUENCE: 17

Pro Lys Lys Lys Arg Lys Val
1               5

<210> SEQ ID NO 18
<211> LENGTH: 16
<212> TYPE: PRT
<213> ORGANISM: Homo sapiens

<400> SEQUENCE: 18

Lys Arg Pro Ala Ala Thr Lys Ala Gly Gln Ala Lys Lys Lys Lys
1               5                   10                  15

<210> SEQ ID NO 19
<211> LENGTH: 9
<212> TYPE: PRT
<213> ORGANISM: Homo sapiens

<400> SEQUENCE: 19

Pro Ala Ala Lys Arg Val Lys Leu Asp
1               5

<210> SEQ ID NO 20
<211> LENGTH: 11
<212> TYPE: PRT
<213> ORGANISM: Homo sapiens

<400> SEQUENCE: 20

Arg Gln Arg Arg Asn Glu Leu Lys Arg Ser Pro
1               5                   10
```

-continued

```
<210> SEQ ID NO 21
<211> LENGTH: 38
<212> TYPE: PRT
<213> ORGANISM: Homo sapiens

<400> SEQUENCE: 21

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
            35

<210> SEQ ID NO 22
<211> LENGTH: 42
<212> TYPE: PRT
<213> ORGANISM: Homo sapiens

<400> SEQUENCE: 22

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 23
<211> LENGTH: 8
<212> TYPE: PRT
<213> ORGANISM: Homo sapiens

<400> SEQUENCE: 23

Val Ser Arg Lys Arg Pro Arg Pro
1               5

<210> SEQ ID NO 24
<211> LENGTH: 8
<212> TYPE: PRT
<213> ORGANISM: Homo sapiens

<400> SEQUENCE: 24

Pro Pro Lys Lys Ala Arg Glu Asp
1               5

<210> SEQ ID NO 25
<211> LENGTH: 8
<212> TYPE: PRT
<213> ORGANISM: Homo sapiens

<400> SEQUENCE: 25

Pro Gln Pro Lys Lys Lys Pro Leu
1               5

<210> SEQ ID NO 26
<211> LENGTH: 12
<212> TYPE: PRT
<213> ORGANISM: Mus musculus

<400> SEQUENCE: 26

Ser Ala Leu Ile Lys Lys Lys Lys Lys Met Ala Pro
1               5                   10
```

```
<210> SEQ ID NO 27
<211> LENGTH: 5
<212> TYPE: PRT
<213> ORGANISM: Influenza virus

<400> SEQUENCE: 27

Asp Arg Leu Arg Arg
1               5

<210> SEQ ID NO 28
<211> LENGTH: 7
<212> TYPE: PRT
<213> ORGANISM: Influenza virus

<400> SEQUENCE: 28

Pro Lys Gln Lys Lys Arg Lys
1               5

<210> SEQ ID NO 29
<211> LENGTH: 10
<212> TYPE: PRT
<213> ORGANISM: Hepatitis D virus

<400> SEQUENCE: 29

Arg Lys Leu Lys Lys Ile Lys Lys Leu
1               5                   10

<210> SEQ ID NO 30
<211> LENGTH: 10
<212> TYPE: PRT
<213> ORGANISM: Mus musculus

<400> SEQUENCE: 30

Arg Glu Lys Lys Lys Phe Leu Lys Arg Arg
1               5                   10

<210> SEQ ID NO 31
<211> LENGTH: 20
<212> TYPE: PRT
<213> ORGANISM: Homo sapiens

<400> SEQUENCE: 31

Lys Arg Lys Gly Asp Glu Val Asp Gly Val Asp Glu Val Ala Lys Lys
1               5                   10                  15

Lys Ser Lys Lys
            20

<210> SEQ ID NO 32
<211> LENGTH: 17
<212> TYPE: PRT
<213> ORGANISM: Homo sapiens

<400> SEQUENCE: 32

Arg Lys Cys Leu Gln Ala Gly Met Asn Leu Glu Ala Arg Lys Thr Lys
1               5                   10                  15

Lys

<210> SEQ ID NO 33
<211> LENGTH: 11
<212> TYPE: PRT
<213> ORGANISM: Homo sapiens
```

<400> SEQUENCE: 33

Leu Tyr Pro Glu Arg Leu Arg Arg Ile Leu Thr
1               5                   10

<210> SEQ ID NO 34
<211> LENGTH: 33
<212> TYPE: DNA
<213> ORGANISM: Homo sapiens

<400> SEQUENCE: 34
ctgtaccctg agcggctgcg gcggatcctg acc                                33

<210> SEQ ID NO 35
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 35
acttgtttaa gt                                                       12

<210> SEQ ID NO 36
<211> LENGTH: 12
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(4)
<223> OTHER INFORMATION: n = any set of nucleotides that is
      complementary to n in position 8-12
<220> FEATURE:
<221> NAME/KEY: misc_feature
<222> LOCATION: (8)..(12)
<223> OTHER INFORMATION: n = any set of nucleotides that is
      complementary to n in position 1-4
<220> FEATURE:
<221> NAME/KEY: misc_feature
<222> LOCATION: (9)..(12)
<223> OTHER INFORMATION: n = any set of nucleotides that is
      complementary to n in position 1-4

<400> SEQUENCE: 36
nnnngtttnn nn                                                       12

<210> SEQ ID NO 37
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 37
ggcaccgagt cggtgc                                                   16

<210> SEQ ID NO 38
<211> LENGTH: 17
<212> TYPE: DNA
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(7)
<223> OTHER INFORMATION: n = any set of nucleotides that is
      complementary to n in position 11-17

```
<220> FEATURE:
<221> NAME/KEY: misc_feature
<222> LOCATION: (11)..(17)
<223> OTHER INFORMATION: n = any set of nucleotides that is
      complementary to n in position 1-7

<400> SEQUENCE: 38
nnnnnnnagt nnnnnnn                                                    17

<210> SEQ ID NO 39
<211> LENGTH: 30
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is a, c, g, or u

<400> SEQUENCE: 39
gyyyyagnnn nnnnnnnnnn aanuurrrru                                      30

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
gagtccgagc agaagaagaa                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gagtcctagc aggagaagaa                                                 20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
gagtctaagc agaagaagaa                                                 20

<210> SEQ ID NO 43
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 43
aataaaagat ctttatttc attagatctg tgtgttggtt ttttgtgtg                  49
```

```
<210> SEQ ID NO 44
<211> LENGTH: 125
<212> TYPE: DNA
<213> ORGANISM: Artificial Sequence
<220> FEATURE:
<223> OTHER INFORMATION: Synthetic Oligonucleotide

<400> SEQUENCE: 44
gtttattgca gcttataatg gttacaaata aagcaatagc atcacaaatt tcacaaataa      60 agcattttt tcactgcatt ctagttgtgg tttgtccaaa ctcatcaatg tatcttatca     120
tgtct                                                                125

<210> SEQ ID NO 45
<211> LENGTH: 273
<212> TYPE: DNA
<213> ORGANISM: Artificial Sequence
<220> FEATURE:
<223> OTHER INFORMATION: Synthetic Oligonucleotide

<400> SEQUENCE: 45
aaattgatga tctattaaac aataaagatg tccactaaaa tggaagtttt ttcctgtcat      60
actttgttaa gaagggtgag aacagagtac ctacattttg aatggaagga ttggagctac     120
gggggtgggg gtggggtggg attagataaa tgcctgctct ttactgaagg ctctttacta    180
ttgctttatg ataatgtttc atagttggat atcataattt aaacaagcaa aaccaaatta    240
agggccagct cattcctcca ctcacgatct ata                                 273

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
acgttgtgtg aggttcctag                                                 20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gattcctttg gatatatacc                                                 20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
aagaggattg ctggataacg                                                 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 49
gactgctgct tagaaattct        20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
ccgtgggaag aaacaaagaa        20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
ccagaagaat agttagtaaa        20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
atgctattgt caggaaagaa        20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
gacaggcatt acaagaacac        20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gcccaatagc aataactttc        20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
caagatttcg ttggcactgt        20

```
<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
tgctggagaa gagatttctc                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 57
tactgtgcct tctctaattg                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
aagtagcaag ggagattctt                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
tgcaaagaag tcacattcac                                              20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
ttatcaactc aaagttctgg                                              20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
gcgagaagat acaagtatac                                              20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 62
tacatatcga aaggaaacct                                           20

<210> SEQ ID NO 63
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 63
taataactgg tattgaggaa                                           20

<210> SEQ ID NO 64
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 64
atatgatcaa agactacctg                                           20

<210> SEQ ID NO 65
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 65
cgtggactgg atgttctctg                                           20

<210> SEQ ID NO 66
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 66
ctgtagacac atttaaacag                                           20

<210> SEQ ID NO 67
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 67
ccacggtgct gccataccgc                                           20

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 68
cccgcgagac agtcgagccc                                           20
```

```
<210> SEQ ID NO 69
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 69
gcgggttctt actcaccgtg                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 70
catctctgtg aagttgcttg                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 71
cacagcatga acttggaggt                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 72
catagcttgg agagctctag                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 73
gagactccag catagccaca                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 74
gacagttggc cacatttgat                                               20

<210> SEQ ID NO 75
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 75
atggaattgt aaacagactg				20

<210> SEQ ID NO 76
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 76
gatgaattat aagctcacat				20

<210> SEQ ID NO 77
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 77
tgaccaggat agcataacta				20

<210> SEQ ID NO 78
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 78
tgaagttcac aacttatcag				20

<210> SEQ ID NO 79
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 79
gccaatcgcg gcccgggagc				20

<210> SEQ ID NO 80
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 80
agtgtgcctg tgtttagctc				20

<210> SEQ ID NO 81
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 81
aaacagaatc tccatccagc				20

```
<210> SEQ ID NO 82
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 82
gcaactgaac tgagtacatt                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
gtttgaaact gcttatcttc                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 84
ttgtcaagca tccatcctcc                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 85
cctcctcgga gcccggagcc                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 86
acaagcaagg gcctacttta                                               20

<210> SEQ ID NO 87
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 87
gggcgctttc aaagggaggt                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 88
gcatttggct cactagaaca                                                    20

<210> SEQ ID NO 89
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 89
ccttacctaa atggttcaaa                                                    20

<210> SEQ ID NO 90
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 90
cataatgatt tctcaatggt                                                    20

<210> SEQ ID NO 91
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 91
tgctccagcc tgggcaacac                                                    20

<210> SEQ ID NO 92
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 92
gggttctcat gataatgtta                                                    20

<210> SEQ ID NO 93
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 93
ccctgtggat acaagaaata                                                    20

<210> SEQ ID NO 94
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 94
ctgaaaaagg aaggagttga                                                    20

```
<210> SEQ ID NO 95
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 95
aagatgaaag gaaaggcgtt                                               20

<210> SEQ ID NO 96
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 96
ccacggtgct gccataccgc                                               20

<210> SEQ ID NO 97
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 97
cccgcgagac agtcgagccc                                               20

<210> SEQ ID NO 98
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 98
gcgggttctt actcaccgtg                                               20

<210> SEQ ID NO 99
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 99
ctgaaaaagg aaggagttga                                               20

<210> SEQ ID NO 100
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 100
ggctggaagc ccccttagac                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 101
gatgatctct gggtccacaa                                              20

<210> SEQ ID NO 102
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 102
aaggaaaggg gccgcaacct                                              20

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
tcgggtgact atgccgactt                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 104
tctgaagact gctttatctc                                              20

<210> SEQ ID NO 105
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 105
gactgagtca caaagctgtt                                              20

<210> SEQ ID NO 106
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 106
ccagagcttg ctacaggctg                                              20

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
gctctcacag tactcgctga                                              20

```
<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
cgctcccgat ctcgcccggg                                                  20

<210> SEQ ID NO 109
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 109
ctcaccattt tctttcgcgc                                                  20

<210> SEQ ID NO 110
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 110
gtcgcttgcc aatccacgca                                                  20

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
ccgtccgccg gttggctcgc                                                  20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
ggtgcatgag ggggctgctc                                                  20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
ctttgggatc atcttccctc                                                  20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 114
ggctggaagc cccttagac					20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
tgacaccttc ttcactgccc					20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
gatgatctct gggtccacaa					20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
caatcagaaa atcctgggga					20

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
cagagcggag cataaatcat					20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
ctgggagtca tggatgaacc					20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
actctctact tgtgtggtct					20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
tgcagaaaag acactgggcc                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
aagaaggtgt cagatcagaa                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
cccgcgagac agtcgagccc                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 124
cgcggcgcgc tgggtgcatg                                              20

<210> SEQ ID NO 125
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 125
gcctagacag tatgtgaatg agtat                                        25

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (20)..(20)
<223> OTHER INFORMATION: 3' Iowa Black quencher

```
<400> SEQUENCE: 126
aaagcagctc acggccacac                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
aagcaagttc ctctgggaag                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
ttttggaaag agagaaaaga                                              20

<210> SEQ ID NO 129
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 129
catcgcatgc ttccagagat a                                            21

<210> SEQ ID NO 130
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (25)..(25)
<223> OTHER INFORMATION: 3' Iowa Black quencher

<400> SEQUENCE: 130
aaatacttcc tctaggtggc agcgc                                        25

<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
ctatggtggg catttggact                                              20
```

```
<210> SEQ ID NO 132
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 132
ttcatttatt tcatacacca c                                              21

<210> SEQ ID NO 133
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 133
aaggacgtag cctttcctaa tc                                             22

<210> SEQ ID NO 134
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (24)..(24)
<223> OTHER INFORMATION: 3' Iowa Black quencher

<400> SEQUENCE: 134
actctgaagg gcaattccag caga                                           24

<210> SEQ ID NO 135
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 135
gtcccagatg tcatggaatg ta                                             22

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
ctgtaggtac tggtattatc                                                20

<210> SEQ ID NO 137
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 137
agagtctgct aaactccctc ta                                              22

<210> SEQ ID NO 138
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal  ZEN quencher
<220> FEATURE:
<221> NAME/KEY: misc_feature
<222> LOCATION: (24)..(4)
<223> OTHER INFORMATION: 3' Iowa Black quencher

<400> SEQUENCE: 138
tcccagagga ctgagaacag gtca                                            24

<210> SEQ ID NO 139
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 139
cttccagatc ctgactccat tc                                              22

<210> SEQ ID NO 140
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 140
ttataaagat ttcagcagat g                                               21

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
gacacagagc ggagcataaa                                                 20

<210> SEQ ID NO 142
<211> LENGTH: 26
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN quencher
```

```
<220> FEATURE:
<221> NAME/KEY: misc_feature
<222> LOCATION: (26)..(26)
<223> OTHER INFORMATION: 3' Iowa Black quencher

<400> SEQUENCE: 142
aacacactgg gagtcatgga tgaacc                                          26

<210> SEQ ID NO 143
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 143
gaccaagacc acacaagtag ag                                              22

<210> SEQ ID NO 144
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 144
ctgttcatca ccgaggaatc tc                                              22

<210> SEQ ID NO 145
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN qencher
<220> FEATURE:
<221> NAME/KEY: misc_feature
<222> LOCATION: (25)..(25)
<223> OTHER INFORMATION: 3' Iowa Black quencher

<400> SEQUENCE: 145
accagagtca gacagaccca tagca                                           25

<210> SEQ ID NO 146
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 146
acagagcttc agaaaggtta gac                                             23

<210> SEQ ID NO 147
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 147
catcaaccac aggtagcaag ta                                              22

<210> SEQ ID NO 148
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' 6-FAM tag
<220> FEATURE:
<221> NAME/KEY: misc_feature
<222> LOCATION: (9)..(10)
<223> OTHER INFORMATION: internal ZEN quencher
<220> FEATURE:
<221> NAME/KEY: misc_feature
<222> LOCATION: (24)..(24)
<223> OTHER INFORMATION: 3' Iowa Black quencher

<400> SEQUENCE: 148
aaagcagaca gtagaggtcg tggc                                            24

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
tcaccaagac aaggcaagag                                                 20

<210> SEQ ID NO 150
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 150
aacacgtcta tacgc                                                      15

<210> SEQ ID NO 151
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 151
tcaagactga tagata                                                     16

<210> SEQ ID NO 152
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 152
cgccaattta cggagg                                                     16
```

```
<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153
tcgtagttag ttgcag                                                   16

<210> SEQ ID NO 154
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 154
acacagaatt agagtc                                                   16

<210> SEQ ID NO 155
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 155
cgaaagaagg acgatc                                                   16

<210> SEQ ID NO 156
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 156
caaagttaag cgcgat                                                   16

<210> SEQ ID NO 157
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 157
ccgagagatt tagagt                                                   16

<210> SEQ ID NO 158
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 158
tcaggaaaga gcgcga                                                   16

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 159
gatgatctct gggtccacaa                                              20

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 160
tcaacaatca gaaaatcctg                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
atgaactgcc tgacacagag                                              20

<210> SEQ ID NO 162
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 162
ctccgtgagg catcgtcag                                               19

<210> SEQ ID NO 163
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 163
atgaccagtc taaggggct                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 164
cacaagtaga gagtggcggg                                              20

<210> SEQ ID NO 165
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa = Aspartic Acid (D) or Glutamic Acid (E)
<220> FEATURE:
<221> NAME/KEY: misc_feature
<222> LOCATION: (4)..(4)
<223> OTHER INFORMATION: Xaa can be any naturally occurring amino acid

```
<400> SEQUENCE: 165

Pro Asp Xaa Xaa Lys
1               5

<210> SEQ ID NO 166
<211> LENGTH: 834
<212> TYPE: DNA
<213> ORGANISM: Homo sapiens

<400> SEQUENCE: 166
gaggccatcc tgatgagtac gaggtggtag agctgcctgc ttttgatta atgtgacgat      60 cacaccctct gcctgggagt tttacagact ggtgatgact ttttgtggca tctcaggaaa     120
gaacataact tcgtggacgt ccttagtcag aatctactca gtgtatctac tcagtatagg    180
ctcacatgag ccctcacctt cccagggagt cacaacctct actatacttc ttctttctgc    240 tctgccccc acaaacggcc ctgccagccc tcaccaccta gagggagatt gggagccggt     300
agaggaaaga caccctgaat ccccgaggtc aagcaaagcc ctggggaggc gccgtgggat    360
ccctgcctcg ggcctgccta gacagtatgt gaatgagtat cccagagatt ctccccgctg    420
tgacctcgag ggccagcctg cctgtgtggc cgtgagctgc tttcttccca gaggaacttg    480
cttgcggcag caggactcca cagcctcagg ggcagcttgg gcctcggcaa agtggggagc    540
tgcctcggtc cagcaggggt ccagatcacc tcctcattta gagggaccat gtctctagag    600
agatgacatg ccaaaaacgg aaacctcaca ggagcttttt gtccacctgc aagcgaggtg    660
cagacacgtt tgagatggtg gatggacttt tttttttctc ttttctctct ttccaaaatc    720
tggacacacc atggcccagt gatggagaag aagtcgagga cctgtcaagg atcttctttc    780
ttaggagtgg cggagggctg accagtctca ataaagcaca gggggagccc ctgt          834

<210> SEQ ID NO 167
<211> LENGTH: 619
<212> TYPE: DNA
<213> ORGANISM: Homo sapiens

<400> SEQUENCE: 167
atttttcagt ctgagccttt tttcagtgct gtaagaaagg acggaggctg ttatctatgg     60
cagatctatc caataaagga gagaaaggac cgcatacgcc tggttctcat catatgcaat    120
aaagagtttg accatctgcc tccaagaaat ggggctgact ttgccatcat ggagatgaag    180
aagctgcttg aggatctggg ttacagtgtg gatgtagaag agaatctgac agccaggata    240
acgtgtccag gagagacagc acaaggggct ccatcttcat cacacaactc atcgcatgct    300
tccagagata ttcctggcgc tgccacctag aggaagtatt ttggaaggtt cagcaagcat    360
ttgaaagtcc ggaggcaaca gtccaaatgc ccaccataga acgagtgtcc atgacaagat    420
atttctacct ctttcctggc aattgaaaat ggttaagcat tgagagttgt tggtggtgta    480
tgaaataaat gaaagtgtga tattggagca ggaaaccaca agcagcccag ccctccttta    540
tcaacttcaa gaaacacctt tactagtaca gattgaatgc ttaacatttt gtatttcaat    600
aaaggtgaag acaaatgaa                                                 619

<210> SEQ ID NO 168
<211> LENGTH: 884
<212> TYPE: DNA
<213> ORGANISM: Homo sapiens
```

<400> SEQUENCE: 168

```
tttctatatt tcctgcccag tactaaaatc agccatttct ccgaggagcc ctgattcctt      60
ttaccatgga agggagctga acttcagca gtgaaaagga ctggagagct cccgcgggtc     120
tcgaaccgcc cagagaggta aaggactgg agagcgccg cggtctcga acaacccaga      180
caggttgctt gtttcaatta agaactgtc gaagtaaccg ctgagctaaa gccagcccgg     240
aggttgcttt cggattatat tttattgact ggtgagaaag acctacgtca caaagagtga     300
gtcaaaaaga gagtgcttca gcatgactca gcgaccagga ctgtccaaca cgcccccgac     360
ctccagacaa ttgaggagtt gtccatctgg ggacacacag cagtgacaag gacgtagcct     420
ttcctaatcc ctgaagagct cttccgcagg tactctgaag ggcaattcca gcagaatgta     480
cattccatga catctgggac tttgatgcgt tgccccagaa gataatacca gtacctacag     540
catgttcacc taagcactgg tcaagtggat attactcaac cagaatgcaa acatttctat     600
tggttttagt aagacctgaa agaggctggg cgcggtggct aacgcctgta atcccagcag     660
tttgggaggc tgaggcgggc ggatcatgag gtcagatgat caagaccatc ctggctaaca     720
tgtgaaaccc cctctctact aaaaatacaa taaaaaaaaa aaatagccgg gcgtggtggc     780
aggcgcctgt aatcccagct actcgggagg ctgaggcagc agaatggcat gaaccaggaa     840
ggtggagctt gcagtgagcc gagatagcgc cactgcactt cagc                     884
```

<210> SEQ ID NO 169
<211> LENGTH: 411
<212> TYPE: DNA
<213> ORGANISM: Homo sapiens

<400> SEQUENCE: 169

```
gaactcccac actctgaatg aacagcccag tgatcaggag ctttgaatca attcttggca      60
cctaacagtt tgtgaagagt ctgctaaact ccctctatca gaaatcccag aggactgaga     120
acaggtcatc cttggagctg tatctgaatg gagtcaggat ctggaagccc aagtctcctt     180
gtcaatgtct gcttggttcc caaggacacc tgtaaatgga gagggggcat agtacacaga     240
agacattgct ggcaagtgtg gtctctttac gatcaggtga gtcatctgct gaaatcttta     300
taatagactt ctaccttgat ggaatggggtt ggactaacga ggaaccacca ttactccaag     360
gcccagagca gagctgggcc atcaactgtc tccacacttc ctgtcttcta g              411
```

<210> SEQ ID NO 170
<211> LENGTH: 1421
<212> TYPE: DNA
<213> ORGANISM: Homo sapiens

<400> SEQUENCE: 170

```
tgggacatga ccagtctaag ggggcttcca gccttgcaga aaagacactg gccagggca      60
gtgaagaagg tgtcagatca gaaaggatga tctctgggtc cacaacgccc acttccaagg    120
cacctagaga gggggaaaca gtttgccttc cccaggattt tctgattgtt gaaaaatacc    180
atgaactgcc tgacacagag cggagcataa atcattggaa aatactcaga ttctagtgga    240
tttactagaa cacactggga gtcatggatg aacctggatt ttaaagctca acccacagcc    300
cgccactctc tacttgtgtg gtcttggtct atctacaacc ttaaagcctc agtattctcc    360
tccgtaaatt ggcggggagc aatatcaccc ttgcagggtg atggttacgg cacaatgaag    420
atcttgaagg gcacacagag agagggaagg caacagaggc aggctttgtt ggacaccaaa    480
tgaatgtact gagccattgt tccaagacag ctctgtattt taaagctcag catgggccaa    540
```

```
attcaacctc tggatgaaat atgtgattct tgtggcattg tcagaagtgg caaatggatt       600
ctctcctcct aaatgtggtg tgactctccc atcaaccaca ggtagcaagt aacggcacac       660
ttgccacgac ctctactgtc tgctttctgt atcactgcct caatcatgcc cctcctcttg       720
ccttgtcttg gtgaagagtg cctggccagc agccctgcct acctctctct tctggcccta       780
gcgccttgct ccagcccatg tggttccagc aagctccact tcaaggggcc caccctccag       840
ggcatgttcc aagcatcacc aaccagaggg cttcttctct gagaatttat acatggacct       900
tgaggtcagc aagcaaggat gatataagcc agagttctct gcagccatcc ccttttcacc       960
tctctcagtt acggatgaac ttatctgtaa aatgggaaaa agaaacgaca agagaagcac      1020
agctgagaga acaccaaaaa gaaagagttg aagacattgt ttgaattcct gcatccagta      1080
gtgcccaaag ccagtgccaa ccctggaatt cctagctaca agagccaatg aagtcccttt      1140
tgctttagtt tgaggtgggc tcctgtcact tgccacagaa actaggagaa agcacagtgt      1200
ctgtgctgca gtgagagagg gctaaagtcc tcaggacaa ccaataaagc acgagagcca      1260
atgaataaat acttgaggtg agcaattaca ggaggcattc tttacatttc ttagagagcc      1320
aagcaaaatt tagccccagt tgcctgaagt ggccatatat attattatta ataatgaata      1380
tagtcaataa cctgtaggca gctcagaaaa aatctcagtc a                          1421

<210> SEQ ID NO 171
<211> LENGTH: 1262
<212> TYPE: DNA
<213> ORGANISM: Homo sapiens

<400> SEQUENCE: 171
cctgactcaa cttaaaggtt tatacagcca gaaaggaaaa cagaagggca aggaagagga        60
gttggccaac agggagcagg agttttcatt gttcaaataa gactctctgc aagagctgaa       120
ggagccctga ccttggggtg aataagtgaa gagcagaatt ggtcccactc atctctttca       180
catggccatg ggtatgccat gaatccaagc aggtcttctg ggacacaact tctccaagca       240
atgagctcac cactccctga gcctccactc tctggctgag cccagggatc catgctctgg       300
ctgagtccag gccccatgaa cctgcacccc ccacagcttc ttctccacag cagagtccag       360 tggcccccact gatatttgtc ttggctgccc caaggactag cagagacgtt cctcccaagt       420
tgatagggcc cttttagaca actttgcata agcacagttc ttctagctga gctgcaagca       480
accatatgaa ctgcttctct agctcaagat atgacatgag cgtcttcttt catattgttt       540
ttaactgatc attcatgtcc tgctatggga agtttagcat ctctctcaag gatgctcctc       600
ctcaccaatt ttctaagaac tgcagagtct gaatcagttt acgggggcat cactgccact       660
tccaaatgca aataaaaggg agaattggag tgccaccaat ttctgaggct acaacttttc       720 attttttgtca gtgtcaaaga ctgggccaat acatctttgt cccctgctaa tgaatgttct       780
tggcccagat gcagtgacgg ccctgtgttt gagataccag gttgcagcta tcttggttta       840
caaggccgca cgcactcatc acatcccaaa gactactgtg atagagggct cccagccaca       900
cacatgtcag accagagcaa gttctcccct accaaggtcc ctaggtcttc atgcttaacc       960
ccatcctcgg cctagttcat tccaaccctg gaacctcatt gtccttccca acccctgggc      1020
ttggttcaca ccaacagatt tccctaactc tgaatatcca ggaacagcag ttggaatctt      1080
tatgccttct ctctcagagg atcctgaggc ccatatgcaa ataaattctt ccacccaccc      1140
aaagatctgt ataccaagag gaagcttccc ctcagtctcg aaaaacaaaa gacttatgac      1200
```

| | |
|---|---:|
| agacacttta tggttgtctt ctatgctgtt catgaaatat ttctggttct tccttctttc | 1260 |
| tg | 1262 |

<210> SEQ ID NO 172
<211> LENGTH: 555
<212> TYPE: DNA
<213> ORGANISM: Homo sapiens

<400> SEQUENCE: 172

| | |
|---|---:|
| aaattttga ctctcaggta gtggtgatcg ttatggtaac ccatgaactc ggatgaattt | 60 |
| cggggcctgc tgtgggtttt ctatgggaca ccatatacca cagtactgta tttcaaaata | 120 |
| ttggatattg attatgaaca ctggaactat ttatgtgtca tcattccaaa gaccattgtg | 180 |
| atctatgaag ctcctttatt tgctggctag attgtccaaa aacaagctca cttgttttg | 240 |
| ggcaatctag ccaaggtgtc acataatgga gaaaaatgca gatggtcctg tggctggtgt | 300 |
| gaatgaagaa tgacctgggc ccaacataga acttttccag tatggtctct gcatgtgggg | 360 |
| agccaaactc tagagaagac atcagtgaac tgctgatttg gagtgactga cacttattcc | 420 |
| tgagagtagg tgattcttca gtatccaaag aaatgtatca agtttgtatt agatggaata | 480 |
| tagcttactt tgttgctgaa acattttta gcactgacta tacttgcaaa tgtaaggcat | 540 |
| agtacatgaa catgg | 555 |

<210> SEQ ID NO 173
<211> LENGTH: 303
<212> TYPE: DNA
<213> ORGANISM: Homo sapiens

<400> SEQUENCE: 173

| | |
|---|---:|
| acagttatgg gagcacattt ttgaacacag gctcccacct tcaacttatc acttccttac | 60 |
| ctttgctggg gtacctgatg actttaaaga gactgtttct ttggagaagg tggaatacgc | 120 |
| ttaaagattg gtcttgcctt taaaacacca ttttaaaaga gaccatttgt tagtgcctga | 180 |
| aatctgtaac tggcttaaaa gctctgtcag ctggaaagga acctgtcagt gtgataatgg | 240 |
| aaaagaagaa gatacatcag agagagctct tctgaggatt aaaggaggta acttaagaag | 300 |
| aag | 303 |

<210> SEQ ID NO 174
<211> LENGTH: 302
<212> TYPE: DNA
<213> ORGANISM: Homo sapiens

<400> SEQUENCE: 174

| | |
|---|---:|
| aactatttta ctattcactt ttggtcgaac tgaacacaaa gccaccagtt aagaggatgg | 60 |
| gttcatcaaa gacatcagag ggaggcactt tccattcaga ggatttttaag ggccgatcct | 120 |
| cattcactta atgtttgtt aattcaaaaa tgaaaatcag tgagctgcat caggacccct | 180 |
| ctgcacatcc tcccagatcc aggggagctc ctggcaatag actgagggcc tgccccaaca | 240 |
| gtggcatcat aaaattattg gacatcagcc tgctctgcga agttgtactg aagtttccag | 300 |
| ag | 302 |

<210> SEQ ID NO 175
<211> LENGTH: 3728
<212> TYPE: DNA
<213> ORGANISM: Homo sapiens

<400> SEQUENCE: 175

```
gagtaattta acctccaact ctctgtacaa tcaggtaata ctattgtact cagttgaggt      60
gagaggcatg gtgcattacc cagcacatgg cggggcacag taagtgtttg tttggctttt     120
tttcttttct ctctctctct ctgtgtgtgt tttttttttgt tttgttttgt tgttttttttg    180
tttttttttt tttttttgaca gggtcttgct gtctcactca ggctggaatg tagtggtatg    240
agcaagctta ctgcagcttc agtagatcga aggtgctgcc caccaccaca cccagctaat    300
tgttttgatt tttagtagag atgaggtctc actacattgc ccaggctggt attgaacatc    360
tgagctcaag taatcctccc acctcagcct cccaaagtat ctgaattaca ggtgagccac    420
tgtgcctggt cagcaggtgg tgttttgagt ccttcctata ataactcttt gttgagcacc    480
aactacatgc tattgtcctg ggcccggccc aagatggtc attactgtgc acattgtaat     540
gcagcaagta tggaatttgc aaccaacacc cagatcttcc gataagttcc tcctcttacc    600
agcatgcaat cctaggcaag tcattttcct tctctgcatc tccatctcct tacctgaaac    660
aagcagagaa gatttacaac actcattgag attatacacc tcatgcagtc ctggcacaag    720
ataggaatta atgtattcat tatttccttc ttccttttcca catgtctgca tcagttatgt    780
gtgctaagta ctccacacag ctcagagatg gaacttttg aaactcttct gatctagtgc     840
aaatgttctg gggatggcga ggatctggag aagtccggac acagagtaaa tcaggttgga    900
gagagatttt tttaaagaca ttgcaattgc ttaggtgagg aagacagaag acttcagagg    960
aatcgaagat gactcctagg tttctggctc gaacaactag gaagaggttg gtgtcaaatg   1020
ctagggaaga attctcttta cctcctgtct tagtcagttt gggctgctgt aaaaaatgct   1080
gtcaaaattt attttctcac agttctggag cttgaaagtc catcaaggtg tcaacattat   1140
tggtttctgg gtgagggctc tcctggcttg cagacagcca cctgctccct gtgtgctcac   1200
atagcctttc cttggcgctt acacctggga gagagtgagg aaactctctg gtgtctctta   1260
ttaaaagagc tttaattcca ttggaccagg accccaccgt catgacctcg tctcatccta   1320
atcaccttca aaggctgtgt ctccaaatac catcaactgg ggattagagc ttccacaaat   1380
gaattttgag agaacacaaa catttgattc ataacacctc cgtattaata agagagaaat   1440
aatgatgacg cgtatcctag tcatcttcct attccaatgg ctttgagcct ctttgattat   1500
ttcaggaggt ggcttgcaag cacatctgtc tacattcgtt tttcttccat aagaaagata   1560
aaggggaaga ggagcctcgg taggtgagtt agggctaagc tatgagttca tagtgaagac   1620
ttttgtgaca caagcataaa aaactaggtt cctaaggacc cagtcaatgt gaggctttga   1680
actagaaact gggatgtccg ctgagtcaga ggcacccttta ccctcaagga tctcacgact   1740
ttgtaaatac atggaggatt ttctcaggaa gttagctgtt tggactctcg tctcaggtca   1800
tgaacatctt gcctctgaat atgaaggtcc ttaagtgtga ctccatcact ttcctgtcca   1860
ggacttcctc aggcagggga tggtctgctt acctgacccc taagtggctt gttaggatga   1920
atcatgttcc agttctctaa gagggtttat gtgttggaaa gaatattctc tttgatctca   1980
tggcttagag tgcataggct ttgtccagtt aatcatgtag ctggcgtcag gctttgccag   2040
tttttatttc tttgaggctt tatggcattt aaagggttgg agactggccc tgtagcgaac   2100
atggttttga cttcaacagc aactgaacct tttctccagc tctttgataa taattgatta   2160
gtctagaagt ccaagcaaag gtgggacttt ctaaagtgcc tcagatctaa ggggtgattg   2220
aagggggtgag tctttaataa ggacgcactc tctcctctcc tctcctgagt cattcccaca   2280
tggttaaaag agctctccca ataaatttga ttttgcctta gtgctttcca tttacaaagt   2340
```

```
acattcattc cactatcaat ttaacctctc aaatcagcct tgagaggtag aaagagcaag    2400
gcaaatgggc ttaattttgc aacagagaaa ttctaacact cattaaatga tttgctcaat    2460
gtctcatggg gtacgagttg tgagaggagc taacatttat tgagggtctg ctatgtgaca    2520
gtttccttgt aaaccctaac ttatatagtc tacaactaac cctgggtggg gggtagatat    2580
tattgtgccc agttgaaaga tgaagacact gagtcatgag acatttaaag agctatttca    2640
aagcctccca gcccttagat attaagccaa cattgacttt ctagtcttct gagagtcagt    2700
ctgttatgct gtttaaactc ctcatgcctg actgtaagaa gataatagta cactatttat    2760
gcttagtcaa atctgggta agaagtgccg taaaaggaaa agaggcccat tttccctctt    2820
tacagagaga tttggaaatt tgctttcctt tacatatgaa atgaaagaag acgcagagac    2880
atggaccagc tgctgcgtgt gcttctctct gaagtctgag ccgagattcc ctaagcttga    2940
ctgcatcgct taagaccaca ggccagggca gcagcccttc tgcgaaaaaa gccacctttt    3000
aaccggcttg ttcgttttct tcttcttgca cactctgtgg tctggcaagg agcaggggg    3060 cctcaatagc aaagccctca caacagcaat ccttctcagt tcccactctg agtgaacccg    3120
gttcaacttc tcgggctaac agagatttta atcgaaatga actgacagag aatttgctaa    3180
gtccaagaac acacagtctc gaggtgactg gacaggaaca gaagcctcta aaagctgaaa    3240
gaatgaggca aaggctttcc cctcggcaga ctctggcctc ccttcttgac acttcctctt    3300
gggctctgtg agtgtttgcc cagggttatt ggcgatgtca ttgggtgtca gctgatcgac    3360
agcgaaaggg agaggagcta gagctactgc aggccaggag cacacacgct ggatctcatc    3420
tcatctccat ctaactccta tgtgaagtgg gctgttggaa ccccttttccc acatttgagg    3480 aaactgaggc tctaaaacgt gcagtacgtc gtctaagctc cctggtcctc cagatgacaa    3540
ctgtgagaga ttgcttggat gcttggggac tttgtgaagt caacattata cagcagccag    3600
agcaaatgcc tcagcttcaa agacaccttc aagaacctgt ctttttccatg ctctgagcat    3660 gcccatgtaa aatcctcacc ttgggtaaga ttgcctcttt gtgtggctgc ctctcttctc    3720
aagggaag                                                            3728
```

<210> SEQ ID NO 176
<211> LENGTH: 369
<212> TYPE: DNA
<213> ORGANISM: Homo sapiens

<400> SEQUENCE: 176

```
gatctccatg acctctatgg ttccttagac tgcactttga gaactattga cgtacaggga     60
aaaatgctct tggtgttcca gttaagcaca gaataaaatc tggactgtgt cagtttgtaa    120
agatcttatg tctacttggt catcagccaa gaagggattc cgaagataga agaggaggca    180
tcaacaccgt gaacatcatg gctgagttat tttgtgagag ggataagcct aaagtaaaaa    240
ccttggattt gcctctgtcc ttgaacatgc tatctggaaa gagttttctt aaaagtattg    300
ttgtgaacac atccattttc ccagtatagt tgaatgcagg gtttaataaa tggaatgaat    360
ctagttttta                                                          369
```

<210> SEQ ID NO 177
<211> LENGTH: 3678
<212> TYPE: DNA
<213> ORGANISM: Homo sapiens

<400> SEQUENCE: 177

```
tttgaacacc gcctcccacc ccgcgggaag tgcgggcttg gtttgtaccg cggtgacccc      60
cgcccccctcc gaagccgcag agccggggcc tcgcgccagc agggctggag atgccttctt    120
ggcggctgag tttatttatt ataggaagtc attcgctcgt gggtattta tgtgatttgg     180
cgagtgatgt gcccggccag cgccctcctt ggctgcagcc ccgcaggagg acccggagta    240
gggtgggatg gagtgggtcg tgggaggagc gcgtcagcgc ctgcccgggg accccagct    300
cccgcgagga cacggaggcg cgcacgccgc tcggttttcc tggaaagtgg agaaggagcg    360
tcctgggcag gtcctctgag ctcatccccc ctcggattgg ggcgggtctg tgacggggtc    420
acttaggaca cgacgtcccc ccgccattcc cttcccccgc ccagggcgtt cgcggtgggc    480
gcccaccgcc aagccccact gttcccaagg atgcgccagg tgcttcccgt agcgtcctgg    540
gttgacccctt aaaaaaacag caccctagg aggtggccgg ccctctcctc caggtctc     600
tccgggtcac gatcttccaa agttcggaaa ctcgcaggat cgcgtgtgca atctcccgct    660
acctcccggg gggccgggga gaggtcagag gagcgagtcc cgcgtccacc ggcctcgctt    720
gccccctgcc cgtttgagga tagttccagg gagcagggtg gagtgtgcgg acatctttgg    780
aggcagtgct ggggcttccc gcgttggcgg cgctccaccc ggcgtggggg gcggctgcac    840
gggccccgc ggtggggacg ctgcgcacgg ggcaaggtct ccctaggaag cgcccgggaa    900
ggagatgggg cccgccagga acccccctca ctgaccagct ttctgcacgc cgtgcaggag    960
ggggccactt cctcggagag tattggcttt taattaaaac aagccctaca attttttacat  1020
cgggctgcca cacttgtgta tcccttcttc cttgaattta accaggagtg agcagtggac   1080
agcttcttcc ctatgagaag gaggtgaagc aggacctgaa atcccgtgct cagctcccac   1140
atgcccgtg tccaggacaa gtcctttgct gaatcagcgg cagacaccac ccggagccct   1200
gcgggagcct ttccctgttc ttccagcatg gatctgaaac tccccttccca ctttctgcag  1260
cctcccagag atagttcagg ctccagcctc atgtgatagc atgaagagaa actggttcca   1320
acagctgtgt gctctgctgc cctcatccca aacaacagtt taaatgcaca attacgcttt   1380
tctctaaggc ccaaaatagg ataggaagaa tcgttttgct atccctgaat gcctgtcacc   1440
cttgtttcgt aagcaggaag tcagtcccag aatagttgtt ctgctccctc ccttctaata   1500
agtgctgcgc tgagtgtgct tgcttttgcca gatggttaaa acagagcagg ggatagaagg   1560
acagatgtct tcaccctcat ggagttcacc ttccagtagg aggaggcgat aggccggggt   1620
ctgcacatgt gcgtgctaca gcctgttcca cggtgcgtgg cgtgcgggc agtagagaca    1680
ggatttcacc atgttggcta ggatggtctc gatctcctga ccttgtgatc cgcccctccc   1740
tcagcctccc aaagtgctgg gattacaggc gtgagccact gcaccctgcc agaaaactca   1800
ttcttctact ccatcctaca gttttcccta agagagaaac aataaaacgc caccacgacc    1860
aatggcaaaa agctggcacc cactccacga cttttcatat ctacacgttt gtacagcttt   1920
attttttaagc attctgaaat tctatgcagg agagaccccca gctaggttta gggagtccta   1980
gggtttgtgg agtaaatgaa gtttctcccct agaattaggg agggtagaga caggcagaga   2040
actgacaatc ctaacagctg ctgtcctcag agccactgtt tctgagagct gctcgctgag   2100
tgcttctagc gagttaaatg gtgttcgccc aaaagacctg ttcacgtcct gatcctggga   2160
acctgtggct gtgatcttat ttggaaaaag ctctacatta cgtctttgca gaagtaatca   2220
tgttaaggat cttgagagga cgtgaccctg aattatccgg ctgtgcttga catccaatga   2280
ctggtgatgt tgtaagagaa agacggaggg agatgtaaga tatgagagaa ggccacgccg   2340
```

```
agactggagt gatgtggccg tgagccgagg aatgcctgga gccaccagaa gctggcaaag    2400
gcagaaggag cctcctctgg accctgtggt gggtacgcag cctggcagat atattcattt    2460
tggacttctg gcctccaggg ctgtgagaga atacatttct gcagttttaa gccacgcaat    2520
ctgtgtccct gggaagccca aatagggcga accttttgc caagtggtct ccaagtgtca     2580
cgtcatcgaa tccttctccc gggcttgtgc catagtcttt ccactttaga gaggaggaaa    2640
cggaggctct ggggcacaaa gccagtcagt ggcggggcct gactttcaac ccagcctgca    2700
tggggtcaga gaacccactt tccccgtggg gcctgcggcc tatgctaagg atgcttgttc    2760
atctctcctg ggcccgggag tggttcttct ggcctagaag caagagaag ccagtctttc     2820 ggtttcaagg tttcccatta gtggagtcaa gcaaaaatgg tgtgttgcgc ttcttcctga    2880
gctcagcctg ggagcacggc cttaacatgc tcagtggatc ccaagacggc agcatggcgg    2940
tgccagcctg gcagccttag ctccttgcag ctgtgcttgt gaagggagca gtgagtggct    3000
tccctctgtg accaccttgg gtcctaagtt tcactgggc tgggatccat gcgtcttgca     3060
attggctagg aatttcccgg gctttccctc ccttccctgt tcagggcact gggtgtgagg    3120
cattgcatcc gttcttctgc tcacctgctt ccccctaaga gtgtgagctg tataaaggca    3180
ggaaccaaac aggagcctcc acgtgttccc agttcaaggg cagtgtccct tgtgtgtttc    3240
ttcaataatt cagtggatga cttattctgc acggacactg cacacactcg gccctgccgt    3300
ctccggagct gggaggtgtg gagctggctc ctgacctatt tacacactga ggagggatgt    3360
ggaaaacagg aggagtccca gggctccaat gcaagagga gcctcttcat tccctctgcc     3420
gtggccgtgc aagggacagc gccttgtggg attgtgtcct ccacccaatt atccttagca    3480
ttagtttgct aaggataatg gcctccagct ccacccatgt ccctgcaaag gacatgatct    3540
cattcctttc tgtgtctgca tagtattcca tggtgtatat gtaccgcgtt ttctttatcg    3600
agtctatcat tgatgggcgc ttcagttgat tccatgtctt tgctactgtg actcgtgctg    3660
caatgagcat tcgcgtgc                                                  3678

<210> SEQ ID NO 178
<211> LENGTH: 726
<212> TYPE: DNA
<213> ORGANISM: Homo sapiens

<400> SEQUENCE: 178
cttttagtat gatctaagat tttttgttac aatttatttc ttcatatgag aataattta      60 accttacttc cacagaactg ttaaaaccgt ataataacca cgtgaatacc ttgctaggat    120
gccctgcagt ctttggaagg acaggggcaa gtgaagaaac ctgaagctga agctccatta    180
gctttgtggc gagtcaaccc tggtcaaggt tggaggtggg gctcagaaga actaaaccaa    240
cagatacttc cagctgtaca cactcatccc agccagcgac acccactctt caggtccatg    300
gtcccaggcc gcagcaaagt tctgagacta agctttccac tcatctttat aaaacagtaa    360
ggacaaaatt aaatgaaatg tgcaaaataa ctgcacaaac tctgtgctgg gtgcctggtg    420
acgcggaacc gtcggctggc acgctgcgcc cccacgtgga agcttgcaag gtttggcccc    480
ctaggcacgg aagttcctat ctggcccctg gaaagcagcc caggggacc aggcttagtg     540 cccaaatgta cgcgctgtgc aaaagagaaa cttatgaagt caaggacctc gtggcgtgtt    600
agacgagagc ccgagggcag gggtggggt gcagtgctga tggggatgtg ggccacaccc     660
gctagctttc ctcccgagc cagagaagat gttcctgtcc ttgaacaaga gagcagacag     720
ttcccc                                                               726
```

<210> SEQ ID NO 179
<211> LENGTH: 215
<212> TYPE: DNA
<213> ORGANISM: Homo sapiens

<400> SEQUENCE: 179

| | | | | |
|---|---|---|---|---|
| caacttaagc ccactggatg gatttaaggt tctcctacat tcccaacacg tctatcataa | 60 |
| agacgccaat gaaaggttat aacccagatg gaaacaagac tccaaatgcc agtaaaccaa | 120 |
| agacaacttg agatcagaga cggggttta ccatgctgct gcacactggt cttgaactcc | 180 |
| tgggctctag tgatccacct gctcagcttc ccaaa | 215 |

<210> SEQ ID NO 180
<211> LENGTH: 2863
<212> TYPE: DNA
<213> ORGANISM: Homo sapiens

<400> SEQUENCE: 180

| | |
|---|---|
| attaacatcc cgctcccggt ggcgcagggg agccggccaa agttcctcgc aaagtggcga | 60 |
| gcgaaggagc gctgagcact gacgtctggg ctggggagga gcgggtccga gcgaggacgg | 120 |
| agagggaca gagggaaagg gaggcgggtg tcttcctcag gaatttgagc tgggatctg | 180 |
| catcctggcc attgcagtcc tttagcatcc tcgccgcgcc ctgagcgcgc tggaggctcg | 240 |
| caggctgcgc cctcccaggg ctgatgccgc gtcctgctcc gccgttctgg gacgtcgggg | 300 |
| acaaaagtgg aggagacggg agagcccggg cagaaaaagc aggacgcgcg tcccaggatg | 360 |
| ctttctgttg cagacatgat cgctggtaac agatgcctgg ttcactctca tcctggccat | 420 |
| acctgaggac tatgctcctc ttctagaagt tcggtgcagt catctgactt aattgattca | 480 |
| gcgcatttat ctgcaggctg gagtacaata gcacgacatc agctcactgc aacatctgcc | 540 |
| tcccgggttc aagcaattct cctgcctcag cttcccgagt tgctgggatt acaggcacct | 600 |
| gccaccatgc ccagctaatt tttgtatttt tagtagagat ggggtttcac catgttggtc | 660 |
| aggctggtct tgaactcctg acctcaggtg atccacttgc ctcggcctcc caaagtgctg | 720 |
| ggattacagg tgtgagccac cgcacctggc ctgtgagatg gttttcttgg gtagaatgaa | 780 |
| agaagcttgg ctactgggtc cattttatgt gaacatgttg ctccctatta tagtcagtcc | 840 |
| ctggaaccca ttgtaaagtc agttctgggt ttttgcttag ctaccatgta gtaacagtca | 900 |
| cagcctgtct cctgtcaccc taacaccatc accattgcca gtggatattt ttaccccctag | 960 |
| tttatagtta ggaagcctga gacccagagg gattaaagag ctttttccaaa atcatatggc | 1020 |
| tggcaacact agtaatctgg gctgcctgag tcctaaacat cattctaccc cagcattgaa | 1080 |
| ttccgaggcc tctagaatct tacctacctt ccctgtttga aatgtatttg tgggggaaca | 1140 |
| attgacctca gaatgagtaa tttgtcacta ctctgagaaa gtttcaccga gtttcacatt | 1200 |
| ttcccattac aaaaggaaaa tgagaaaata tgtcctagat actacagaga aaaatacttc | 1260 |
| attgtcttaa ttgcctttct atttcaatca aggaaggcat ttaattatttt ctgaactaca | 1320 |
| ttcaaaactc tctctcaaga atattactct ccccaggtga gttaaccaaa gctgtgcaca | 1380 |
| acatttctca atctgaataa taacatcaaa aaatttattg agcacttttt atatgccaaa | 1440 |
| ctagtcaatt ctttctgttt atgacctcat tgattcctca tggcaagttt atgaagtgga | 1500 |
| agcaatcatt ctctcttcta acaaatgagg aaactgaggc acagagggat gagatagttt | 1560 |
| gtctaagatt gtaaggcatt aggtggtgaa gtcagcattg gatcccaggc caagcccgag | 1620 |
| gccatcactc caccatgctg cctctcaaga gaaagattca gtttccccctt tgagatatcc | 1680 |

| | |
|---|---|
| atttataagt acatgtgcca aagcaatgtg aagaaaccaa cccagatgac ttgattaagc | 1740 |
| tacagaaggg acatctgggg tctcaagcct ctggaaatca aggtggagca tgtagaggtt | 1800 |
| atgggatcag gagagacaga gtttgacttc tttgttttt ctttgagacc aagtcttgct | 1860 |
| ctgttgccca ggctggagtg cagtggtgtg atcttggctc aatacaacct ccacctcctg | 1920 |
| ggttcaagtg attctcctgc ctcgggctac tgagtagctg ggattacagg cgcacgccat | 1980 |
| caggccggct aattttgta tttttagtag acacggggtt tcaccatgtt ggtcaggctg | 2040 |
| gtctcgaact cctgacctcg tgatccacct gcctcggcct cccaaagtgc tgggattaca | 2100 |
| ggcatgagcc accgtgcccg gcctgggttt gacttcttaa gcaacctgag gaatgatgtc | 2160 |
| cttgctgctg agcacagctg ccctgggccc tggaaaaccc acatgacact cactcagcac | 2220 |
| ccaatgctgg cttcattgtg gctgttggaa accatgtgga aaagaaataa ctttttttgt | 2280 |
| gatctgtacg ttatggctat tattttttta cctcgcttag cttttcaaga gaatgaagac | 2340 |
| cagtcgactt agtatttgta ctctgaaatc gaatggcatg aacacatgtg ttgtataagt | 2400 |
| gagaagaagt attctcttgt gtgatggact atagccttca gaaagcacct actattaaac | 2460 |
| agaatagaga ttggattttg aaatatgtag gccacatcag taggaaagtt gacacttcaa | 2520 |
| attgctcaca aggactttaa actctacaat aggtaaaatg tggagtaccct tatgtttca | 2580 |
| gaccaaatga ttttgtaatt tgaattcaaa atttttttag tcttcacagt agtcttagca | 2640 |
| ttaaaagcat agttattttt aatattttga taaaatattc tatttcatta attttgtata | 2700 |
| agggcatgtg tgagaagcat tgatattttt aaaatataaa aatacagcct ctttctaata | 2760 |
| agcaagagca attgttgatt tttaaatttt gtgttttgg aggcttccat tcacaaatct | 2820 |
| gattgtttaa ataaatctgt ctccagtaaa tatgttggca ctt | 2863 |

<210> SEQ ID NO 181
<211> LENGTH: 4426
<212> TYPE: DNA
<213> ORGANISM: Homo sapiens

<400> SEQUENCE: 181

| | |
|---|---|
| gtggtttgat cttggctcac tgcagtctca acctctcagg ctcaagctat ccttctgcct | 60 |
| cagactctgg ggtagctggg acaacagcct cagccaagat gtctcaccct actctctatg | 120 |
| atgcaacaag aagcccctgg ggaatgtttc agtcccagtc tgtactattg tcatgtgctc | 180 |
| atcacagtct ggtggaattt aaatgacctt ttatcaagat ggataaacgc aagtttccca | 240 |
| gtgctggaat acagaaaatg gatggacaaa cagggtcttg ctctgttgtc caggctggag | 300 |
| tgcggtagtg ctatcacagc tgactgcatc ctcaacctct caggctcaag cagtcctccc | 360 |
| acctcagcct cccaggtggc tgagactgta cgtgcttgcc acaatgccca actaataatt | 420 |
| tggactttc ctatacatgg gttccaaagg gctgactgcg aaacgaagtg acctcacaat | 480 |
| gactcaagct accacttagt gttgattgtg atgaaatgcc agctgtggca tatgccttgg | 540 |
| gagctaagtg gctgctgcac ttgaccacta tgaagactgg tgtggaaggg tccttctgga | 600 |
| tgtacttggg cagggtcccc aacgccagag ccatggaact gtaaggagcc acacagccgg | 660 |
| aggtgaatgt tgttgaatga gggaagcttc atctgtgttt acagccactc cccattgctc | 720 |
| acattcctgc ctgagctctg ccttctctca gatcagcagc agcattagat tctcatagga | 780 |
| gcatgcaccc cattgtgaac catgcatgtg agggatctac gttgcgctgt ccctatgaga | 840 |
| atctaatgcc tgatgctctg tcactttctc caatattatc ttcaagtgag ccactcctgg | 900 |
| cccaattcct gtctcccgtt ggcctataga ggccaagcct ctgcctcatg atggcctctg | 960 |

```
caggtcaagc tcctcctcct ggttccgtct acaggcccaa cacttccctc aaataaactc    1020
ttctgcccag ctcctgtcca gctcacggca gccactgtcg gcatgaaaat tcctcaattc    1080
aagctctcta ggcccacctt ctgcctccca ctggcctgga cacgcccagc tccaacctga    1140
caatggtctc tacaggccca gctcatcggg ctctgaggga cctctccagg ccaagctctt    1200
acctcacgga ggcttctcca ggtcgtttct ccctgtcttc aggcagtggt gacaggtcag    1260
ctcctcctcc acagtggcct cgtttgggca ggtcctgcct cttgcagcct ctcaaagccc    1320
agctcctgcc tctgagtggc ttctgcgcac ccaaatgtcc tccagtcagc ctgtcctggc    1380
tgagctcctg cgacctggct gagctcctgc ctcctgtcgg cctctataaa cccagcctct    1440
gctgtatggt ggcttcttca ggcccagctc ttcctcctgg cggtgtatac aggtccaact    1500
cctgcttccc aatggactct ttaggccagg ctcatgcctt acggcagcct ttcctggccc    1560
agcttttgcc tgttggcata ccctccaggc ccacaatgta ctcagatcag ccactccatt    1620
cccagctctt cttcctggct gtgtctacag gcccaactgc tgcctcacaa cccctctttt    1680
tggcccagct cctgcccagc acctggtggc ctctatatgc cccagacttc ttaaagtcaa    1740
ctttgctagg cccacctttg gcctcccagc ggctttgaca ggaccagctc ttgcctcatg    1800
gcagcttccc aacgccaggt ttctgcctgc attgtggcat ccttgatgga cccaactctt    1860
gctttatgcc ggccttccca caccaagttt ctgcctgcct catggcagga tccgataggc    1920
ccagctcctg cctctaatgg cctggttagg ctcatctcat ccctcaaggt ggccacccca    1980
gatgaagctc ctgccttttg gcagccttta gaggcccagc tcatgcatct cattgcctct    2040
tgaagcccag ctcattcctc aaaacggcct atccacgccc agcttttccc tttggtggct    2100
tctccaggcc cagaaattcc tcagttcggc ttcgcaaggt gaagttgctg cctccctgtg    2160
ccttctccag gcccagttct tcctcccagc tgggtctaca gtcccatctc ctgactcaaa    2220
acaacctatt ttggctcggc tcctgcccag cacctggcgg cctttgtagg cctaaagctt    2280
cctcaagtca agcgttccag gcccagatca tgctgcccag gggccttcac aggcccagct    2340
actgcctgac gatggcttcc ccaggcccag gtcttgcctt cccccagcct cccgaggccc    2400
agcccttgcc tcacagttgc tttcccagtc cacgttacag cctgttaccc gacggccttg    2460
acagaccaaa ctcttccttc acactggaca gtttaggaca agctcatacg tcttccagcc    2520
tctccaggtc aagctcctgc tcacactgg cctctatagg cccaggtgct gaatcgcaat    2580 ggtctgtttta ggtccatctc atgcctttct cagactctcc aagcgacgat ctggcctgac    2640
acttgcttct gtgggccatg tgatcactca cactggcctc tttaggatca ggggatgcct    2700
ctccacaggc cgagatcctg cctgttgtag gccccttcag gatgcgccgc tgcctgacag    2760
tggaccctcc aggcctagat gttacgtgat catggcctct gcaggtcaag aatttaaatt    2820
ttcgcagcct ctataggcca ggctactgcc tcctgataat ggcttctgca ggcccaaatc    2880
gtcctgaaat aagcctcgcc aggaacagca cgtgtgttgg atgcccgaac aaccatagct    2940
tctcccgcac agtggcccat gggggccggg ctcttgcctc agcctggcca cctcaggccc    3000
agttcttgcc tgttggcggc cgctccaggc ccggctcctg ccctcggcc tcctctccag    3060 gcccagaact ggttcccgtc ggcctctcca ggcccagctc tccggccac ctccacgggc    3120 ccagctcctg cctcacgaca accacgttcg gcccagctcc tgcccagctc ctggcagccg    3180
ttgtaggccc caggcttccc tgcgttcagg cctcccggac ccaccttcgg ctttccggcg    3240
gccctgagag accggctcc tgcctgccag cggcctctcc cggcccagct gcggcctcac    3300
gtcggcctcc ccaggccacg tttccgcctg cctcacggca gccccggcag gcccggctcc    3360
```

```
cgcctgccgg gggcctcttg aggaggctca tctcgtgccc ggccgcggcc tccccaggcc      3420
aggctcctgc ctgccggcag gcgccacaag cccagctcct gcgtcccgaa ggcttctcta      3480
ggcccggctc gtgcctcgct gcggcctctt gaggcccagc tttcccttg tggtggcctc       3540 tccaggccca gaacttcctc aagtcggcct cccccggtcc agtggctgcc tcccggcctc     3600
ctctccgggc ccagctcttt gctcgcgtct gcgcccgtgg gcccagctcc cgtctccaaa     3660
cagcctcctt cgactcggct cctgcccagc tcccggcggc cttcgtaggc ccgaagcctc      3720
ctccagtcca gctctccagg gccgcgtctt gcctcgcctc gcctcccctc accttgcctc     3780
acctcgcagc agcctttcca ggcccagctc ccgcctcccg gcggccttcc cctgccacgc     3840
tcgtgccggc ctcccggcag cctccaccag cccggctcct gcctcacgct ggcccctctg     3900
ggcccagctc atgcctcgcg gtggcctctc cgggcccagc tcccacccag cctgacggcg     3960
cctcccggcc ccaagctgcc ttcctcgatg tggcccaaag tggcccaaag cgtcccaaag    4020
taggcctcgc caggcccacc tcctgcccgg cgtaggccct gaggggcgcg gccctgccc     4080 catactggcc tcttttgggc cctctcttac accagcccct gtctcaggat tgtctcttca     4140
cgcccatctt ctgcctcata gtggtcactc aaggcctcgc ttttgcctga tgattgcgtt     4200
ttctggtttt gctcttgcct tgtattccct tcttcgggat acagctttta cgtcttccat     4260
ggtgaacctc atcaaggaga ctaaatcttc cctggtctgt catttttttc acttcacacc     4320
agagtgcctt gggaaaaccc catctcttct tttaaccttg agagtggatt tctgacgaat     4380
tgataataaa ttttttctct gtggtttcag tgatttctgt tttaaa                    4426
```